US012168049B2

(12) United States Patent
Coleman et al.

(10) Patent No.: US 12,168,049 B2
(45) Date of Patent: Dec. 17, 2024

(54) ATTENUATED FLAVIVIRUSES

(71) Applicant: Codagenix Inc., Farmingdale, NY (US)

(72) Inventors: John Robert Coleman, Blauvelt, NY (US); Steffen Mueller, Great Neck, NY (US); Ying Wang, South Setauket, NY (US)

(73) Assignee: Codagenix Inc., Farmingdale, NY (US)

( * ) Notice: Subject to any disclaimer, the term of this patent is extended or adjusted under 35 U.S.C. 154(b) by 67 days.

(21) Appl. No.: 16/976,220

(22) PCT Filed: Dec. 21, 2018

(86) PCT No.: PCT/US2018/067114
§ 371 (c)(1),
(2) Date: Aug. 27, 2020

(87) PCT Pub. No.: WO2019/172982
PCT Pub. Date: Sep. 12, 2019

(65) Prior Publication Data
US 2021/0000939 A1   Jan. 7, 2021

Related U.S. Application Data

(60) Provisional application No. 62/640,355, filed on Mar. 8, 2018.

(51) Int. Cl.
*A61K 39/12* (2006.01)
*A61P 31/14* (2006.01)
*C12N 7/00* (2006.01)
*A61K 39/00* (2006.01)

(52) U.S. Cl.
CPC .............. *A61K 39/12* (2013.01); *A61P 31/14* (2018.01); *C12N 7/00* (2013.01); *A61K 2039/5254* (2013.01); *A61K 2039/575* (2013.01); *C12N 2770/24121* (2013.01); *C12N 2770/24162* (2013.01)

(58) Field of Classification Search
None
See application file for complete search history.

(56) References Cited

U.S. PATENT DOCUMENTS

| 5,494,671 A | 2/1996 | Lai et al. |
| 5,744,140 A | 4/1998 | Paoletti et al. |
| 5,824,506 A | 10/1998 | Chan et al. |
| 8,846,051 B2 | 9/2014 | Kew et al. |
| 9,476,032 B2 | 10/2016 | Wimmer et al. |
| 9,957,486 B2 | 5/2018 | Collins et al. |
| 10,023,845 B2 | 7/2018 | Wimmer et al. |
| 10,316,294 B2 | 6/2019 | Mueller et al. |
| 10,695,414 B2 | 6/2020 | Kew et al. |
| 10,808,012 B2 | 10/2020 | Lenouen et al. |
| 2008/0118530 A1 | 5/2008 | Om et al. |
| 2008/0286848 A1 | 11/2008 | Skiadopoulos et al. |
| 2009/0092635 A1 | 4/2009 | Clarke et al. |
| 2010/0008946 A1 | 1/2010 | Szalay et al. |
| 2010/0062532 A1 | 3/2010 | Jin et al. |
| 2010/0166769 A1 | 7/2010 | Hsiao et al. |
| 2012/0009215 A1 | 1/2012 | Yang et al. |
| 2014/0023680 A1 | 1/2014 | Yang et al. |
| 2014/0242102 A1 | 8/2014 | Yang et al. |
| 2014/0356962 A1 | 12/2014 | Wimmer et al. |
| 2015/0307851 A1 | 10/2015 | Kawaoka et al. |
| 2015/0368622 A1 | 12/2015 | Collins et al. |
| 2016/0367656 A9 | 12/2016 | Bonaldo et al. |
| 2017/0067030 A1 | 3/2017 | Wimmer et al. |
| 2017/0143780 A1 | 5/2017 | Zitvogel et al. |
| 2017/0290808 A1 | 10/2017 | Charo et al. |
| 2018/0008689 A1 | 1/2018 | Vignuzzi et al. |
| 2018/0201908 A1 | 7/2018 | Chung et al. |
| 2018/0207295 A1 | 7/2018 | Fotin-Mleczek et al. |
| 2018/0208906 A1 | 7/2018 | Collins et al. |
| 2019/0002837 A1 | 1/2019 | Wimmer et al. |
| 2019/0275139 A1 | 9/2019 | Yu et al. |
| 2020/0268865 A1 | 8/2020 | Kew et al. |
| 2021/0228705 A1 | 7/2021 | Coleman et al. |
| 2022/0160863 A1 | 5/2022 | Muster et al. |

(Continued)

FOREIGN PATENT DOCUMENTS

| CA | 3091508 A | 12/2019 |
| CN | 104204196 A | 12/2014 |

(Continued)

OTHER PUBLICATIONS

Pattnaik et al., Vaccines, 2020, 8:266, 19 pages. (Year: 2020).*
Supplementary European Search Report for EP 18908620 dated Dec. 23, 2021.
Li et al., Zika Virus Attenuation by Codon Pair Deoptimization Induces Sterilizing Immunity in Mouse Models, Journal of Virology, 2018, vol. 92(17), pp. 1-16.
Asif et al., Zika Virus: Immune Evasion Mechanisms, Currently Available Therapeutic Regimens, and Vaccines, Viral Immunology, 2017, vol. 30(10), pp. 682-690.
Extended Europen Search Report for EP 18891144 dated Mar. 3, 2022, 2 pages.
Burns et al., Genetic Inactivation of Poliovirus Infectivity by Increasing the Frequencies of CpG and UpA Dinucleotides within and across Synonymous Capsid Region Codons, Journal of Virology, 2009, vol. 83(19), pp. 9957-9969.

(Continued)

*Primary Examiner* — Stacy B Chen
(74) *Attorney, Agent, or Firm* — Nixon Peabody LLP; Linda B. Huber

(57) ABSTRACT

The present invention provides for modified Flavivirus such as a modified Zika virus. The modification according to various aspects of the invention results in reduced viral proteins compared to a parent virus, wherein the reduction in expression is the result of recoding one or more regions of the virus. For example, the prM, or envelope (E) region, or the nonstructural protein 3 (NS3) region or both the E and NS3 regions can be recoded. In various embodiments one or more regions are recoded by reducing the codon pair bias or codon usage bias of the protein-encoding sequence. These modified Flavivirus are used as vaccine compositions to provide a protective immune response.

12 Claims, 10 Drawing Sheets

Specification includes a Sequence Listing.

(56) References Cited

U.S. PATENT DOCUMENTS

| | | | |
|---|---|---|---|
| 2023/0000971 | A1 | 1/2023 | Rockman et al. |
| 2023/0340423 | A1 | 10/2023 | Coleman et al. |

FOREIGN PATENT DOCUMENTS

| | | | |
|---|---|---|---|
| CN | 102753200 | B2 | 11/2017 |
| CN | 108290932 | A | 7/2018 |
| CN | 111481663 | A | 8/2020 |
| CN | 112040977 | A | 12/2020 |
| EP | 2465927 | B1 | 6/2012 |
| EP | 3727442 | | 10/2020 |
| EP | 3762021 | | 1/2021 |
| EP | 3515930 | A1 | 9/2022 |
| EP | 4061930 | A1 | 9/2022 |
| IN | 202027030412 | A | 10/2020 |
| IN | 202027038754 | A | 10/2020 |
| JP | 2000502889 | A | 3/2000 |
| JP | 2002513575 | A | 5/2002 |
| JP | 2009518007 | A | 5/2009 |
| JP | 2009534039 | A | 9/2009 |
| JP | 2010523086 | A | 7/2010 |
| JP | 2011505863 | A | 3/2011 |
| JP | 4771959 | B2 | 9/2011 |
| JP | 2012510283 | A | 5/2012 |
| JP | 4980895 | B2 | 7/2012 |
| JP | 2012519484 | A | 8/2012 |
| JP | 2012531205 | A | 12/2012 |
| JP | 2013179943 | A | 9/2013 |
| JP | 5349049 | B2 | 11/2013 |
| JP | 2015501141 | A | 1/2015 |
| JP | 2015502158 | A | 1/2015 |
| JP | 2015091247 | A | 5/2015 |
| JP | 2015524266 | A | 8/2015 |
| JP | 2017524693 | A | 8/2017 |
| JP | 2020502080 | A | 1/2020 |
| JP | 2021508696 | A | 3/2021 |
| KR | 2020103020 | | 9/2020 |
| WO | 2007104782 | A1 | 9/2007 |
| WO | 2011044561 | A1 | 4/2011 |
| WO | 2013090795 | A1 | 6/2013 |
| WO | 2013138670 | A1 | 9/2013 |
| WO | 2016037187 | A1 | 3/2016 |
| WO | WO 2016/120412 | A1 * | 8/2016 |
| WO | 2017/078577 | A1 | 5/2017 |
| WO | 2019126690 | A | 6/2019 |
| WO | 2019172982 | A1 | 9/2019 |
| WO | 2020232254 | A1 | 11/2020 |
| WO | 2020263850 | A1 | 12/2020 |
| WO | 2022011032 | A1 | 1/2022 |
| WO | 2022051327 | A1 | 3/2022 |
| WO | 2023102520 | A1 | 6/2023 |
| WO | 2023205689 | A2 | 10/2023 |

OTHER PUBLICATIONS

International Search Report and Written Opinion for PCT/US2021/040716 dasted Oct. 26, 2021, 10 pages.
Supplementary European Search Report for EP 18891144 dated Oct. 20, 2021, 10 pages.
Exam Report for SA 520412310 dated Jun. 8, 2022.
Search Report for RU 2020124143 dated Feb. 28, 2022, 4 pages.
Search Report and Written Opinion for SG 11202008126Q dated Mar. 31, 2022.
International Search Report and Written Opinion for PCT/US2018/67114 dated May 23, 2019, 15 pages.
International Search Report and Written Opinion of PCT/US2018/67174, dated May 17, 2019, 15 Pages.
International Search Report and Written Opinion of PCT/US2020/32901, dated Sep. 1, 2020, 8 Pages.
Woodson et al., Infection of hepatocytes with 17-D vaccine-strain yellow fever virus induces a strong pro-inflammatory host response, Journal of General Virology, 2011, vol. 92(10), pp. 2262-2271.
International Search Report and Written Opinion of PCT/US2020/39166, dated Sep. 24, 2020, 12 Pages.
Nouen et al., Attenuation of human respiratory syncytial virus by genome-scale codon-pair deoptimization, PNAS, 2014, vol. 111(36), pp. 13169-13174.
Yun

(56) References Cited

OTHER PUBLICATIONS

Production of Viral Vaccines for Infectious Disease Indications, U.S. Department of Health and Human Services Food and Drug Administration Center for Biologics Evaluation and Research, 2010, pp. 1-47.

Gao et al., HP-PRRSV is attenuated by de-optimization of codon pair bias in its RNA-dependent RNA polymerase nsp9 gene, Virology 485, 2015, pp. 135-144.

Influenza A virus (A/Gs/HK/739.2/02(H5N1)) nucleocapsit protein (NP) gene, complete cds, GenBank: AY575907.2, Mar. 31, 2008, 2 pages.

Martrus et al., Changes in codon-pair bias of human immunodeficiency virus type 1 have profound effects on virus replication in cell culture, Retrovirology, 2013, vol. 10(78), pp. 1-12.

Influenza A virus (A/PuertoRico/8/34/Mount Sinai (H1N1)) segment 5, complete sequence, GenBank: AF389119.1, Sep. 19, 2002, 2 pages.

Influenza A virus (A/swine/Germany/SIV05/2007(H1N1)) segement 5, complete sequence, genomic RNA, GenBank: FN429082.1, Jan. 7, 2010, 2 pages.

Gao et al., HP-PRRSV is attenuated by de-optimization of codon pair bias in its RNA-dependent RNA polymerase nsp9 gene, Virology 485, 2015, pp. 135-144, Supplementary table.

Guo et al., Oncolytic Immunotherapy: Conceptual Evolution, Current Strategies, and Future Perspectives, Frontiers in Immunology, 2017, vol. 8(555), pp. 1-15.

Masemann et al., "Oncolytic influenza virus infection restores immunocompetence of lung tumor-associated alveolar macrophages", OncoImmunology, 2018, vol. 7, No. 5, e1423171, 13 pp.

Hock et al., "Oncolytic influenza a virus expressing interleukin-15 decreases tumor growth in vivo", Surgery, Mar. 2017 (EPub Oct. 21, 2016) 161(3), 735-746 pp.

Bergmann et al., "A Genetically Engineered Influenza A Virus with ras-Dependent Oncolytic Properties", Cancer Research; Nov. 15, 2001, 61, 8188-8193 pp.

Search Report in Malaysia Application No. PI2020004620 dated Dec. 13, 2023, 4 pp.

Search Report in UAE Ministry of Economy Application No. P6001272/2020 mailing date Feb. 1, 2024, 2 pp.

\* cited by examiner

PR15 E-Min

5'—|C|M| E | NS1 |NS2A|NS2B| NS3 |NS4A|NS4B| NS5 |—3'

PR15 NS3-Min

5'—|C|M| E | NS1 |NS2A|NS2B| NS3 |NS4A|NS4B| NS5 |—3'

PR15 E+NS3-Min

5'—|C|M| E | NS1 |NS2A|NS2B| NS3 |NS4A|NS4B| NS5 |—3'

MR766 WT

5'—|C|M| E | NS1 |NS2A|NS2B| NS3 |NS4A|NS4B| NS5 |—3'

MR766 E-Min

5'—|C|M| E | NS1 |NS2A|NS2B| NS3 |NS4A|NS4B| NS5 |—3'

MR766 NS3-Min

5'—|C|M| E | NS1 |NS2A|NS2B| NS3 |NS4A|NS4B| NS5 |—3'

MR766 E+NS3-Min

[Diagram showing four genome constructs:]

Wild-type: 5'—[prM + E genes | NS Genes]—3'

E-Min, 2014 bp deoptimized: 5'—[prM + E genes | NS Genes]—3'

W-E-Min, 997 bp deoptimized: 5'—[prM + E genes | NS Genes]—3'

W-W-E-Min, 664 bp deoptimized: 5'—[prM + E genes | NS Genes]—3'

☐ = deoptimized sequence

▨ = wildtype sequence

FIG. 8

- ○ $10^2$ 766-E*hMin*
- ■ $10^4$ 766-E*hMin*
- △ $10^4$ 766-NS3*hMin*
- ▲ $10^2$ PR15-E*hMin*
- ● $10^4$ PR15-E*hMin*
- ☐ $10^4$ PR15-NS3/E*hMin*
- ● Mock

SEQUENCE LISTING

```
<160> NUMBER OF SEQ ID NOS: 12

<210> SEQ ID NO 1
<211> LENGTH: 10808
<212> TYPE: DNA
<213> ORGANISM: Zika

<400> SEQUENCE: 1
agttgttgat ctgtgtgaat cagactgcga cagttcgagt ttgaagcgaa agctagcaac      60
agtatcaaca ggtttatttt tggatttgga aacgagagtt tctggtcatg aaaaacccaa     120
aaaagaaatc cggaggattc cggattgtca atatgctaaa acgcggagta gcccgtgtga     180
gccccttggg gggcttgaag aggctgccag ccggacttct gctgggtcat gggcccatca     240
```

```
ggatggtctt ggcgattcta gccttttga gattcacggc aatcaagcca tcactgggtc      300
tcatcaatag atggggttca gtggggaaaa aagaggctat ggaataata aagaagttca      360 agaaagatct ggctgccatg ctgagaataa tcaatgctag gaaggagaag aagagacgag      420
gcgcagatac tagtgtcgga attgttggcc tcctgctgac cacagctatg gcagcggagg      480
tcactagacg tgggagtgca tactatatgt acttggacag aaacgatgct ggggaggcca      540
tatcttttcc aaccacattg gggatgaata agtgttatat acagatcatg gatcttggac      600
acatgtgtga tgccaccatg agctatgaat gccctatgct ggatgagggg gtggaaccag      660
atgacgtcga ttgttggtgc aacacgacgt caacttgggt tgtgtacgga acctgccatc      720
acaaaaaagg tgaagcacgg agatctagaa gggctgtgac gctcccctcc cattccacca      780
ggaagctgca aacgcggtcg caaacctggt tggaatcaag agaatacaca aagcacttga      840
ttagagtcga aaattggata ttcaggaacc ctggcttcgc gttagcagca gctgccatcg      900
cttggctttt gggaagctca acgagccaaa aagtcatata cttggtcatg atactgctga      960
ttgccccggc atacagcatc aggtgcatag gagtcagcaa tagggacttt gtggaaggta     1020
tgtcaggtgg gacttgggtt gatgttgtct tggaacatgg aggttgtgtc accgtaatgg     1080
cacaggacaa accgactgtc gacatagagc tggttacaac aacagtcagc aacatggcgg     1140
aggtaagatc ctactgctat gaggcatcaa tatcagacat ggcttctgac agccgctgcc     1200
caacacaagg tgaagcctac cttgacaagc aatcagacac tcaatatgtc tgcaaaagaa     1260
cgttagtgga cagaggctgg ggaaatggat gtggactttt tggcaaaggg agcctggtga     1320
catgcgctaa gtttgcatgc tccaagaaaa tgaccggcaa gagcatccag ccagagaatc     1380
tggagtaccg gataatgctg tcagttcatg ctcccagca cagtgggatg atcgttaatg     1440
acacaggaca tgaaactgat gagaatagag cgaaagttga gataacgccc aattcaccga     1500
gagccgaagc caccctgggg ggttttggaa gcctaggact tgattgtgaa ccgaggacag     1560
gccttgactt tcagatttg tattacttga ctatgaataa caagcactgg ttggttcaca     1620
aggagtggtt ccacgacatt ccattacctt ggcacgctgg ggcagacacc ggaactccac     1680
actggaacaa caaagaagca ctggtagagt tcaaggacgc acatgccaaa aggcaaactg     1740
tcgtggttct agggagtcaa gaaggagcag ttcacacggc ccttgctgga gctctggagg     1800
ctgagatgga tggtgcaaag ggaaggctgt cctctggcca cttgaaatgt cgcctgaaaa     1860
tggataaact tagattgaag ggcgtgtcat actccttgtg tactgcagcg ttcacattca     1920
ccaagatccc ggctgaaaca ctgcacggga cagtcacagt ggaggtacag tacgcaggga     1980
cagatggacc ttgcaaggtt ccagctcaga tggcggtgga catgcaaact ctgacccag     2040 ttgggaggtt gataaccgct aaccccgtaa tcactgaaag cactgagaac tctaagatga     2100
tgctggaact tgatccacca tttggggact cttacattgt cataggagtc ggggagaaga     2160
agatcaccca ccactggcac aggagtggca gcaccattgg aaaagcattt gaagccactg     2220
tgagaggtgc caagagaatg gcagtcttgg agacacagc tgggactttt ggatcagttg     2280
gaggcgctct caactcattg ggcaagggca tccatcaaat ttttggagca gctttcaaat     2340
cattgtttgg aggaatgtcc tggttctcac aaattctcat tggaacgttg ctgatgtggt     2400
tgggtctgaa cacaaagaat ggatctattt cccttatgtg cttggcctta gggggagtgt     2460
tgatcttctt atccacagcc gtctctgctg atgtggggtg ctcggtggac ttctcaaaga     2520
aggagacgag atgcggtaca ggggtgttcg tctataacga cgttaagcc tggagggaca     2580 ggtacaagta ccatcctgac tcccccgta gattggcagc agcagtcaag caagcctggg     2640
```

```
aagatggtat ctgcgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctggaaggct tgggggaaat cgtatttcgt cagagcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcatta gagtgtgatc cagccgttat tggaacagct gttaagggaa    3060
aggaggctgt acacagtgat ctaggctact ggattgagag tgagaagaat gacacatgga    3120
ggctgaagag ggcccatctg atcgagatga aacatgtga atggccaaag tcccacacat    3180
tgtggacaga tggaatagaa gagagtgatc tgatcatacc caagtcttta gctgggccac    3240
tcagccatca caataccaga gagggctaca ggacccaaat gaaagggcca tggcacagtg    3300
aagaacttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgccccccac tgtcgttccg ggctaaagat ggctgttggt    3480
atggaatgga gataaggccc aggaaagaac cagaaagcaa cttagtaagg tcaatggtga    3540
ctgcaggatc aactgatcac atggaccact tctcccttgg agtgcttgtg atcctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcacctt ggcaatcctg gctgctctga    4020
caccactggc ccggggcaca ctgcttgtgg cgtggagagc aggccttgct acttgcgggg    4080
ggtttatgct cctctctctg aagggaaaag gcagtgtgaa gaagaactta ccatttgtca    4140
tggccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgg tctgctaatt gtcagttacg tggtgtcagg aaagagtgtg gacatgtaca    4380
ttgaaagagc aggagacatc acatgggaaa aagatgcgga agtcactgga aacagtcccc    4440
ggctcgatgt ggcgctagat gagagtgtg atttctccct ggtggaggat gacggtcccc    4500
ccatgagaga gatcatactc aaggtggtcc tgatgaccat ctgtggcatg aacccaatag    4560
ccataccctt tgcagctgga gcgtggtacg tatacgtgaa gactggaaaa aggagtggtg    4620
ctctatggga tgtgcctgct cccaaggaag taaaaagg ggaaaccaca gatggagtgt    4680
acagagtaat gactcgtaga ctgctaggtt caacacaagt tggagtggga gttatgcaag    4740 aggggtctt tcacactatg tggcacgtca caaaaggatc cgcgctgaga agcggtgaag    4800
ggagacttga tccatactgg ggagatgtca agcaggatct ggtgtcatac tgtggtccat    4860
ggaagctaga tgccgcctgg gatgggcaca gcgaggtgca gctcttggcc gtgcccccg    4920 gagagagagc gaggaacatc cagactctgc ccggaatatt taagacaaag gatggggaca    4980
```

|  |  |  |  |  |  |
|---|---|---|---|---|---|
| ttggagcggt | tgcgctggat | tacccagcag | gaacttcagg | atctccaatc | ctagacaagt | 5040 |
| gtgggagagt | gataggactt | tatggcaatg | gggtcgtgat | caaaaacggg | agttatgtta | 5100 |
| gtgccatcac | ccaagggagg | agggaggaag | agactcctgt | tgagtgcttc | gagccctcga | 5160 |
| tgctgaagaa | gaagcagcta | actgtcttag | acttgcatcc | tggagctggg | aaaaccagga | 5220 |
| gagttcttcc | tgaaatagtc | cgtgaagcca | taaaaacaag | actccgtact | gtgatcttag | 5280 |
| ctccaaccag | ggttgtcgct | gctgaaatgg | aggaggccct | tagagggctt | ccagtgcgtt | 5340 |
| atatgacaac | agcagtcaat | gtcacccact | ctggaacaga | aatcgtcgac | ttaatgtgcc | 5400 |
| atgccacctt | cacttcacgt | ctactacagc | caatcagagt | ccccaactat | aatctgtata | 5460 |
| ttatggatga | ggcccacttc | acagatccct | caagtatagc | agcaagagga | tacatttcaa | 5520 |
| caagggttga | gatgggcgag | gcggctgcca | tcttcatgac | cgccacgcca | ccaggaaccc | 5580 |
| gtgacgcatt | tccggactcc | aactccaccaa | ttatggacac | cgaagtggaa | gtcccagaga | 5640 |
| gagcctggag | ctcaggcttt | gattgggtga | cggatcattc | tggaaaaaca | gtttggtttg | 5700 |
| ttccaagcgt | gaggaacggc | aatgagatcg | cagcttgtct | gacaaaggct | ggaaaacggg | 5760 |
| tcatacagct | cagcagaaag | acttttgaga | cagagttcca | gaaaacaaaa | catcaagagt | 5820 |
| gggactttgt | cgtgacaact | gacatttcag | agatgggcgc | caactttaaa | gctgaccgtg | 5880 |
| tcatagattc | caggagatgc | ctaaagccgg | tcatacttga | tggcgagaga | gtcattctgg | 5940 |
| ctggacccat | gcctgtcaca | catgccagcg | ctgcccagag | gaggggcgc | ataggcagga | 6000 |
| atcccaacaa | acctggagat | gagtatctgt | atggaggtgg | gtgcgcagag | actgacgaag | 6060 |
| accatgcaca | ctggcttgaa | gcaagaatgc | tccttgacaa | tatttacctc | caagatggcc | 6120 |
| tcatagcctc | gctctatcga | cctgaggccg | acaaagtagc | agccattgag | ggagagttca | 6180 |
| agcttaggac | ggagcaaagg | aagacctttg | tggaactcat | gaaaagagga | gatcttcctg | 6240 |
| tttggctggc | ctatcaggtt | gcatctgccg | gaataaccta | cacagataga | agatggtgct | 6300 |
| ttgatggcac | gaccaacaac | accataatgg | aagacagtgt | gccggcagag | gtgtggacca | 6360 |
| gacacggaga | gaaaagagtg | ctcaaaccga | ggtggatgga | cgccagagtt | tgttcagatc | 6420 |
| atgcggccct | gaagtcattc | aaggagtttg | ccgctgggaa | aagaggagcg | gcttttggag | 6480 |
| tgatggaagc | cctgggaaca | ctgccaggac | acatgacaga | gagattccag | gaagccattg | 6540 |
| acaacctcgc | tgtgctcatg | cgggcagaga | ctggaagcag | gccttacaaa | gccgcggcgg | 6600 |
| cccaattgcc | ggagacacta | gagacaataa | tgcttttggg | gttgctggga | acagtctcgc | 6660 |
| tgggaatctt | cttcgtcttg | atgaggaaca | agggcatagg | gaagatgggc | tttggaatgg | 6720 |
| tgactcttgg | ggccagcgca | tggctcatgt | ggctctcgga | aattgagcca | gccagaattg | 6780 |
| catgtgtcct | cattgttgtg | ttcctattgc | tggtggtgct | catacctgag | ccagaaaagc | 6840 |
| aaagatctcc | ccaggacaac | caaatggcaa | tcatcatcat | ggtagcagta | ggtcttctgg | 6900 |
| gcttgattac | cgccaatgaa | ctcggatggt | tggagagaac | aaaagtgac | ctaagccatc | 6960 |
| taatgggaag | gagagaggag | ggggcaacca | taggattctc | aatggacatt | gacctgcggc | 7020 |
| cagcctcagc | ttgggccatc | tatgctgcct | tgacaacttt | cattaccccca | gccgtccaac | 7080 |
| atgcagtgac | cacctcatac | aacaactact | ccttaatggc | gatggccacg | caagctggag | 7140 |
| tgttgtttgg | catgggcaaa | gggatgccat | tctacgcatg | ggactttgga | gtcccgctgc | 7200 |
| taatgatagg | ttgctactca | caattaacac | ccctgaccct | aatagtggcc | atcattttgc | 7260 |
| tcgtggcgca | ctacatgtac | ttgatcccag | ggctgcagge | agcagctgcg | cgtgctgccc | 7320 |
| agaagagaac | ggcagctggc | atcatgaaga | accctgttgt | ggatggaata | gtggtgactg | 7380 |

```
acattgacac aatgacaatt gaccccccaag tggagaaaaa gatgggacag gtgctactca    7440
tagcagtagc cgtctccagc gccatactgt cgcggaccgc ctgggggtgg ggggaggctg    7500
gggctctgat cacagccgca acttccactt tgtgggaagg ctctccgaac aagtactgga    7560
actcctctac agccacttca ctgtgtaaca ttttaggggg aagttacttg gctggagctt    7620
ctctaatcta cacagtaaca agaaacgctg gcttggtcaa gagacgtggg ggtggaacag    7680
gagaaaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggatacctg cagccctatg aaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatggggag    8280 gactggtcag agtgccactc tcccgcaact ctacacatga gatgtactgg gtgtctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct tgacgagaa ccacccatat aggacatggg    8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt gtcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatgggaga gagaactcag    9180 gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
```

-continued

| | |
|---|---|
| atatgggaaa agttaggaag acacacaag agtggaaacc ctcaactgga tgggacaact | 9780 |
| gggaagaagt tccgttttgc tcccaccact tcaacaagct ccatctcaag gacgggaggt | 9840 |
| ccattgtggt tccctgccgc caccaagatg aactgattgg ccgggcccgc gtctctccag | 9900 |
| gggcgggatg gagcatccgg gagactgctt gcctagcaaa atcatatgcg caaatgtggc | 9960 |
| agctccttta tttccacaga agggacctcc gactgatggc caatgccatt tgttcatctg | 10020 |
| tgccagttga ctgggttcca actgggagaa ctacctggtc aatccatgga aagggagaat | 10080 |
| ggatgaccac tgaagacatg cttgtggtgt ggaacagagt gtggattgag gagaacgacc | 10140 |
| acatggaaga caagacccca gttacgaaat ggacagacat tccctatttg gaaaaaggg | 10200 |
| aagacttgtg gtgtggatct ctcataggc acagaccgcg caccacctgg gctgagaaca | 10260 |
| ttaaaaacac agtcaacatg gtgcgcagga tcataggtga tgaagaaaag tacatggact | 10320 |
| acctatccac ccaagttcgc tacttgggtg aagaagggtc tacacctgga gtgctgtaag | 10380 |
| caccaatctt aatgttgtca ggcctgctag tcagccacag cttggggaaa gctgtgcagc | 10440 |
| ctgtgacccc cccaggagaa gctgggaaac caagcctata gtcaggccga aacgccatg | 10500 |
| gcacggaaga agccatgctg cctgtgagcc cctcagagga cactgagtca aaaaacccca | 10560 |
| cgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| ccccggaaaa cgcaaaacag catattgacg ctggaaagga ccagagactc catgagtttc | 10740 |
| caccacgctg gccgccaggc acagatcgcc gaacagcggc ggccggtgtg gggaaatcca | 10800 |
| tggtttct | 10808 |

<210> SEQ ID NO 2
<211> LENGTH: 10808
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| agttgttgat ctgtgtgaat cagactgcga cagttcgagt ttgaagcgaa agctagcaac | 60 |
| agtatcaaca ggttttattt tggatttgga acgagagtt tctggtcatg aaaaacccaa | 120 |
| aaaagaaatc cggaggattc cggattgtca atatgctaaa acgcggagta gcccgtgtga | 180 |
| gccccttgg gggcttgaag aggctgccag ccggacttct gctgggtcat gggcccatca | 240 |
| ggatggtctt ggcgattcta gccttttga gattcacggc aatcaagcca tcactgggtc | 300 |
| tcatcaatag atggggttca gtggggaaaa aagaggctat ggaaataata agaagttca | 360 |
| agaaagatct ggctgccatg ctgagaataa tcaatgctag gaaggagaag aagagacgag | 420 |
| gcgcagatac tagtgtcgga attgttggcc tcctgctgac cacagctatg gcagccgaag | 480 |
| tgactagacg cggatccgct tactatatgt atctcgatag aaacgacgct ggcgaagcga | 540 |
| taagctttcc gactacactc ggtatgaata agtgttacat acagattatg gacttagggc | 600 |
| atatgtgcga cgctactatg tcatacgaat gccctatgct tgacgaggga gtcgaaccag | 660 |
| acgacgtcga ttgttggtgc aatacgacta gcacttgggt cgtttacggt acatgccatc | 720 |
| acaaaaaggg cgaagctaga cggtctagac gcgcagtgac actgcctagt cactctacga | 780 |
| gaaagttgca gactaggtca cagacatggt tggagtctag agtacact aagcatctga | 840 |
| ttaggggtcga gaattggatt tttagaaacc cagggttcgc actagccgca gccgcaatcg | 900 |
| catggttgtt ggggtctagc actagccaaa aagtgatata tctggttatg atactgttga | 960 |

```
tcgctcccgc atactctatt aggtgcatag gcgttagcaa tagggacttt gtcgagggaa    1020
tgtccggggg gacatgggtc gacgtcgtgc ttgagcacgg ggggtgcgtt acggttatgg    1080
cacaagacaa accgacagtc gacatagagt tggttacgac tacagtgagt aatatggctg    1140
aggttaggtc atactgttac gaagcgtcaa ttagcgatat ggctagcgat agtaggtgtc    1200
cgacacaggg cgaagcatac ttagacaaac aatccgatac gcaatacgta tgcaaacgga    1260
ctctggtcga taggggtgg ggtaacggat gcggattgtt cggtaagggg tcactggtta    1320
catgcgctaa attcgcatgc tctaaaaaaa tgaccggtaa gtcaatccaa cccgaaaacc    1380
ttgagtatag gattatgctt agcgtacacg datcccaaca ctccggtatg atcgttaacg    1440
ataccggaca cgaaaccgac gagaataggg ctaaggtcga gattacgcct aactccccta    1500
gagccgaagc gacattgggc ggattcggat cactgggact ggattgcgaa ccagaaccg     1560
gattggactt tagcgatctg tattacttga ctatgaacaa taagcattgg ttggtgcaca    1620
aagagtggtt tcacgacata ccgttgccat ggcacgccgg agccgatacc ggaacgccac    1680
attggaataa caaagaggca ttggtcgagt ttaaggacgc tcacgctaaa cggcaaaccg    1740
tagtcgtgtt agggtcacag gagggagccg tacacaccgc attggccggc gcactcgaag    1800
ccgaaatgga cggagctaag gggagactgt ctagcggaca ccttaagtgt agactgaaaa    1860
tggacaaact gagacttaag ggagtgtcat actcactgtg tactgccgca tttacgttta    1920
cgaagatacc cgccgaaaca ttgcacggaa ccgttacagt cgaagtgcaa tacgccggaa    1980
ccgacggacc atgtaaggtg ccagcgcaaa tggcagtcga tatgcaaaca ctgacaccag    2040
tcggtagact gattaccgct aacccagtga taaccgaatc cactgagaat tcgaaaatga    2100
tgcttgagct tgacccacca ttcggcgata gctatatcgt tatcggagtc ggcgaaaaaa    2160
agattacaca ccattggcat agatccggat ctacaatcgg taaggcattc gaagctaccg    2220
ttaggggcgc taagcgtatg gccgtattgg gcgataccgc ttgggatttc ggatccgtcg    2280
gaggcgcact gaattcccta ggtaagggga tacaccaaat attcggcgca gcgtttaagt    2340
cattgttcgg agggatgtca tggtttagtc agatactgat cggaacattg cttatgtggt    2400
tagggttgaa cactaagaac ggatcaatct cattgatgtg tcttgcgtta ggggggggtgt    2460
tgatctttct gtcaaccgcc gttagcgcag atgtggggtg ctcggtggac ttctcaaaga    2520
aggagacgag atgcggtaca ggggtgttcg tctataacga cgttaagcc tggagggaca    2580
ggtacaagta ccatcctgac tcccccgta gattggcagc agcagtcaag caagcctggg    2640
aagatggtat ctgcgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctgaaggct tggggaaat cgtatttcgt cagagcagca aagacaaata    2880
acagctttgt cgtggatggt gacacactga aggaatgccc actcaaacat agagcatgga    2940
acagctttct tgtggaggat catgggttcg gggtatttca cactagtgtc tggctcaagg    3000
ttagagaaga ttattcatta gagtgtgatc cagccgttat tggaacagct gttaagggaa    3060
aggaggctgt acacagtgat ctaggctact ggattgagag tgagaagaat gacacatgga    3120
ggctgaagag ggcccatctg atcgagatga aaacatgtga atggccaaag tcccacacat    3180
tgtggacaga tggaatagaa gagagtgatc tgatcatacc caagtctta gctgggccac    3240
tcagccatca caataccaga gagggctaca ggacccaaat gaaagggcca tggcacagtg    3300
```

```
aagaacttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgccccac tgtcgttccg ggctaaagat ggctgttggt     3480
atggaatgga gataaggccc aggaaagaac cagaaagcaa cttagtaagg tcaatggtga    3540
ctgcaggatc aactgatcac atggaccact tctcccttgg agtgcttgtg atcctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcacctt ggcaatcctg gctgctctga    4020
caccactggc ccggggcaca ctgcttgtgg cgtggagagc aggccttgct acttgcgggg    4080
ggtttatgct cctctctctg aagggaaaag gcagtgtgaa gaagaactta ccatttgtca    4140
tggccctggg actaaccgct gtgaggctgg tcgaccccat caacgtggtg ggactgctgt    4200
tgctcacaag gagtgggaag cggagctggc cccctagcga agtactcaca gctgttggcc    4260
tgatatgcgc attggctgga gggttcgcca aggcagatat agagatggct gggcccatgg    4320
ccgcggtcgg tctgctaatt gtcagttacg tggtgtcagg aaagagtgtg acatgtaca     4380
ttgaaagagc aggagacatc acatgggaaa aagatgcgga agtcactgga acagtccccc    4440
ggctcgatgt ggcgctagat gagagtggtg atttctccct ggtggaggat gacggtcccc    4500
ccatgagaga gatcatactc aaggtggtcc tgatgaccac ctgtggcatg aacccaatag    4560
ccataccctt tgcagctgga gcgtggtacg tatacgtgaa gactggaaaa aggagtggtg    4620
ctctatggga tgtgcctgct cccaaggaag taaaaagggg ggaaaccaca gatggagtgt    4680
acagagtaat gactcgtaga ctgctaggtt caacacaagt tggagtggga gttatgcaag    4740
agggggtctt tcacactatg tggcacgtca caaaaggatc cgcgctgaga gcggtgaag     4800
ggagacttga tccatactgg ggagatgtca agcaggatct ggtgtcatac tgtggtccat    4860
ggaagctaga tgccgcctgg gatgggcaca gcgaggtgca gctcttggcc gtgccccccg    4920
gagagagagc gaggaacatc cagactctgc ccggaatatt taagacaaag gatggggaca    4980
ttggagcggt tgcgctggat tacccagcag gaacttcagg atctccaatc ctagacaagt    5040
gtgggagagt gataggactt tatggcaatg gggtcgtgat caaaaacggg agttatgtta    5100
gtgccatcac ccaagggagg agggaggaag agactcctgt tgagtgcttc gagccctcga    5160
tgctgaagaa gaagcagcta actgtcttag acttgcatcc tggagctggg aaaaccagga    5220
gagttcttcc tgaaatagtc cgtgaagcca taaaaacaag actccgtact gtgatcttag    5280
ctccaaccag ggttgtcgct gctgaaatgg aggaggccct tagagggctt ccagtgcgtt    5340
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
```

```
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag agggggcgc ataggcagga     6000 atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300 tgatggcac gaccaacaac accataatgg aagacagtgt gccggcagag gtgtggacca     6360
gacacggaga gaaagagtg ctcaaaccga ggtggatgga cgccagagtt tgttcagatc     6420
atgcggccct gaagtcattc aaggagtttg ccgctgggaa aagaggagcg gcttttggag    6480
tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacacta gagacaataa tgcttttggg gttgctggga acagtctcgc    6660
tgggaatctt cttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag agagaggag ggggcaacca taggattctc aatggacatt gacctgcggc     7020
cagcctcagc ttgggccatc tatgctgcct tgacaacttt cattaccca gccgtccaac      7080 atgcagtgac cacctcatac aacaactact ccttaatggc gatggccacg caagctggag    7140
tgttgtttgg catgggcaaa gggatgccat tctacgcatg ggacttttga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gaccccaag tggagaaaaa gatgggacag gtgctactca    7440
tagcagtagc cgtctccagc gccatactgt cgcggaccgc ctgggggtgg ggggaggctg    7500
gggctctgat cacagccgca acttccactt tgtgggaagg ctctccgaac aagtactgga    7560
actcctctac agccacttca ctgtgtaaca tttttaggg aagttacttg gctggagctt     7620
ctctaatcta cacagtaaca agaaacgctg cttggtcaa gagacgtggg ggtggaacag     7680
gagaaaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggataccta cagccctatg aaaggtcat tgatcttgga tgtggcagag     7920
ggggctggag ttactacgcc gccaccatcc gcaaagttca gaagtgaaa ggatacacaa     7980 aaggaggccc tggtcatgaa gaacccgtgt tggtgcaaag ctatgggtgg aacatagtcc    8040
```

```
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtgtctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt gtcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacgatgggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggccgc gtctctccag    9900
gggcgggatg gagcatccgg gagactgctt gcctagcaaa atcatatgcg caaatgtggc    9960
agctccttta tttccacaga agggaccttc gactgatggc caatgccatt tgttcatctg    10020
tgccagttga ctgggttcca actggagaa ctacctggtc aatccatgga aagggagaat    10080
ggatgaccac tgaagacatg cttgtggtgt ggaacagagt gtggattgag gagaacgacc    10140
acatggaaga caagaccca gttacgaaat ggacagacat tccctatttg ggaaaaaggg    10200
aagacttgtg tgtgtggatct ctcataggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctgtaag    10380
caccaatctt aatgttgtca ggcctgctag tcagccacag cttggggaaa gctgtgcagc    10440
```

-continued

| | |
|---|---|
| ctgtgacccc cccaggagaa gctgggaaac aagcctata gtcaggccga gaacgccatg | 10500 |
| gcacggaaga agccatgctg cctgtgagcc cctcagagga cactgagtca aaaaccccca | 10560 |
| cgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| ccccggaaaa cgcaaaacag catattgacg ctgggaaaga ccagagactc catgagtttc | 10740 |
| caccacgctg gccgccaggc acagatcgcc aacagcggc ggccggtgtg gggaaatcca | 10800 |
| tggtttct | 10808 |

<210> SEQ ID NO 3
<211> LENGTH: 10808
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| agttgttgat ctgtgtgaat cagactgcga cagttcgagt ttgaagcgaa agctagcaac | 60 |
| agtatcaaca ggttttattt tggatttgga acgagagtt tctggtcatg aaaaacccaa | 120 |
| aaaagaaatc cggaggattc cggattgtca atatgctaaa acgcggagta gcccgtgtga | 180 |
| gcccctttgg gggcttgaag aggctgccag ccggacttct gctgggtcat gggcccatca | 240 |
| ggatggtctt ggcgattcta gccttttga gattcacggc aatcaagcca tcactgggtc | 300 |
| tcatcaatag atggggttca gtggggaaaa aagaggctat ggaataata aagaagttca | 360 |
| agaaagatct ggctgccatg ctgagaataa tcaatgctag gaaggagaag aagagacgag | 420 |
| gcgcagatac tagtgtcgga attgttggcc tcctgctgac cacagctatg gcagcggagg | 480 |
| tcactagacg tgggagtgca tactatatgt acttggacag aaacgatgct ggggaggcca | 540 |
| tatcttttcc aacccattg gggatgaata agtgttatat acagatcatg gatcttggac | 600 |
| acatgtgtga tgccaccatg agctatgaat gccctatgct ggatgagggg gtggaaccag | 660 |
| atgacgtcga ttgttggtgc aacacgacgt caacttgggt tgtgtacgga acctgccatc | 720 |
| acaaaaaagg tgaagcacgg agatctagaa gggctgtgac gctcccctcc cattccacca | 780 |
| ggaagctgca aacgcggtcg caaacctggt tggaatcaag agaatacaca aagcacttga | 840 |
| ttagagtcga aaattggata ttcaggaacc ctggcttcgc gttagcagca gctgccatcg | 900 |
| cttggctttt gggaagctca acgagccaaa aagtcatata cttggtcatg atactgctga | 960 |
| ttgccccggc atacagcatc aggtgcatag gagtcagcaa tagggacttt gtggaaggta | 1020 |
| tgtcaggtgg gacttgggtt gatgttgtct tggaacatgg aggttgtgtc accgtaatgg | 1080 |
| cacaggacaa accgactgtc gacatagagc tggttacaac aacagtcagc aacatggcgg | 1140 |
| aggtaagatc ctactgctat gaggcatcaa tatcagacat ggcttctgac agccgctgcc | 1200 |
| caacacaagg tgaagcctac cttgacaagc aatcagacac tcaatatgtc tgcaaaagaa | 1260 |
| cgttagtgga cagaggctgg ggaaatggat gtggactttt tggcaaaggg agcctggtga | 1320 |
| catgcgctaa gtttgcatgc tccaagaaaa tgaccggcaa gagcatccag ccagagaatc | 1380 |
| tggagtaccg gataatgctg tcagttcatg gctcccagca cagtgggatg atcgttaatg | 1440 |
| acacaggaca tgaaactgat gagaatagag cgaaagttga gataacgccc aattcaccga | 1500 |
| gagccgaagc caccctgggg ggttttgaa gcctaggact tgattgtgaa ccgaggacag | 1560 |
| gccttgactt ttcagatttg tattacttga ctatgaataa caagcactgg ttggttcaca | 1620 |

-continued

```
aggagtggtt ccacgacatt ccattacctt ggcacgctgg ggcagacacc ggaactccac    1680
actggaacaa caaagaagca ctggtagagt tcaaggacgc acatgccaaa aggcaaactg    1740
tcgtggttct agggagtcaa gaaggagcag ttcacacggc ccttgctgga gctctggagg    1800
ctgagatgga tggtgcaaag ggaaggctgt cctctggcca cttgaaatgt cgcctgaaaa    1860
tggataaact tagattgaag ggcgtgtcat actccttgtg tactgcagcg ttcacattca    1920
ccaagatccc ggctgaaaca ctgcacggga cagtcacagt ggaggtacag tacgcaggga    1980
cagatggacc ttgcaaggtt ccagctcaga tggcggtgga catgcaaact ctgaccccag    2040
ttgggaggtt gataaccgct aaccccgtaa tcactgaaag cactgagaac tctaagatga    2100
tgctggaact tgatccacca tttggggact cttacattgt cataggagtc ggggagaaga    2160
agatcaccca ccactggcac aggagtggca gcaccattgg aaaagcattt gaagccactg    2220
tgagaggtgc caagagaatg gcagtcttgg gagacacagc ctgggacttt ggatcagttg    2280
gaggcgctct caactcattg gcaagggca tccatcaaat ttttggagca gctttcaaat    2340
cattgtttgg aggaatgtcc tggttctcac aaattctcat tggaacgttg ctgatgtggt    2400
tgggtctgaa cacaaagaat ggatctattt cccttatgtg cttggcctta ggggagtgt    2460 tgatcttctt atccacagcc gtctctgctg atgtggggtg ctcggtggac ttctcaaaga    2520
aggagacgag atgcggtaca ggggtgttcg tctataacga cgttgaagcc tggagggaca    2580
ggtacaagta ccatcctgac tcccccgta gattggcagc agcagtcaag caagcctggg    2640
aagatggtat ctgcgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccacgg ctgaaaggct gggggaaat cgtatttcgt cagagcagca agacaaata    2880 acagctttgt cgtggatggt gacacactga aggaatgccc actcaaacat agagcatgga    2940 acagcttttct tgtggaggat catgggttcg gggtatttca cactagtgtc tggctcaagg    3000
ttagagaaga ttattcatta gagtgtgatc cagccgttat tggaacagct gttaagggaa    3060
aggaggctgt acacagtgat ctaggctact ggattgagag tgagaagaat gacacatgga    3120
ggctgaagag ggcccatctg atcgagatga aaacatgtga atggccaaag tcccacacat    3180
tgtggacaga tggaatagaa gagagtgatc tgatcatacc caagtctttta gctgggccac    3240 tcagccatca caataccaga gagggctaca ggacccaaat gaagggccca tggcacagtg    3300
aagaacttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgccccccac tgtcgttccg ggctaaagat ggctgttggt    3480
atggaatgga gataaggccc aggaaagaac cagaaagcaa cttagtaagg tcaatggtga    3540
ctgcaggatc aactgatcac atggaccact tctcccttgg agtgcttgtg atcctgctca    3600
tggtgcagga agggctgaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgtagct catctggcgc    3780
tgatagcggc attcaaagtc agaccagcgt tgctggtatc tttcatcttc agagctaatt    3840
ggacaccccg tgaaagcatg ctgctggcct tggcctcgtg tcttttgcaa actgcgatct    3900
ccgccttgga aggcgacctg atggttctca tcaatggttt tgctttggcc tggttggcaa    3960
tacgagcgat ggttgttcca cgcactgata acatcaccctt ggcaatcctg ctgctctga    4020
```

```
caccactggc cgggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtgtcagg aaagagtgtg acatgtaca   4380
ttgaaagagc aggagacatc acatgggaaa agatgcggaa agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccatacccctt tgcagctgga gcgtggtacg tatacgtgaa gactggaaaa aggtcaggcg   4620
cactatggga cgtacccgca cctaaagagg tcaaaaaagg cgagactacc gacggagtgt   4680
atagagtgat gacacgtaga ctgttagggt caacacaggt cggagtcggc gttatgcagg   4740
agggagtgtt tcatacaatg tggcacgtta cgaaagggtc agcgcttagg tcaggcgaag   4800
ggagactcga tccatattgg ggggacgtta agcaagacct agtgtcatat tgcggaccat   4860
ggaaactcga cgccgcatgg gacggacact ctgaggtcca actgttagcc gtaccacccg   4920
gagagagagc gagaaacata cagacactgc cagggatttt taagactaag gacggcgata   4980
tcggagccgt cgcactcgat taccctgccg gaactagcgg atcaccgata ctcgataaat   5040
gcggacgggt tatcggactg tacgaaacg gagtcgttat caaaaacgga tcatacgtta   5100
gcgctattac acagggcgt agagaggagg agacaccagt cgagtgtttc gaacctagta   5160
tgcttaaaaa aaaacagttg accgtactcg atctgcatcc cggagccggt aagacacgta   5220
gagtgttgcc cgagatagtg agagaggcta ttaagactag actgagaacc gtgatactcg   5280
cacctactag agtcgtcgcc gccgaaatgg aggaggcact tagggggtta cccgttaggt   5340
atatgacaac cgccgttaac gttacgcata gcggaaccga gatagtcgat ctgatgtgtc   5400
acgctacatt tacatctaga ctactgcaac cgattagggt gcctaattac aatctgtata   5460
taatggacga agcgcatttt accgatccgt catcaatcgc cgctaggggg tacatatcga   5520
ctagggtcga gatgggcgaa gccgccgcaa tctttatgac cgctacacct cccggaacta   5580
gagacgcttt tcccgattcg aatagtccaa ttatggatac cgaggtcgag gtccccgaac   5640
gcgcatggtc atccgggttc gattgggtta ccgatcattc cggtaagacc gtttggtttg   5700
tgcctagcgt taggaacggt aacgagatag ccgcatgcct tacgaaagcc ggtaagagag   5760
tgatacagct atctagaaag acattcgaaa ccgagtttca gaaaactaag catcaggagt   5820
gggatttcgt cgttacaacc gatattagcg aaatgggcgc taactttaaa gccgataggg   5880
tgatcgatag taggcgatgc cttaagccag tgatactcga cggagagaga gtgatactag   5940
ccggaccaat gccagtgaca cacgctagcg ctgcgcaacg tagggggaga atcggacgta   6000
atccgaataa gccaggcgac gaatacctat acggggggg gtgcgccgag actgacgagg   6060
atcacgctca ttggctcgaa gcgagaatgc tactcgataa catatatctg caagacggac   6120
taatcgctag tctgtataga cccgaagccg ataaggtcgc cgcaatcgaa ggcgaattta   6180
agcttagaac cgagcaacgt aagacattcg tcgagcttat gaaaaggggg gatctgccag   6240
tgtggcttgc gtatcaggtc gctagtgccg gaattacata taccgatagg agatggtgtt   6300
tcgacggaac aactaacaat acgattatgg aggactcagt cccagccgaa gtgtggacta   6360
```

```
ggcacggaga gaaaagagtg cttaagccta gatggatgga cgctagggtg tgttccgatc    6420
acgccgcact taagtctttt aaagagttcg cagccggtaa gcgtggagcg gcttttggag    6480
tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacacta gagacaataa tgcttttggg gttgctggga acagtctcgc    6660
tgggaatctt cttcgtcttg atgaggaaca agggcatagg gaagatgggc tttgaatgg     6720 tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag gagagaggag ggggcaacca taggattctc aatggacatt gacctgcggc    7020
cagcctcagc ttgggccatc tatgctgcct tgacaacttt cattacccca gccgtccaac    7080
atgcagtgac cacctcatac aacaactact ccttaatggc gatggccacg caagctggag    7140
tgttgtttgg catgggcaaa gggatgccat tctacgcatg ggactttgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gaccccccaag tggagaaaaa gatgggacag gtgctactca    7440
tagcagtagc cgtctccagc gccatactgt cgcggaccgc ctgggggtgg ggggaggctg    7500
gggctctgat cacagccgca acttccactt tgtgggaagg ctctccgaac aagtactgga    7560
actcctctac agccacttca ctgtgtaaca ttttttagggg aagttacttg gctggagctt    7620
ctctaatcta cacagtaaca agaaacgctg gcttggtcaa gagacgtggg ggtggaacag    7680
gagaaaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggataccta cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tgggggtgga cgtctttcata tggcggctga gccgtgtgac acgttgctgt    8100
gtgacatagg tgagtcatca tctagtcctg aagtggaaga agcacggacg ctcagagtcc    8160
tctccatggt ggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtgtctggag    8340
cgaaaagcaa caccataaaa agtgtgtcca ccacgagcca gctcctcttg ggcgcatgg    8400 acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccaccatat aggacatggg    8580 cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
```

```
cagaccccca agaaggcact cgtcaggtta tgagcatggt gtcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatgggaga gagaactcag     9180 gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960
agctccttta tttccacaga agggacctcc gactgatggc caatgccatt tgttcatctg    10020
tgccagttga ctgggttcca actgggagaa ctacctggtc aatccatgga aagggagaat    10080
ggatgaccac tgaagacatg cttgtggtgt ggaacagagt gtggattgag gagaacgacc    10140
acatggaaga caagccccca gttacgaaat ggacagacat tccctatttg gaaaaagggg    10200
aagacttgtg gtgtggatct ctcatagggc acagaccgcg caccacctgg gctgagaaca    10260
ttaaaaacac agtcaacatg gtgcgcagga tcataggtga tgaagaaaag tacatggact    10320
acctatccac ccaagttcgc tacttgggtg aagaagggtc tacacctgga gtgctgtaag    10380
caccaatctt aatgttgtca ggcctgctag tcagccacag cttggggaaa gctgtgcagc    10440
ctgtgacccc cccaggagaa gctgggaaac caagcctata gtcaggccga aacgccatg    10500 gcacggaaga agccatgctg cctgtgagcc ctcagagga cactgagtca aaaaacccca    10560
cgcgcttgga ggcgcaggat gggaaaagaa ggtggcgacc ttcccacccc ttcaatctgg    10620
ggcctgaact ggagatcagc tgtggatctc cagaagaggg actagtggtt agaggagacc    10680
ccccggaaaa cgcaaaacag catattgacg ctgggaaaga ccagagactc catgagtttc    10740
caccacgctg gccgccaggc acagatcgcc gaacagcggc ggccggtgtg gggaaatcca    10800
tggtttct                                                             10808
```

<210> SEQ ID NO 4
<211> LENGTH: 10808
<212> TYPE: DNA
<213> ORGANISM: Artificial Sequence
<220> FEATURE:
<223> OTHER INFORMATION: Synthetic Construct

```
<400> SEQUENCE: 4
agttgttgat ctgtgtgaat cagactgcga cagttcgagt ttgaagcgaa agctagcaac      60
agtatcaaca ggttttattt tggatttgga aacgagagtt tctggtcatg aaaaacccaa     120
aaaagaaatc cggaggattc cggattgtca atatgctaaa acgcggagta gcccgtgtga     180 gccccttttgg gggcttgaag aggctgccag ccggacttct gctgggtcat gggcccatca    240
ggatggtctt ggcgattcta gccttttga gattcacggc aatcaagcca tcactgggtc      300
tcatcaatag atggggttca gtggggaaaa aagaggctat ggaataata aagaagttca      360 agaaagatct ggctgccatg ctgagaataa tcaatgctag aaggagaag aagagacgag       420 gcgcagatac tagtgtcgga attgttggcc tcctgctgac cacagctatg gcagcggagg     480
tcactagacg tgggagtgca tactatatgt acttggacag aaacgatgct ggggaggcca     540 tatctttttcc aaccacattg gggatgaata agtgttatat acagatcatg gatcttggac    600
acatgtgtga tgccaccatg agctatgaat gccctatgct ggatgagggg gtggaaccag     660
atgacgtcga ttgttggtgc aacacgacgt caacttgggt tgtgtacgga acctgccatc    720
acaaaaaagg tgaagcacgg agatctagaa gggctgtgac gctcccctcc cattccacca    780
ggaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg    1080
cacaggacaa accgactgtc gacatagagc tggttacaac aacagtcagc aacatggcgg    1140
aggtaagatc ctactgctat gaggcatcaa tatcagacat ggcttctgac agccgctgcc    1200
caacacaagg tgaagcctac cttgacaagc aatcagacac tcaatatgtc tgcaaaagaa    1260
cgttagtgga cagaggctgg ggaaatggat gtggactttt tggcaaaggg agcctggtga    1320
catgcgctaa gtttgcatgc tccaagaaaa tgaccggcaa gagcatccag ccagagaatc    1380
tggagtaccg gataatgctg tcagttcatg gctcccagca cagtgggatg atcgttaatg    1440
acacaggaca tgaaactgat gagaatagag cgaaagttga gataacgcct aactccccta    1500
gagccgaagc gacattgggc ggattcggat cactgggact ggattgcgaa ccagaaccg     1560 gattggactt tagcgatctg tattacttga ctatgaacaa taagcattgg ttggtgcaca    1620
aagagtggtt tcacgacata ccgttgccat ggcacgccgg agccgatacc ggaacgccac    1680
attggaataa caaagaggca ttggtcgagt ttaaggacgc tcacgctaaa cggcaaaccg    1740
tagtcgtgtt agggtcacag gagggagccg tacacaccgc attggccggc gcactcgaag    1800
ccgaaatgga cggagctaag gggagactgt ctagcggaca ccttaagtgt agactgaaaa    1860
tggacaaact gagacttaag ggagtgtcat actcactgtg tactgccgca tttacgttta    1920
cgaagatacc cgccgaaaca ttgcacggaa ccgttacagt cgaagtgcaa tacgccggaa    1980
ccgacggacc atgtaaggtg ccagcgcaaa tggcagtcga tatgcaaaca ctgacaccag    2040
tcggtagact gattaccgct aacccagtga taaccgaatc cactgagaat tcgaaaatga    2100
tgcttgagct tgacccacca ttcggcgata gctatatcgt tatcggagtc ggcgaaaaaa    2160
agattacaca ccattggcat agatccggat ctacaatcgg taaggcattc gaagctaccg    2220
ttaggggcgc taagcgtatg gccgtattgg gcgataccgc ttgggatttc ggatccgtcg    2280
gaggcgcact gaattcccta ggtaagggga tacaccaaat attcggcgca gcgtttaagt    2340
```

```
cattgttcgg agggatgtca tggtttagtc agatactgat cggaacattg cttatgtggt  2400 taggggttgaa cactaagaac ggatcaatct cattgatgtg tcttgcgtta gggggggtgt  2460
tgatctttct gtcaaccgcc gttagcgcag atgtggggtg ctcggtggac ttctcaaaga  2520
aggagacgag atgcggtaca ggggtgttcg tctataacga cgttgaagcc tggagggaca  2580
ggtacaagta ccatcctgac tcccccgta gattggcagc agcagtcaag caagcctggg  2640
aagatggtat ctgcgggatc tcctctgttt caagaatgga aaacatcatg tggagatcag  2700
tagaagggga gctcaacgca atcctggaag agaatggagt tcaactgacg gtcgttgtgg  2760
gatctgtaaa aaacccccatg tggagaggtc cacagagatt gcccgtgcct gtgaacgagc  2820
tgccccacgg ctggaaggct tgggggaaat cgtatttcgt cagagcagca aagacaaata  2880
acagctttgt cgtggatggt gacacactga aggaatgccc actcaaacat agagcatgga  2940
acagctttct tgtggaggat catgggttcg gggtatttca cactagtgtc tggctcaagg  3000
ttagagaaga ttattcatta gagtgtgatc agccgttat tggaacagct gttaagggaa  3060
aggaggctgt acacagtgat ctaggctact ggattgagag tgagaagaat gacacatgga  3120
ggctgaagag ggcccatctg atcgagatga aacatgtga atggccaaag tcccacacat  3180
tgtggacaga tggaatagaa gagagtgatc tgatcatacc caagtctta gctgggccac  3240 tcagccatca aataccaga gagggctaca ggacccaaat gaaagggcca tggcacagtg  3300
aagaacttga aattcggttt gaggaatgcc caggcactaa ggtccacgtg gaggaaacat  3360
gtggaacaag aggaccatct ctgagatcaa ccactgcaag cggaagggtg atcgaggaat  3420
ggtgctgcag ggagtgcaca atgccccac tgtcgttccg ggctaaagat ggctgttggt  3480
atggaatgga gataaggccc aggaaagaac cagaaagcaa cttagtaagg tcaatggtga  3540
ctgcaggatc aactgatcac atggaccact ctcccttgg agtgcttgtg atcctgctca  3600
tggtgcagga agggctgaag aagagaatga ccacaaagat catcataagc acatcaatgg  3660
cagtgctggt agctatgatc ctgggaggat tttcaatgag tgacctggct aagcttgcaa  3720
ttttgatggg tgccaccttc gcggaaatga acactggagg agatgtagct catctggcgc  3780
tgatagcggc attcaaagtc agaccagcgt tgctggtatc tttcatcttc agagctaatt  3840
ggacaccccg tgaaagcatg ctgctggcct tggcctcgtg tcttttgcaa actgcgatct  3900
ccgccttgga aggcgacctg atggttctca tcaatggttt tgctttggcc tggttggcaa  3960
tacgagcgat ggttgttcca cgcactgata acatcacctt ggcaatcctg gctgctctga  4020
caccactggc ccgggggcaca ctgcttgtgg cgtggagagc aggccttgct acttgcgggg  4080
ggtttatgct cctctctctg aagggaaag gcagtgtgaa gaagaactta ccatttgtca  4140
tggcctgggg actaaccgct gtgaggctgg tcgaccccat caacgtggtg ggactgctgt  4200
tgctcacaag gagtgggaag cggagctggc ccctagcga agtactcaca gctgttggcc  4260
tgatatgcgc attggctgga gggttcgcca aggcagatat agagatggct gggcccatgg  4320
ccgcggtcgg tctgctaatt gtcagttacg tggtgtcagg aaagagtgtg acatgtaca  4380 ttgaaagagc aggagacatc acatgggaaa aagatgcgga agtcactgga aacagtcccc  4440
ggctcgatgt ggcgctagat gagagtggtg atttctccct ggtggaggat gacggtcccc  4500
ccatgagaga gatcatactc aaggtggtcc tgatgaccat ctgtggcatg aacccaatag  4560
ccatacccct tgcagctgga gcgtggtacg tatacgtgaa gactggaaaa aggagtggtg  4620
ctctatggga tgtgcctgct cccaaggaag taaaaaaggg ggaaaccaca gatggagtgt  4680
```

```
acagagtaat gactcgtaga ctgctaggtt caacacaagt tggagtggga gttatgcaag    4740 aggggtctt tcacactatg tggcacgtca caaaaggatc cgcgctgaga agcggtgaag     4800
ggagacttga tccatactgg ggagatgtca agcaggatct ggtgtcatac tgtggtccat    4860
ggaagctaga tgccgcctgg gatgggcaca gcgaggtgca gctcttggcc gtgcccccg     4920 gagagagagc gaggaacatc cagactctgc ccggaatatt taagacaaag gatggggaca    4980
ttggagcggt tgcgctggat tacccagcag gaacttcagg atctccaatc ctagacaagt    5040
gtgggagagt gataggactt tatggcaatg gggtcgtgat caaaaacggg agttatgtta    5100
gtgccatcac ccaagggagg agggaggaag agactcctgt tgagtgcttc gagccctcga    5160
tgctgaagaa gaagcagcta actgtcttag acttgcatcc tggagctggg aaaaccagga    5220
gagttcttcc tgaaatagtc cgtgaagcca taaaaacaag actccgtact gtgatcttag    5280
ctccaaccag ggttgtcgct gctgaaatgg aggaggccct tagagggctt ccagtgcgtt    5340
atatgacaac agcagtcaat gtcacccact ctggaacaga aatcgtcgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag actttttgaga cagagttcca gaaaacaaaa catcaagagt    5820
gggactttgt cgtgacaact gacatttcag agatgggcgc caacttttaa gctgaccgtg    5880
tcatagattc caggagatgc ctaaagccgg tcatacttga tggcgagaga gtcattctgg    5940
ctggacccat gcctgtcaca catgccagcg ctgcccagag gagggggcgc ataggcagga    6000
atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagacctttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gacacggaga gaaaagagtg ctcaaaccga ggtggatgga cgccagagtt tgttcagatc    6420
atgcggccct gaagtcattc aaggagtttg ccgctgggaa aagaggagcg cttttggag    6480 tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacacta gagacaataa tgctttgggg gttgctggga acagtctcgc    6660
tgggaatctt cttcgtcttg atgaggaaca agggcatagg gaagatgggc tttgaatgg    6720 tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaaagagtgac ctaagccatc    6960 taatgggaag gagagaggag ggggcaacca taggattctc aatggacatt gacctgcggc    7020
cagcctcagc ttgggccatc tatgctgcct tgacaacttt cattacccca gccgtccaac    7080
```

```
atgcagtgac cacctcatac aacaactact ccttaatggc gatggccacg caagctggag    7140
tgttgtttgg catgggcaaa gggatgccat tctacgcatg ggactttgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc cgtctccagc gccatactgt cgcggaccgc ctgggggtgg gggaggctg    7500 gggctctgat cacagccgca acttccactt tgtgggaagg ctctccgaac aagtactgga    7560
actcctctac agccacttca ctgtgtaaca ttttagggg aagttacttg gctggagctt    7620
ctctaatcta cacagtaaca agaaacgctg gcttggtcaa gagacgtggg ggtggaacag    7680
gagaaaccct gggagagaaa tggaaggccc gcttgaacca gatgtcggcc ctggagttct    7740
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggataccctg cagccctatg gaaaggtcat tgatcttgga gtgtggcagag    7920 ggggctggag ttactacgcc gccaccatcc gcaaagttca agaagtgaaa ggatacacaa    7980
aaggaggccc tggtcatgaa gaacccgtgt ggtgcaaag ctatgggtgg aacatagtcc    8040
gtcttaagag tggggtggac gtcttccata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc ctttgtata aagtgttgt    8220 gcccatacac cagcactatg atggaaaccc tggagcgact gcagcgtagg tatgggggag    8280
gactggtcag agtgccactc tcccgcaact ctacacatga gatgtactgg gtgtctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccaccatat aggacatggg    8580 cttaccatgg aagctatgag ccccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760 cagacccccca agaaggcact cgtcaggtta tgagcatggt gtcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggaaaatgaa gctctaatca ccaaccaaat ggaaaagggg cacagggcct    9360
tggcattggc cataatcaag tacacatacc aaaacaaagt ggtaaaggtc cttagaccag    9420
```

| | |
|---|---:|
| ctgaaaaagg gaaaacagtt atggacatta tttcgagaca agaccaaagg gggagcggac | 9480 |
| aagttgtcac ttacgctctt aacacattta ccaacctagt ggtgcaactc attcggaata | 9540 |
| tggaggctga ggaagttcta gagatgcaag acttgtggct gctgcggagg tcagagaaag | 9600 |
| tgaccaactg gttgcagagc aacggatggg ataggctcaa acgaatggca gtcagtggag | 9660 |
| atgattgcgt tgtgaagcca attgatgata ggtttgcaca tgccctcagg ttcttgaatg | 9720 |
| atatgggaaa agttaggaag gacacacaag agtggaaacc ctcaactgga tgggacaact | 9780 |
| gggaagaagt tccgttttgc tcccaccact tcaacaagct ccatctcaag gacgggaggt | 9840 |
| ccattgtggt tccctgccgc caccaagatg aactgattgg ccgggcccgc gtctctccag | 9900 |
| gggcgggatg gagcatccgg gagactgctt gcctagcaaa atcatatgcg caaatgtggc | 9960 |
| agctcctttta tttccacaga agggacctcc gactgatggc caatgccatt tgttcatctg | 10020 |
| tgccagttga ctgggttcca actgggagaa ctacctggtc aatccatgga aagggagaat | 10080 |
| ggatgaccac tgaagacatg cttgtggtgt ggaacagagt gtggattgag gagaacgacc | 10140 |
| acatggaaga caagaccccca gttacgaaat ggacagacat tccctatttg ggaaaaaggg | 10200 |
| aagacttgtg gtgtggatct ctcatagggc acagaccgcg caccacctgg gctgagaaca | 10260 |
| ttaaaaacac agtcaacatg gtgcgcagga tcataggtga tgaagaaaag tacatggact | 10320 |
| acctatccac ccaagttcgc tacttgggtg aagaagggtc tacacctgga gtgctgtaag | 10380 |
| caccaatctt aatgttgtca ggcctgctag tcagccacag cttggggaaa gctgtgcagc | 10440 |
| ctgtgacccc cccaggagaa ctgggaaaca agcctata gtcaggccga gaacgccatg | 10500 |
| gcacggaaga agccatgctg cctgtgagcc cctcagagga cactgagtca aaaaccccca | 10560 |
| cgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| ccccggaaaa cgcaaaacag catattgacg ctgggaaaga ccagagactc catgagtttc | 10740 |
| caccacgctg gccgccaggc acagatcgcc gaacagcggc ggccggtgtg gggaaatcca | 10800 |
| tggtttct | 10808 |

<210> SEQ ID NO 5
<211> LENGTH: 10808
<212> TYPE: DNA
<213> ORGANISM: Artificial Sequence
<220> FEATURE:
<223> OTHER INFORMATION: Synthetic Construct

<400> SEQUENCE: 5

| | |
|---|---:|
| agttgttgat ctgtgtgaat cagactgcga cagttcgagt ttgaagcgaa agctagcaac | 60 |
| agtatcaaca ggttttattt tggatttgga aacgagagtt tctggtcatg aaaaacccaa | 120 |
| aaaagaaatc cggaggattc cggattgtca atatgctaaa acgcggagta gcccgtgtga | 180 |
| gccccttttgg gggcttgaag aggctgccag ccggacttct gctgggtcat gggcccatca | 240 |
| ggatggtctt ggcgattcta gccttttga gattcacggc aatcaagcca tcactgggtc | 300 |
| tcatcaatag atggggttca gtggggaaaa aagaggctat ggaaataata aagaagttca | 360 |
| agaaagatct ggctgccatg ctgagaataa tcaatgctag gaaggagaag aagagacgag | 420 |
| gcgcagatac tagtgtcgga attgttggcc tcctgctgac cacagctatg gcagcggagg | 480 |
| tcactagacg tggagtgcaa tactatatgt acttggacag aaacgatgct ggggaggcca | 540 |
| tatcttttcc aaccacattg gggatgaata agtgttatat acagatcatg gatcttggac | 600 |
| acatgtgtga tgccaccatg agctatgaat gccctatgct ggatgagggg gtggaaccag | 660 |

```
atgacgtcga ttgttggtgc aacacgacgt caacttgggt tgtgtacgga acctgccatc    720
acaaaaaagg tgaagcacgg agatctagaa gggctgtgac gctccctcc cattccacca     780 ggaagctgca acgcggtcg caaacctggt tggaatcaag agaatacaca aagcacttga     840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttctgac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccggcaa gagcatccag ccagagaatc   1380
tggagtaccg ataatgctg tcagttcatg ctcccagca cagtgggatg atcgttaatg     1440
acacaggaca tgaaactgat gagaatagag cgaaagttga gataacgccc aattcaccga   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag gggagactgt ctagcggaca ccttaagtgt agactgaaaa   1860
tggacaaact gagacttaag ggagtgtcat actcactgtg tactgccgca tttacgttta   1920
cgaagatacc cgccgaaaca ttgcacggaa ccgttacagt cgaagtgcaa tacgccggaa   1980
ccgacggacc atgtaaggtg ccagcgcaaa tggcagtcga tatgcaaaca ctgacaccag   2040
tcggtagact gattaccgct aacccagtga taaccgaatc cactgagaat tcgaaaatga   2100
tgcttgagct tgacccacca ttcggcgata gctatatcgt tatcggagtc ggcgaaaaaa   2160
agattacaca ccattggcat agatccggat ctacaatcgg taaggcattc gaagctaccg   2220
ttaggggcgc taagcgtatg gccgtattgg gcgataccgc ttgggatttc ggatccgtcg   2280
gaggcgcact gaattcccta ggtaagggga taccaaat attcggcgca gcgtttaagt     2340
cattgttcgg agggatgtca tggtttagtc agatactgat cggaacattg cttatgtggt   2400
tagggttgaa cactaagaac ggatcaatct cattgatgtg tcttgcgtta ggggggtgt     2460 tgatctttct gtcaaccgcc gttagcgcag atgtgggtg ctcggtggac ttctcaagga    2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgcgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtatttcgt cagagcagca aagacaaata   2880
acagctttgt cgtggatggt gacacactga aggaatgccc actcaaacat agagcatgga   2940
acagctttct tgtggaggat catgggttcg gggtatttca cactagtgtc tggctcaagg   3000
```

-continued

| | |
|---|---|
| ttagagaaga ttattcatta gagtgtgatc cagccgttat tggaacagct gttaagggaa | 3060 |
| aggaggctgt acacagtgat ctaggctact ggattgagag tgagaagaat gacacatgga | 3120 |
| ggctgaagag ggcccatctg atcgagatga aaacatgtga atggccaaag tcccacacat | 3180 |
| tgtggacaga tggaatagaa gagagtgatc tgatcatacc caagtcttta gctgggccac | 3240 |
| tcagccatca caataccaga gagggctaca ggacccaaat gaaagggcca tggcacagtg | 3300 |
| aagaacttga aattcggttt gaggaatgcc caggcactaa ggtccacgtg gaggaaacat | 3360 |
| gtggaacaag aggaccatct ctgagatcaa ccactgcaag cggaagggtg atcgaggaat | 3420 |
| ggtgctgcag ggagtgcaca atgcccccac tgtcgttccg ggctaaagat ggctgttggt | 3480 |
| atggaatgga gataaggccc aggaaagaac cagaaagcaa cttagtaagg tcaatggtga | 3540 |
| ctgcaggatc aactgatcac atggaccact tctcccttgg agtgcttgtg atcctgctca | 3600 |
| tggtgcagga agggctgaag aagagaatga ccacaaagat catcataagc acatcaatgg | 3660 |
| cagtgctggt agctatgatc ctgggaggat tttcaatgag tgacctggct aagcttgcaa | 3720 |
| ttttgatggg tgccaccttc gcggaaatga acactggagg agatgtagct catctggcgc | 3780 |
| tgatagcggc attcaaagtc agaccagcgt tgctggtatc tttcatcttc agagctaatt | 3840 |
| ggacaccccg tgaaagcatg ctgctggcct tggcctcgtg tcttttgcaa actgcgatct | 3900 |
| ccgccttgga aggcgacctg atggttctca tcaatggttt tgctttggcc tggttggcaa | 3960 |
| tacgagcgat ggttgttcca cgcactgata acatcacctt ggcaatcctg gctgctctga | 4020 |
| caccactggc ccggggcaca ctgcttgtgg cgtggagagc aggccttgct acttgcgggg | 4080 |
| ggtttatgct cctctctctg aagggaaaag gcagtgtgaa gaagaactta ccatttgtca | 4140 |
| tggccctggg actaaccgct gtgaggctgg tcgaccccat caacgtggtg ggactgctgt | 4200 |
| tgctcacaag gagtgggaag cggagctggc cccctagcga agtactcaca gctgttggcc | 4260 |
| tgatatgcgc attggctgga gggttcgcca aggcagatat agagatggct gggcccatgg | 4320 |
| ccgcggtcgg tctgctaatt gtcagttacg tggtgtcagg aaagagtgtg acatgtaca | 4380 |
| ttgaaagagc aggagacatc acatgggaaa agatgcggga agtcactgga aacagtcccc | 4440 |
| ggctcgatgt ggcgctagat gagagtggtg atttctccct ggtggaggat gacggtcccc | 4500 |
| ccatgagaga gatcatactc aaggtggtcc tgatgaccat ctgtggcatg aacccaatag | 4560 |
| ccataccctt tgcagctgga gcgtggtacg tatacgtgaa gactggaaaa aggagtggtg | 4620 |
| ctctatggga tgtgcctgct cccaaggaag taaaaaaggg ggaaaccaca gatggagtgt | 4680 |
| acagagtaat gactcgtaga ctgctaggtt caacacaagt tggagtggga gttatgcaag | 4740 |
| aggggtctt tcacactatg tggcacgtca caaaaggatc cgcgctgaga agcggtgaag | 4800 |
| ggagacttga tccatactgg ggagatgtca agcaggatct ggtgtcatac tgtggtccat | 4860 |
| ggaagctaga tgccgcctgg gatgggcaca gcgaggtgca gctcttggcc gtgccccccg | 4920 |
| gagagagagc gaggaacatc cagactctgc ccggaatatt taagacaaag gatgggcaca | 4980 |
| ttggagcggt tgcgctggat tacccagcag gaacttcagg atctccaatc ctagacaagt | 5040 |
| gtgggagagt gataggactt tatggcaatg gggtcgtgat caaaaacggg agttatgtta | 5100 |
| gtgccatcac ccaagggagg agggaggaag agactcctgt tgagtgcttc gagccctcga | 5160 |
| tgctgaagaa gaagcagcta actgtcttag acttgcatcc tggagctggg aaaaccagga | 5220 |
| gagttcttcc tgaaatagtc cgtgaagcca taaaaacaag actccgtact gtgatcttag | 5280 |
| ctccaaccag ggttgtcgct gctgaaatgg aggaggccct tagagggctt ccagtgcgtt | 5340 |
| atatgacaac agcagtcaat gtcacccact ctggaacaga aatcgtcgac ttaatgtgcc | 5400 |

```
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac cgccacgcca ccaggaaccc    5580
gtgacgcatt tccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaacggc aatgagatcg cagcttgtct gacaaaggct ggaaaacggg    5760
tcatacagct cagcagaaag acttttgaga cagagttcca gaaaacaaaa catcaagagt    5820
gggactttgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000 atcccaacaa acctggagat gagtatctgt atggaggtgg gtgcgcagag actgacgaag    6060
accatgcaca ctggcttgaa gcaagaatgc tccttgacaa tatttacctc caagatggcc    6120
tcatagcctc gctctatcga cctgaggccg acaaagtagc agccattgag ggagagttca    6180
agcttaggac ggagcaaagg aagaccttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gacacggaga gaaagagtg ctcaaaccga ggtggatgga cgccagagtt tgttcagatc    6420
atgcggccct gaagtcattc aaggagtttg ccgctgggaa agaggagcg gcttttggag    6480 tgatggaagc cctgggaaca ctgccaggac acatgacaga gagattccag gaagccattg    6540
acaacctcgc tgtgctcatg cgggcagaga ctggaagcag gccttacaaa gccgcggcgg    6600
cccaattgcc ggagacacta gagacaataa tgcttttggg gttgctggga acagtctcgc    6660
tgggaatctt cttcgtcttg atgaggaaca agggcatagg gaagatgggc tttggaatgg    6720
tgactcttgg ggccagcgca tggctcatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagta ggtcttctgg    6900
gcttgattac cgccaatgaa ctcggatggt tggagagaac aaagagtgac ctaagccatc    6960
taatgggaag agagaggag ggggcaacca taggattctc aatggacatt gacctgcggc    7020
cagcctcagc ttgggccatc tatgctgcct tgacaacttt cattaccccca gccgtccaac    7080 atgcagtgac caccctcata acaactact ccttaatggc gatggccacg caagctggag    7140
tgttgtttgg catgggcaaa gggatgccat tctacgcatg gactttgga gtcccgctgc    7200 taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc cgtctccagc gccatactgt cgcggaccgc ctgggggtgg ggggaggctg    7500
gggctctgat cacagccgca acttccactt tgtgggaagg ctctccgaac aagtactgga    7560
actcctctac agccacttca ctgtgtaaca ttttaggg aagttacttg gctggagctt    7620
ctctaatcta cacagtaaca agaaacgctg gcttggtcaa gagacgtggg ggtggaacag    7680
gagaaaccct gggagagaaa tggaaggccc gcttgaacca gatgtcggcc ctggagttct    7740
```

```
actcctacaa aaagtcaggc atcaccgagg tgtgcagaga agaggcccgc cgcgccctca    7800
aggacggtgt ggcaacggga ggccatgctg tgtcccgagg aagtgcaaag ctgagatggt    7860
tggtggagcg gggatacctg cagccctatg gaaaggtcat tgatcttgga tgtggcagag    7920
ggggctggag ttactacgcc gccaccatcc gcaaagttca agaagtgaaa ggatacacaa    7980
aaggaggccc tggtcatgaa gaacccgtgt tggtgcaaag ctatgggtgg aacatagtcc    8040
gtcttaagag tggggtggac gtctttcata tggcggctga gccgtgtgac acgttgctgt    8100
gtgacatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtgtctggag    8340
cgaaaagcaa caccataaaa agtgtgtcca ccacgagcca gctcctcttg gggcgcatgg    8400
acgggcctag gaggccagtg aaatatgagg aggatgtgaa tctcggctct ggcacgcggg    8460
ctgtggtaag ctgcgctgaa gctcccaaca tgaagatcat tggtaaccgc attgaaagga    8520
tccgcagtga gcacgcggaa acgtggttct ttgacgagaa ccacccatat aggacatggg    8580
cttaccatgg aagctatgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt gtcttcctgg ttgtggaaag    8820
agctaggcaa acacaaacgg ccacgagtct gcaccaaaga agagttcatc aacaaggttc    8880
gtagcaatgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaaggc agccgcgcca tctggtatat gtggctaggg gctagatttc    9120
tagagttcga agcccttgga ttcttgaacg aggatcactg gatggggaga gagaactcag    9180
gaggtggtgt tgaagggctg ggattacaaa gactcggata tgtcctagaa gagatgagtc    9240
gtataccagg aggaaggatg tatgcagatg acactgctgg ctgggacacc cgcattagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaaaacagtt atggacatta tttcgagaca agaccaaagg gggagcggac    9480
aagttgtcac ttacgctctt aacacattta ccaacctagt ggtgcaactc attcggaata    9540
tggaggctga ggaagttcta gagatgcaag acttgtggct gctgcggagg tcagagaaag    9600
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact caacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960 agctcctta tttccacaga agggacctcc gactgatggc caatgccatt tgttcatctg   10020
tgccagttga ctgggttcca actggagaa ctacctggtc aatccatgga aagggagaat   10080
ggatgaccac tgaagacatg cttgtggtgt ggaacagagt gtggattgag gagaacgacc   10140
```

| | | |
|---|---|---|
| acatggaaga caagacccca gttacgaaat ggacagacat tccctatttg ggaaaaaggg | 10200 |
| aagacttgtg gtgtggatct ctcatagggc acagaccgcg cacccctgg gctgagaaca | 10260 |
| ttaaaaacac agtcaacatg gtgcgcagga tcataggtga tgaagaaaag tacatggact | 10320 |
| acctatccac ccaagttcgc tacttgggtg aagaagggtc tacacctgga gtgctgtaag | 10380 |
| caccaatctt aatgttgtca ggcctgctag tcagccacag cttggggaaa gctgtgcagc | 10440 |
| ctgtgacccc cccaggagaa gctgggaaac caagcctata gtcaggccga gaacgccatg | 10500 |
| gcacggaaga agccatgctg cctgtgagcc cctcagagga cactgagtca aaaaacccca | 10560 |
| cgcgcttgga ggcgcaggat gggaaaagaa ggtggcgacc ttccccaccc ttcaatctgg | 10620 |
| ggcctgaact ggagatcagc tgtggatctc cagaagaggg actagtggtt agaggagacc | 10680 |
| ccccggaaaa cgcaaaacag catattgacg ctgggaaaga ccagagactc catgagtttc | 10740 |
| caccacgctg gccgccaggc acagatcgcc gaacagcggc ggccggtgtg gggaaatcca | 10800 |
| tggtttct | 10808 |

<210> SEQ ID NO 6
<211> LENGTH: 10807
<212> TYPE: DNA
<213> ORGANISM: Zika

<400> SEQUENCE: 6

| | | |
|---|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaaacccaaa | 120 |
| gaagaaatcc ggaggattcc ggattgtcaa tatgctaaaa cgcggagtag cccgtgtaaa | 180 |
| ccccttggga ggtttgaaga ggttgccagc cggacttctg ctgggtcatg gacccatcag | 240 |
| aatggttttg gcgatactag cctttttgag atttacagca atcaagccat cactgggcct | 300 |
| tatcaacaga tggggttccg tggggaaaaa gagggctatg gaaataataa gaagttcaa | 360 |
| gaaagatctt gctgccatgt tgagaataat caatgctagg aaagagagga gagacgtgg | 420 |
| cgcagacacc agcatcggaa tcattggcct cctgctgact acagccatgg cagcagagat | 480 |
| cactagacgc gggagtgcat actacatgta cttggatagg agcgatgccg ggaaggccat | 540 |
| ttcgtttgct accacattgg gagtgaacaa gtgccacgta cagatcatgg acctcgggca | 600 |
| catgtgtgac gccaccatga gttatgagtg ccctatgctg gatgagggag tggaaccaga | 660 |
| tgatgtcgat tgctggtgca acacgacatc aacttgggtt gtgtacggaa cctgtcatca | 720 |
| caaaaaggt gaggcacggc gatctaggag agccgtgacg ctcccttctc actctacaag | 780 |
| gaagttgcaa acgcggtcgc agacctggtt agaatcaaga gaatacacga agcacttgat | 840 |
| caaggttgaa aactggatat tcaggaaccc cgggtttgcg ctagtggccg ttgccattgc | 900 |
| ctggcttttg ggaagctcga cgagccaaaa agtcatatac ttggtcatga tactgctgat | 960 |
| tgccccggca tacagtatca ggtgcattgg agtcagcaat agagacttcg tggagggcat | 1020 |
| gtcaggtggg acctgggttg atgttgtctt ggaacatgga ggctgcgtta ccgtgatggc | 1080 |
| acaggacaag ccaacagttg acatagagtt ggtcacgacg acggttagta acatggccga | 1140 |
| ggtaagatcc tattgctacg aggcatcgat atcggacatg gcttcggaca gtcgttgccc | 1200 |
| aacacaaggt gaagcctacc ttgacaagca atcagacact caatatgtct gcaaaagaac | 1260 |
| attagtggac agaggttggg gaaacggttg tggactttt ggcaaaggga gcttggtgac | 1320 |
| atgtgccaag tttacgtgtt ctaagaagat gaccggcaag agcattcaac cggaaaatct | 1380 |

-continued

```
ggagtatcgg ataatgctat cagtgcatgg ctcccagcat agcgggatga ttgtcaatga   1440
tacaggatat gaaactgacg aaaatagagc gaaagtcgag gttacgccta attcaccaag   1500
agcggaagca accttgggag gctttggaag cttaggactt gactgtgaac caaggacagg   1560
ccttgacttt tcagatctgt attacctgac catgaacaat aagcattggt tggtgcacaa   1620
agagtggttt catgacatcc cattgccttg gcatgctggg gcagacaccg gaactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg gaaggctgtt ctctggccat ttgaaatgcc gcctaaaaat   1860
ggacaagctt agattgaagg gcgtgtcata ttccttgtgc actgcggcat tcacattcac   1920
caaggtccca gctgaaacac tgcatggaac agtcacagtg gaggtgcagt atgcagggac   1980
agatggaccc tgcaagatcc cagtccagat ggcggtggac atgcagaccc tgaccccagt   2040
tggaaggctg ataaccgcca accccgtgat tactgaaagc actgagaact caaagatgat   2100
gttggagctt gacccaccat tgggggattc ttacattgtc ataggagttg gggacaagaa   2160
aatcacccac cactggcata ggagtggtag caccatcgga aaggcatttg aggccactgt   2220
gagaggcgcc aagagaatgg cagtcctggg ggatacagcc tgggacttcg gatcagtcgg   2280
gggtgtgttc aactcactgg gtaagggcat tcaccagatt tttggagcag ccttcaaatc   2340
actgtttgga ggaatgtcct ggttctcaca gatcctcata ggcacgctgc tagtgtggtt   2400
aggtttgaac acaaagaatg gatctatctc cctcacatgc ttggccctgg ggggagtgat   2460
gatcttcctc tccacggctg tttctgctga cgtggggtgc tcagtggact ctctcaaaaaa   2520 ggaaacgaga tgtggcacgg gggtattcat ctataatgat gttgaagcct ggagggaccg   2580
gtacaagtac catcctgact ccccccgcag attggcagca gcagtcaagc aggcctggga   2640
agaggggatc tgtgggatct catccgtttc aagaatggaa aacatcatgt ggaaatcagt   2700 agaagggag ctcaatgcta tcctagagga gaatggagtt caactgacag ttgttgtggg   2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940 tagtttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa acatgtgaa tggccaaagt ctcacacatt   3180
gtggacagat ggagtagaag aaagtgatct tatcataccc aagtctttag ctggtccact   3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgcccccact atcgtttcga gcaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac cacaaagatc atcatgagca catcaatggc   3660
agtgctggta gtcatgatct tgggaggatt ttcaatgagt gacctggcca agcttgtgat   3720
cctgatgggt gctactttcg cagaaatgaa cactggagga gatgtagctc acttggcatt   3780
```

```
ggtagcggca tttaaagtca gaccagcctt gctggtgtcc ttcattttca gagccaattg   3840
gacaccccgt gagagcatgc tgctagccct ggcttcgtgt cttctgcaaa ctgcgatctc   3900
tgctcttgaa ggtgacttga tggtcctcat taatggattt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga aagggaaagg tagtgtgaag aagaacctgc catttgtcat   4140
ggccctggga ttgacagctg tgagggtagt agaccctatt aatgtggtag gactactgtt   4200
actcacaagg agtgggaagc ggagctggcc ccctagtgaa gttctcacag ccgttggcct   4260
gatatgtgca ctggccggag ggtttgccaa ggcagacatt gagatggctg acccatggc   4320 tgcagtaggc ttgctaattg tcagctatgt ggtgtcggga aagagtgtgg acatgtacat   4380
tgaaagagca ggagacatca catgggaaaa ggacgcggaa gtcactggaa acagtcctcg   4440
gcttgacgtg gcactggatg agagtggtga tttctccttg gtagaggaag atggtccacc   4500
catgagagag atcatactca aggtggtcct gatggccatc tgtggcatga acccaatagc   4560
tatacctttt gctgcaggag cgtggtatgt gtatgtgaag actgggaaaa ggagtggcgc   4620
cctctgggac gtgcctgctc ccaaagaagt gaagaaagga gaaccacag atggagtgta   4680 cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag cttttggccg tacctcccgg   4920
agagagggcc agaaacattc agaccctgcc tggaatattc aagacaaagg acggggacat   4980
cggagcagtt gctctggact accctgcagg gacctcagga tctccgatcc tagacaaatg   5040
tggaagagtg ataggactct atggcaatgg ggttgtgatc aagaatggaa gctatgttag   5100
tgctataacc caggaaaga gggaggagga gactccggtt gaatgtttcg aaccctcgat   5160
gctgaagaag aagcagctaa ctgtcttgga tctgcatcca ggagccggaa aaaccaggag   5220
agttcttcct gaaatagtcc gtgaagccat aaaaaagaga ctccggacag tgatcttggc   5280
accaactagg gttgtcgctg ctgagatgga ggaggccttg agaggacttc cggtgcgtta   5340
catgacaaca gcagtcaacg tcacccattc tgggacagaa atcgttgatt tgatgtgcca   5400
tgccactttc acttcacgct actacaaacc catcagagtc cctaattaca atctcaacat   5460
catggatgaa gcccacttca cagaccccctc aagtatagct gcaagaggat acatatcaac   5520
aagggttgaa atgggcgagg cggctgccat ttttatgact gccacaccac caggaacccg   5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg aaagcgggt   5760 catacagctc agcaggaaga cttttgagac agaatttcag aaaacaaaaa atcaagagtg   5820 ggacttttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
```

```
catagcctcg ctctatcggc ctgaggccga taaggtagcc gccattgagg gagagtttaa    6180
gctgaggaca gagcaaagga agaccttcgt ggaactcatg aagagagggg accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagactctag agacaattat gctcttaggt ttgctgggaa cagtttcact    6660
ggggatcttc ttcgtcttga tgcggaataa gggcatcggg aagatgggct ttggaatggt    6720
aaccctgggg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccag ctgtccaaca    7080
tgcggtaacc acttcataca caactactc cttaatggcg atggccacac aagctggagt    7140
gctgtttggc atgggcaaag ggatgccatt ttatgcatgg gaccttggag tcccgctgct    7200
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccaggt ggagaagaag atgggacaag tgttactcat    7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg    8280
attagtcaga gtgccattgt ctcgcaactc cacacatgag atgtactggg tgtctggggc    8340
aaagagcaac atcataaaaa gtgtgtccac cacaagtcag ctcctcctgg acgcatgga    8400
tggcccagg aggccagtga atatgaggag ggatgtgaac ctcggctcgg gtacacgagc    8460
tgtggcaagc tgtgctgagg ctcctaacat gaaaatcatc ggcaggcgca ttgagagaat    8520
```

```
ccgcaatgaa catgcagaaa catggtttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaaggt tttgggccct agtggatagg agagagaaac accacctgag    9000
aggagagtgt cacagctgtg tgtacaacat gatgggaaaa agagaaaaga gcaaggaga    9060 gttcgggaaa gcaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta ccggaacat    9540 ggaagctgag gaagtgttag agatgcaaga cttatggttg ttgaggaagc cagagaaagt    9600
gaccagatgg ttgcagagca atggatggga tagactcaaa cgaatggcgg tcagtggaga    9660
tgactgcgtt gtgaagccaa tcgatgatag gtttgcacat gccctcaggt tcttgaatga    9720
catgggaaaa gttaggaaag acacacagga gtggaaaccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960 gctccttat ttccacagaa gggaccttcg actgatggct aatgccattt gctcggctgt   10020
gccagttgac tgggttccaa ctgggagaac cacctggtca atccatgaa agggagaatg   10080 gatgaccact gaggacatgc tcatggtgtg aatagagtg tggattgagg agaacgacca   10140
tatggaggac aagactcctg taacaaaatg gacagacatt ccctatctag gaaaaaggga   10200
ggacttatgg tgtggatccc ttatagggca cagaccccgc accacttggg ctgaaaacat   10260
caaagacaca gtcaacatgg tgcgcaggat cataggtgat gaagaaaagt acatggacta   10320
tctatccacc caagtccgct acttgggtga ggaagggtcc acaccggag tgttgtaagc   10380 accaattta gtgttgtcag gcctgctagt cagccacagt ttggggaaag ctgtgcagcc   10440
tgtaaccccc ccaggagaag ctgggaaacc aagctcatag tcaggccgag aacgccatgg   10500
cacggaagaa gccatgctgc ctgtgagccc ctcagaggac actgagtcaa aaacccac   10560 gcgcttggaa gcgcaggatg ggaaaagaag gtggcgacct tccccaccct tcaatctggg   10620
gcctgaactg gagactagct gtgaatctcc agcagggga ctagtggtta gaggagaccc   10680
cccggaaaac gcacaacagc atattgacgc tgggaaagac cagagactcc atgagtttcc   10740
accacgctgg ccgccaggca cagatcgccg aacttcggcg gccggtgtgg ggaaatccat   10800
ggtttct                                                             10807
```

<210> SEQ ID NO 7
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 7

```
agttgttgat ctgtgtgagt cagactgcga cagttcgagt ctgaagcgag agctaacaac      60
agtatcaaca ggtttaattt ggatttggaa acgagagttt ctggtcatga aaaacccaaa     120
gaagaaatcc ggaggattcc ggattgtcaa tatgctaaaa cgcggagtag cccgtgtaaa     180
cccctthggga ggtttgaaga ggttgccagc cggacttctg ctgggtcatg gacccatcag    240
aatggttttg gcgatactag ccttttttgag atttacagca atcaagccat cactgggcct    300
tatcaacaga tgggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagccgaaat    480
tacgagaagg gggtccgcat actatatgta tctggatagg tccgacgccg gtaaggcaat    540
ctcattcgca acgacactcg gagtgaataa gtgtcacgtt cagattatgg acttagggca    600
tatgtgcgac gctactatgt catacgaatg ccctatgctt gacgaaggcg ttgagccaga    660
cgacgtcgac tgttggtgca atacgactag cacatgggtc gtgtacggta catgccatca    720
caaaagggc gaagcgagac ggtctagaag ggccgttacg ttgccgtcac actctacgag    780
aaagttgcag actaggtctc agacttggtt ggagtcacgc gaatacacta agcatctgat    840
taaggtcgag aattggattt ttaggaaccc agggttcgca ctagtcgccg tcgcaatcgc    900
ttggttgttg gggtctagta cgagtcagaa agtgatatac ttagtgatga tactgttgat    960
cgcacccgca tactctatta ggtgtatcgg agtgagtaat cgcgatttcg tcgagggtat   1020
gagcggaggg acatgggtcg acgttgtgct tgagcacggg gggtgcgtta ccgttatggc   1080
ccaagacaaa ccgacagtcg atatcgaact ggttacgact accgtttcga acatggccga   1140
agtgagatcg tattgttacg aggctagcat aagcgatatg gctagcgata gtaggtgccc   1200
aacacagggc gaagcgtatc tcgataagca atccgatacg caatacgttt gcaaacggac   1260
attggtcgat aggggggtggg gtaacggatg cggactgttc ggtaagggt cactagtgac    1320
atgcgctaag tttacatgct ctaaaaaaat gaccggtaag tcaatccaac ccgaaaacct   1380
tgagtatagg attatgttga gcgtacacgg atcgcaacac tccggtatga tcgttaacga   1440
taccggatac gagactgacg agaatagggc taaggtcgag gtgacaccta actcacctag   1500
agccgaagcg acattggggg ggttcggatc tctcggactg gattgcgaac ctagaaccgg   1560
attggacttt agcgatctgt actatctgac tatgaacaat aagcattggt tggtgcataa   1620
ggagtggttt cacgacatac cactgccatg gcacgccgga gccgataccg gtacgccaca   1680
ttggaataac aaagaggcac tagtcgagtt taaggacgct cacgctaaga gacagaccgt   1740
agtcgtgttg gggtcacagg agggagccgt gcataccgca ctagccggcg cactcgaggc   1800
cgaaatggac ggagcgaaag ggagactgtt tagcggacac cttaagtgta gactgaaaat   1860
ggacaagttg cgacttaagg gcgttagcta tagcctatgt accgccgcat ttacgtttac   1920
gaaagtgcca gccgaaacgt tgcacggaac cgttaccgtc gaggtgcaat acgccggaac   1980
cgacggacca tgcaagatac ccgtgcaaat ggccgtcgat atgcagacac tgacaccagt   2040
cggacggttg attaccgcta acccagtgat aaccgagtca accgaaaact ctaagatgat   2100
```

```
gctcgagctt gacccaccat tcggcgactc atatatcgtt atcggagtcg gcgacaaaaa   2160
gattacgcat cattggcata gatccggatc gacaatcggt aaggcattcg aagcgacagt   2220
gagaggcgct aagcgtatgg ccgtattggg cgataccgca tgggacttcg gatccgtcgg   2280
cggagtgttt aactcactcg gtaagggat acaccagata ttcggagccg cattcaaatc    2340
gttgttcggc ggaatgtcat ggtttagtca gatactgatc ggaacactgc ttgtgtggtt   2400
ggggttgaac actaagaacg gatcgattag tctgacatgc ttagccttag gcggagtgat   2460
gatttttctg tcaaccgccg ttagcgcaga cgtggggtgc tcagtggact ctcaaaaaa    2520 ggaaacgaga tgtggcacgg gggtattcat ctataatgat gttgaagcct ggagggaccg   2580
gtacaagtac catcctgact cccccgcag attggcagca gcagtcaagc aggcctggga    2640
agaggggatc tgtgggatct catccgtttc aagaatggaa acatcatgt ggaaatcagt    2700 agaaggggag ctcaatgcta tcctagagga gaatggagtt caactgacag ttgttgtggg   2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgaa tggccaaagt ctcacacatt   3180
gtggacagat ggagtagaag aaagtgatct tatcataccc aagtctttag ctggtccact   3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgcccccact atcgtttcga gcaaaagacg gctgctggta   3480
tggaatggag ataaggcccca ggaaagaacc agagagcaac ttagtgaggt caatggtgac   3540 agcgggtca accgatcata tggaccactt ctctcttgga gtgcttgtga ttctactcat    3600
ggtgcaggag gggttgaaga agagaatgac cacaaagatc atcatgagca catcaatggc   3660
agtgctggta gtcatgatct gggaggatt ttcaatgagt gacctggcca agcttgtgat    3720
cctgatgggt gctactttcg cagaaatgaa cactggagga gatgtagctc acttggcatt   3780
ggtagcggca tttaaagtca gaccagcctt gctggtgtcc ttcattttca gagccaattg   3840
gacaccccgt gagagcatgc tgctagccct ggcttcgtgt cttctgcaaa ctgcgatctc   3900
tgctcttgaa ggtgacttga tggtcctcat taatggattt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga aagggaaagg tagtgtgaag aagaacctgc catttgtcat   4140
ggccctggga ttgacagctg tgaggatagt agaccctatt aatgtggtag gactactgtt   4200
actcacaagg agtgggaagc ggagctggcc ccctagtgaa gttctcacag ccgttggcct   4260
gatatgtgca ctggccggag ggtttgccaa ggcagacatt gagatggctg gacccatggc   4320
tgcagtaggc ttgctaattg tcagctatgt ggtgtcggga aagagtgtgg acatgtacat   4380
tgaaagagca ggagacatca catgggaaaa ggacgcggaa gtcactggaa acagtcctcg   4440
```

```
gcttgacgtg gcactggatg agagtggtga tttctccttg gtagaggaag atggtccacc    4500
catgagagag atcatactca aggtggtcct gatggccatc tgtggcatga acccaatagc    4560
tataccttt  gctgcaggag cgtggtatgt gtatgtgaag actgggaaaa ggagtggcgc    4620
cctctgggac gtgcctgctc ccaaagaagt gaagaaagga gaaaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg tgtcatact  gtgggccttg    4860
gaagttggat gcagcttggg atggactcag cgaggtacag cttttggccg tacctcccgg    4920
agagagggcc agaaacattc agaccctgcc tggaatattc aagacaaagg acgggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc cagggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctcaacat    5460
catggatgaa gcccacttca cagacccctc aagtatagct gcaagaggat acatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg gaaagcgggt    5760
catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga agaccttcgt ggaactcatg aagagagggg accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagactctag acaattat   gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc atacccgagc cagagaagca    6840
```

```
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agagaagaag gagcaaccat gggattctca atggacattg atctgcggcc   7020
agcctccgcc tgggctatct atgccgcatt gacaactctc atcacccag ctgtccaaca   7080 tgcggtaacc acttcataca acaactactc cttaatggcg atggccacac aagctggagt   7140
gctgtttggc atgggcaaag ggatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag accccaggt ggagaagaag atgggacaag tgttactcat   7440
agcagtagcc atctccagtg ctgtgctgct gcggaccgcc tggggatggg gggaggctgg   7500
agctctgatc acagcagcga cctccacctt gtgggaaggc tctccaaaca aatactggaa   7560
ctcctctaca gccacctcac tgtgcaacat cttcagagga agctatctgg caggagcttc   7620
ccttatctat acagtgacga gaaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag gacatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga acatagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatggtg ggggactggc ttgaaaaaag accagggcc ttctgtataa aggtgctgtg   8220
cccatacacc agcactatga tggaaaccat ggagcgactg caacgtaggc atggggagg   8280 attagtcaga gtgccattgt ctcgcaactc cacacatgag atgtactggg tgtctggggc   8340
aaagagcaac atcataaaaa gtgtgtccac cacaagtcag ctcctcctgg gacgcatgga   8400
tggccccagg aggccagtga atatgaggag ggatgtgaac ctcggctcgg gtacacgagc   8460
tgtggcaagc tgtgctgagg ctcctaacat gaaaatcatc ggcaggcgca ttgagagaat   8520
ccgcaatgaa catgcagaaa catggttct tgatgaaaac cacccataca ggacatgggc   8580
ctaccatggg agctacgaag ccccacgca aggatcagcg tcttccctcg tgaacggggt   8640
tgttagactc ctgtcaaagc cttggacgt ggtgactgga gttacaggaa tagccatgac   8700
tgacaccaca ccatacggcc aacaaagagt cttcaaagaa aaagtggaca ccagggtgcc   8760
agatccccaa gaaggcactc gccaggtaat gaacatagtc tcttcctggc tgtgaagga   8820 gctggggaaa cgcaagcggc cacgcgtctg caccaaagaa gagtttatca caaggtgcg   8880 cagcaatgca gcactgggag caatatttga agaggaaaaa gaatggaaga cggctgtgga   8940
agctgtgaat gatccaaggt tttgggccct agtggatagg gagagagaac accacctgag   9000
aggagagtgt cacagctgtg tgtacaacat gatgggaaaa agagaaaaga agcaaggaga   9060
gttcgggaaa gcaaaggta gccgcgccat ctggtacatg tggttgggag ccagattctt   9120
ggagtttgaa gcccttggat tcttgaacga ggaccattgg atgggaagag aaaactcagg   9180
```

| | |
|---|---|
| aggtggagtc gaagggttag gattgcaaag acttggatac attctagaag aaatgaatcg | 9240 |
| ggcaccagga ggaaagatgt acgcagatga cactgctggc tgggacaccc gcattagtaa | 9300 |
| gtttgatctg gagaatgaag ctctgattac caaccaaatg gaggaagggc acagaactct | 9360 |
| ggcgttggcc gtgattaaat acacatacca aaacaaagtg gtgaaggttc tcagaccagc | 9420 |
| tgaaggagga aaaacagtta tggacatcat ttcaagacaa gaccagagag ggagtggaca | 9480 |
| agttgtcact tatgctctca acacattcac caacttggtg gtgcagctta tccggaacat | 9540 |
| ggaagctgag gaagtgttag agatgcaaga cttatggttg ttgaggaagc cagagaaagt | 9600 |
| gaccagatgg ttgcagagca atggatggga tagactcaaa cgaatggcgg tcagtggaga | 9660 |
| tgactgcgtt gtgaagccaa tcgatgatag gtttgcacat gccctcaggt tcttgaatga | 9720 |
| catgggaaaa gttaggaaag acacacagga gtggaaaccc tcgactggat ggagcaattg | 9780 |
| ggaagaagtc ccgttctgct cccaccactt caacaagctg tacctcaagg atgggagatc | 9840 |
| cattgtggtc ccttgccgcc accaagatga actgattggc cgagctcgcg tctcaccagg | 9900 |
| ggcaggatgg agcatccggg agactgcctg tcttgcaaaa tcatatgcgc agatgtggca | 9960 |
| gctcctttat ttccacagaa gggaccttcg actgatggct aatgccattt gctcggctgt | 10020 |
| gccagttgac tgggttccaa ctgggagaac cacctggtca atccatggaa agggagaatg | 10080 |
| gatgaccact gaggacatgc tcatggtgtg aatagagtg tggattgagg agaacgacca | 10140 |
| tatggaggac aagactcctg taacaaaatg gacagacatt ccctatctag aaaaaggga | 10200 |
| ggacttatgg tgtggatccc ttatagggca cagaccccgc accacttggg ctgaaaacat | 10260 |
| caaagacaca gtcaacatgg tgcgcaggat cataggtgat gaagaaaagt acatggacta | 10320 |
| tctatccacc caagtccgct acttgggtga ggaagggtcc acacccggag tgttgtaagc | 10380 |
| accaattta tgtgttgtcag gcctgctagt cagccacagt ttggggaaag ctgtgcagcc | 10440 |
| tgtaaccccc ccaggagaag ctgggaaacc aagctcatag tcaggccgag aacgccatgg | 10500 |
| cacggaagaa gccatgctgc ctgtgagccc tcagaggac actgagtcaa aaaccccac | 10560 |
| gcgcttggaa gcgcaggatg ggaaaagaag gtggcgacct tccccaccct tcaatctggg | 10620 |
| gcctgaactg gagactagct gtgaatctcc agcagggga ctagtggtta gaggagaccc | 10680 |
| cccggaaaac gcacaacagc atattgacgc tgggaaagac cagagactcc atgagtttcc | 10740 |
| accacgctgg ccgccaggca cagatcgccg aacttcggcg gccggtgtgg ggaaatccat | 10800 |
| ggtttct | 10807 |

<210> SEQ ID NO 8
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaaacccaaa | 120 |
| gaagaaatcc ggaggattcc ggattgtcaa tatgctaaaa cgcggagtag cccgtgtaaa | 180 |
| ccccttggga ggtttgaaga ggttgccagc cggacttctg ctgggtcatg gacccatcag | 240 |
| aatggttttg cgatactag ccttttttgag atttacagca atcaagccat cactgggcct | 300 |
| tatcaacaga tggggttccg tggggaaaaa agaggctatg gaaataataa agaagttcaa | 360 |
| gaaagatctt gctgccatgt tgagaataat caatgctagg aaagagagga agagacgtgg | 420 |

```
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720 caaaaaggt gaggcacggc gatctaggag agccgtgacg ctcccttctc actctacaag    780
gaagttgcaa acgcggtcgc agacctggtt agaatcaaga aatacacga agcacttgat    840 caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagttg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggactttt ggcaaaggga gcttggtgac   1320
atgtgccaag tttacgtgtt ctaagaagat gaccggcaag agcattcaac cggaaaatct   1380
ggagtatcgg ataatgctat cagtgcatgg ctcccagcat agcgggatga ttgtcaatga   1440
tacaggatat gaaactgacg aaaatagagc gaaagtcgag gttacgccta actcacctag   1500
agccgaagcg acattggggg ggttcggatc tctcggactg gattgcgaac ctagaaccgg   1560
attggacttt agcgatctgt actatctgac tatgaacaat aagcattggt tggtgcataa   1620
ggagtggttt cacgacatac cactgccatg gcacgccgga gccgataccg gtacgccaca   1680
ttggaataac aaagaggcac tagtcgagtt taaggacgct cacgctaaga gacagaccgt   1740
agtcgtgttg gggtcacagg agggagccgt gcataccgca ctagccggcg cactcgaggc   1800
cgaaatggac ggagcgaaag ggagactgtt tagcggacac cttaagtgta gactgaaaat   1860
ggacaagttg cgacttaagg gcgttagcta tagcctatgt accgccgcat ttacgtttac   1920
gaaagtgcca gccgaaacgt tgcacggaac cgttaccgtc gaggtgcaat acgccggaac   1980
cgacggacca tgcaagatac ccgtgcaaat ggccgtcgat atgcagacac tgacaccagt   2040
cggacggttg attaccgcta acccagtgat aaccgagtca accgaaaact ctaagatgat   2100
gctcgagctt gacccaccat tcggcgactc atatatcgtt atcggagtcg gcgacaaaaa   2160
gattacgcat cattggcata gatccggatc gacaatcggt aaggcattcg aagcgacagt   2220
gagaggcgct aagcgtatgg ccgtattggg cgataccgca tgggacttcg gatccgtcgg   2280
cggagtgttt aactcactcg gtaaggggat acaccagata ttcggagccg cattcaaatc   2340
gttgttcggc ggaatgtcat ggtttagtca gatactgatc ggaacactgc ttgtgtggtt   2400
ggggttgaac actaagaacg gatcgattag tctgacatgc ttagccttag cggagtgat   2460 gattttctg tcaaccgccg ttagcgcaga cgtggggtgc tcagtggact tctcaaaaaa   2520
ggaaacgaga tgtggcacgg gggtattcat ctataatgat gttgaagcct ggagggaccg   2580
gtacaagtac catcctgact ccccccgcag attggcagca gcagtcaagc aggcctggga   2640
agaggggatc tgtgggatct catccgtttc aagaatggaa acatcatgt ggaaatcagt   2700 agaagggag ctcaatgcta tcctagagga gaatggagtt caactgacag ttgttgtggg   2760
```

```
atctgtaaaa aacccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa aacatgtgaa tggccaaagt ctcacacatt   3180
gtggacagat ggagtagaag aaagtgatct tatcataccc aagtctttag ctggtccact   3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgcccccact atcgtttcga gcaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac cacaaagatc atcatgagca catcaatggc   3660
agtgctggta gtcatgatct tgggaggatt ttcaatgagt gacctggcca agcttgtgat   3720
cctgatgggt gctactttcg cagaaatgaa cactggagga gatgtagctc acttggcatt   3780
ggtagcggca tttaaagtca accagcctt gctggtgtcc ttcattttca gagccaattg   3840
gacaccccgt gagagcatgc tgctagccct ggcttcgtgt cttctgcaaa ctgcgatctc   3900
tgctcttgaa ggtgacttga tggtcctcat taatggatt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga aagggaaagg tagtgtgaag aagaacctgc catttgtcat   4140 ggcccctggga ttgacagctg tgagggtagt agaccctatt aatgtggtag gactactgtt   4200
actcacaagg agtgggaagc ggagctggcc ccctagtgaa gttctcacag ccgttggcct   4260
gatatgtgca ctggccggag ggtttgccaa ggcagacatt gagatggctg acccatggc   4320 tgcagtaggc ttgctaattg tcagctatgt ggtgtcggga aagagtgtgg acatgtacat   4380
tgaaagagca ggagacatca catgggaaaa ggacgcggaa gtcactggaa acagtcctcg   4440
gcttgacgtg gcactggatg agagtggtga tttctccttg gtagaggaag atggtccacc   4500
catgagagag atcatactca aggtggtcct gatggccatc tgtggcatga cccaatagc   4560 tataccttt gctgcaggag cgtggtatgt gtatgtgaag actgggaaaa ggagtggcgc   4620
cctctgggac gtgcctgctc ccaaagaagt gaagaaagga gaaccacag atggagtgta   4680 cagagtgatg actcgcagac tgctaggttc aacacaggtt ggagtgggag tcatgcaaga   4740
gggagtcttc cacaccatgt ggcacgttac aaaaggagcc gcactgagga gcggtgaggg   4800
aagacttgat ccatactggg gggatgtcaa gcaggacttg gtgtcatact gtgggccttg   4860
gaagttggat gcagcttggg atggactcag cgaggtacag cttttggccg tacctccgg   4920 agagagggcc agaaacattc agaccctgcc tggaatattc aagacaaagg acgggacat   4980 cggagcagtt gctctggact acccctgcagg gacctcagga tctccgatcc tagacaaatg   5040
tggaagagtg ataggactct atggcaatgg ggttgtgatc aagaatgaa gctatgttag   5100 tgctataacc cagggaaaga gggaggagga gactccggtt gaatgtttcg aaccctcgat   5160
```

```
gctgaagaag aagcagctaa ctgtcttgga tctgcatcca ggagccggaa aaaccaggag   5220
agttcttcct gaaatagtcc gtgaagccat aaaaaagaga ctccggacag tgatcttggc   5280
accaactagg gttgtcgctg ctgagatgga ggaggccttg agaggacttc cggtgcgtta   5340
catgacaaca gcagtcaacg tcacccattc tgggacagaa atcgttgatt tgatgtgcca   5400
tgccactttc acttcacgct tactacaacc catcagagtc cctaattaca atctcaacat   5460
catggatgaa gcccacttca cagacccctc aagtatagct gcaagaggat acatatcaac   5520
aagggttgaa atgggcgagg cggctgccat ttttatgact gccacaccac caggaacccg   5580
tgatgcgttt cctgactcta actcaccaat catggacaca gaagtggaag tcccagagag   5640
agcctggagc tcaggctttg attgggtgac agaccattct gggaaaacag tttggttcgt   5700
tccaagcgtg agaaacggaa atgaaatcgc agcctgtctg acaaaggctg aaagcgggt   5760 catacagctc agcaggaaga cttttgagac agaatttcag aaaacaaaaa atcaagagtg   5820
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagagggg accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca aagaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg cctttataagg cagcggcagc   6600 ccaactgccg gagactctag agacaattat gctcttaggt ttgctgggaa cagtttcact   6660
ggggatcttc ttcgtcttga tgcggaataa gggcatcggg aagatgggct ttggaatggt   6720
aaccctgggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agaagaagg gagcaaccat gggattctca atggacattg atctgcggcc   7020
agcctccgcc tgggctatct atgccgcatt gacaactctc atcacccag ctgtccaaca   7080 tgcggtaacc acttcataca acaactactc cttaatggcg atgccacac aagctggagt   7140 gctgtttggc atgggcaaag ggatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag accccaggt ggagaagaag atgggacaag tgttactcat   7440
agcagtagcc atctccagtg ctgtgctgct gcggaccgcc tggggatggg gggaggctgg   7500
```

```
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag acatgccgt atcccgggga agtgcaaagc tcagatggtt     7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atgggggagg    8280
attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggtttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga gcaaggaga    9060
gttcgggaaa gcaaaggta ccgcgccat ctggtacatg tggttgggag ccagattctt     9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta ccgaacat     9540
ggaagctgag gaagtgttag agatgcaaga cttatggttg ttgaggaagc cagagaaagt    9600
gaccagatgt tgcagagca atggatggga tagactcaaa cgaatggcgg tcagtggaga    9660
tgactgcgtt gtgaagccaa tcgatgatag gtttgcacat gccctcaggt tcttgaatga    9720
catgggaaaa gttaggaaag acacacagga gtggaaccc tcgactggat ggagcaattg    9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
```

```
ggcaggatgg agcatccggg agactgcctg tcttgcaaaa tcatatgcgc agatgtggca    9960
gctcctttat ttccacagaa gggaccttcg actgatggct aatgccattt gctcggctgt   10020
gccagttgac tgggttccaa ctgggagaac cacctggtca atccatggaa agggagaatg   10080
gatgaccact gaggacatgc tcatggtgtg aatagagtg tggattgagg agaacgacca    10140
tatggaggac aagactcctg taacaaaatg gacagacatt ccctatctag gaaaagggga   10200
ggacttatgg tgtggatccc ttatagggca gacccccgc accacttggg ctgaaaacat    10260
caaagacaca gtcaacatgg tgcgcaggat cataggtgat gaagaaaagt acatggacta   10320
tctatccacc caagtccgct acttgggtga ggaagggtcc acaccggag tgttgtaagc     10380
accaatttta gtgttgtcag gcctgctagt cagccacagt ttggggaaag ctgtgcagcc   10440
tgtaaccccc ccaggagaag ctgggaaacc aagctcatag tcaggccgag aacgccatgg   10500
cacggaagaa gccatgctgc ctgtgagccc ctcagaggac actgagtcaa aaacccac     10560
gcgcttggaa gcgcaggatg gaaaagaag gtggcgacct tccccacct tcaatctggg     10620
gcctgaactg gagactagct gtgaatctcc agcagaggga ctagtggtta gaggagaccc   10680
cccggaaaac gcacaacagc atattgacgc tgggaaagac cagagactcc atgagtttcc   10740
accacgctgg ccgccaggca cagatcgccg aacttcggcg gccggtgtgg ggaaatccat   10800
ggtttct                                                             10807

<210> SEQ ID NO 9
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 9
agttgttgat ctgtgtgagt cagactgcga cagttcgagt ctgaagcgag agctaacaac      60
agtatcaaca ggtttaattt ggatttggaa acgagagttt ctggtcatga aaacccaaa     120
gaagaaatcc ggaggattcc ggattgtcaa tatgctaaaa cgcggagtag cccgtgtaaa    180
ccccttggga ggtttgaaga ggttgccagc cggacttctg ctgggtcatg acccatcag    240
aatggttttg gcgatactag cctttttgag atttacagca atcaagccat cactgggcct    300
tatcaacaga tggggttccg tggggaaaaa agaggctatg gaaataataa gaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720
caaaaaaggt gaggcacggc gatctaggag agccgtgacg ctcccttctc actctacaag    780
gaagttgcaa acgcggtcgc agacctggtt agaatcaaga aatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
```

-continued

```
acaggacaag ccaacagttg acatagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggacttttt ggcaaaggga gcttggtgac   1320
atgtgccaag tttacgtgtt ctaagaagat gaccggcaag agcattcaac cggaaaatct   1380
ggagtatcgg ataatgctat cagtgcatgg ctcccagcat agcgggatga ttgtcaatga   1440
tacaggatat gaaactgacg aaaatagagc gaaagtcgag gttacgccta attccccaag  1500
agcggaagca accttgggag ctttggaag cttaggactt gactgtgaac caaggacagg   1560
ccttgacttt tcagatctgt attacctgac catgaacaat aagcattggt tggtgcacaa   1620
agagtggttt catgacatcc cattgccttg gcatgctggg gcagacaccg gaactccaca   1680
ctggaacaac aaagaggcat tggtagaatt caaggatgcc cacgccaaga ggcaaaccgt   1740
cgtcgttctg gggagccagg aaggagccgt tcacacggct ctcgctggag ctctagaggc   1800
tgagatggat ggtgcaaagg ggagactgtt tagcggacac cttaagtgta gactgaaaat   1860
ggacaagttg cgacttaagg gcgttagcta tagcctatgt accgccgcat ttacgtttac   1920
gaaagtgcca gccgaaacgt tgcacggaac cgttaccgtc gaggtgcaat acgccggaac   1980
cgacggacca tgcaagatac ccgtgcaaat ggccgtcgat atgcagacac tgacaccagt   2040
cggacggttg attaccgcta acccagtgat aaccgagtca accgaaaact ctaagatgat   2100
gctcgagctt gacccaccat tcggcgactc atatatcgtt atcggagtcg gcgacaaaaa   2160
gattacgcat cattggcata gatccggatc gacaatcggt aaggcattcg aagcgacagt   2220
gagaggcgct aagcgtatgg ccgtattggg cgataccgca tgggacttcg gatccgtcgg   2280
cggagtgttt aactcactcg gtaaggggat acaccagata ttcggagccg cattcaaatc   2340
gttgttcggc ggaatgtcat ggtttagtca gatactgatc ggaacactgc ttgtgtggtt   2400
ggggttgaac actaagaacg gatcgattag tctgacatgc ttagccttag gcggagtgat   2460
gatttttctg tcaaccgccg ttagcgcaga cgtggggtgc tcagtggact tctcaaaaaa   2520
ggaaacgaga tgtggcacgg gggtattcat ctataatgat gttgaagcct ggagggaccg   2580
gtacaagtac catcctgact cccccgcag attggcagca gcagtcaagc aggcctggga   2640
agaggggatc tgtgggatct catccgtttc aagaatggaa acatcatgt ggaaatcagt   2700
agaaggggag ctcaatgcta tcctagagga gaatggagtt caactgacag ttgttgtggg   2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa acatgtgaa tggccaaagt ctcacacatt   3180
gtggacagat ggagtagaag aaagtgatct tatcataccc aagtctttag ctggtccact   3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgccccact atcgtttcga gcaaaagacg gctgctggta   3480
```

```
tggaatggag ataaggccca ggaaagaacc agagagcaac ttagtgaggt caatggtgac    3540 agcgggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctgccggag gtttgccaa ggcagacatt gagatggctg acccatggc    4320 tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560 tataccttt gctgcaggag cgtggtatgt gtatgtgaag actgggaaaa ggagtggcgc    4620
cctctgggac gtgcctgctc ccaaagaagt gaagaaagga gaaaccacag atggagtgta    4680
cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acgggacat    4980 cggagcagtt gctctggact accctgcagg gacctcagga tctccgatcc tagacaaatg    5040
tggaagagtg ataggactct atggcaatgg ggttgtgatc aagaatgaa gctatgttag    5100 tgctataacc caggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct actacaaacc catcagagtc cctaattaca atctcaacat    5460
catggatgaa gcccacttca cagacccctc aagtatagct gcaagaggat acatatcaac    5520
aagggttgaa atgggcgagg cggctgccat ttttatgact gccacaccac caggaaccc    5580 tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg aaagcgggt    5760 catacagctc agcaggaaga cttttgagac agaatttcag aaaacaaaaa atcaagagtg    5820
```

-continued

```
ggactttgtc ataacaactg acatctcaga gatgggcgcc aacttcaagg ctgaccgggt   5880
catagactct aggagatgcc taaaaccagt catacttgat ggtgagagag tcatcttggc   5940
tgggcccatg cctgtcacgc atgctagtgc tgctcagagg agaggacgta taggcaggaa   6000
ccctaacaaa cctggagatg agtacatgta tggaggtggg tgtgcagaga ctgatgaagg   6060
ccatgcacac tggcttgaag caagaatgct tcttgacaac atctacctcc aggatggcct   6120
catagcctcg ctctatcggc ctgaggccga taaggtagcc gccattgagg gagagtttaa   6180
gctgaggaca gagcaaagga agaccttcgt ggaactcatg aagagagggg accttcccgt   6240
ctggctagcc tatcaggttg catctgccgg aataacttac acagacagaa gatggtgctt   6300
tgatggcaca accaacaaca ccataatgga agacagcgta ccagcagagg tgtggacaaa   6360
gtatggagag aagagagtgc tcaaaccgag atggatggat gctagggtct gttcagacca   6420
tgcggccctg aagtcgttca agaattcgc cgctggaaaa agaggagcgg ctttgggagt   6480
aatggaggcc ctgggaacac tgccaggaca catgacagag aggtttcagg aagccattga   6540
caacctcgcc gtgctcatgc gagcagagac tggaagcagg ccttataagg cagcggcagc   6600
ccaactgccg gagactctag agacaattat gctcttaggt ttgctgggaa cagtttcact   6660
ggggatcttc ttcgtcttga tgcggaataa gggcatcggg aagatgggct ttggaatggt   6720
aaccccttggg gccagtgcat ggctcatgtg gctttcggaa attgaaccag ccagaattgc   6780
atgtgtcctc attgttgtgt ttttattact ggtggtgctc atacccgagc cagagaagca   6840
aagatctccc caagataacc agatggcaat tatcatcatg gtggcagtgg gccttctagg   6900
tttgataact gcaaacgaac ttggatggct ggaaagaaca aaaaatgaca tagctcatct   6960
aatgggaagg agagaagaag gagcaaccat gggattctca atggacattg atctgcggcc   7020
agcctccgcc tgggctatct atgccgcatt gacaactctc atcaccccag ctgtccaaca   7080
tgcggtaacc acttcataca acaactactc cttaatggcg atgccacac aagctggagt   7140
gctgtttggc atgggcaaag gatgccatt ttatgcatgg gaccttggag tcccgctgct   7200
aatgatgggt tgctattcac aattaacacc cctgactctg atagtagcta tcattctgct   7260
tgtggcgcac tacatgtact tgatcccagg cctacaagcg gcagcagcgc gtgctgccca   7320
gaaaaggaca gcagctggca tcatgaagaa tcccgttgtg gatggaatag tggtaactga   7380
cattgacaca atgacaatag accccaggt ggagaagaag atgggacaag tgttactcat   7440
agcagtagcc atctccagtg ctgtgctgct gcggaccgcc tggggatggg gggaggctgg   7500
agctctgatc acagcagcga cctccacctt gtgggaaggc tctccaaaca atactggaa   7560
ctcctctaca gccacctcac tgtgcaacat cttcagagga agctatctgg caggagcttc   7620
ccttatctat acagtgacga gaacgctgg cctggttaag agacgtggag gtgggacggg   7680
agagactctg ggagagaagt ggaaagctcg tctgaatcag atgtcggccc tggagttcta   7740
ctcttataaa aagtcaggta tcactgaagt gtgtagagag gaggctcgcc gtgccctcaa   7800
ggatggagtg gccacaggag acatgccgt atcccgggga agtgcaaagc tcagatggtt   7860
ggtggagaga ggatatctgc agccctatgg gaaggttgtt gacctcggat gtggcagagg   7920
gggctggagc tattatgccg ccaccatccg caaagtgcag gaggtgagag gatacacaaa   7980
gggaggtccc ggtcatgaag aacccatgct ggtgcaaagc tatgggtgga catagttcg   8040
tctcaagagt ggagtggacg tcttccacat ggcggctgag ccgtgtgaca ctctgctgtg   8100
tgacataggt gagtcatcat ctagtcctga agtggaagag acacgaacac tcagagtgct   8160
ctctatggtg ggggactggc ttgaaaaaag accaggggcc ttctgtataa aggtgctgtg   8220
```

```
cccatacacc agcactatga tggaaaccat ggagcgactg caacgtaggc atggggagg    8280
attagtcaga gtgccattgt ctcgcaactc cacacatgag atgtactggg tgtctgggc    8340
aaagagcaac atcataaaaa gtgtgtccac cacaagtcag ctcctcctgg gacgcatgga   8400
tggcccagg aggccagtga aatatgagga ggatgtgaac ctcggctcgg gtacacgagc    8460
tgtggcaagc tgtgctgagg ctcctaacat gaaaatcatc ggcaggcgca ttgagagaat   8520
ccgcaatgaa catgcagaaa catggtttct tgatgaaaac cacccataca ggacatgggc   8580
ctaccatggg agctacgaag cccccacgca aggatcagcg tcttccctcg tgaacggggt   8640
tgttagactc ctgtcaaagc cttggacgt ggtgactgga gttacaggaa tagccatgac    8700
tgacaccaca ccatacggcc aacaaagagt cttcaaagaa aaagtggaca ccagggtgcc   8760
agatccccaa gaaggcactc gccaggtaat gaacatagtc tcttcctggc tgtggaagga   8820
gctgggaaaa cgcaagcggc cacgcgtctg caccaaagaa gagtttatca acaaggtgcg   8880
cagcaatgca gcactgggag caatatttga agaggaaaaa gaatggaaga cggctgtgga   8940
agctgtgaat gatccaaggt ttgggccct agtggatagg gagagagaac accacctgag    9000
aggagagtgt cacagctgtg tgtacaacat gatgggaaaa agagaaaaga agcaaggaga   9060
gttcgggaaa gcaaaaggta gccgcgccat ctggtacatg tggttgggag ccagattctt   9120
ggagtttgaa gcccttggat tcttgaacga ggaccattgg atgggaagag aaaactcagg   9180
aggtggagtc gaagggttag gattgcaaag acttggatac attctagaag aaatgaatcg   9240
ggcaccagga ggaaagatgt acgcagatga cactgctggc tgggacaccc gcattagtaa   9300
gtttgatctg gagaatgaag ctctgattac caaccaaatg gaggaagggc acagaactct   9360
ggcgttggcc gtgattaaat acacatacca aaacaaagtg gtgaaggttc tcagaccagc   9420
tgaaggagga aaaacagtta tggacatcat ttcaagacaa gaccagagag ggagtggaca   9480
agttgtcact tatgctctca acacattcac caacttggtg gtgcagctta tccggaacat   9540
ggaagctgag gaagtgttag agatgcaaga cttatggttg ttgaggaagc cagagaaagt   9600
gaccagatgg ttgcagagca atggatggga tagactcaaa cgaatggcgg tcagtggaga   9660
tgactgcgtt gtgaagccaa tcgatgatag gtttgcacat gccctcaggt tcttgaatga   9720
catgggaaaa gttaggaaag acacacagga gtggaaaccc tcgactggat ggagcaattg   9780
ggaagaagtc ccgttctgct cccaccactt caacaagctg tacctcaagg atgggagatc   9840
cattgtggtc ccttgccgcc accaagatga actgattggc cgagctcgcg tctccaccagg   9900
ggcaggatgg agcatccggg agactgcctg tcttgcaaaa tcatatgcgc agatgtggca   9960
gctcctttat ttccacagaa gggaccttcg actgatggct aatgccattt gctcggctgt  10020
gccagttgac tgggttccaa ctgggagaac cacctggtca atccatggaa agggagaatg  10080
gatgaccact gaggacatgc tcatggtgtg aatagagtg tggattgagg agaacgacca   10140
tatggaggac aagactcctg taacaaaatg gacagacatt ccctatctag aaaaaggga   10200
ggacttatgg tgtggatccc ttatagggca cagacccgc accacttggg ctgaaaacat    10260
caaagacaca gtcaacatgg tgcgcaggat cataggtgat gaagaaaagt acatggacta  10320
tctatccacc caagtccgct acttgggtga ggaagggtcc acacccggag tgttgtaagc  10380
accaatttta gtgttgtcag gcctgctagt cagccacagt ttggggaaag ctgtgcagcc  10440
tgtaaccccc ccaggagaag ctgggaaacc aagctcatag tcaggccgag aacgccatgc  10500
cacggaagaa gccatgctgc ctgtgagccc ctcagaggac actgagtcaa aaaccccac   10560
```

| | |
|---|---|
| gcgcttggaa gcgcaggatg ggaaaagaag gtggcgacct tccccacccct tcaatctggg | 10620 |
| gcctgaactg gagactagct gtgaatctcc agcagaggga ctagtggtta gaggagaccc | 10680 |
| cccggaaaac gcacaacagc atattgacgc tgggaaagac cagagactcc atgagtttcc | 10740 |
| accacgctgg ccgccaggca cagatcgccg aacttcggcg gccggtgtgg ggaaatccat | 10800 |
| ggtttct | 10807 |

<210> SEQ ID NO 10
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| agttgttgat ctgtgtgagt cagactgcga cagttcgagt ctgaagcgag agctaacaac | 60 |
| agtatcaaca ggtttaattt ggatttggaa acgagagttt ctggtcatga aaaacccaaa | 120 |
| gaagaaatcc ggaggattcc ggattgtcaa tatgctaaaa cgcggagtag cccgtgtaaa | 180 |
| cccccttggga ggtttgaaga ggttgccagc cggacttctg ctgggtcatg gacccatcag | 240 |
| aatggttttg gcgatactag cctttttgag atttacagca atcaagccat cactgggcct | 300 |
| tatcaacaga tggggttccg tggggaaaaa agaggctatg gaaataataa gaagttcaa | 360 |
| gaaagatctt gctgccatgt tgagaataat caatgctagg aaagagagga agagacgtgg | 420 |
| cgcagacacc agcatcggaa tcattggcct cctgctgact acagccatgg cagcagagat | 480 |
| cactagacgc gggagtgcat actacatgta cttggatagg agcgatgccg ggaaggccat | 540 |
| ttcgtttgct accacattgg gagtgaacaa gtgccacgta cagatcatgg acctcgggca | 600 |
| catgtgtgac gccaccatga gttatgagtg ccctatgctg gatgagggag tggaaccaga | 660 |
| tgatgtcgat tgctggtgca acacgacatc aacttgggtt gtgtacggaa cctgtcatca | 720 |
| caaaaaggt gaggcacggc gatctaggag agccgtgacg ctcccttctc actctacaag | 780 |
| gaagttgcaa acgcggtcgc agacctggtt agaatcaaga gaatacacga agcacttgat | 840 |
| caaggttgaa aactggatat tcaggaaccc cgggtttgcg ctagtggccg ttgccattgc | 900 |
| ctggcttttg ggaagctcga cgagccaaaa agtcatatac ttggtcatga tactgctgat | 960 |
| tgccccggca tacagtatca ggtgcattgg agtcagcaat agagacttcg tggagggcat | 1020 |
| gtcaggtggg acctgggttg atgttgtctt ggaacatgga ggctgcgtta ccgtgatggc | 1080 |
| acaggacaag ccaacagttg acatagagtt ggtcacgacg acggttagta acatggccga | 1140 |
| ggtaagatcc tattgctacg aggcatcgat atcggacatg gcttcggaca gtcgttgccc | 1200 |
| aacacaaggt gaagcctacc ttgacaagca atcagacact caatatgtct gcaaaagaac | 1260 |
| attagtggac agaggttggg gaaacggttg tggactttt ggcaaaggga gcttggtgac | 1320 |
| atgtgccaag tttacgtgtt ctaagaagat gaccggcaag agcattcaac cggaaaatct | 1380 |
| ggagtatcgg ataatgctat cagtgcatgg ctcccagcat agcgggatga ttgtcaatga | 1440 |
| tacaggatat gaaactgacg aaaatagagc gaaagtcgag gttacgccta attccaccaag | 1500 |
| agcggaagca accttgggag ctttggaag cttaggactt gactgtgaac caaggacagg | 1560 |
| ccttgacttt tcagatctgt attacctgac catgaacaat aagcattggt tggtgcacaa | 1620 |
| agagtggttt catgacatcc cattgccttg gcatgctggg gcagacaccg gaactccaca | 1680 |
| ctggaacaac aaagaggcat tggtagaatt caaggatgcc cacgccaaga ggcaaacccgt | 1740 |
| cgtcgttctg gggagccagg aaggagccgt tcacacggct ctcgctggag ctctagaggc | 1800 |

```
tgagatggat ggtgcaaagg gaaggctgtt ctctggccat ttgaaatgcc gcctaaaaat    1860
ggacaagctt agattgaagg gcgtgtcata ttccttgtgc actgcggcat tcacattcac    1920
caaggtccca gctgaaacac tgcatggaac agtcacagtg gaggtgcagt atgcagggac    1980
agatggaccc tgcaagatcc cagtccagat ggcggtggac atgcagaccc tgaccccagt    2040
tggaaggctg ataaccgcca accccgtgat tactgaaagc actgagaact caaagatgat    2100
gttggagctt gacccaccat tggggattc  ttacattgtc ataggagttg gggacaagaa    2160
aatcacccac cactggcata ggagtggtag caccatcgga aaggcatttg aggccactgt    2220
gagaggcgcc aagagaatgg cagtcctggg ggatacagcc tgggacttcg gatcagtcgg    2280
gggtgtgttc aactcactgg gtaagggcat tcaccagatt tttggagcag ccttcaaatc    2340
actgtttgga ggaatgtcct ggttctcaca gatcctcata ggcacgctgc tagtgtggtt    2400
aggtttgaac acaaagaatg gatctatctc cctcacatgc ttggccctgg ggggagtgat    2460
gatcttcctc tccacggctg tttctgctga cgtgggggtgc tcagtggact tctcaaaaaa    2520
ggaaacgaga tgtggcacgg gggtattcat ctataatgat gttgaagcct ggagggaccg    2580
gtacaagtac catcctgact cccccccgcag attggcagca gcagtcaagc aggcctggga    2640
agagggatc  tgtgggatct catccgtttc aagaatggaa aacatcatgt ggaaatcagt    2700
agaaggggag ctcaatgcta tcctagagga gaatggagtt caactgacag ttgttgtggg    2760
atctgtaaaa aaccccatgt ggagaggtcc acaaagattg ccagtgcctg tgaatgagct    2820
gccccatggc tggaaagcct ggggggaaatc gtattttgtt agggcggcaa agaccaacaa    2880
cagttttgtt gtcgacggtg acacactgaa ggaatgtccg cttgagcaca gagcatggaa    2940
tagttttctt gtggaggatc acgggtttgg agtcttccac accagtgtct ggcttaaggt    3000
cagagaagat tactcattag aatgtgaccc agccgtcata ggaacagctg ttaagggaag    3060
ggaggccgcg cacagtgatc tgggctattg gattgaaagt gaaaagaatg acacatggag    3120
gctgaagagg gcccacctga ttgagatgaa acatgtgaa  tggccaaagt ctcacacatt    3180
gtggacagat ggagtagaag aaagtgatct tatcatacc  aagtctttag ctggtccact    3240
cagccaccac aacaccagag agggttacag aacccaagtg aaagggccat ggcacagtga    3300
agaacttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt tcaatgagt  gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
```

```
ggccctggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctggccggag ggtttgccaa ggcagacatt gagatggctg gacccatggc    4320
tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560
tataccttt gctgcaggag cgtggtatgt gtatgtgaag actgggaaaa ggtctggcgc    4620
actatgggac gtacccgctc ctaaagaggt caaaaaaggc gaaacaaccg acggagtgta    4680
tagggttatg actagacggt tgctcggatc gacacaggtc ggagtcggag tgatgcaaga    4740
gggagtgttt catacaatgt ggcatgtgac taagggagcc gcacttagat caggcgaagg    4800
gagactcgat ccatactggg gggacgttaa gcaggaccta gtctcatatt gcggaccttg    4860
gaaactcgac gccgcatggg acggactgtc agaggtccaa ctgttagccg taccaccagg    4920
cgaaagagcg agaaacatac agacattgcc cggaatcttt aagactaagg acggagacat    4980
aggcgcagtc gcactcgatt accctgccgg aactagcgga tcaccgatac tcgataagtg    5040
cggaagggtt atcggattgt acggaaacgg agtcgttatc aaaaacggat catacgttag    5100
cgctataaca caggggaaac gcgaagagga gacaccagtc gagtgtttcg aacctagtat    5160
gcttaaaaaa aaacagctaa ccgtactcga tctgcatccc ggagccggta agacacgtag    5220
agtgttgccc gaaatcgtta gggaggctat caaaaaacgg ttgcgtacag tgatactcgc    5280
acctactagg gtcgtcgccg ccgaaatgga ggaagcgctt aggggttgc ccgttaggta    5340
tatgacaacc gccgttaacg ttacgcatag cggaacagag atagtcgatc tgatgtgtca    5400
cgctacattt acatctagac tgttgcagcc aattagggtg cctaattaca atctgaatat    5460
aatggacgaa gcgcatttta ccgatccgtc atcaatcgcc gctaggggt acatatcgac    5520
tagagtcgag atgggcgaag ccgccgcaat ctttatgacc gctacacctc ccggaactag    5580
ggacgcattc ccagactcta actcacctat tatggatacc gaagtcgagg tccccgaacg    5640
cgcttggtct agcggattcg attgggttac cgatcatagc ggtaagaccg tttggttcgt    5700
acctagcgtt agaaacggaa acgagatagc cgcatgtctg actaaggccg gtaagagagt    5760
gatacagcta tctagaaaga cattcgaaac agagtttcag aagactaaga atcaggagtg    5820
ggacttcgtt ataacaaccg atatctctga gatgggcgct aactttaagg ccgatagggt    5880
gatcgatagt agacggtgtc ttaagccagt gatactcgac ggagagagag tgatactcgc    5940
cggacctatg ccagtgacac acgctagcgc cgcacaacgt aggggagaa tcggacggaa    6000
tcctaacaaa ccgggagacg aatatatgta cggggggggg tgcgctgaga cagacgaagg    6060
gcacgctcat tggcttgagg ctagaatgct actcgataac atatacttgc aggacggact    6120
aatcgctagt ctgtatagac cggaagccga taaggtcgcc gctatcgagg gagagtttaa    6180
gcttagaacc gagcaacgta agacattcgt cgagcttatg aaaagaggcg atctgccagt    6240
gtggctcgca taccaggtcg ctagtgccgg aataacatat accgatagga gatggtgttt    6300
cgacggaaca actaacaata caattatgga ggactcagtc ccagccgaag tgtggactaa    6360
gtacggcgaa aagagagtgc ttaagcctag atggatggac gctagggtgt gttcggatca    6420
cgccgcactt aagtcattca aagagttcgc agccggtaag agaggagcgg ctttgggagt    6480
aatggaggcc ctgggaacac tgccaggaca catgacagag aggtttcagg aagccattga    6540
```

```
caacctcgcc gtgctcatgc gagcagagac tggaagcagg ccttataagg cagcggcagc    6600
ccaactgccg gagactctag agacaattat gctcttaggt ttgctgggaa cagtttcact    6660
ggggatcttc ttcgtcttga tgcggaataa gggcatcggg aagatgggct ttggaatggt    6720
aacccttggg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccccag ctgtccaaca    7080
tgcggtaacc acttcataca caactactc cttaatggcg atggccacac aagctggagt    7140
gctgtttggc atgggcaaag ggatgccatt ttatgcatgg gaccttggag tcccgctgct    7200
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag acccccaggt ggagaagaag atgggacaag tgttactcat    7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag acatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag atacacaaaa    7980
gggaggtccc ggtcatgaag aacccatgct ggtgcaaagc tatgggtgga catagttcg    8040
tctcaagagt ggagtggacg tcttccacat ggcggctgag ccgtgtgaca ctctgctgtg    8100
tgacatggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atgggggagg    8280
attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggttcct tgatgaaaac caccccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtgaagga     8820
gctggggaaa cgcaagcggc cacgcgtctg caccaaagaa gagtttatca acaaggtgcg    8880
```

```
cagcaatgca gcactgggag caatatttga agaggaaaaa gaatggaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga agcaaggaga    9060
gttcgggaaa gcaaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta ccggaacat     9540
ggaagctgag gaagtgttag agatgcaaga cttatggttg ttgaggaagc cagagaaagt    9600
gaccagatgg ttgcagagca atggatggga tagactcaaa cgaatggcgg tcagtggaga    9660
tgactgcgtt gtgaagccaa tcgatgatag gtttgcacat gccctcaggt tcttgaatga    9720
catgggaaaa gttaggaaag acacacagga gtggaaaccc tcgactggat ggagcaattg    9780
ggaagaagtc ccgttctgct cccaccactt caacaagctg tacctcaagg atggggagatc   9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960
gctcctttat ttccacagaa gggaccttcg actgatggct aatgccattt gctcggctgt   10020
gccagttgac tgggttccaa ctgggagaac cacctggtca atccatggaa agggagaatg   10080
gatgaccact gaggacatgc tcatggtgtg gaatagagtg tggattgagg agaacgacca   10140
tatggaggac aagactcctg taacaaaatg gacagacatt ccctatctag aaaaaggga    10200
ggacttatgg tgtggatccc ttatagggca cagacccgc accacttggg ctgaaaacat   10260
caaagacaca gtcaacatgg tgcgcaggat cataggtgat gaagaaaagt acatggacta   10320
tctatccacc caagtccgct acttgggtga ggaagggtcc acacccggag tgttgtaagc   10380
accaatttta gtgttgtcag gcctgctagt cagccacagt ttggggaaag ctgtgcagcc   10440
tgtaaccccc ccaggagaag ctgggaaacc aagctcatag tcaggccgag aacgccatgg   10500
cacggaagaa gccatgctgc ctgtgagccc ctcagaggac actgagtcaa aaacccccac   10560
gcgcttggaa gcgcaggatg ggaaaagaag gtggcgacct tccccacccct tcaatctggg   10620
gcctgaactg gagactagct gtgaatctcc agcagaggga ctagtggtta gaggagaccc   10680
cccgaaaac gcacaacagc atattgacgc tgggaaagac cagagactcc atgagtttcc   10740
accacgctgg ccgccaggca cagatcgccg aacttcggcg ccggtgtgg ggaaatccat   10800
ggtttct                                                            10807

<210> SEQ ID NO 11
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 11
agttgttgat ctgtgtgagt cagactgcga cagttcgagt ctgaagcgag agctaacaac      60
agtatcaaca ggtttaattt ggatttggaa acgagagttt ctggtcatga aaacccaaa     120
```

```
gaagaaatcc ggaggattcc ggattgtcaa tatgctaaaa cgcggagtag cccgtgtaaa    180 cccttggga ggtttgaaga ggttgccagc cggacttctg ctgggtcatg gacccatcag    240
aatggttttg gcgatactag ccttttgag atttacagca atcaagccat cactgggcct    300
tatcaacaga tggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720 caaaaaggt gaggcacggc gatctaggag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagttg catagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggactttt ggcaaaggga gcttggtgac   1320
atgtgccaag tttacgtgtt ctaagaagat gaccggcaag agcattcaac cggaaaatct   1380
ggagtatcgg ataatgctat cagtgcatgg ctcccagcat agcgggatga ttgtcaatga   1440
tacaggatat gaaactgacg aaaatagagc gaaagtcgag gttacgccta actcacctag   1500
agccgaagcg acattggggg ggttcggatc tctcggactg gattgcgaac ctagaaccgg   1560
attggacttt agcgatctgt actatctgac tatgaacaat aagcattggt tggtgcataa   1620
ggagtggttt cacgacatac cactgccatg gcacgccgga gccgataccg gtacgccaca   1680
ttggaataac aaagaggcac tagtcgagtt taaggacgct cacgctaaga cagaccgt    1740 agtcgtgttg ggtcacagg agggagccgt gcataccgca ctagccggcg cactcgaggc   1800
cgaaatggac ggagcgaaag ggagactgtt tagcggacac cttaagtgta gactgaaaat   1860
ggacaagttg cgacttaagg gcgttagcta tagcctatgt accgccgcat ttacgtttac   1920
gaaagtgcca gccgaaacgt tgcacggaac cgttaccgtc gaggtgcaat acgccggaac   1980
cgacggacca tgcaagatac ccgtgcaaat ggccgtcgat atgcagacac tgacaccagt   2040
cggacggttg attaccgcta acccagtgat aaccgagtca accgaaaact ctaagatgat   2100
gctcgagctt gacccaccat tcggcgactc atatatcgtt atcggagtcg gcgacaaaaa   2160
gattacgcat cattggcata gatccggatc gacaatcggt aaggcattcg aagcgacagt   2220
gagaggcgct aagcgtatgg ccgtattggg cgataccgca tggacttcg gatccgtcgg   2280 cggagtgttt aactcactcg gtaaggggat acaccagata ttcggagccg cattcaaatc   2340
gttgttcggc ggaatgtcat ggtttagtca gatactgatc ggaacactgc ttgtgtggtt   2400
ggggttgaac actaagaacg gatcgattag tctgacatgc ttagccttag gcggagtgat   2460
```

```
gatttttctg tcaaccgccg ttagcgcaga cgtggggtgc tcagtggact tctcaaaaaa    2520
ggaaacgaga tgtggcacgg gggtattcat ctataatgat gttgaagcct ggagggaccg    2580
gtacaagtac catcctgact cccccgcag attggcagca gcagtcaagc aggcctggga    2640
agagggatc tgtgggatct catccgtttc aagaatggaa acatcatgt ggaaatcagt     2700
agaaggggag ctcaatgcta tcctagagga gaatggagtt caactgacag ttgttgtggg   2760
atctgtaaaa aaccccatgt ggagaggtcc acaaagattg ccagtgcctg tgaatgagct   2820
gccccatggc tggaaagcct gggggaaatc gtattttgtt agggcggcaa agaccaacaa   2880
cagttttgtt gtcgacggtg acacactgaa ggaatgtccg cttgagcaca gagcatggaa   2940
tagttttctt gtggaggatc acgggtttgg agtcttccac accagtgtct ggcttaaggt   3000
cagagaagat tactcattag aatgtgaccc agccgtcata ggaacagctg ttaagggaag   3060
ggaggccgcg cacagtgatc tgggctattg gattgaaagt gaaaagaatg acacatggag   3120
gctgaagagg gcccacctga ttgagatgaa acatgtgaa tggccaaagt ctcacacatt    3180
gtggacagat ggagtagaag aaagtgatct tatcatacc aagtctttag ctggtccact    3240
cagccaccac aacaccagag agggttacag aacccaagtg aaagggccat ggcacagtga   3300
agaacttgaa atccggtttg aggaatgtcc aggcaccaag gtttacgtgg aggagacatg   3360
cggaactaga ggaccatctc tgagatcaac tactgcaagt ggaagggtca ttgaggaatg   3420
gtgctgtagg gaatgcacaa tgcccccact atcgtttcga gcaaaagacg gctgctggta   3480
tggaatggag ataaggccca ggaaagaacc agagagcaac ttagtgaggt caatggtgac   3540
agcggggtca accgatcata tggaccactt ctctcttgga gtgcttgtga ttctactcat   3600
ggtgcaggag gggttgaaga agagaatgac cacaaagatc atcatgagca catcaatggc   3660
agtgctggta gtcatgatct tgggaggatt ttcaatgagt gacctggcca agcttgtgat   3720
cctgatgggt gctactttcg cagaaatgaa cactggagga gatgtagctc acttggcatt   3780
ggtagcggca tttaaagtca gaccagcctt gctggtgtcc ttcatttca gagccaattg    3840
gacaccccgt gagagcatgc tgctagccct ggcttcgtgt cttctgcaaa ctgcgatctc   3900
tgctcttgaa ggtgacttga tggtcctcat taatggattt gctttggcct ggttggcaat   3960
tcgagcaatg gccgtgccac gcactgacaa catcgctcta ccaatcttgg ctgctctaac   4020
accactagct cgaggcacac tgctcgtggc atggagagcg ggcctggcta cttgtggagg   4080
gatcatgctc ctctccctga agggaaagg tagtgtgaag aagaacctgc catttgtcat    4140
ggcccctgga ttgacagctg tgagggtagt agaccctatt aatgtggtag actactgtt    4200
actcacaagg agtgggaagc ggagctggcc ccctagtgaa gttctcacag ccgttggcct   4260
gatatgtgca ctggccggag gtttgccaa ggcagacatt gagatggctg acccatggc    4320
tgcagtaggc ttgctaattg tcagctatgt ggtgtcggga aagagtgtgg acatgtacat   4380
tgaaagagca ggagacatca catgggaaaa ggacgcggaa gtcactggaa acagtcctcg   4440
gcttgacgtg gcactggatg agagtggtga tttctccttg gtagaggaag atggtccacc   4500
catgagagag atcatactca aggtggtcct gatggccatc tgtggcatga acccaatagc   4560
tataccttt gctgcaggag cgtggtatgt gtatgtgaag actgggaaaa ggagtggcgc   4620
cctctgggac gtgcctgctc ccaaagaagt gaagaaagga gaaccacag atggagtgta    4680
cagagtgatg actcgcagac tgctaggttc aacacaggt ggagtgggag tcatgcaaga   4740
gggagtcttc cacaccatgt ggcacgttac aaaaggagcc gcactgagga cggtgagggg   4800
aagacttgat ccatactggg gggatgtcaa gcaggacttg gtgtcatact gtgggccttg   4860
```

-continued

```
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatgaa gctatgttag     5100 tgctataacc cagggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggccttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctcaacat    5460
catggatgaa gcccacttca cagacccctc aagtatagct gcaagaggat acatatcaac    5520
aagggttgaa atgggcgagg cggctgccat ttttatgact gccacaccac caggaacccg    5580
tgatgcgttt cctgactcta actcaccaat catggacaca gaagtggaag tcccagagag    5640
agcctggagc tcaggctttg attgggtgac agaccattct gggaaaacag tttggttcgt    5700
tccaagcgtg agaaacggaa atgaaatcgc agcctgtctg acaaaggctg gaaagcgggt    5760
catacagctc agcaggaaga cttttgagac agaatttcag aaaacaaaaa atcaagagtg    5820
ggactttgtc ataacaactg acatctcaga gatgggcgcc aacttcaagg ctgaccgggt    5880
catagactct aggagatgcc taaaaccagt catacttgat ggtgagagag tcatcttggc    5940
tgggcccatg cctgtcacgc atgctagtgc tgctcagagg agaggacgta taggcaggaa    6000
ccctaacaaa cctggagatg agtacatgta tggaggtggg tgtgcagaga ctgatgaagg    6060
ccatgcacac tggcttgaag caagaatgct tcttgacaac atctacctcc aggatggcct    6120
catagcctcg ctctatcggc ctgaggccga taaggtagcc gccattgagg gagagtttaa    6180
gctgaggaca gagcaaagga agaccttcgt ggaactcatg aagagagggg accttcccgt    6240
ctggctagcc tatcaggttg catctgccgg aataacttac acagacagaa gatggtgctt    6300
tgatggcaca accaacaaca ccataatgga agacagcgta ccagcagagg tgtggacaaa    6360
gtatggagag aagagagtgc tcaaaccgag atggatggat gctagggtct gttcagacca    6420
tgcggccctg aagtcgttca aagaattcgc cgctggaaaa agaggagcgg ctttgggagt    6480
aatggaggcc ctgggaacac tgccaggaca catgacagag aggtttcagg aagccattga    6540
caacctcgcc gtgctcatgc gagcagagac tggaagcagg ccttataagg cagcggcagc    6600
ccaactgccg gagactctag agacaattat gctcttaggt ttgctgggaa cagtttcact    6660
ggggatcttc ttcgtcttga tgcggaataa gggcatcggg aagatgggct ttggaatggt    6720
aaccctgggg gccagtgcat ggctcatgtg gctttcggaa attgaaccag ccagaattgc    6780
atgtgtcctc attgttgtgt ttttattact ggtggtgctc atacccgagc cagagaagca    6840
aagatctccc caagataacc agatggcaat tatcatcatg gtggcagtgg gccttctagg    6900
tttgataact gcaaacgaac ttggatggct ggaaagaaca aaaaatgaca tagctcatct    6960
aatgggaagg agagaagaag gagcaaccat gggattctca atggacattg atctgcggcc    7020
agcctccgcc tgggctatct atgccgcatt gacaactctc atcacccag ctgtccaaca     7080 tgcggtaacc acttcataca acaactactc cttaatggcg atggccacac aagctggagt    7140
gctgtttggc atgggcaaag ggatgccatt ttatgcatgg gaccttggag tcccgctgct    7200
```

```
aatgatgggt tgctattcac aattaacacc cctgactctg atagtagcta tcattctgct    7260
tgtggcgcac tacatgtact tgatcccagg cctacaagcg gcagcagcgc gtgctgccca    7320
gaaaaggaca gcagctggca tcatgaagaa tcccgttgtg gatggaatag tggtaactga    7380
cattgacaca atgacaatag accccccaggt ggagaagaag atgggacaag tgttactcat    7440
agcagtagcc atctccagtg ctgtgctgct gcggaccgcc tggggatggg gggaggctgg    7500
agctctgatc acagcagcga cctccacctt gtgggaaggc tctccaaaca aatactggaa    7560
ctcctctaca gccacctcac tgtgcaacat cttcagagga agctatctgg caggagcttc    7620
ccttatctat acagtgacga gaaacgctgg cctggttaag agacgtggag gtgggacggg    7680
agagactctg ggagagaagt ggaaagctcg tctgaatcag atgtcggccc tggagttcta    7740
ctcttataaa aagtcaggta tcactgaagt gtgtagagag gaggctcgcc gtgccctcaa    7800
ggatggagtg gccacaggag gacatgccgt atcccgggga agtgcaaagc tcagatggtt    7860
ggtggagaga ggatatctgc agccctatgg gaaggttgtt gacctcggat gtggcagagg    7920
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagag acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg    8280 attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggtttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatgaaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga agcaaggaga    9060
gttcgggaaa gcaaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta tccggaacat    9540
ggaagctgag gaagtgttag agatgcaaga cttatggttg ttgaggaagc cagagaaagt    9600
```

| | | | | | |
|---|---|---|---|---|---|
| gaccagatgg | ttgcagagca | atggatggga | tagactcaaa | cgaatggcgg | tcagtggaga | 9660 |
| tgactgcgtt | gtgaagccaa | tcgatgatag | gtttgcacat | gccctcaggt | tcttgaatga | 9720 |
| catgggaaaa | gttaggaaag | acacacagga | gtggaaaccc | tcgactggat | ggagcaattg | 9780 |
| ggaagaagtc | ccgttctgct | cccaccactt | caacaagctg | tacctcaagg | atgggagatc | 9840 |
| cattgtggtc | ccttgccgcc | accaagatga | actgattggc | cgagctcgcg | tctcaccagg | 9900 |
| ggcaggatgg | agcatccggg | agactgcctg | tcttgcaaaa | tcatatgcgc | agatgtggca | 9960 |
| gctcctttat | ttccacagaa | gggaccttcg | actgatggct | aatgccattt | gctcggctgt | 10020 |
| gccagttgac | tgggttccaa | ctgggagaac | cacctggtca | atccatggaa | agggagaatg | 10080 |
| gatgaccact | gaggacatgc | tcatggtgtg | aatagagtg | tggattgagg | agaacgacca | 10140 |
| tatggaggac | aagactcctg | taacaaaatg | gacagacatt | ccctatctag | gaaaaaggga | 10200 |
| ggacttatgg | tgtggatccc | ttatagggca | cagaccccgc | accacttggg | ctgaaaacat | 10260 |
| caaagacaca | gtcaacatgg | tgcgcaggat | cataggtgat | gaagaaaagt | acatggacta | 10320 |
| tctatccacc | caagtccgct | acttgggtga | ggaagggtcc | acacccggag | tgttgtaagc | 10380 |
| accaattta | gtgttgtcag | gcctgctagt | cagccacagt | ttggggaaag | ctgtgcagcc | 10440 |
| tgtaaccccc | ccaggagaag | ctgggaaacc | aagctcatag | tcaggccgag | aacgccatgg | 10500 |
| cacggaagaa | gccatgctgc | ctgtgagccc | ctcagaggac | actgagtcaa | aaacccccac | 10560 |
| gcgcttggaa | gcgcaggatg | ggaaaagaag | gtggcgacct | tccccaccct | tcaatctggg | 10620 |
| gcctgaactg | gagactagct | gtgaatctcc | agcagaggga | ctagtggtta | gaggagaccc | 10680 |
| cccggaaaac | gcacaacagc | atattgacgc | tgggaaagac | cagagactcc | atgagtttcc | 10740 |
| accacgctgg | ccgccaggca | cagatcgccg | aacttcggcg | gccggtgtgg | ggaaatccat | 10800 |
| ggtttct | | | | | 10807 |

<210> SEQ ID NO 12
<211> LENGTH: 10807
<212> TYPE: DNA
<213> ORGANISM: Artificial Sequence
<220> FEATURE:
<223> OTHER INFORMATION: Synthetic Construct

<400> SEQUENCE: 12

| | | | | | |
|---|---|---|---|---|---|
| agttgttgat | ctgtgtgagt | cagactgcga | cagttcgagt | ctgaagcgag | agctaacaac | 60 |
| agtatcaaca | ggtttaattt | ggatttggaa | acgagagttt | ctggtcatga | aaaacccaaa | 120 |
| gaagaaatcc | ggaggattcc | ggattgtcaa | tatgctaaaa | cgcggagtag | cccgtgtaaa | 180 |
| ccccttggga | ggtttgaaga | ggttgccagc | cggacttctg | ctgggtcatg | gacccatcag | 240 |
| aatggttttg | gcgatactag | cctttttgag | atttacagca | atcaagccat | cactgggcct | 300 |
| tatcaacaga | tggggttccg | tggggaaaaa | agaggctatg | gaaataataa | agaagttcaa | 360 |
| gaaagatctt | gctgccatgt | tgagaataat | caatgctagg | aaagagagga | agagacgtgg | 420 |
| cgcagacacc | agcatcggaa | tcattggcct | cctgctgact | acagccatgg | cagcagagat | 480 |
| cactagacgc | gggagtgcat | actacatgta | cttggatagg | agcgatgccg | ggaaggccat | 540 |
| ttcgtttgct | accacattgg | gagtgaacaa | gtgccacgta | cagatcatgg | acctcgggca | 600 |
| catgtgtgac | gccaccatga | gttatgagtg | ccctatgctg | gatgagggag | tggaaccaga | 660 |
| tgatgtcgat | tgctggtgca | acacgacatc | aacttgggtt | gtgtacggaa | cctgtcatca | 720 |
| caaaaaggt | gaggcacggc | gatctaggag | agccgtgacg | ctcccttctc | actctacaag | 780 |

```
gaagttgcaa acgcggtcgc agacctggtt agaatcaaga gaatacacga agcacttgat      840
caaggttgaa aactggatat tcaggaaccc cgggtttgcg ctagtggccg ttgccattgc      900
ctggcttttg ggaagctcga cgagccaaaa agtcatatac ttggtcatga tactgctgat      960
tgccccggca tacagtatca ggtgcattgg agtcagcaat agagacttcg tggagggcat     1020
gtcaggtggg acctgggttg atgttgtctt ggaacatgga ggctgcgtta ccgtgatggc     1080
acaggacaag ccaacagttg acatagagtt ggtcacgacg acggttagta acatggccga     1140
ggtaagatcc tattgctacg aggcatcgat atcggacatg gcttcggaca gtcgttgccc     1200
aacacaaggt gaagcctacc ttgacaagca atcagacact caatatgtct gcaaaagaac     1260
attagtggac agaggttggg gaaacggttg tggactttt ggcaagggga gcttggtgac      1320
atgtgccaag tttacgtgtt ctaagaagat gaccggcaag agcattcaac cggaaaatct     1380
ggagtatcgg ataatgctat cagtgcatgg ctcccagcat agcgggatga ttgtcaatga     1440
tacaggatat gaaactgacg aaaatagagc gaaagtcgag gttacgccta attcaccaag     1500
agcggaagca accttgggag ctttggaag cttaggactt gactgtgaac caaggacagg      1560
ccttgacttt tcagatctgt attacctgac catgaacaat aagcattggt tggtgcacaa     1620
agagtggttt catgacatcc cattgccttg gcatgctggg gcagacaccg gaactccaca     1680
ctggaacaac aaagaggcat tggtagaatt caaggatgcc cacgccaaga ggcaaaccgt     1740
cgtcgttctg gggagccagg aaggagccgt tcacacggct ctcgctggag ctctagaggc     1800
tgagatggat ggtgcaaagg gaaggctgtt ctctggccat ttgaaatgcc gcctaaaaat     1860
ggacaagctt agattgaagg gcgtgtcata ttccttgtgc actgcggcat tcacattcac     1920
caaggtccca gctgaaacac tgcatggaac agtcacagtg gaggtgcagt atgcagggac     1980
agatggaccc tgcaagatcc cagtccgat ggcggtggac atgcagaccc tgaccccagt      2040
tggaaggctg ataaccgcca ccccgtgat tactgaaagc actgagaact caaagatgat      2100
gttggagctt gacccaccat tggggattc ttacattgtc ataggagttg gggacaagaa      2160
aatcacccac cactggcata ggagtggtag caccatcgga aaggcatttg aggccactgt     2220
gagaggcgcc aagagaatgg cagtcctggg ggatacagcc tgggacttcg gatcagtcgg     2280
gggtgtgttc aactcactgg gtaagggcat tcaccagatt tttggagcag ccttcaaatc     2340
actgtttgga ggaatgtcct ggttctcaca gatcctcata gcacgctgc tagtgtggtt      2400 aggtttgaac acaaagaatg gatctatctc cctcacatgc ttggccctgg ggagtgat      2460 gatcttcctc tccacggctg tttctgctga cgtgggtgc tcagtggact tctcaaaaaa      2520
ggaaacgaga tgtggcacgg gggtattcat ctataatgat gttgaagcct ggagggaccg     2580
gtacaagtac catcctgact cccccgcag attggcagca gcagtcaagc aggcctggga      2640
agaggggatc tgtgggatct catccgtttc aagaatggaa aacatcatgt ggaaatcagt     2700
agaaggggag ctcaatgcta tcctagagga gaatggagtt caactgacag ttgttgtggg     2760
atctgtaaaa aaccccatgt ggagaggtcc acaaagattg ccagtgcctg tgaatgagct     2820
gccccatggc tggaaagcct gggggaaatc gtattttgtt agggcggcaa agaccaacaa     2880
cagttttgtt gtcgacggtg acacactgaa ggaatgtccg cttgagcaca gcatggaa      2940 tagttttctt gtggaggatc acgggtttgg agtcttccac accagtgtct ggcttaaggt     3000
cagagaagat tactcattag aatgtgaccc agccgtcata ggaacagctg ttaagggaag     3060
ggaggccgcg cacagtgatc tgggctattg gattgaaagt gaaaagaatg acacatggag     3120
gctgaagagg gcccacctga ttgagatgaa acatgtgaa tggccaaagt ctcacacatt      3180
```

```
gtggacagat ggagtagaag aaagtgatct tatcataccc aagtctttag ctggtccact    3240
cagccaccac aacaccagag agggttacag aacccaagtg aaagggccat ggcacagtga    3300
agaacttgaa atccggtttg aggaatgtcc aggcaccaag gtttacgtgg aggagacatg    3360
cggaactaga ggaccatctc tgagatcaac tactgcaagt ggaagggtca ttgaggaatg    3420
gtgctgtagg gaatgcacaa tgcccccact atcgtttcga gcaaaagacg gctgctggta    3480
tggaatggag ataaggccca ggaaagaacc agagagcaac ttagtgaggt caatggtgac    3540
agcggggtca accgatcata tggaccactt ctctcttgga gtgcttgtga ttctactcat    3600
ggtgcaggag gggttgaaga agagaatgac cacaaagatc atcatgagca catcaatggc    3660
agtgctggta gtcatgatct tgggaggatt ttcaatgagt gacctggcca agcttgtgat    3720
cctgatgggt gctactttcg cagaaatgaa cactggagga gatgtagctc acttggcatt    3780
ggtagcggca tttaaagtca gaccagcctt gctggtgtcc ttcattttca gagccaattg    3840
gacaccccgt gagagcatgc tgctagccct ggcttcgtgt cttctgcaaa ctgcgatctc    3900
tgctcttgaa ggtgacttga tggtcctcat taatggattt gctttggcct ggttggcaat    3960
tcgagcaatg gccgtgccac gcactgacaa catcgctcta ccaatcttgg ctgctctaac    4020
accactagct cgaggcacac tgctcgtggc atggagagcg ggcctggcta cttgtggagg    4080
gatcatgctc ctctccctga aagggaaagg tagtgtgaag aagaacctgc catttgtcat    4140
ggccctggga ttgacagctg tgagggtagt agaccctatt aatgtggtag gactactgtt    4200
actcacaagg agtgggaagc ggagctggcc ccctagtgaa gttctcacag ccgttggcct    4260
gatatgtgca ctggccggag ggtttgccaa ggcagacatt gagatggctg gacccatggc    4320
tgcagtaggc ttgctaattg tcagctatgt ggtgtcggga aagagtgtgg acatgtacat    4380
tgaaagagca ggagacatca catgggaaaa ggacgcggaa gtcactggaa acagtcctcg    4440
gcttgacgtg gcactggatg agagtggtga tttctccttg gtagaggaag atggtccacc    4500
catgagagag atcatactca aggtggtcct gatggccatc tgtggcatga acccaatagc    4560 tataccttt gctgcaggag cgtggtatgt gtatgtgaag actgggaaaa ggagtggcgc    4620
cctctgggac gtgcctgctc ccaaagaagt gaagaaagga gaaccacag atggagtgta    4680 cagagtgatg actcgcagac tgctaggttc aacacaggtt ggagtgggag tcatgcaaga    4740
gggagtcttc cacaccatgt ggcacgttac aaaaggagcc gcactgagga gcggtgaggg    4800
aagacttgat ccatactggg gggatgtcaa gcaggacttg gtgtcatact gtgggccttg    4860
gaagttggat gcagcttggg atggactcag cgaggtacag cttttggccg tacctcccgg    4920
agagagggcc agaaacattc agaccctgcc tggaatattc aagacaaagg acggggacat    4980
cggagcagtt gctctggact accctgcagg gacctcagga tctccgatcc tagacaaatg    5040
tggaagagtg ataggactct atggcaatgg ggttgtgatc aagaatggaa gctatgttag    5100
tgctataacc caggggaaaga gggaggagga gactccggtt gaatgtttcg aaccctcgat    5160
gctgaagaag aagcagctaa ctgtcttgga tctgcatcca ggagccggaa aaaccaggag    5220
agttcttcct gaaatagtcc gtgaagccat aaaaaagaga ctccggacag tgatcttggc    5280
accaactagg gttgtcgctg ctgagatgga ggaggcttg agaggacttc cggtgcgtta    5340
catgacaaca gcagtcaacg tcacccattc tgggacagaa atcgttgatt tgatgtgcca    5400
tgccactttc acttcacgct tactacaacc catcagagtc cctaattaca atctcaacat    5460
catggatgaa gcccacttca cagacccctc aagtatagct gcaagaggat acatatcaac    5520
```

-continued

| | |
|---|---|
| aagggttgaa atgggcgagg cggctgccat ttttatgact gccacaccac caggaacccg | 5580 |
| tgatgcgttt cctgactcta actcaccaat catggacaca gaagtggaag tcccagagag | 5640 |
| agcctggagc tcaggctttg attgggtgac agaccattct gggaaaacag tttggttcgt | 5700 |
| tccaagcgtg agaaacggaa atgaaatcgc agcctgtctg acaaaggctg aaagcgggt | 5760 |
| catacagctc agcaggaaga cttttgagac agaatttcag aaaacaaaaa atcaagagtg | 5820 |
| ggactttgtc ataacaactg acatctctga gatgggcgct aactttaagg ccgatagggt | 5880 |
| gatcgatagt agacggtgtc ttaagccagt gatactcgac ggagagagag tgatactcgc | 5940 |
| cggacctatg ccagtgacac acgctagcgc cgcacaacgt aggggagaa tcggacggaa | 6000 |
| tcctaacaaa ccgggagacg aatatatgta cggggggggg tgcgctgaga cagacgaagg | 6060 |
| gcacgctcat tggcttgagg ctagaatgct actcgataac atatacttgc aggacggact | 6120 |
| aatcgctagt ctgtatagac cggaagccga taaggtcgcc gctatcgagg gagagtttaa | 6180 |
| gcttagaacc gagcaacgta agacattcgt cgagcttatg aaaagaggcg atctgccagt | 6240 |
| gtggctcgca taccaggtcg ctagtgccgg aataacatat accgatagga gatggtgttt | 6300 |
| cgacggaaca actaacaata caattatgga ggactcagtc ccagccgaag tgtggactaa | 6360 |
| gtacggcgaa aagagagtgc ttaagcctag atggatggac gctagggtgt gttcggatca | 6420 |
| cgccgcactt aagtcattca aagagttcgc agccggtaag agaggagcgg ctttgggagt | 6480 |
| aatggaggcc ctgggaacac tgccaggaca catgacagag aggtttcagg aagccattga | 6540 |
| caacctcgcc gtgctcatgc gagcagagac tggaagcagg ccttataagg cagcggcagc | 6600 |
| ccaactgccg gagactctag agacaattat gctcttaggt ttgctgggaa cagtttcact | 6660 |
| ggggatcttc ttcgtcttga tgcggaataa gggcatcggg aagatgggct ttggaatggt | 6720 |
| aacccttggg gccagtgcat ggctcatgtg gctttcggaa attgaaccag ccagaattgc | 6780 |
| atgtgtcctc attgttgtgt ttttattact ggtggtgctc atacccgagc cagagaagca | 6840 |
| aagatctccc caagataacc agatggcaat tatcatcatg gtggcagtgg gccttctagg | 6900 |
| tttgataact gcaaacgaac ttggatggct ggaaagaaca aaaaatgaca tagctcatct | 6960 |
| aatgggaagg agagaagaag gagcaaccat gggattctca atggacattg atctgcggcc | 7020 |
| agcctccgcc tgggctatct atgccgcatt gacaactctc atcacccag ctgtccaaca | 7080 |
| tgcggtaacc acttcataca acaactactc cttaatggcg atggccacac aagctggagt | 7140 |
| gctgtttggc atgggcaaag ggatgccatt ttatgcatgg gaccttggag tcccgctgct | 7200 |
| aatgatgggt tgctattcac aattaacacc cctgactctg atagtagcta tcattctgct | 7260 |
| tgtggcgcac tacatgtact tgatcccagg cctacaagcg gcagcagcgc gtgctgccca | 7320 |
| gaaaaggaca gcagctggca tcatgaagaa tcccgttgtg gatggaatag tggtaactga | 7380 |
| cattgacaca atgacaatag accccaggt ggagaagaag atgggacaag tgttactcat | 7440 |
| agcagtagcc atctccagtg ctgtgctgct gcggaccgcc tggggatggg gggaggctgg | 7500 |
| agctctgatc acagcagcga cctccaccct gtgggaaggc tctccaaaca aatactggaa | 7560 |
| ctcctctaca gccacctcac tgtgcaacat cttcagagga agctatctgg caggagcttc | 7620 |
| ccttatctat acagtgacga gaacgctgg cctggttaag agacgtggag gtgggacggg | 7680 |
| agagactctg ggagagaagt ggaaagctcg tctgaatcag atgtcggccc tggagttcta | 7740 |
| ctcttataaa aagtcaggta tcactgaagt gtgtagagag gaggctcgcc gtgccctcaa | 7800 |
| ggatggagtg gccacaggag gacatgccgt atcccgggga agtgcaaagc tcagatggtt | 7860 |
| ggtggagaga ggatatctgc agccctatgg gaaggttgtt gacctcggat gtggcagagg | 7920 |

```
gggctggagc tattatgccg ccaccatccg caaagtgcag gaggtgagag gatacacaaa    7980
gggaggtccc ggtcatgaag aacccatgct ggtgcaaagc tatgggtgga acatagttcg    8040
tctcaagagt ggagtggacg tcttccacat ggcggctgag ccgtgtgaca ctctgctgtg    8100
tgacataggt gagtcatcat ctagtcctga agtggaagac acacgaacac tcagagtgct    8160
ctctatggtg ggggactggc ttgaaaaaag accaggggcc ttctgtataa aggtgctgtg    8220
cccatacacc agcactatga tggaaaccat ggagcgactg caacgtaggc atggggagg     8280 attagtcaga gtgccattgt ctcgcaactc cacacatgag atgtactggg tgtctggggc    8340
aaagagcaac atcataaaaa gtgtgtccac cacaagtcag ctcctcctgg gacgcatgga    8400
tggccccagg aggccagtga aatatgagga ggatgtgaac ctcggctcgg gtacacgagc    8460
tgtggcaagc tgtgctgagg ctcctaacat gaaaatcatc ggcaggcgca ttgagagaat    8520
ccgcaatgaa catgcagaaa catggtttct tgatgaaaac cacccataca ggacatgggc    8580
ctaccatggg agctacgaag cccccacgca aggatcagcg tcttccctcg tgaacggggt    8640
tgttagactc ctgtcaaagc cttgggacgt ggtgactgga gttacaggaa tagccatgac    8700
tgacaccaca ccatacggcc aacaaagagt cttcaaagaa aaagtggaca ccagggtgcc    8760
agatccccaa gaaggcactc gccaggtaat gaacatagtc tcttcctggc tgtggaagga    8820
gctggggaaa cgcaagcggc cacgcgtctg caccaaagaa gagtttatca acaaggtgcg    8880
cagcaatgca gcactgggag caatatttga agaggaaaaa gaatggaaga cggctgtgga    8940
agctgtgaat gatccaaggt tttgggccct agtggatagg gagagagaac accacctgag    9000
aggagagtgt cacagctgtg tgtacaacat gatgggaaaa agagaaaaga gcaaggaga    9060 gttcgggaaa gcaaaggta gccgcgccat ctggtacatg tggttgggag ccagattctt    9120
ggagtttgaa gcccttggat tcttgaacga ggaccattgg atgggaagag aaaactcagg    9180
aggtggagtc gaagggttag gattgcaaag acttggatac attctagaag aaatgaatcg    9240
ggcaccagga ggaaagatgt acgcagatga cactgctggc tgggacaccc gcattagtaa    9300
gtttgatctg gagaatgaag ctctgattac caaccaaatg gaggaagggc acagaactct    9360
ggcgttggcc gtgattaaat acacatacca aaacaaagtg gtgaaggttc tcagaccagc    9420
tgaaggagga aaaacagtta tggacatcat ttcaagacaa gaccagagag ggagtggaca    9480
agttgtcact tatgctctca acacattcac caacttggtg gtgcagctta ccgaacat    9540 ggaagctgag gaagtgttag agatgcaaga cttatggttg ttgaggaagc cagagaaagt    9600
gaccagatgg ttgcagagca atggatggga tagactcaaa cgaatggcgg tcagtggaga    9660
tgactgcgtt gtgaagccaa tcgatgatag gtttgcacat gccctcaggt tcttgaatga    9720
catgggaaaa gttaggaaag acacacagga gtggaaccc tcgactggat ggagcaattg     9780
ggaagaagtc ccgttctgct cccaccactt caacaagctg tacctcaagg atgggagatc    9840
cattgtggtc ccttgccgcc accaagatga actgattggc cgagctcgcg tctcaccagg    9900
ggcaggatgg agcatccggg agactgcctg tcttgcaaaa tcatatgcgc agatgtggca    9960
gctcctttat ttccacagaa gggaccttcg actgatggct aatgccattt gctcggctgt   10020
gccagttgac tgggttccaa ctgggagaac cacctggtca atccatgaa agggagaatg    10080 gatgaccact gaggacatgc tcatggtgtg aatagagtg tggattgagg agaacgacca     10140
tatggaggac aagactcctg taacaaaatg gacagacatt ccctatctag gaaaagggga   10200
ggacttatgg tgtggatccc ttataggca cagacccgc accacttggg ctgaaaacat      10260
```

```
caaagacaca gtcaacatgg tgcgcaggat cataggtgat gaagaaaagt acatggacta   10320
tctatccacc caagtccgct acttgggtga ggaagggtcc acacccggag tgttgtaagc   10380
accaatttta gtgttgtcag gcctgctagt cagccacagt ttggggaaag ctgtgcagcc   10440
tgtaaccccc ccaggagaag ctgggaaacc aagctcatag tcaggccgag aacgccatgg   10500
cacggaagaa gccatgctgc ctgtgagccc ctcagaggac actgagtcaa aaaccccac    10560 gcgcttggaa gcgcaggatg ggaaaagaag gtggcgacct tccccaccct tcaatctggg   10620
gcctgaactg gagactagct gtgaatctcc agcagaggga ctagtggtta gaggagaccc   10680
cccggaaaac gcacaacagc atattgacgc tgggaaagac cagagactcc atgagtttcc   10740
accacgctgg ccgccaggca cagatcgccg aacttcggcg gccggtgtgg ggaaatccat   10800
ggtttct                                                             10807
```

ATTENUATED FLAVIVIRUSES

CROSS-REFERENCE TO RELATED APPLICATIONS

This application is a National Phase of International Application No. PCT/US2018/067114 filed Dec. 21, 2018, which designated the U.S. and that International Application was published under PCT Article 21 (2) in English, which includes a claim of priority under 35 U.S.C. § 119 (e) to U.S. provisional patent application No. 62/640,355 filed Mar. 8, 2018, the entirety of which is hereby incorporated by reference.

FIELD OF THE INVENTION

This invention provides highly attenuated flaviviruses and particularly, Zika viruses and vaccines. The attenuated viruses and vaccines proliferate well and have high safety factors. The attenuated viruses providing protective immunity from challenge by virus of the same lineage, as well as cross protection against heterologous viruses.

BACKGROUND OF THE INVENTION

Zika virus (ZIKV) is a single-stranded positive-sense RNA virus belonging to the Flaviviridae family, in the same genus (Flavivirus) that includes dengue virus (DENV), West Nile virus (WNV), and yellow fever virus (YFV). It is closely related phylogenetically to DENV and shares a common mosquito vector, *Aedes aegypti*, with both DENV and Chikungunya virus (an alphavirus). Although first isolated from a sentinel rhesus macaque in Uganda in 1947, ZIKV has remained fairly obscure until a few years ago. Despite sporadic evidence of human infection in Africa (3) and Indonesia (4) ZIKV was not associated with any major outbreaks or epidemics until it first emerged in the island of Yap in the South Pacific where it then jumped from island to island, spreading throughout Polynesia and to Southeast Asia. In 2014 and 2015, ZIKV spread to the Americas. Recently, there is active transmission of ZIKV throughout Central and South America as well as on the African islands of Cape Verde and several U.S. territories, including U.S. Virgin Islands, Puerto Rico, and American Samoa. Infection with ZIKV is usually mild with a rash, muscle aches, and conjunctivitis being the most widely reported symptoms. Of public health concern, however, is the association of ZIKV infection with neurological sequelae (Guillain-Barre Syndrome) observed in French Polynesia and microcephaly cases in Brazil. In a preliminary case-control study, up to 30% of fetuses in infected mothers displayed microcephaly, some of which were fatal. Unusual for mosquito-transmitted viruses, ZIKV is capable of vertical (mother to fetus) transmission and possible horizontal (sexual) transmission. The WHO raised a state of alarm as ZIKV continues to spread "explosively" throughout the Americas. There is special concern for tourists at risk for ZIKV infection, with an added concern of importation and spread of the epidemic to places like the southern U.S. The vector for ZIKV, *Aedes aegypti*, is found throughout the southern U.S. *Aedes albopictus*, the Asian tiger mosquito, is also competent for transmitting ZIKV and has been implicated as a vector for transmission in Singapore. If ZIKV enters *A. albopictus* populations in the U.S., it will have a vastly expanded range extending into the American Midwest and Northeast.

Accordingly, there remains a need in the art to develop a vaccine to prevent or reduce infection.

Flavivirus vaccine development is compounded by the phenomenon of Antibody-Dependent Enhancement (ADE). ADE occurs when prior infection with one flavivirus predisposes an individual to an enhanced severity of disease upon re-infection with a different serotype. During ADE, antibodies against the first virus bind, but do not neutralize the second virus, instead increasing its infectivity. ZIKV is prevalent in DENV endemic countries, thus any vaccine strategy must consider the impact on a population with established dengue immunity. There is in vitro evidence for cross-flavivirus enhancement of ZIKV infection by dengue immune serum. It is therefore important that an inactivated anti-ZIKV vaccine does not predispose the vaccine recipient to ADE from a subsequent DENV infection. Conversely, it is worth noting that people with underlying DENV immunity could experience increased adverse events from a live ZIKV vaccine, since their DENV immunity could enhance infectivity of the ZIKV vaccine strain, leading to increased adverse events. Both of these are plausible scenarios that needs to be considered when developing a ZIKV vaccine, whether live, inactivated or antigen/VLP/backbone carrier-based. Because of the high likelihood of enhancing flavivirus infection due to ADE, all vaccine development strategies need to consider how any given ZIKV vaccine might interact with existing antibodies to a flavivirus or a subsequent flavivirus infection.

Zika virus is a virus belonging to the Spondweni serogroup of the mosquito-borne Flaviviruses in the family Flaviviridae. Zika viruses are enveloped viruses with an icosahedral virion comprised of C (Core), M (Membrane), and E (Envelope) glycoproteins that is 40-65 nanometers in diameter. The Zika virus genome is a single positive-strand RNA molecule of 10,000-11,000 bases in length encoding structural (C, prM, E) and nonstructural (NS1, NS2, NS3, NS4, and NS5) proteins. Zika viruses transcribe and replicate their genome in the cell cytoplasm, with the genome translated into a single polypeptide that is cleaved and processed by both host and viral proteins. Zika virus is an emerging agent of international concern in the tropics that has been divided in African and Asian lineages, although both lineages are fairly homologous and no individual serotypes have yet to be identified.

SUMMARY OF THE INVENTION

The following embodiments and aspects thereof are described and illustrated in conjunction with compositions and methods which are meant to be exemplary and illustrative, not limiting in scope.

It is described herein that recoded Zika viruses made by modification of the E and NS3 regions by large numbers of synonymous nucleotide mutations are highly effective in providing protective immunity against lethal wild type challenge and cross protection against different lineages. Further, the viruses have exceptional safety profiles.

Accordingly, the invention provides an attenuated Zika virus in which expression of viral proteins is reduced through codon-pair deoptimization of the E and NS3 coding regions. In certain embodiments, E and NS3 are the only virus protein coding regions targeted. In other embodiments of the invention, the expression of one or more other virus protein encoding regions may also be reduced, such as, for example, C, prM, NS1, NS2, NS4, or NS5. In certain embodiments, when another Zika virus protein encoding region other than E and NS3 is deoptimized, the reduction is small compared to the reduction of E and NS3. According to the invention, reduction in expression of virus proteins of the invention is accomplished by changes in protein encoding sequence, for example by lowering the codon pair bias of the protein-encoding sequence, substituting rare codons, modifying G+C content, modifying CG and/or TA (or UA) dinucleotide content, or combinations. Reduced expression can also be accomplished by modifications to the regulatory sequences of the proteins.

In one such embodiment, reducing the codon-pair bias can comprise identifying a codon pair in the parent protein-encoding sequence having a codon-pair score that can be reduced, and reducing the codon-pair bias by substituting the codon pair with a codon pair that has a lower codon-pair score. In another such embodiment, reducing the codon-pair bias can comprise rearranging the codons of a parent protein-encoding sequence. In certain embodiments, the E protein-encoding sequence and the NS3 protein-encoding sequence individually have a codon pair bias less than −0.1, or less than −0.2, or less than −0.3, or less than −0.4. Codon pair bias of a protein-encoding sequence (i.e., an open reading frame) is calculated as described in Coleman et al., 2000 and herein.

In an embodiment of the invention, expression of one or both of the E protein-encoding sequence and the NS3 protein-encoding sequence is reduced by replacing one or more codons with synonymous codons that are less frequent in the host.

The invention further provides a Zika vaccine composition for inducing a protective immune response in a subject, wherein the vaccine composition comprises virus in which viral translation is reduced while maintaining antigenic identity with wt virus.

The invention also provides a method of eliciting a protective immune response in a subject comprising administering to the subject a prophylactically or therapeutically effective dose of a vaccine composition comprising an attenuated Zika virus, wherein expression of viral proteins is reduced. In an embodiment of the invention, an immune response is elicited that is effective against Zika virus of the same lineage as the attenuated virus of the vaccine. In another embodiment, an immune response is elicited that is effective against a heterologous Zika virus.

The invention also provides a method of making an attenuated Zika virus genome comprising a) obtaining the genomic nucleotide b) recoding the envelope-encoding nucleotide sequence to reduce expression and recoding the nonstructural protein 3-encoding nucleotide sequence to reduce expression, and substituting the recoded nucleotide sequences into a Zika virus genome to make an attenuated Zika virus genome. In certain embodiments, only the E and NS3 regions are targeted. In some embodiments, expression of another virus protein encoding region is also reduced.

The invention also provides a method of constructing template Zika virus DNA sequences for transcription of infectious viral RNA genomes by T7 polymerase using overlapping PCR. All Zika genomes were divided into three fragments starting from 5' end (fragment 1: nt1-3596; fragment 2: nt3030-6959, and fragment 3: nt: nt6851-end) and chemically/biochemically synthesized. Instead of constructing an infectious cDNA clone, a novel overlap extension PCR strategy (or: long PCR-based fusion strategy) was used to obtain full-length Zika genome (or: the syn-wt and min Zika genomes simultaneously).

Various embodiments of the invention provide for a modified Zika virus in which expression of viral proteins is reduced compared to a parent virus, wherein the reduction in expression is the result of recoding the prM, or envelope (E) region, or the nonstructural protein 3 (NS3) region or both the E and NS3 regions.

In various embodiments, one or both of the E protein-encoding sequence and the NS3 protein-encoding sequence can be recoded by reducing the codon pair bias or codon usage bias of the protein-encoding sequence. In various embodiments, reducing the codon-pair bias can comprise identifying a codon pair in the parent protein-encoding sequence having a codon-pair score that can be reduced, and reducing the codon-pair bias by substituting the codon pair with a codon pair that has a lower codon-pair score. In various embodiments, reducing the codon-pair bias can comprise rearranging the codons of a parent protein-encoding sequence.

In various embodiments, one or both of the E protein-encoding sequence and the NS3 protein-encoding sequence can be recoded by increasing the number of CpG or UpA di-nucleotides compared to a parent virus.

In various embodiments, each of the recoded prM/E protein-encoding sequence and the recoded NS3 protein-encoding sequence can have a codon pair bias less than, −0.05, −0.1, or less than −0.2, or less than −0.3, or less than −0.4.

In various embodiments, one or both of the E protein-encoding sequence and the NS3 protein-encoding sequence can be recoded by replacing one or more codons with synonymous codons that are less frequent in the host.

Various embodiments of the invention provide for a Zika vaccine composition for inducing a protective immune response in a subject, comprising a modified virus of the present application as described herein.

Various embodiments of the invention provide for a method of eliciting a protective immune response in a subject, comprising: administering to the subject a prophylactically or therapeutically effective dose of a vaccine composition comprising a modified virus of the present application as described herein.

In various embodiments, the method can further comprise administering to the subject at least one adjuvant.

In various embodiments, the immune response is cross-protective against a heterologous Zika virus.

Various embodiments of the invention provide a method of making a modified Zika virus genome comprising: obtaining the nucleotide sequence encoding the envelope protein of a Zika virus and the nucleotide sequence encoding the nonstructural 3 proteins of a Zika virus; recoding the envelope encoding nucleotide sequence to reduce protein expression and recoding the nonstructural protein 3-encoding nucleotide sequence to reduce protein expression, and substituting a nucleic acid having the recoded envelope-encoding nucleotide sequence and a nucleic acid having the recoded nonstructural protein 3-encoding nucleotide sequence into a parent Zika virus genome to make a modified Zika virus genome; whereby expression of the recoded envelope-encoding nucleotide sequence and expression of the recoded nonstructural protein 3-encoding nucleotide sequence is reduced compared to the parent virus.

Various embodiments of the invention provide a modified Flavivirus virus in which expression of viral proteins is reduced compared to a parent virus, wherein the reduction in expression is the result of recoding the prM, or envelope (E) region, or the nonstructural protein 3 (NS3) region or both the E and NS3 regions.

In various embodiments, one or both of the E protein-encoding sequence and the NS3 protein-encoding sequence can be recoded by reducing the codon pair bias or codon usage bias of the protein-encoding sequence.

In various embodiments, reducing the codon-pair bias can comprise identifying a codon pair in the parent protein-encoding sequence having a codon-pair score that can be reduced, and reducing the codon-pair bias by substituting the codon pair with a codon pair that has a lower codon-pair score.

In various embodiments, reducing the codon-pair bias can comprise rearranging the codons of a parent protein-encoding sequence.

In various embodiments, one or both of the E protein-encoding sequence and the NS3 protein-encoding sequence can be recoded by increasing the number of CpG or UpA di nucleotides compared to a parent virus.

In various embodiments, each of the recoded prM/E protein-encoding sequence and the recoded NS3 protein-encoding sequence can have a codon pair bias less than, −0.05, −0.1, or less than −0.2, or less than −0.3, or less than −0.4.

In various embodiments, one or both of the E protein-encoding sequence and the NS3 protein-encoding sequence can be recoded by replacing one or more codons with synonymous codons that are less frequent in the viral host.

In various embodiments, the parent virus can be a Flavivirus selected from the group consisting of dengue fever virus, West Nile virus, yellow fever virus, Japanese encephalitis virus, Spondweni virus, Saint Louis encephalitis virus, and Powassan virus. In various embodiments, the parent virus can be a natural isolate. In various embodiments, the parent virus can be a mutant of a natural isolate.

Various embodiments of the invention provide for a Flavivirus vaccine composition for inducing a protective immune response in a subject, which comprises a modified virus of the present invention as described herein.

Various embodiments of the invention provide for a method of eliciting a protective immune response in a subject comprising administering to the subject a prophylactically or therapeutically effective dose of a vaccine composition comprising a modified virus of the present invention as described herein. In various embodiments, the method can further comprise administering to the subject at least one adjuvant.

In various embodiments, the immune response can be cross-protective against a heterologous Flavivirus virus.

Various embodiments of the present invention provide for a method of making a modified Flavivirus virus genome comprising: obtaining the nucleotide sequence encoding the envelope protein of a Flavivirus virus and the nucleotide sequence encoding the nonstructural 3 proteins of a Flavivirus virus; recoding the envelope encoding nucleotide sequence to reduce protein expression and recoding the nonstructural protein 3-encoding nucleotide sequence to reduce protein expression, and substituting a nucleic acid having the recoded envelope-encoding nucleotide sequence and a nucleic acid having the recoded nonstructural protein 3-encoding nucleotide sequence into a parent Flavivirus virus genome to make a modified Flavivirus virus genome; whereby expression of the recoded envelope-encoding nucleotide sequence and expression of the recoded nonstructural protein 3-encoding nucleotide sequence is reduced compared to the parent virus.

Various embodiments of the present invention provide for a method of eliciting an immune response in a subject in need thereof, comprising: administering a prime dose of an attenuated Flavivirus produced by a method other than codon-pair deoptimization or a modified Flavivirus in which expression of viral proteins is reduced compared to a parent virus, wherein the reduction in expression is the result of recoding the prM, or envelope (E) region, or the nonstructural protein 3 (NS3) region or both the E and NS3 regions; and administering one or more boost dose of the attenuated Flavivirus by methods other than codon-pair deoptimization or the modified Flavivirus to the subject in need thereof, wherein at least the prime dose or the one or more boost dose is the modified virus.

In various embodiments, a first of the one or more boost dose can be administered about 2 weeks after the prime dose.

In various embodiments, the Flavivirus can be a Zika virus.

In various embodiments, the Flavivirus can be selected from the group consisting of dengue fever virus, West Nile virus, yellow fever virus, Japanese encephalitis virus, Spondweni virus, Saint Louis encephalitis virus, and Powassan virus.

In various embodiments, one or both of the E protein-encoding sequence and the NS3 protein-encoding sequence can be recoded by reducing the codon pair bias or codon usage bias of the protein-encoding sequence.

In various embodiments, one or both of the E protein-encoding sequence and the NS3 protein-encoding sequence can be recoded by increasing the number of CpG or UpA di nucleotides compared to a parent virus.

In various embodiments, reducing the codon-pair bias can comprise identifying a codon pair in the parent protein-encoding sequence having a codon-pair score that can be reduced, and reducing the codon-pair bias by substituting the codon pair with a codon pair that has a lower codon-pair score.

In various embodiments, reducing the codon-pair bias can comprise rearranging the codons of a parent protein-encoding sequence.

In various embodiments, each of the recoded prM/E protein-encoding sequence and the recoded NS3 protein-encoding sequence can have a codon pair bias less than, −0.05, −0.1, or less than −0.2, or less than −0.3, or less than −0.4.

In various embodiments, one or both of the E protein-encoding sequence and the NS3 protein-encoding sequence can be recoded by replacing one or more codons with synonymous codons that are less frequent in the viral host.

Other features and advantages of the invention will become apparent from the following detailed description, taken in conjunction with the accompanying drawings, which illustrate, by way of example, various features of embodiments of the invention

BRIEF DESCRIPTION OF THE FIGURES

FIG. 1A-1B depicts Rapid Construction of six SAVE-deoptimized, live-attenuated Zika vaccine candidate in less than 1 month with growth in Vero cells under animal component-free conditions. (1A) Codon pair bias of the Zika prM/E and NS3 genes and their SAVE-deoptimized counterparts in relation to the human ORFeome. Codon-Pair Bias (CPB) is expressed as the average codon pair score of a given gene's open reading frame (ORF). Positive and negative CPB value signifies the predominance of statistically over- or under-represented codon-pairs, respectively in an ORF. Red circles indicate the CPB of each of the 14,795 human ORFs, representing the majority of the known, annotated human genes at the time of our analysis (ORFeome). The CPB of wild-type prM/E and NS3 genes fall within the normal range of human host cell's genes. Following codon pair-'deoptimization' via SAVE, the resulting deoptimized prM/E and NS3 gene segments were now encoded predominantly by under-represented human codon-pairs as evident by their extremely negative CPB, and are drastically different from any human gene. (1B) cDNA genomes of wild-type and synthetically 'de-optimized' chimeric Zika vaccine variants. The SAVE-deoptimized synthetic prM/E and NS3 from FIG. 1A were synthesized de novo and using overlapping PCR subcloned individually into the WT PR15 or MR766 genomes—yielding six independent cDNA genomes each containing a synthetically 'de-optimized' fragment(s). We constructed infectious cDNA genomes for wt PR15 and MR766 in 7 days and then recovered fully infectious, replicating virus for the six deoptimized ZIKV vaccine candidates in 27 days via transfection of RNA into Vero or BHK cells.

FIG. 2 shows a diagram of subcloning strategies for decreasing attenuation or increasing immunogenicity by reducing the length of deoptimized sequence in the prM+E encoding region. The second generation of Zika vaccine candidates leverages the flexibility of the SAVE platform to reduce the deoptimized region from 2014 bp (E-min) to 997 bp (W-E-Min) or further to 664 bp (W-W-E-Min) while keeping the amino acid sequence 100% identical.

FIG. 8 depicts survival post-lethal ZIKV challenge. AG129 Mice were vaccinated on day 28 and boosted on Day 49. Mice were then challenged with a lethal dose ($10^{2.3}$ $CCID_{50}$/animal) of Wt PR15 PRVABC59 ZIKV virus in 0.1 mL delivered s.c. Vaccination was successful in preventing or reducing mortality and weight loss (not shown) compared to unvaccinated controls. Lead candidate MR 766 E-Min, PR-15-EMin, and MR766 NS3-Min vaccinated mice were all protected at a dose of $10^4$ PFU.

DETAILED DESCRIPTION

Figure 1A:
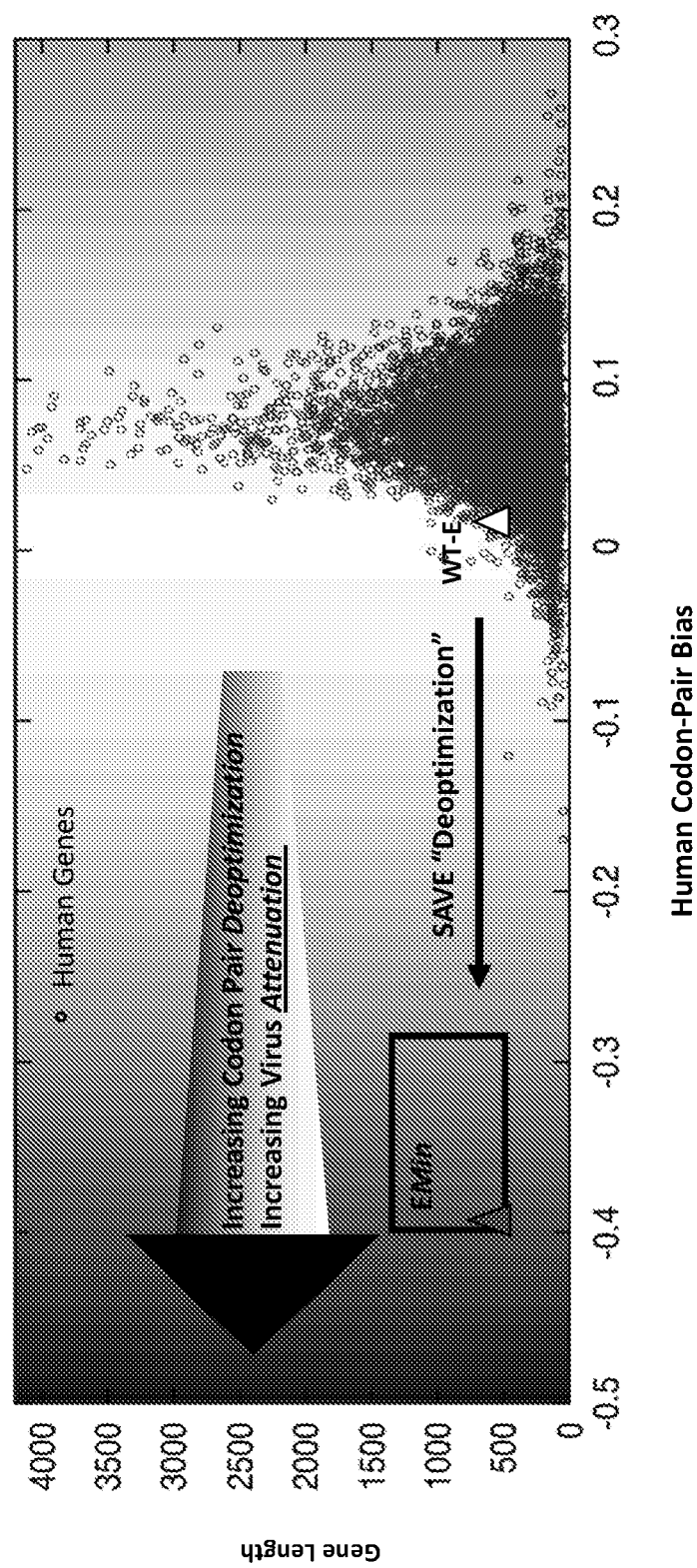

The present invention relates to the production of attenuated Zika viruses that can be used to protect against viral infection and disease. A basic premise in vaccination is adequate delivery of protective antigens to vaccine recipients assuming that a very high dose ("Peptide or Virus-Like Particle") or a dose corresponding to live viral infection ("ChimeriVax") of these traditionally dominant antigenic polypeptides alone are sufficient for adequate vaccine efficacy. Those expectations aside, the present invention benefits from a contrary approach. The invention provides attenuated Zika viruses in which expression of viral proteins is reduced, which have excellent growth properties useful to vaccine production, yet possess an extraordinary safety profile and enhanced protective characteristics. The attenuated viruses proliferate nearly as well as wild type virus, have highly attenuated phenotypes, as revealed by $LD_{50}$ values, are unusually effective in providing protective immunity against challenge by Zika virus of the same strain, and also provide protective immunity against challenge by Zika virus of other strains.

In certain embodiments of the invention, the attenuated Zika viruses of the invention comprise a recoded pre-membrane/Envelope (E) encoding region, a recoded non-structural protein 3 (NS3) encoding region, or both E and NS3 encoding regions. That the C, NS1, NS2, NS4, or NS5 protein encoding regions are not recoded does not exclude mutations and other variations in those sequences, but only means that any mutations or variations made in those sequences have little or no effect on attenuation. Little or no effect on attenuation includes one or both of the following: 1) The mutations or variations in the That the C, NS1, NS2, NS4, or NS5 encoding regions do not reduce viral replication or viral infectivity more than 20% when the variant C, NS1, NS2, NS4, or NS5 encoding region is the only variant in a test Zika virus; 2) Mutations or variations in any of the C, NS1, NS2, NS4, or NS5 encoding regions represent fewer than 10% of the nucleotides in that coding sequence.

The viruses of the invention are highly attenuated. In embodiments of the invention, compared to wild type, the viruses are at least 5,000 fold attenuated, or at least 10,000 fold attenuated, or at least 20,000 fold attenuated, or at least 33,000 fold attenuated, or at least 50,000 fold attenuated, of at least 100,000 fold attenuated in the AG129 mouse model compared to a wild type virus having proteins of the same sequence but encoded by a different nucleotide sequence.

The attenuated viruses are also highly protective against wild type virus of the same strain. In embodiments of the invention, the protective dose ($PD_{50}$) of the viruses is less than 1,000 PFU, or less than 100 PFU, or less than 50 PFU, or less than 20 PFU, or less than 10 PFU, or less than 5 PFU, when measured by a mouse model, such as exemplified herein.

The attenuated viruses of the invention also exhibit a large margin of safety (i.e., the difference between $LD_{50}$ and $PD_{50}$), thus have high safety factors, defined herein as the ratio of $LD_{50}/PD_{50}$. In certain embodiments of the invention, the safety factor is at least $10^2$, or at least $10^3$, or at least $10^4$, or at least $10^5$, or at least $2 \times 10^5$, or at least $5 \times 10^5$, or at least $10^6$, or at least $2 \times 10^6$, or at least $5 \times 10^6$. In certain embodiments, the safety factor is from $10^2$ to $10^3$, or from $10^3$ to $10^4$, or from $10^4$ to $10^5$, or from $10^5$ to $10^6$.

The attenuated viruses of the invention are also highly protective against heterologous strains of the Zika virus. In certain embodiments of the invention, the protective dose ($PD_{50}$) of an attenuated virus of the invention is less than 1000 PFU, or less than 500 PFU, or less than 200 PFU, or less than 100 PFU, when measured by a mouse model, such as exemplified herein.

The recoding of E and NS3 protein encoding sequences of the attenuated viruses of the invention can have been made utilizing any algorithm or procedure known in the art or newly devised for recoding a protein encoding sequence. According to the invention, nucleotide substitutions are engineered in multiple locations in the E and NS3 coding sequences, wherein the substitutions introduce a plurality of synonymous codons into the genome. In certain embodiments, the synonymous codon substitutions alter codon bias, codon pair bias, the density of infrequent codons or infrequently occurring codon pairs, RNA secondary structure, CG and/or TA (or UA) dinucleotide content, C+G content, translation frameshift sites, translation pause sites, the presence or absence of microRNA recognition sequences or any combination thereof, in the genome. The codon substitutions may be engineered in multiple locations distributed throughout the E and NS3 coding sequences, or in the multiple locations restricted to a portion of the E and NS3 coding sequences. Because of the large number of defects (i.e., nucleotide substitutions) involved, the invention provides a means of producing stably attenuated viruses and live vaccines.

As discussed further below, in some embodiments, a virus coding sequence is recoded by substituting one or more codon with synonymous codons used less frequently in the Zika host (e.g., humans, mosquitoes). In some embodiments, a virus coding sequence is recoded by substituting one or more codons with synonymous codons used less frequently in the Zika virus. In certain embodiments, the number of codons substituted with synonymous codons is at least 5. In some embodiments, at least 10, or at least 20 codons are substituted with synonymous codons.

In some embodiments, virus codon pairs are recoded to reduce (i.e., lower the value of) codon-pair bias. In certain embodiments, codon-pair bias is reduced by identifying a codon pair in an E or NS3 coding sequence having a codon-pair score that can be reduced and reducing the codon-pair bias by substituting the codon pair with a codon pair that has a lower codon-pair score. In some embodiments, this substitution of codon pairs takes the form of rearranging existing codons of a sequence. In some such embodiments, a subset of codon pairs is substituted by rearranging a subset of synonymous codons. In other embodiments, codon pairs are substituted by maximizing the number of rearranged synonymous codons. It is noted that while rearrangement of codons leads to codon-pair bias that is reduced (made more negative) for the virus coding sequence overall, and the rearrangement results in a decreased CPS at many locations, there may be accompanying CPS increases at other locations, but on average, the codon pair scores, and thus the CPB of the modified sequence, is reduced. In some embodiments, recoding of codons or codon-pairs can take into account altering the G+C content of the E and NS3 coding sequences. In some embodiments, recoding of codons or codon-pairs can take into account altering the frequency of CG and/or TA dinucleotides in the E and NS3 coding sequences.

In certain embodiments, the recoded E protein-encoding sequence has a codon pair bias less than −0.1, or less than −0.2, or less than −0.3, or less than −0.4. In certain embodiments, the recoded (i.e., reduced-expression) NS3 protein-encoding sequence has a codon pair bias less than −0.1, or less than −0.2, or less than −0.3, or less than −0.4. In certain embodiments, the codon pair bias of the recoded HA protein encoding sequence is reduced by at least 0.1, or at least 0.2, or at least 0.3, or at least 0.4, compared to the parent E protein encoding sequence from which it is derived. In certain embodiments, the codon pair bias of the recoded NS3 protein encoding sequence is reduced by at least 0.1, or at least 0.2, or at least 0.3, or at least 0.4, compared to the parent NS3 protein encoding sequence from which it is derived. In certain embodiments, rearrangement of synonymous codons of the E protein-encoding sequence provides a codon-pair bias reduction of at least 0.1, or at least 0.2, or at least 0.3, or at least 0.4, parent E protein encoding sequence from which it is derived. In certain embodiments, rearrangement of synonymous codons of the NS3 protein-encoding sequence provides a codon-pair bias reduction of at least 0.1, or at least 0.2, or at least 0.3, or at least 0.4, parent NS3 protein encoding sequence from which it is derived.

Usually, these substitutions and alterations are made and reduce expression of the encoded virus proteins without altering the amino acid sequence of the encoded protein. In certain embodiments, the invention also includes alterations in the E and/or NS3 coding sequences that result in substitution of non-synonymous codons and amino acid substitutions in the encoded protein, which may or may not be conservative.

Most amino acids are encoded by more than one codon. See the genetic code in Table 1. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy.

TABLE 1

Genetic Code

| U | C | A | G | | |
|---|---|---|---|---|---|
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

[a]The first nucleotide in each codon encoding a particular amino acid is shown in the left-most column; the second nucleotide is shown in the top row; the third nucleotide is shown in the right-most column.

Codon Bias

As used herein, a "rare" codon is one of at least two synonymous codons encoding a particular amino acid that is present in an mRNA at a significantly lower frequency than the most frequently used codon for that amino acid. Thus, the rare codon may be present at about a 2-fold lower frequency than the most frequently used codon. Preferably, the rare codon is present at least a 3-fold, more preferably at least a 5-fold, lower frequency than the most frequently used codon for the amino acid. Conversely, a "frequent" codon is one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid. For example, human genes use the leucine codon CTG 40% of the time, but use the synonymous CTA only 7% of the time (see Table 2). Thus, CTG is a frequent codon, whereas CTA is a rare codon. Roughly consistent with these frequencies of usage, there are 6 copies in the genome for the gene for the tRNA recognizing CTG, whereas there are only 2 copies of the gene for the tRNA recognizing CTA. Similarly, human genes use the frequent codons TCT and TCC for serine 18% and 22% of the time, respectively, but the rare codon TCG only 5% of the time. TCT and TCC are read, via wobble, by the same tRNA, which has 10 copies of its gene in the genome, while TCG is read by a tRNA with only 4 copies. It is well known that those mRNAs that are very actively translated are strongly biased to use only the most frequent codons. This includes genes for ribosomal proteins and glycolytic enzymes. On the other hand, mRNAs for relatively non-abundant proteins may use the rare codons.

TABLE 2

Codon usage in *Homo sapiens* (source: www.kazusa.or.jp/codon/)

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |

TABLE 2-continued

Codon usage in Homo sapiens
(source: www.kazusa.or.jp/codon/)

| Amino Acid | Codon | Number | /1000 | Fraction |
|---|---|---|---|---|
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

The propensity for highly expressed genes to use frequent codons is called "codon bias." A gene for a ribosomal protein might use only the 20 to 25 most frequent of the 61 codons, and have a high codon bias (a codon bias close to 1), while a poorly expressed gene might use all 61 codons, and have little or no codon bias (a codon bias close to 0). It is thought that the frequently used codons are codons where larger amounts of the cognate tRNA are expressed, and that use of these codons allows translation to proceed more rapidly, or more accurately, or both. The PV capsid protein, for example, is very actively translated, and has a high codon bias.

Codon Pair Bias

In addition, a given organism has a preference for the nearest codon neighbor of a given codon A, referred to a bias in codon pair utilization. A change of codon pair bias, without changing the existing codons, can influence the rate of protein synthesis and production of a protein.

Codon pair bias may be illustrated by considering the amino acid pair Ala-Glu, which can be encoded by 8 different codon pairs. If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is the most comprehensive representation of human coding sequences. Using this set of genes, the frequencies of codon usage were re-calculated by dividing the number of occurrences of a codon by the number of all synonymous codons coding for the same amino acid. As expected, the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/ codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 3 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.097 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 3; observed frequency). Frequency and observed/ expected values for the complete set of 3721 ($61^2$) codon pairs, based on the set of 14,795 human genes, are provided herewith as Table 3.

TABLE 3

Codon Pair Scores Exemplified by the Amino Pair Ala-Glu

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |
| AE | GCTGAA | 0.112 | 0.145 | 1.29 |
| AE | GCTGAG | 0.150 | 0.206 | 1.37 |
| Total | | 1.000 | 1.000 | |

If the ratio of observed frequency/expected frequency of the codon pair is greater than one the codon pair is said to be overrepresented. If the ratio is smaller than one, it is said to be underrepresented. In the example, the codon pair GCA-GAA is overrepresented 1.65 fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

As discussed more fully below, codon pair bias takes into account the score for each codon pair in a coding sequence averaged over the entire length of the coding sequence. According to the invention, codon pair bias is determined by $$CPB = \sum_{i=1}^{k} \frac{CPSi}{K-1}$$

Accordingly, similar codon pair bias for a coding sequence can be obtained, for example, by minimized codon pair scores over a subsequence or moderately diminished codon pair scores over the full length of the coding sequence.

Calculation of Codon Pair Bias

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair. The detailed equations used to calculate CPB are disclosed in WO 2008/121992 and WO 2011/044561, which are incorporated by reference.

$$S(P_{ij}) = \ln\left(\frac{N_O(P_{ij})}{N_E(P_{ij})}\right) = \ln\left(\frac{N_O(P_{ij})}{F(C_i)F(C_j)N_O(X_{ij})}\right)$$

In the calculation, $P_{ij}$ is a codon pair occurring with a frequency of $No(P_{ij})$ in its synonymous group. $C_i$ and $C_j$ are the two codons comprising $P_{ij}$, occurring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=No(C_i)/No(X_i)$, where $No(C_i)$ and $No(X_i)$ are the observed number of occurrences of codon $C_i$ and amino acid $X_i$ respectively. $F(C_j)$ is calculated accordingly. Further, $No(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $N_o(P_{ij})$ over the expected number of occurrences of $N_e(P_{ij})$.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions.

The "combined" codon pair bias of an individual coding sequence was calculated by averaging all codon pair scores according to the following formula:

$$S(P_{ij}) = \sum_{i=1}^{k} \frac{S(P_{ij})l}{k-1}$$

The codon pair bias of an entire coding region is thus calculated by adding all of the individual codon pair scores comprising the region and dividing this sum by the length of the coding sequence.

Calculation of Codon Pair Bias, Implementation of Algorithm to Alter Codon-Pair Bias.

An algorithm was developed to quantify codon pair bias. Every possible individual codon pair was given a "codon pair score", or "CPS". CPS is defined as the natural log of the ratio of the observed over the expected number of occurrences of each codon pair over all human coding regions, where humans represent the host species of the instant vaccine virus to be recoded.

$$CPS = \ln\left(\frac{F(AB)_O}{\frac{F(A) \times F(B)}{F(X) \times F(Y)} \times F(XY)}\right)$$

Although the calculation of the observed occurrences of a particular codon pair is straightforward (the actual count within the gene set), the expected number of occurrences of a codon pair requires additional calculation. We calculate this expected number to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k} \frac{CPSi}{k-1}$$

The CPB has been calculated for all annotated human genes using the equations shown and plotted (FIG. 1). Each point in the graph corresponds to the CPB of a single human gene. The peak of the distribution has a positive codon pair bias of 0.07, which is the mean score for all annotated human genes. Also, there are very few genes with a negative codon pair bias. Equations established to define and calculate CPB were then used to manipulate this bias.

Algorithm for Reducing Codon-Pair Bias.

Recoding of protein-encoding sequences may be performed with or without the aid of a computer, using, for example, a gradient descent, or simulated annealing, or other minimization routine. An example of the procedure that rearranges codons present in a starting sequence can be represented by the following steps:

(1) Obtain wildtype viral genome sequence.
(2) Select protein coding sequences to target for attenuated design.
(3) Lock down known or conjectured DNA segments with non-coding functions.
(4) Select desired codon distribution for remaining amino acids in redesigned proteins.
(5) Perform random shuffle of at least two synonymous unlocked codon positions and calculate codon-pair score.
(6) Further reduce (or increase) codon-pair score optionally employing a simulated annealing procedure.
(7) Inspect resulting design for excessive secondary structure and unwanted restriction site:
if yes->go to step (5) or correct the design by replacing problematic regions with wildtype sequences and go to step (8).
(8) Synthesize DNA sequence corresponding to virus design.
(9) Create viral construct and assess viral phenotype:
if too attenuated, prepare subclone construct and go to 9;
if insufficiently attenuated, go to 2.

Attenuation of viruses by reducing codon pair bias is disclosed in WO 2008/121992 and WO 2011/044561, which are incorporated by reference.

Methods of obtaining full-length Flavivirus or Zika genome sequence or codon pair deoptimized sequences embedded in a wild-type Flavivirus or Zika genome sequence can include for example, constructing an infectious cDNA clone, using an overlap extension PCR strategy, or long PCR-based fusion strategy.

Modified Flavivirus

Various embodiments of the invention provide for a modified Flavivirus virus in which expression of viral proteins is reduced compared to a parent virus. The reduction in expression is the result of recoding the prM, or envelope (E) region, or the nonstructural protein 3 (NS3) region or both the E and NS3 regions.

In various embodiments, one or both of the E protein-encoding sequence and the NS3 protein-encoding sequence are recoded by reducing the codon pair bias or codon usage bias of the protein-encoding sequence. In various embodiments, reducing the codon-pair bias comprises identifying a codon pair in the parent protein-encoding sequence having a codon-pair score that can be reduced, and reducing the codon-pair bias by substituting the codon pair with a codon pair that has a lower codon-pair score. In other embodiments embodiments, reducing the codon-pair bias comprises rearranging the codons of a parent protein-encoding sequence.

In various embodiments, each of the recoded prM/E protein-encoding sequence and the recoded NS3 protein-encoding sequence have a codon pair bias less than, −0.05, −0.1, or less than −0.2, or less than −0.3, or less than −0.4.

In various embodiments, one or both of the E protein-encoding sequence and the NS3 protein-encoding sequence are recoded by increasing the number of CpG or UpA di nucleotides compared to a parent virus.

In various embodiments, one or both of the E protein-encoding sequence and the NS3 protein-encoding sequence are recoded by replacing one or more codons with synonymous codons that are less frequent in the viral host.

In various embodiments, the parent virus is a Flavivirus selected from the group consisting of dengue fever virus, West Nile virus, yellow fever virus, Japanese encephalitis virus, Spondweni virus, Saint Louis encephalitis virus, and Powassan virus. In various embodiments, the parent virus is a natural isolate. In various embodiments, the parent virus a mutant of a natural isolate.

Modified Zika Viruses

Various embodiments of the present invention provide for modified Zika viruses as the modified Flavivirus.

In various embodiments, a modified Zika virus is provided in which expression of viral proteins is reduced compared to a parent virus, wherein the reduction in expression is the result of recoding the prM, or envelope (E) region, or the nonstructural protein 3 (NS3) region or both the E and NS3 regions.

In various embodiments, one or both of the E protein-encoding sequence and the NS3 protein-encoding sequence are recoded by reducing the codon pair bias or codon usage bias of the protein-encoding sequence. In various embodiments, reducing the codon-pair bias comprises identifying a codon pair in the parent protein-encoding sequence having a codon-pair score that can be reduced, and reducing the codon-pair bias by substituting the codon pair with a codon pair that has a lower codon-pair score. In various embodiments, reducing the codon-pair bias comprises rearranging the codons of a parent protein-encoding sequence.

In various embodiments, one or both of the E protein-encoding sequence and the NS3 protein-encoding sequence are recoded by increasing the number of CpG or UpA di-nucleotides compared to a parent virus. In various embodiments, each of the recoded prM/E protein-encoding sequence and the recoded NS3 protein-encoding sequence have a codon pair bias less than, −0.05, −0.1, or less than −0.2, or less than −0.3, or less than −0.4. In various embodiments, one or both of the E protein-encoding sequence and the NS3 protein-encoding sequence are recoded by replacing one or more codons with synonymous codons that are less frequent in the host.

Various embodiments of the present invention provide for a method of making a modified Flavivirus virus genome. The method comprises obtaining the nucleotide sequence encoding the envelope protein of a Flavivirus virus and the nucleotide sequence encoding the nonstructural 3 proteins of a Flavivirus virus; recoding the envelope encoding nucleotide sequence to reduce protein expression and recoding the nonstructural protein 3-encoding nucleotide sequence to reduce protein expression, and substituting a nucleic acid having the recoded envelope-encoding nucleotide sequence and a nucleic acid having the recoded nonstructural protein 3-encoding nucleotide sequence into a parent Flavivirus virus genome to make a modified Flavivirus virus genome; whereby expression of the recoded envelope-encoding nucleotide sequence and expression of the recoded nonstructural protein 3-encoding nucleotide sequence is reduced compared to the parent virus.

Various embodiments of the present invention provide for a method of making a modified Zika virus genome comprising: obtaining the nucleotide sequence encoding the envelope protein of a Zika virus and the nucleotide sequence encoding the nonstructural 3 proteins of a Zika virus; recoding the envelope encoding nucleotide sequence to reduce protein expression and recoding the nonstructural protein 3-encoding nucleotide sequence to reduce protein expression, and substituting a nucleic acid having the recoded envelope-encoding nucleotide sequence and a nucleic acid having the recoded nonstructural protein 3-encoding nucleotide sequence into a parent Zika virus genome to make a modified Zika virus genome; whereby expression of the recoded envelope-encoding nucleotide sequence and expression of the recoded nonstructural protein 3-encoding nucleotide sequence is reduced compared to the parent virus.

According to various embodiments the invention, viral attenuation is accomplished by reducing expression viral proteins through codon pair deoptimization of E and NS3 coding sequences. One way to reduce expression of the coding sequences is by a reduction in codon pair bias, but other methods can also be used, alone or in combination. While codon bias may be changed, adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties.

Codon pair bias of a protein-encoding sequence (i.e., an open reading frame) is calculated as set forth above and described in Coleman et al., 2008.

Viral attenuation and induction or protective immune responses can be confirmed in ways that are well known to one of ordinary skill in the art, including but not limited to, the methods and assays disclosed herein. Non-limiting examples include plaque assays, growth measurements, reduced lethality in test animals, and protection against subsequent infection with a wild type virus.

In preferred embodiments, the invention provides viruses that are highly attenuated, and induce immunity against a plurality of Zika types and/or subtypes. Such Zika virus varieties include viruses in the so-called African and Asian lineages. Examples of attenuated Zika protein coding sequences are provided below.

TABLE 4

Reduced-Expression Zika Virus Genes

| Gene | WT Coding Sequence SEQ ID NO: | Recoded Coding Sequence SEQ ID NO: |
|---|---|---|
| PR15 Syn WT | 1 | |
| PR15 E-Min | | 2 |
| PR15 N53-Min | | 3 |
| PR15 E-W/min | | 4 |
| PR15 E-W/W/min | | 5 |
| MR766 Syn WT | 6 | |
| MR766 E-Min | | 7 |
| MR766 E-W/Min | | 8 |
| MR766 E-W/W/min | | 9 |
| MR766 N53-Min | | 10 |
| MR766 NS3-W/Min | | 11 |
| MR766 N53-W/W/Min | | 12 |

Vaccine Compositions

Various embodiments provide for a Flavivirus vaccine composition for inducing a protective immune response in a subject, which comprises the modified Flavivirus of the present invention as described herein.

Various embodiments of the present invention provide for a Zika vaccine composition for inducing a protective immune response in a subject, comprising the modified Zika virus of the present invention. Non-limiting examples of modified Zika viruses are provided:

PR15 Syn WT

SEQ ID NO: 1

Agttgttgatctgtgtgaatcagactgcgacagttcgagtttgaagcgaaagctagcaacagtatcaacaggttttattttggatttgg
aaacgagagtttctggtcatgaaaaacccaaaaagaaatccggaggattccggattgtcaatatgctaaaacgcggagtagcccgtgt
gagcccattgggggcttgaagaggctgccagccggacttctgctgggtcatgggcccatcaggatggtcttggcgattctagccttttt
gagattcacggcaatcaagccatcactgggtctcatcaatagatggggttcagtggggaaaaagaggctatggaaaTaataaagaagt
tcaagaaagatctggctgccatgctgagaataatcaatgctaggaaggagaagaagagacgaggcgcagatactagtgtcggaattgtt
ggcctcctgctgaccacagctatggcagcggaggtcactagacgtgggagtgcatactatatgtacttggacagaaacgatgctgggga
ggccatatcttttccaaccacattggggatgaataagtgttatatacagatcatggatcttggacacatgtgtgatgccaccatgagct
atgaatgccctatgctggatgaggggtggaaccagatgacgtcgattgttggtgcaacacgacgtcaacttgggttgtgtacggaacc
tgccatcacaaaaaggtgaagcacggagatctagaagGgctgtgacgctcccctcccattccaccaggaagctgcaaacgcggtcgca
aacctggttggaatcaagagaatacacaaagcacttgattagagtcgaaaattggatattcaggaaccctggcttcgcgttagcagcag
ctgccatcgcttggcttttgggaagctcaacgagccaaaaagtcatatacttggtcatgatactgctgattgccccggcatacagcatc
aggtgcataggagtcagcaatagggactttgtggaaggtatgtcaggtgggacttgggttgatgttgtcttggaacatggaggttgtgt
caccgtaatggcacaggacaaaccgactgtcgacatagagctggttacaacaacagtcagcaacatggcggaggtaagatcctactgct
atgaggcatcaatatcagacatggcttctgacagccgctgcccaacacaaggtgaagcctaccttgacaagcaatcagacactcaatat
gtctgcaaaagaacgttagtggacagaggctggggaaatggatgtggactttttggcaaagggagcctggtgacatgcgctaagtttgc
atgctccaagaaaatgaccggCaagagcatccagccagagaatctgagtaccggataatgctgtcagttcatggctcccagcacagtg
ggatgatcgttaatgacacaggacatgaaactgatgagaatagagcgaaagttgagataacgcccaattcaccgagagccgaagccacc
ctgggggtttggaagcctaggacttgattgtgaaccgaggacaggccttgacttttcagatttgtattacttgactatgaataacaa
gcactggttggttcacaaggagtggttccacgacattccattaccttggcacgctggggcagacaccggaactccacactggaacaaca
agaagcactggtagagttcaaggacgcacatgccaaaaggcaaactgtcgtggttctagggagtcaagaaggagcagttcacacggcc
cttgctggagctctggaggctgagatggatggtgcaaagggaaggctgtcctctggccacttgaaatgtcgcctgaaaatggataaact
tagattgaagggcgtgtcatactccttgtgtactgcagcgttcacattcaccaagatcccggctgaaacactgcacgggacagtcacag
tggaggtacagtacgcagggacagatggaccttgcaaggttccagctcagatggcggtggacatgcaaactctgaccccagttgggagg
ttgataaccgctaaccccgtaatcactgaaagcactgagaactctaagatgatgctggaacttgatccaccatttgggactcttacat
tgtcataggagtcggggagaagaagatcacccaccactggcacaggagtggcagcaccattggaaaagcatttgaagccactgtgagag
gtgccaagagaatggcagtcttgggagacacagcctgggactttggatcagttggaggcgctctcaactcattgggcaagggcatccat
caaattttggagcagattcaaatcattgtttggaggaatgtcctggttctcacaaattctcattggaacgttgctgatgtggttgggt
ctgaacacaaagaatggatctatttcccttatgtgcttggccttaggggagtgttgatcttcttatccacagccgtctctgctgatgt
ggggtgctcggtggacttctcaaagaaggagacgagatgcggtacaggggtgttcgtctataacgacgttgaagcctggagggacaggt
acaagtaccatcctgactccccccgtagattggcagcagcagtcaagcaagcctgggaagatggtatctgcgggatctcctctgtttca
agaatggaaaacatcatgtggagatcagtagaaggggagctcaacgcaatcctggaagagaatggagttcaactgacggtcgttgtggg
atctgtaaaaaaccccatgtggagaggtccacagagattgcccgtgcctgtgaacgagctgccccacggctggaaggcttggggaaat
cgtatttcgtcagagcagcaaagacaaataacagattgtcgtggatggtgacacactgaaggaatgcccactcaaacatagagcatgga
acagattcttgtggaggatcatgggttcggggtatttcacactagtgtctggctcaaggttagagaagattattcattagagtgtgatc
cagccgttattggaacagctgttaaggaaaggaggctgtacacagtgatctaggctactggattgagagtgagaagaatgacacatgg
aggctgaagagggcccatctgatcgagatgaaaacatgtgaatggccaaagtcccacacattgtggacagatggaatagaagagagtga
tctgatcatacccagtctttagctgggccactcagccatcacaataccagagagggctacaggacccaaatgaagggccatggcaca
gtgaagaActtgaaattcggtttgaggaatgcccaggcactaaggtccacgtggaggaaacatgtggaacaagaggaccatctctgaga
tcaaccactgcaagcggaagggtgatcgaggaatggtgctgcaggagtgcacaatgcccccactgtcgttccgggctaaagatggctg
ttggtatggaatggagataaggcccaggaaagaaccagaaagcaacttagtaaggtcaatggtgactgcaggatcaactgatcacatgg -continued

```
accacttctcccttggagtgcttgtgatcctgctcatggtgcaggaagggctgaagaagagaatgaccacaaagatcatcataagcaca tcaatggcagtgctggtagctatgatcctggaggattttcaatgagtgacctggctaagcttgcaattttgatgggtgccaccttcgc ggaaatgaacactggaggagatgtagctcatctggcgctgatagcggcattcaaagtcagaccagcgttgctggtatattcatcttcag agctaattggacaccccgtgaaagcatgctgctggccttggcctcgtgtatttgcaaactgcgatctccgccttggaaggcgacctgat ggttctcatcaatggttttgattggcctggttggcaatacgagcgatggttgttccacgcactgataacatccccttggcaatcctggc tgctctgacaccactggcccggggcacactgcttgtggcgtggagagcaggccttgctacttgcgggggggtttatgctcctctctctga agggaaaaggcagtgtgaagaagaacttaccatttgtcatggccctgggactaaccgctgtgaggctggtcgacccatcaacgtggtg ggactgctgttgctcacaaggagtgggaagcggagctggcccccctagcgaagtactcacagctgttggcctgatatgcgcattggctgg agggttcgccaaggcagatatagagatggctgggcccatggccgcggtcggtctgctaattgtcagttacgtggtGtcaggaaagagtg tggacatgtacattgaaagagcaggAgacatcacatgggaaaaagatgcggaagtcactggaaacagtcccggctcgatgtggcgcta gatgagagtggtgatttctccctggtggaggatgacggtcccccatgagagagatcatactcaaggtggtcctgatgaccatctgtgg catgaacccaatagccataccattgcagctggagcgtggtacgtatacgtgaagactggaaaaaggagtggtgctctatgggatgtgcc tgctcccaaggaagtaaaaaaggggggaAaccacagatggagtgtacagagtaatgactcgtagactgctaggttcaacacaagttggag tgggagttatgcaagagggggtattcacactatgtggcacgtcacaaaaggatccgcgctgagaagcggtgaagggagacttgatccat actggggagatgtcaagcaggatctggtgtcatactgtggtccatggaagctagatgccgcctgggatgggcacagcgaggtgcagctc ttggccgtgcccccggagagagagcgaggaacatccagactctgcccggaatatttaagacaaaggatggggacattggagcggttgc gctggattacccagcaggaacttcaggatctccaatcctagacaagtgtgggagagtgataggactttatggcaatggggtcgtgatca aaaacgggagttatgttagtgccatcacccaaggggaggggggaggaagagactcctgttgagtgcttcgagccctcgatgctgaagaag aagcagctaactgtcttagacttgcatcctggagctgggaaaaccaggagagttcttcctgaaatagtccgtgaagccataaaaacaag actccgtactgtgatcttagctccaaccagggttgtcgctgctgaaatggaggaggcccttagagggcttccagtgcgttatatgacaa cagcagtcaatgtcaccccactctggaacagaaatcgtcgacttaatgtgccatgccaccttcacttcacgtctactacagccaatcaga gtccccaactataatctgtatattatggatgaggcccacttcacagatccctcaagtatagcagcaagaggatacatttcaacaagggt tgagatgggcgaggcggctgccatcttcatgaccgccacgccaccaggaacccgtgacgcatttccggactccaactcaccaattatgg acaccgaagtggaagtcccagagagagcctggagctcaggattgattgggtgacggatcattctggaaaaacagtttggtttgttccaa gcgtgaggaacggcaatgagatcgcagcttgtctgacaaaggctggaaaacgggtcatacagctcagcagaaagacttttgagacagag ttccagaaaacaaaacatcaagagtgggactttgtcgtgacaactgacatttcagagatgggcgccaactttaaagctgaccgtgtcat agattccaggagatgcctaaagccggtcatacttgatggcgagagagtcattctggctggacccatgcctgtcacacatgccagcgctg cccagaggaggggggcgcataggcaggaatcccaacaaacctggagatgagtatctgtatggaggtgggtgcgcagagactgacgaagac catgcacactggcttgaagcaagaatgctccttgacaatatttacctccaagatggcctcatagcctcgctctatcgacctgaggccga caaagtagcagccattgagggagagttcaagcttaggacggagcaaggaagacctttgtggaactcatgaaaagaggagatcttcctg tttggctggcctatcaggttgcatctgccggaataacctacacagatagaagatggtgattgatggcacgaccaacaacaccataatgg aagacagtgtgccggcagaggtgtggaccagacacggagagaaaagagtgctcaaaccgaggtggatggacgccagagtttgttcagat catgcggccctgaagtcattcaaggagtttgccgctgggaaaagaggagcggcttttggagtgatggaagccctgggaacactgccagg acacatgacagagagattccaggaagccattgacaacctcgctgtgctcatgcgggcagagactggaagcaggccttacaaagccgcgg cggcccaattgccggagacActagagacAataatgcttttgggttgctgggaacagtctcgctgggaatcttcttcgtcttgatgagg aacaagggcatagggaagatgggattggaatggtgactcttggggccagcgcatggctcatgtggctctcggaaattgagccagccaga attgcatgtgtcctcattgttgtgttcctattgctggtggtgctcatacctgagccagaaaagcaaagatctccccaggacaaccaaat ggcaatcatcatcatggtagcagtaggtcttctgggcttgattaccgccaatgaactcggatggttggagagaacaaagagtgacctaa gccatctaatgggaaggagagaggaggggggcaaccataggattctcaatggacattgacctgcggcagcctcagcttgggccatctat gctgccttgacaactttcattaccccagccgtccaacatgcagtgaccacctcatacaacaactactccttaatggcgatggccacgca
```

-continued agctggagtgttgtttggcatgggcaaagggatgccattctacgcatgggactttggagtcccgctgctaatgataggttgctactcac
aattaacacccctgaccctaatagtggccatcattttgctcgtggcgcactacatgtacttgatcccagggctgcaggcagcagctgcg
cgtgctgcccagaagagaacggcagctggcatcatgaagaaccctgttgtggatggaatagtggtgactgacattgacacaatgacaat
tgaccccaagtggagaaaaagatgggacaggtgctactcatagcagtagccgtctccagcgccatactgtcgcggaccgcctgggggt
gggggaggctgggctctgatcacagccgcaacttccactttgtgggaaggctctccgaacaagtactggaactcctctacagccact
tcactgtgtaacattttagggaagttacttggctggagcttctctaatctacacagtaacaagaaacgctggcttggtcaagacg
tgggggtggaacaggagaAaccctgggagagaaatggaaggcccgcttgaaccagatgtcggccctggagttctactcctacaaaagt
caggcatcaccgaggtgtgcagagaagaggcccgccgcgccctcaaggacggtgtggcaacgggaggccatgctgtgtcccgaggaagt
gcaaagctgagatggttggtggagcgggatacctgcagccctatggaaaggtcattgatcttggatgtggcagaggggctggagtta
ctacgCcgccaccatccgcaaagttcaagaagtgaaaggatacacaaaaggaggccctggtcatgaagaacccgtgttggtgcaaagct
atgggtggaacatagtccgtcttaagagtggggtggacgtattcatatggcggctgagccgtgtgacacgttgctgtgtgacataggtg
agtcatcatctagtcctgaagtggaagaagcacggacgctcagagtcctctccatggtggggattggcttgaaaaaagaccaggagcc
ttttgtataaaagtgttgtgcccatacaccagcactatgatggaaacctggagcgactgcagcgtaggtatgggggaggactggtcag
agtgccactctcccgcaactctacacatgagatgtactgggtGtctggagcgaaaagcaacaccataaaaagtgtgtccaccacgagcc
agctcctcttggggcgcatggacgggcctaggaggccagtgaaatatgaggaggatgtgaatctcggctctggcacgcgggctgtggta
agctgcgctgaagctcccaacatgaagatcattggtaaccgcattgaaaggatccgcagtgagcacgcggaaacgtggttattgacgag
aaccacccatataggacatgggcttaccatggaagctatgaggcccccacacaagggtcagcgtcctctctaataaacggggttgtcag
gctcctgtcaaaaccctgggatgtggtgactggagtcacaggaatagccatgaccgacaccacaccgtatggtcagcaaagagttttca
aggaaaaagtggacactagggtgccagacccccaagaaggcactcgtcaggttatgagcatggtGtcttcctggttgtggaaagagcta
ggcaaacacaaacggccacgagtctgcaccaaagaagagttcatcaacaaggttcgtagcaatgcagcattagggcaatatttgaaga
ggaaaaagagtggaagactgcagtggaagctgtgaacgatccaaggtctgggctctagtggacaaggaaagagagcaccacctgagag
gagagtgccagagctgtgtgtacaacatgatgggaaaaagagaaaagaaacaaggggaatttggaaaggccaagggcagccgcgccatc
tggtatatgtggctaggggctagatttctagagttcgaagcccttggattcttgaacgaggatcactggatggggagagagaactcagg
aggtggtgttgaagggctgggattacaaagactcggatatgtcctagaagagatgagtcgtataccaggaggaaggatgtatgcagatg
acactgctggctgggacacccgcattagcaggtttgatctggagaatgaagctctaatcaccaaccaaatggagaaagggcacagggcc
ttggcattggccataatcaagtacacataccaaaacaaagtggtaaaggtccttagaccagctgaaaagggaaaacagttatggacat
tatttcgagacaagaccaaaggggagcggacaagttgtcacttacgctcttaacacatttaccaacctagtggtgcaactcattcgga
atatggaggctgaggaagttctagagatgcaagacttgtggctgctgcggaggtcagagaaagtgaccaactggttgcagagcaacgga
tgggataggctcaaacgaatggcagtcagtggagatgattgcgttgtgaagccaattgatgataggtttgcacatgccctcaggttctt
gaatgatatgggaaaagttaggaaggacacacaagagtggaaaccctcaactggatgggacaactgggaagaagttccgttttgctccc
accacttcaacaagctccatctcaaggacgggaggtccattgtggttccctgccgccaccaagatgaactgattggccgggcccgcgtc
tctccaggggcgggatggagcatccgggagactgcttgcctagcaaaatcatatgcgcaaatgtggcagctcctttatttccacagaag
ggacctccgactgatggccaatgccatttgttcatctgtgccagttgactgggttccaactgggagaactacctggtcaatccatggaa
agggagaatggatgaccactgaagacatgcttgtggtgtggaacagagtgtggattgaggagaacgaccacatggaagacaagacccca
gttacgaaatggacagacattccctatttgggaaaaagggaagacttgtggtgtggatctctcatagggcacagaccgcgcaccacctg
ggctgagaacattaaaaacacagtcaacatggtgcgcaggatcataggtgatgaagaaaagtacatggactacctatccacccaagttc
gctacttgggtgaagaagggtctacacctggagtgctgtaagcaccaatcttaatgttgtcaggcctgctagtcagccacagcttgggg
aaagctgtgcagcctgtgaccccccaggagaagctgggaaaccaagcctatagtcaggccgagaacgccatggcacggaagaagccat -continued gctgcctgtgagcccctcagaggacactgagtcaaaaaaccccacgcgcttggaggcgcaggatgggaaaagaaggtggcgaccttccc caccttcaatctggggcctgaactggagatcagctgtggatctccagaagagggactagtggttagaggaGACCCCCCGGAAAACGCA AAACAGCATATTGACGCTGGGAAAGACCAGAGACTCCATGAGTTTCCaccacgctggccgccaggcacagatcgccgaacagcggcggc cggtgtggggaaatccatggtttct PR15 E-Min

SEQ ID NO: 2

AGTTGTTGATCTGTGTGAATCAGACTGCGACAGTTCGAGTTTGAAGCGAAAGCTAGCAACAGTATCAACAGGTTTTATTTTGGATTTGG

AAACGAGAGTTTCTGGTCATGAAAAACCCAAAAAAGAAATCCGGAGGATTCCGGATTGTCAATATGCTAAAACGCGGAGTAGCCCGTGT

GAGCCCCTTTGGGGGCTTGAAGAGGCTGCCAGCCGGACTTCTGCTGGGTCATGGGCCCATCAGGATGGTCTTGGCGATTCTAGCCTTTT

TGAGATTCACGGCAATCAAGCCATCACTGGGTCTCATCAATAGATGGGGTTCAGTGGGGAAAAAAGAGGCTATGGAAATAATAAAGAAG

TTCAAGAAAGATCTGGCTGCCATGCTGAGAATAATCAATGCTAGGAAGGAGAAGAAGAGACGAGGCGCAGATACTAGTGTCGGAATTGT

TGGCCTCCTGCTGACCACAGCTATGGCAGCCGAAGTGACTAGACGCGGATCCGCTTACTATATGTATCTCGATAGAAACGACGCTGGCG

AAGCGATAAGCTTTCCGACTACACTCGGTATGAATAAGTGTTACATACAGATTATGGACTTAGGGCATATGTGCGACGCTACTATGTCA

TACGAATGCCCTATGCTTGACGAGGGAGTCGAACCAGACGACGTCGATTGTTGGTGCAATACGACTAGCACTTGGGTCGTTTACGGTAC

ATGCCATCACAAAAAGGGCGAAGCTAGACGGTCTAGACGCGCAGTGACACTGCCTAGTCACTCTACGAGAAAGTTGCAGACTAGGTCAC

AGACATGGTTGGAGTCTAGAGAGTACACTAAGCATCTGATTAGGGTCGAGAATTGGATTTTTAGAAACCCAGGGTTCGCACTAGCCGCA

GCCGCAATCGCATGGTTGTTGGGGTCTAGCACTAGCCAAAAAGTGATATATCTGGTTATGATACTGTTGATCGCTCCCGCATACTCTAT

TAGGTGCATAGGCGTTAGCAATAGGGACTTTGTCGAGGGAATGTCCGGGGGGACATGGGTCGACGTCGTGCTTGAGCACGGGGGGTGCG

TTACGGTTATGGCACAAGACAAACCGACAGTCGACATAGAGTTGGTTACGACTACAGTGAGTAATATGGCTGAGGTTAGGTCATACTGT

TACGAAGCGTCAATTAGCGATATGGCTAGCGATAGTAGGTGTCCGACACAGGGCGAAGCATACTTAGACAAACAATCCGATACGCAATA

CGTATGCAAACGGACTCTGGTCGATAGGGGGTGGGGTAACGGATGCGGATTGTTCGGTAAGGGGTCACTGGTTACATGCGCTAAATTCG

CATGCTCTAAAAAAATGACCGGTAAGTCAATCCAACCCGAAAACCTTGAGTATAGGATTATGCTTAGCGTACACGGATCCCAACACTCC

GGTATGATCGTTAACGATACCGGACACGAAACCGACGAGAATAGGGCTAAGGTCGAGATTACGCCTAACTCCCCTAGAGCCGAAGCGAC

ATTGGGCGGATTCGGATCACTGGGACTGGATTGCGAACCGAGAACCGGATTGGACTTTAGCGATCTGTATTACTTGACTATGAACAATA

AGCATTGGTTGGTGCACAAAGAGTGGTTTCACGACATACCGTTGCCATGGCACGCCGGAGCCGATACCGGAACGCCACATTGGAATAAC

AAAGAGGCATTGGTCGAGTTTAAGGACGCTCACGCTAAACGGCAAACCGTAGTCGTGTTAGGGTCACAGGAGGGAGCCGTACACACCGC

ATTGGCCGGCGCACTCGAAGCCGAAATGGACGGAGCTAAGGGGAGACTGTCTAGCGGACACCTTAAGTGTAGACTGAAAATGGACAAAC

TGAGACTTAAGGGAGTGTCATACTCACTGTGTACTGCCGCATTTACGTTTACGAAGATACCGCCGAAACATTGCACGGAACCGTTACA

GTCGAAGTGCAATACGCCGGAACCGACGGACCATGTAAGGTGCCAGCGCAAATGGCAGTCGATATGCAAACACTGACACCAGTCGGTAG

ACTGATTACCGCTAACCCAGTGATAACCGAATCCACTGAGAATTCGAAAATGATGCTTGAGCTTGACCCACCATTCGGCGATAGCTATA

TCGTTATCGGAGTCGGCGAAAAAAAGATTACACACCATTGGCATAGATCCGGATCTACAATCGGTAAGGCATTCGAAGCTACCGTTAGG

GGCGCTAAGCGTATGGCCGTATTGGGCGATACCGCTTGGGATTTCGGATCCGTCGGAGGCGCACTGAATTCCCTAGGTAAGGGGATACA

CCAAATATTCGGCGCAGCGTTTAAGTCATTGTTCGGAGGGATGTCATGGTTTAGTCAGATACTGATCGGAACATTGCTTATGTGGTTAG

GGTTGAACACTAAGAACGGATCAATCTCATTGATGTGTCTTGCGTTAGGGGGGGTGTTGATCTTTCTGTCAACCGCCGTTAGCGCAGAT

GTGGGGTGCTCGGTGGACTTCTCAAAGAAGGAGACGAGATGCGGTACAGGGGTGTTCGTCTATAACGACGTTGAAGCCTGGAGGGACAG

GTACAAGTACCATCCTGACTCCCCCCGTAGATTGGCAGCAGCAGTCAAGCAAGCCTGGGAAGATGGTATCTGCGGGATCTCCTCTGTTT

CAAGAATGGAAAACATCATGTGGAGATCAGTAGAAGGGGAGCTCAACGCAATCCTGGAAGAGAATGGAGTTCAACTGACGGTCGTTGTG

GGATCTGTAAAAAACCCCATGTGGAGAGGTCCACAGAGATTGCCCGTGCCTGTGAACGAGCTGCCCCACGGCTGGAAGGCTTGGGGGAA

ATCGTATTTCGTCAGAGCAGCAAAGACAAATAACAGCTTTGTCGTGGATGGTGACACACTGAAGGAATGCCCACTCAAACATAGAGCAT

GGAACAGCTTTCTTGTGGAGGATCATGGGTTCGGGTATTTCACACTAGTGTCTGGCTCAAGGTTAGAGAAGATTATTCATTAGAGTGT

GATCCAGCCGTTATTGGAACAGCTGTTAAGGGAAAGGAGGCTGTACACAGTGATCTAGGCTACTGGATTGAGAGTGAGAAGAATGACAC

ATGGAGGCTGAAGAGGGCCCATCTGATCGAGATGAAAACATGTGAATGGCCAAAGTCCCACACATTGTGGACAGATGGAATAGAAGAGA

-continued

```
GTGATCTGATCATACCCAAGTCTTTAGCTGGGCCACTCAGCCATCACAATACCAGAGAGGGCTACAGGACCCAAATGAAAGGGCCATGG

CACAGTGAAGAACTTGAAATTCGGTTTGAGGAATGCCCAGGCACTAAGGTCCACGTGGAGGAAACATGTGGAACAAGAGGACCATCTCT

GAGATCAACCACTGCAAGCGGAAGGGTGATCGAGGAATGGTGCTGCAGGGAGTGCACAATGCCCCCACTGTCGTTCCGGGCTAAAGATG

GCTGTTGGTATGGAATGGAGATAAGGCCCAGGAAAGAACCAGAAAGCAACTTAGTAAGGTCAATGGTGACTGCAGGATCAACTGATCAC

ATGGACCACTTCTCCCTTGGAGTGCTTGTGATCCTGctcatggtgcaggaagggctgaagaagagaatgaccacaaagatcatcataag cacatcaatggcagtgctggtagctatgatcctggaggattttcaatgagtgacctggctaagcttgcaattttgatgggtgccacct tcgcggaaatgaacactggaggagatgtagctcatctggcgctgatagcggcattcaaagtcagaccagcgttgctggtatattcatct tcagagctaattggacaccccgtgaaagcatgctgctggccttggcctcgtgtatttgcaaactgcgatctccgccttggaaggcgacc tgatggttctcatcaatggttttgctttggcctggttggcaatacgagcgatggttgttccacgcactgataacatcaccttggcaatc ctggctgctctgacaccactggcccggggcacactgcttgtggcgtggagagcaggccttgctacttgcgggggggtttatgctcctctc tctgaagggaaaaggcagtgtgaagaagaacttaccatttgtcatggccctgggactaaccgctgtgaggctggtcgaccccatcaacg tggtgggactgctgttgctcacaaggagtgggaagcggagctggcccccctagcgaagtactcacagctgttggcctgatatgcgcattg gctggagggttcgccaaggcagatatagagatggctgggcccatggccgcggtcggtctgctaattgtcagttacgtggtGtcaggaaa gagtgtggacatgtacattgaaagagcaggAgacatcacatgggaaaaagatgcggaagtcactggaaacagtccccggctcgatgtgg cgctagatgagagtggtgatttctccctggtggaggatgacggtcccccatgagagagatcatactcaaggtggtcctgatgaccatc tgtggcatgaacccaatagccataccattgcagctggagcgtggtacgtatacgtgaagactggaaaaaggagtggtgctctatgggat gtgcctgctcccaaggaagtaaaaaaggggggaAaccacagatggagtgtacagagtaatgactcgtagactgctaggttcaacacaagt tggagtgggagttatgcaagagggggtattcacactatgtggcacgtcacaaaaggatccgcgctgagaagcggtgaagggagacttga tccatactggggagatgtcaagcaggatctggtgtcatactgtggtccatggaagctagatgccgcctgggatgggcacagcgaggtgc agctcttggccgtgccccccggagagagagcgaggaacatccagactctgcccggaatatttaagacaaaggatggggacattggagcg gttgcgctggattacccagcaggaacttcaggatctccaatcctagacaagtgtgggagagtgataggactttatggcaatgggtcgt gatcaaaaacgggagttatgttagtgccatcacccaagggaggagggaggaagagactcctgttgagtgcttcgagccctcgatgctga agaagaagcagctaactgtcttagacttgcatcctggagctgggaaaaccaggagagttcttcctgaaatagtccgtgaagccataaaa acaagactccgtactgtgatcttagctccaaccagggttgtcgctgctgaaatggaggaggcccttagagggcttccagtgcgttatat gacaacagcagtcaatgtcacccactctggaacagaaatcgtcgacttaatgtgccatgccaccttcacttcacgtctactacagccaa tcagagtccccaactataatctgtatattatggatgaggcccacttcacagatccctcaagtatagcagcaagaggatacatttcaaca agggttgagatgggcgaggcggctgccatcttcatgaccgccacgccaccaggaacccgtgacgcatttccggactccaactcaccaat tatggacaccgaagtggaagtcccagagagagcctggagctcaggattgattgggtgacggatcattctggaaaaacagtttggtttgt tccaagcgtgaggaacggcaatgagatcgcagcttgtctgacaaaggctggaaaacgggtcatacagctcagcagaaagacttttgaga cagagttccagaaaacaaaacatcaagagtgggactttgtcgtgacaactgacatttcagagatgggcgccaactttaaagctgaccgt gtcatagattccaggagatgcctaaagccggtcatacttgatggcgagagagtcattctggctggacccatgcctgtcacacatgccag cgctgcccagaggaggggcgcataggcaggaatcccaacaaacctggagatgagtatctgtatggaggtgggtgcgcagagactgacg aagaccatgcacactggcttgaagcaagaatgctccttgacaatatttacctccaagatggcctcatagcctcgctctatcgacctgag gccgacaaagtagcagccattgagggagagttcaagcttaggacggagcaaaggaagacctttgtggaactcatgaaaagaggagatct tcagtttggctggcctatcaggttgcatctgccggaataacctacacagatagaagatggtgattgatggcacgaccaacaacaccata atggaagacagtgtgccggcagaggtgtggaccagacacggagagaaaagagtgctcaaaccgaggtggatggacgccagagtttgttc agatcatgcggccctgaagtcattcaaggagtttgccgctgggaaaagaggagcggcttttggagtgatggaagccctgggaacactgc caggacacatgacagagagattccaggaagccattgacaacctcgctgtgctcatgcgggcagagactggaagcaggccttacaaagcc gcggcggcccaattgccggagacActagagacAataatgctttttggggttgctgggaacagtctcgctgggaatcttcttcgtcttgat gaggaacaagggcatagggaagatgggattggaatggtgactcttggggccagcgcatggctcatgtggctctcggaaattgagccagc
```

```
cagaattgcatgtgtcctcattgttgtgttcctattgctggtggtgctcatacctgagccagaaaagcaaagatctccccaggacaacc
aaatggcaatcatcatcatggtagcagtaggtcttctgggcttgattaccgccaatgaactcggatggttggagagaacaaagagtgac
ctaagccatctaatgggaaggagagaggaggggggcaaccataggattctcaatggacattgacctgcggccagcctcagcttgggccat
ctatgctgccttgacaactttcattacccccagccgtccaacatgcagtgaccacctcatacaacaactactccttaatggcgatggcca
cgcaagctggagtgttgtttggcatgggcaaagggatgccattctacgcatgggactttggagtcccgctgctaatgataggttgctac
tcacaattaacaccctgaccctaatagtggccatcattttgctcgtggcgcactacatgtacttgatcccagggctgcaggcagcagc
tgcgcgtgctgcccagaagagaacggcagctggcatcatgaagaaccctgttgtggatggaatagtggtgactgacattgacacaatga
caattgaccccaagtggagaaaaagatgggacaggtgctactcatagcagtagccgtctccagcgccatactgtcgcggaccgcctgg
gggtgggggaggctggggctctgatcacagccgcaacttccactttgtgggaaggctctccgaacaagtactggaactcctctacagc
cacttcactgtgtaacattttagggaagttacttggctggagcttctctaatctacacagtaacaagaaacgctggcttggtcaaga
gacgtgggggtggaacaggagaAaccctgggagagaaatggaaggcccgcttgaaccagatgtcggccctggagttctactcctacaaa
aagtcaggcatcaccgaggtgtgcagagaagaggcccgccgcgccctcaaggacggtgtggcaacgggaggccatgctgtgtcccgagg
aagtgcaaagctgagatggttggtggagcgggatacctgcagccctatggaaaggtcattgatcttggatgtggcagaggggctgga
gttactacgCcgccaccatccgcaaagttcaagaagtgaaaggatacacaaaaggaggccctggtcatgaagaacccgtgttggtgcaa
agctatgggtggaacatagtccgtcttaagagtggggtggacgtattcatatggcggctgagccgtgtgacacgttgctgtgtgacata
ggtgagtcatcatctagtcctgaagtggaagaagcacggacgctcagagtcctctccatggtgggggattggcttgaaaaaagaccagg
agccttttgtataaaagtgttgtgcccatacaccagcactatgatggaaaccctggagcgactgcagcgtaggtatggggggaggactgg
tcagagtgccactctcccgcaactctacacatgagatgtactgggGtctggagcgaaaagcaacaccataaaaagtgtgtccaccacg
agccagctcctcttggggcgcatggacgggcctaggaggccagtgaaatatgaggaggatgtgaatctcggctctggcacgcgggctgt
ggtaagctgcgctgaagctcccaacatgaagatcattggtaaccgcattgaaaggatccgcagtgagcacgcggaaacgtggttattga
cgagaaccacccatataggacatgggcttaccatggaagctatgaggcccccacacaagggtcagcgtcctctctaataaacgggttg
tcaggctcctgtcaaaaccctgggatgtggtgactggagtcacaggaatagccatgaccgacaccacaccgtatggtcagcaaagagtt
ttcaaggaaaaagtggacactagggtgccagaccccaagaaggcactcgtcaggttatgagcatggtGtcttcctggttgtggaaaga
gctaggcaaacacaaacggccacgagtctgcaccaaagaagagttcatcaacaaggttcgtagcaatgcagcattaggggcaatatttg
aagaggaaaaagagtggaagactgcagtggaagctgtgaacgatccaaggttctgggctctagtggacaaggaaagagagcaccacctg
agaggagagtgccagagctgtgtgtacaacatgatgggaaaaagagaaaagaaacaaggggaatttggaaaggccaagggcagccgcgc
catctggtatatgtggctaggggctagatttctagagttcgaagcccttggattcttgaacgaggatcactggatggggagagagaact
caggaggtggtgttgaagggctgggattacaaagactcggatatgtcctagaagagatgagtcgtataccaggaggaaggatgtatgca
gatgacactgctggctgggacacccgcattagcaggtttgatctggagaatgaagctctaatcaccaaccaaatggagaaagggcacag
ggccttggcattggccataatcaagtacacataccaaaacaaagtggtaaaggtccttagaccagctgaaaaagggaaaacagttatgg
acattatttcgagacaagaccaaaggggggagcggacaagttgtcacttacgctcttaacacatttaccaacctagtggtgcaactcatt
cggaatatggaggctgaggaagttctagagatgcaagacttgtggctgctgcggaggtcagagaaagtgaccaactggttgcagagcaa
cggatgggataggctcaaacgaatggcagtcagtggagatgattgcgttgtgaagccaattgatgataggtttgcacatgccctcagt
tcttgaatgatatgggaaaagttaggaaggacacacaagagtggaaaccctcaactggatgggacaactgggaagaagttccgttttgc
tcccaccacttcaacaagctccatctcaaggacggggaggtccattgtggttccctgccgccaccaagatgaactgattggccgggccg
cgtctctccaggggcgggatggagcatccgggagactgcttgcctagcaaaatcatatgcgcaaatgtggcagctcctttatttccaca
gaagggacctccgactgatggccaatgccatttgttcatctgtgccagttgactgggttccaactgggagaactacctggtcaatccat
ggaaaggagaatggatgaccactgaagacatgcttgtggtgtgaacagagtgtggattgaggagaacgaccacatggaagacaagac
cccagttacgaaatggacagacattccctatttggaaaaagggaagacttgtggtgtggatctctcatagggcacagaccgcgcacca
cctgggctgagaacattaaaaacacagtcaacatggtgcgcaggatcataggtgatgaagaaaagtacatggactacctatccacccaa
gttcgctacttgggtgaagaagggtctacacctggagtgctgtaagcaccaatcttaatgttgtcaggcctgctagtcagccacagctt
```

-continued ggggaaagctgtgcagcctgtgacccccccaggagaagctgggaaaccaagcctatagtcaggccgagaacgccatggcacggaagaag ccatgctgcctgtgagcccctcagaggacactgagtcaaaaaaccccacgcgcttggaggcgcaggatgggaaaagaaggtggcgacct tccccacccttcaatctggggcctgaactggagatcagctgtggatctccagaagagggactagtggttagaggaGACCCCCCGGAAAA CGCAAAACAGCATATTGACGCTGGGAAAGACCAGAGACTCCATGAGTTTCCaccacgctggccgccaggcacagatcgccgaacagcgg cggccggtgtggggaaatccaTggtttct PR15 NS3-Min

SEQ ID NO: 3

Agttgttgatctgtgtgaatcagactgcgacagttcgagtttgaagcgaaagctagcaacagtatcaacaggttttattttggatttgg aaacgagagtttctggtcatgaaaaacccaaaaaagaaatccggaggattccggattgtcaatatgctaaaacgcggagtagcccgtgt gagccccttggggcttgaagaggctgccagccggacttctgctgggtcatgggcccatcaggatggtcttggcgattctagccttttt tgagattcacggcaatcaagccatcactgggtctcatcaatagatggggttcagtggggaaaaaagaggctatgaaaTaataaagaag ttcaagaaagatctggctgccatgctgagaataatcaatgctaggaaggagaagaagagacgaggcgcagatactagtgtcggaattgt tggcctcctgctgaccacagctatggcagcggaggtcactagacgtgggagtgcatactatatgtacttggacagaaacgatgctgggg aggccatatcttttccaaccacattggggatgaataagtgttatatacagatcatggatcttggacacatgtgtgatgccaccatgagc tatgaatgccctatgctggatgaggggtggaaccagatgacgtcgattgttggtgcaacacgacgtcaacttgggtgtgtacggaac ctgccatcacaaaaaggtgaagcacggagatctagaagGctgtgacgctcccctcccattccaccaggaagctgcaaacgcggtcgc aaacctggttggaatcaagagaatacacaaagcacttgattagagtcgaaaattggatattcaggaaccctggcttcgcgttagcagca gctgccatcgcttggcttttgggaagctcaacgagccaaaaagtcatatacttggtcatgatactgctgattgccccggcatacagcat caggtgcataggagtcagcaatagggactttgtggaaggtatgtcaggtgggacttgggttgatgttgtcttggaacatggaggttgtg tcaccgtaatggcacaggacaaaccgactgtcgacatagagctggttacaacaacagtcagcaacatggcggaggtaagatcctactgc tatgaggcatcaatatcagacatggcttctgacagccgctgcccaacacaaggtgaagcctaccttgacaagcaatcagacactcaata tgtctgcaaaagaacgttagtggacagaggctggggaaatggatgtggacttttttggcaaagggagcctggtgacatgcgctaagtttg catgctccaagaaaatgaccggCaagagcatccagccagagaatctggagtaccggataatgctgtcagttcatggctcccagcacagt gggatgatcgttaatgacacaggacatgaaactgatgagaatagagcgaaagttgagataacgcccaattcaccgagagccgaagccac cctgggggttttggaagcctaggacttgattgtgaaccgaggacaggccttgacttttcagatttgtattacttgactatgaataaca agcactggttggttcacaaggagtggttccacgacattccattaccttggcacgctggggcagacaccggaactccacactggaacaac aaagaagcactggtagagttcaaggacgcacatgccaaaaggcaaactgtcgtggttctagggagtcaagaaggagcagttcacacggc ccttgctggagctctgtgaggctgagatggatggtgcaaagggaaggctgtcctctggccacttgaaatgtcgcctgaaaatggataaac ttagattgaagggcgtgtcatactccttgtgtactgcagcgttcacattcaccaagatcccggctgaaacactgcacgggacagtcaca gtggaggtacagtacgcagggacagatggaccttgcaaggttccagctcagatggcggtggacatgcaaactctgaccccagttgggag gttgataaccgctaaccccgtaatcactgaaagcactgagaactctaagatgatgctggaacttgatccaccatttgggactcttaca ttgtcataggagtcggggagaagaagatcaccccaccactggcacaggagtggcagcaccattggaaaagcatttgaagccactgtgaga ggtgccaagagaatggcagtcttgggagacacagcctgggactttggatcagttggaggcgctctcaactcattgggcaagggcatcca tcaaattttttggagcagctttcaaatcattgtttggaggaatgtcctggttctcacaaattctcattggaacgttgctgatgtggttgg gtctgaacacaaagaatggatctatttcccttatgtgcttggccttagggggagtgttgatcttcttatccacagccgtctctgctgat gtggggtgctcggtggacttctcaaagaaggagacgagatgcggtacaggggtgttcgtctataacgacgttgaagcctggagggacag gtacaagtaccatcctgactcccccgtagattggcagcagcagtcaagcaagcctgggaagatggtatctgcgggatctcctctgtttt caagaatggaaaacatcatgtggagatcagtagaaggggagctcaacgcaatcctggaagagaatggagttcaactgacggtcgttgtg ggatctgtaaaaaacccatgtggagaggtccacagagattgcccgtgcctgtgaacgagctgccccacggctggaaggcttggggaa atcgtatttcgtcagagcagcaaagacaaataacagattgtcgtggatggtgacacactgaaggaatgcccactcaaacatagagcatg gaacagattcttgtggaggatcatgggttcggggtatttcacactagtgtctggctcaaggttagagaagattattcattagagtgtga -continued

```
tCCAGCCGTTATTGGAACAGCTGTTAAGGGAAAGGAGGCTGTACACAGTGATCTAGGCTACTGGATTGAGAGTGAGAAGAATGACACAT

GGAGGCTGAAGAGGGCCCATCTGATCGAGATGAAAACATGTGAATGGCCAAAGTCCCACACATTGTGGACAGATGGAATAGAAGAGAGT

GATCTGATCATACCCAAGTCTTTAGCTGGGCCACTCAGCCATCACAATACCAGAGAGGGCTACAGGACCCAAATGAAAGGGCCATGGCA

CAGTGAAGAACTTGAAATTCGGTTTGAGGAATGCCCAGGCACTAAGGTCCACGTGGAGGAAACATGTGGAACAAGAGGACCATCTCTGA

GATCAACCACTGCAAGCGGAAGGGTGATCGAGGAATGGTGCTGCAGGGAGTGCACAATGCCCCCACTGTCGTTCCGGGCTAAAGATGGC

TGTTGGTATGGAATGGAGATAAGGCCCAGGAAAGAACCAGAAAGCAACTTAGTAAGGTCAATGGTGACTGCAGGATCAACTGATCACAT

GGACCACTTCTCCCTTGGAGTGCTTGTGATCCTGCTCATGGTGCAGGAAGGGCTGAAGAAGAGAATGACCACAAAGATCATCATAAGCA

CATCAATGGCAGTGCTGGTAGCTATGATCCTGGGAGGATTTTCAATGAGTGACCTGGCTAAGCTTGCAATTTTGATGGGTGCCACCTTC

GCGGAAATGAACACTGGAGGAGATGTAGCTCATCTGGCGCTGATAGCGGCATTCAAAGTCAGACCAGCGTTGCTGGTATCTTTCATCTT

CAGAGCTAATTGGACACCCCGTGAAAGCATGCTGCTGGCCTTGGCCTCGTGTCTTTTGCAAACTGCGATCTCCGCCTTGGAAGGCGACC

TGATGGTTCTCATCAATGGTTTTGCTTTGGCCTGGTTGGCAATACGAGCGATGGTTGTTCCACGCACTGATAACATCACCTTGGCAATC

CTGGCTGCTCTGACACCACTGGCCCGGGGCACACTGCTTGTGGCGTGGAGAGCAGGCCTTGCTACTTGCGGGGGGTTTATGCTCCTCTC

TCTGAAGGGAAAAGGCAGTGTGAAGAAGAACTTACCATTTGTCATGGCCCTGGGACTAACCGCTGTGAGGCTGGTCGACCCCATCAACG

TGGTGGGACTGCTGTTGCTCACAAGGAGTGGGAAGCGGAGCTGGCCCCCTAGCGAAGTACTCACAGCTGTTGGCCTGATATGCGCATTG

GCTGGAGGGTTCGCCAAGGCAGATATAGAGATGGCTGGGCCCATGGCCGCGGTCGGTCTGCTAATTGTCAGTTACGTGGTGTCAGGAAA

GAGTGTGGACATGTACATTGAAAGAGCAGGAGACATCACATGGGAAAAAGATGCGGAAGTCACTGGAAACAGTCCCCGGCTCGATGTGG

CGCTAGATGAGAGTGGTGATTTCTCCCTGGTGGAGGATGACGGTCCCCCCATGAGAGAGATCATACTCAAGGTGGTCCTGATGACCATC

TGTGGCATGAACCCAATAGCCATACCCTTTGCAGCTGGAGCGTGGTACGTATACGTGAAGACTGGAAAAAGGTCAGGCGCACTATGGGA

CGTACCCGCACCTAAAGAGGTCAAAAAAGGCGAGACTACCGACGGAGTGTATAGAGTGATGACACGTAGACTGTTAGGGTCAACACAGG

TCGGAGTCGGCGTTATGCAGGAGGGAGTGTTTCATACAATGTGGCACGTTACGAAAGGGTCAGCGCTTAGGTCAGGCGAAGGGAGACTC

GATCCATATTGGGGGGACGTTAAGCAAGACCTAGTGTCATATTGCGGACCATGGAAACTCGACGCCGCATGGGACGGACACTCTGAGGT

CCAACTGTTAGCCGTACCACCCGGAGAGAGAGCGAGAAACATACAGACACTGCCAGGGATTTTTAAGACTAAGGACGGCGATATCGGAG

CCGTCGCACTCGATTACCCTGCCGGAACTAGCGGATCACCGATACTCGATAAATGCGGACGGGTTATCGGACTGTACGGAAACGGAGTC

GTTATCAAAAACGGATCATACGTTAGCGCTATTACACAGGGGCGTAGAGAGGAGGAGACACCAGTCGAGTGTTTCGAACCTAGTATGCT

TAAAAAAAAACAGTTGACCGTACTCGATCTGCATCCCGGAGCCGGTAAGACACGTAGAGTGTTGCCCGAGATAGTGAGAGAGGCTATTA

AGACTAGACTGAGAACCGTGATACTCGCACCTACTAGAGTCGTCGCCGCCGAAATGGAGGAGGCACTTAGGGGGTTACCCGTTAGGTAT

ATGACAACCGCCGTTAACGTTACGCATAGCGGAACCGAGATAGTCGATCTGATGTGTCACGCTACATTTACATCTAGACTACTGCAACC

GATTAGGGTGCCTAATTACAATCTGTATATAATGGACGAAGCGCATTTTACCGATCCGTCATCAATCGCCGCTAGGGGGTACATATCGA

CTAGGGTCGAGATGGGCGAAGCCGCCGCAATCTTTATGACCGCTACACCTCCCGGAACTAGAGACGCTTTTCCCGATTCGAATAGTCCA

ATTATGGATACCGAGGTCGAGGTCCCCGAACGCGCATGGTCATCCGGGTTCGATTGGGTTACCGATCATTCCGGTAAGACCGTTTGGTT

TGTGCCTAGCGTTAGGAACGGTAACGAGATAGCCGCATGCCTTACGAAAGCCGGTAAGAGAGTGATACAGCTATCTAGAAAGACATTCG

AAACCGAGTTTCAGAAAACTAAGCATCAGGAGTGGGATTTCGTCGTTACAACCGATATTAGCGAAATGGGCGCTAACTTTAAAGCCGAT

AGGGTGATCGATAGTAGGCGATGCCTTAAGCCAGTGATACTCGACGGAGAGAGAGTGATACTAGCCGGACCAATGCCAGTGACACACGC

TAGCGCTGCGCAACGTAGGGGGAGAATCGGACGTAATCCGAATAAGCCAGGCGACGAATACCTATACGGGGGGGGTGCGCCGAGACTG

ACGAGGATCACGCTCATTGGCTCGAAGCGAGAATGCTACTCGATAACATATATCTGCAAGACGGACTAATCGCTAGTCTGTATAGACCC

GAAGCCGATAAGGTCGCCGCAATCGAAGGCGAATTTAAGCTTAGAACCGAGCAACGTAAGACATTCGTCGAGCTTATGAAAAGGGGGA

TCTGCCAGTGTGGCTTGCGTATCAGGTCGCTAGTGCCGGAATTACATATACCGATAGGAGATGGTGTTTCGACGGAACAACTAACAATA

CGATTATGGAGGACTCAGTCCCAGCCGAAGTGTGGACTAGGCACGGAGAGAAAAGAGTGCTTAAGCCTAGATGGATGGACGCTAGGGTG

TGTTCCGATCACGCCGCACTTAAGTCTTTTAAAGAGTTCGCAGCCGGTAAGCGTGGAGCGGCTTTTGGAGTGATGGAAGCCCTGGGAAC

ACTGCCAGGACACATGACAGAGAGATTCCAGGAAGCCATTGACAACCTCGCTGTGCTCATGCGGGCAGAGACTGGAAGCAGGCCTTACA

AAGCCGCGGCGGCCCAATTGCCGGAGACACTAGAGACAATAATGCTTTTGGGGTTGCTGGGAACAGTCTCGCTGGGAATCTTCTTCGTC
```

-continued

```
TTGATGAGGAACAAGGGCATAGGGAAGATGGGCTTTGGAATGGTGACTCTTGGGGCCAGCGCATGGCTCATGTGGCTCTCGGAAATTGA
GCCAGCCAGAATTGCATGTGTCCTCATTGTTGTGTTCCTATTGCTGGTGGTGCTCATACCTGAGCCAGAAAAGCAAAGATCTCCCCAGG
ACAACCAAATGGCAATCATCATCATGGTAGCAGTAGGTCTTCTGGGCTTGATTACCGCCAATGAACTCGGATGGTTGGAGAGAACAAAG
AGTGACCTAAGCCATCtaatgggaaggagagaggaggggggcaaccataggattctcaatggacattgacctgcggccagcctcagcttg
ggccatctatgctgccttgacaactttcattaccccagccgtccaacatgcagtgaccacctcatacaacaactactccttaatggcga
tggccacgcaagctggagtgttgtttggcatgggcaaagggatgccattctacgcatgggactttggagtcccgctgctaatgatAggt
tgctactcacaattaacacccctgaccctaatagtggccatcattttgctcgtggcgcactacatgtacttgatcccagggctgcaggc
agcagctgcgcgtgctgcccagaagagaacggcagctggcatcatgaagaaccctgttgtggatggaatagtggtgactgacattgaca
caatgacaattgaccccaagtggagaaaaagatgggacaggtgctactcatagcagtagccgtctccagcgccatactgtcgcggacc
gcctgggggtgggggaggctgggcgctctgatcacagccgcaacttccactttgtgggaaggctctccgaacaagtactggaactcctc
tacagccacttcactgtgtaacatttnaggggaagttacttggctggagcttctctaatctacacagtaacaagaaacgctggcttggt
caagagacgtggggtggaacaggagaAaccctgggagagaaatggaaggcccgcttgaaccagatgtcggccctggagttctactcct
acaaaaagtcaggcatcaccgaggtgtgcagagaagaggcccgccgcgccctcaaggacggtgtggcaacgggaggccatgctgtgtcc
cgaggaagtgcaaagctgagatggttggtggagcgggatacctgcagcccatggaaaggtcattgatcttggatgtggcagaggggg
ctggagttactacgCcgccaccatccgcaaagttcaagaagtgaaaggatacacaaaaggaggccctggtcatgaagaacccgtgttgg
tgcaaagctatgggtggaacatagtccgtcttaagagtggggtggacgtattcatatggcggctgagccgtgtgacacgttgctgtgtg
acataggtgagtcatcatctagtcctgaagtggaagaagcacggacgctcagagtcctctccatggtggggattggcttgaaaaaaga
ccaggagccttttgtataaaagtgttgtgcccatacaccagcactatgatggaaaccctggagcgactgcagcgtaggtatgggggagg
actggtcagagtgccactctcccgcaactctacacatgagatgtactgggGtctggagcgaaaagcaacaccataaaaagtgtgtcca
ccacgagccagctcctcttggggcgcatggacgggcctaggaggccagtgaaatatgaggaggatgtgaatctcggctctggcacgcgg
gctgtggtaagctgcgctgaagctcccaacatgaagatcattggtaaccgcattgaaaggatccgcagtgagcacgcggaaacgtggtt
attgacgagaaccacccatataggacatgggcttaccatggaagctatgaggccccccacacaagggtcagcgtcctctctaataaacgg
ggttgtcaggctcctgtcaaaaccctgggatgtggtgactggagtcacaggaatagccatgaccgacaccacaccgtatggtcagcaaa
gagttttcaaggaaaaagtggacactagggtgccagaccccaagaaggcactcgtcaggttatgagcatggtGtcttcctggttgtgg
aaagagctaggcaaacacaaacggccacgagtctgcaccaaagaagagttcatcaacaaggttcgtagcaatgcagcattaggggcaat
atttgaagaggaaaaagagtggaagactgcagtggaagctgtgaacgatccaaggttctgggctctagtggacaaggaaagagagcacc
acctgagaggagtgccagagctgtgtgtacaacatgatgggaaaaagagaaaagaaacaaggggaatttggaaaggccaagggcagc
cgcgccatctggtatatgtggctagggggctagatttctagagttcgaagcccttggattcttgaacgaggatcactggatggggagaga
gaactcaggaggtggtgttgaagggctgggattacaaagactcggatatgtcctagaagagatgagtcgtataccaggaggaaggatgt
atgcagatgacactgctggctgggacacccgcattagcaggtttgatctggagaatgaagctctaatcaccaaccaaatggagaaaggg
cacagggccttggcattggccataatcaagtacacataccaaaacaaagtggtaaaggtccttagaccagctgaaaaagggaaaacagt
tatggacattatttcgagacaagaccaaaggggagcggacaagttgtcacttacgctcttaacacatttaccaacctagtggtgcaac
tcattcggaatatggagctgaggaagttctagagatgcaagacttgtggctgctgcggaggtcagagaaagtgaccaactggttgcag
agcaacggatgggataggctcaaacgaatggcagtcagtggagatgattgcgttgtgaagccaattgatgataggtttgcacatgccct
caggttcttgaatgatatgggaaaagttaggaaggacacacaagagtggaaaccctcaactggatgggacaactgggaagaagttccgt
tttgctccaccacttcaacaagctccatctcaaggacgggaggtccattgtggttccctgccgccaccaagatgaactgattggccgg
gcccgcgtctctccaggggcgggatggagcatccgggagactgcttgcctagcaaaatcatatgcgcaaatgtggcagctcctttatttt
ccacagaagggacctccgactgatggccaatgccatttgttcatctgtgccagttgactgggttccaactgggagaactacctggtcaa
tccatggaaagggagaatggatgaccactgaagacatgcttgtggtgtgaacagagtgtggattgaggagaacgaccacatggaagac
aagaccccagttacgaaatggacagacattccctatttgggaaaaagggaagacttgtggtgtggatctctcataggcacagaccgcg
```

-continued
caccacctgggctgagaacattaaaaacacagtcaacatggtgcgcaggatcataggtgatgaagaaaagtacatggactacctatcca cccaagttcgctacttgggtgaagaagggtctacacctggagtgctgtaagcaccaatcttaatgttgtcaggcctgctagtcagccac agcttggggaaagctgtgcagcctgtgaccccccaggagaagctgggaaaccaagcctatagtcaggccgagaacgccatggcacgga agaagccatgctgcctgtgagcccctcagaggacactgagtcaaaaaacccacgcgcttggaggcgcaggatgggaaagaaggtggc gaccttccccacccttcaatctggggcctgaactggagatcagctgtggatctccagaagagggactagtggttagaggaGACCCCCCG GAAAACGCAAAACAGCATATTGACGCTGGGAAAGACCAGAGACTCCATGAGTTTCCaccacgctggccgccaggcacagatcgccgaac agcggcggccggtgtggggaaatccatggtttct PR15 E-W/Min
SEQ ID NO: 4
Agttgttgatctgtgtgaatcagactgcgacagttcgagtttgaagcgaaagctagcaacagtatcaacaggttttattttggatttgg aaacgagagtttctggtcatgaaaaacccaaaaaagaaatccggaggattccggattgtcaatatgctaaaacgcggagtagcccgtgt gagccccttggggcttgaagaggctgccagccggacttctgctgggtcatgggccatcaggatggtcttggcgattctagccttt tgagattcacggcaatcaagccatcactgggtctcatcaatagatggggttcagtggggaaaaagaggctatggaaaTaataaagaag ttcaagaaagatctggctgccatgctgagaataatcaatgctaggaaggagaagaagagacgaggcgcagatactagtgtcggaattgt tggcctcctgctgaccacagctatggcagcggaggtcactagacgtgggagtgcatactatatgtacttggacagaaacgatgctgggg aggccatatcttttccaaccacattggggatgaataagtgttatatacagatcatggatcttggacacatgtgtgatgccaccatgagc tatgaatgccctatgctggatgagggggtggaaccagatgacgtcgattgttggtgcaacacgacgtcaacttgggttgtgtacggaac ctgccatcacaaaaaggtgaagcacggagatctagaagGgctgtgacgctcccctcccattccaccaggaagctgcaaacgcggtcgc aaacctggttggaatcaagagaatacacaaagcacttgattagagtcgaaaattggatattcaggaaccctggcttcgcgttagcagca gctgccatcgcttggcttttgggaagctcaacagagccaaaaagtcatatacttggtcatgatactgctgattgcccggcatacagcat caggtgcataggagtcagcaatagggactttgtggaaggtatgtcaggtgggacttgggttgatgttgtcttggaacatggaggttgtg tcaccgtaatggcacaggacaaaccgactgtcgacatagagctggttacaacaacagtcagcaacatggcggaggtaagatcctactgc tatgaggcatcaatatcagacatggcttctgacagccgctgcccaacacaaggtgaagcctaccttgacaagcaatcagacactcaata tgtctgcaaaagaacgttagtggacagaggctggggaaatggatgtggactttttggcaaagggagcctggtgacatgcgctaagtttg catgctccaagaaaatgaccggCaagagcatccagccagagaatctggagtaccggataatgctgtcagttcatggctcccagcacagt gggatgatcgttaatgacacaggacatgaaactgatgagaatagagcgaaagttgagataacGCCTAACTCCCCTAGAGCCGAAGCGAC ATTGGGCGGATTCGGATCACTGGGACTGGATTGCGAACCGAGAACCGGATTGGACTTTAGCGATCTGTATTACTTGACTATGAACAATA AGCATTGGTTGGTGCACAAAGAGTGGTTTCACGACATACCGTTGCCATGGCACGCCGGAGCCGATACCGGAACGCCACATTGGAATAAC AAAGAGGCATTGGTCGAGTTTAAGGACGCTCACGCTAAACGGCAAACCGTAGTCGTGTTAGGGTCACAGGAGGGAGCCGTACACACCGC ATTGGCCGGCGCACTCGAAGCCGAAATGGACGGAGCTAAGGGAGACTGTCTAGCGGACACCTTAAGTGTAGACTGAAAATGGACAAAC TGAGACTTAAGGGAGTGTCATACTCACTGTGTACTGCCGCATTTACGTTTACGAAGATACCCGCCGAAACATTGCACGGAACCGTTACA GTCGAAGTGCAATACGCCGGAACCGACGGACCATGTAAGGTGCCAGCGCAAATGGCAGTCGATATGCAAACACTGACACCAGTCGGTAG ACTGATTACCGCTAACCCAGTGATAACCGAATCCACTGAGAATTCGAAAATGATGCTTGAGCTTGACCCACCATTCGGCGATAGCTATA TCGTTATCGGAGTCGGCGAAAAAAAGATTACACACCATTGGCATAGATCCGGATCTACAATCGGTAAGGCATTCGAAGCTACCGTTAGG GGCGCTAAGCGTATGGCCGTATTGGGCGATACCGCTTGGGATTTCGGATCCGTCGGAGGCGCACTGAATTCCCTAGGTAAGGGGATACA CCAAATATTCGGCGCAGCGTTTAAGTCATTGTTCGGAGGGATGTCATGGTTTAGTCAGATACTGATCGGAACATTGCTTATGTGGTTAG GGTTGAACACTAAGAACGGATCAATCTCATTGATGTGTCTTGCGTTAGGGGGGTGTTGATCTTTCTGTCAACCGCCGTTAGCGCAgat gtggggtgctcggtggacttctcaaagaaggagacgagatgcggtacaggggtgttcgtctataacgacgttgaagcctggagggacag gtacaagtaccatcctgactcccccgtagattggcagcagcagtcaagcaagcctgggaagatggtatctgcgggatctcctctgttt caagaatggaaaacatcatgtggagatcagtagaaggggagctcaacgcaatcctggaagagaatggagttcaactgacggtcgttgtg ggatctgtaaaaaaccccatgtggagaggtccacagagattgcccgtgcctgtgaacgagctgccccacggctggaaggcttgggggaa atcgtatttcgtcagagcagcaaagacaaataacagattgtcgtggatggtgacacactgaaggaatgcccactcaaacatagagcatg -continued

```
gaacagctttcttgtggaggatcatgggttcggggtatttcacactagtgtctggctcaaggttagagaagattattcattagagtgtg
atccagccgttattggaacagctgttaagggaaaggaggctgtacacagtgatctaggctactggattgagagtgagaagaatgacaca
tggaggctgaagagggcccatctgatcgagatgaaaacatgtgaatggccaaagtcccacacattgtggacagatggaatagaagagag
tgatctgatcatacccaagtattagctgggccactcagccatcacaataccagagagggctacaggacccaaatgaaagggccatggca
cagtgaagaActtgaaattcggtttgaggaatgcccaggcactaaggtccacgtggaggaaacatgtggaacaagaggaccatctctga
gatcaaccactgcaagcggaagggtgatcgaggaatggtgctgcagggagtgcacaatgcccccactgtcgttccgggctaaagatggc
tgttggtatggaatggagataaggcccaggaaagaaccagaaagcaacttagtaaggtcaatggtgactgcaggatcaactgatcacat
ggaccacttctcccttggagtgcttgtgatcctgctcatggtgcaggaagggctgaagaagagaatgaccacaaagatcatcataagca
catcaatggcagtgctggtagctatgatcctggaggattttcaatgagtgacctggctaagcttgcaattttgatgggtgccaccttc
gcggaaatgaacactggaggagatgtagctcatctggcgctgatagcggcattcaaagtcagaccagcgttgctggtatattcatcttc
agagctaattggacaccccgtgaaagcatgctgctggccttggcctcgtgtatttgcaaactgcgatctccgccttggaaggcgacctg
atggttctcatcaatggttttgattggcctggttggcaatacgagcgatggttgttccacgcactgataacatccacttggcaatcctg
gctgctctgacaccactggcccggggcacactgcttgtggcgtggagagcaggccttgctacttgcgggggggtttatgctcctctctct
gaagggaaaaggcagtgtgaagaagaacttaccatttgtcatggccctgggactaaccgctgtgaggctggtcgaccccatcaacgtgg
tgggactgctgttgctcacaaggagtgggaagcggagctggcccctagcgaagtactcacagctgttggcctgatatgcgcattggct
ggagggttcgccaaggcagatatagagatggctgggcccatggccgcggtcggtctgctaattgtcagttacgtggtGtcaggaaagag
tgtggacatgtacattgaaagagcaggAgacatcacatgggaaaagatgcggaagtcactggaaacagtccccggctcgatgtggcgc
tagatgagagtggtgatttctccctggtggaggatgacggtcccccatgagagagatcatactcaaggtggtcctgatgaccatctgt
ggcatgaacccaatagccataccattgcagctggagcgtggtacgtatacgtgaagactggaaaaaggagtggtgctctatgggatgtg
cctgctcccaaggaagtaaaaaagggggaAaccacagatggagtgtacagagtaatgactcgtagactgctaggttcaacacaagttgg
agtgggagttatgcaagaggggtattcacactatgtggcacgtcacaaaaggatccgcgctgagaagcggtgaagggagacttgatcc
atactggggagatgtcaagcaggatctggtgtcatactgtggtccatggaagctagatgccgcctgggatgggcacagcgaggtgcagc
tcttggccgtgccccccggagagagagcgaggaacatccagactctgcccggaatatttaagacaaaggatggggacattggagcggtt
gcgctggattacccagcaggaacttcaggatctccaatcctagacaagtgtgggagagtgataggactttatggcaatggggtcgtgat
caaaaacgggagttatgttagtgccatcacccaagggaggagggaggaagagactcctgttgagtgcttcgagccctcgatgctgaaga
agaagcagctaactgtcttagacttgcatcctggagctgggaaaaccaggagagttcttcctgaaatagtccgtgaagccataaaaaca
agactccgtactgtgatcttagctccaaccagggttgtcgctgctgaaatgagggaggcccttagagggcttccagtgcgttatatgac
aacagcagtcaatgtcacccactctggaacagaaatcgtcgacttaatgtgccatgccaccttcacttcacgtctactacagccaatca
gagtccccaactataatctgtatattatggatgaggcccacttcacagatccctcaagtatagcagcaagaggatacatttcaacaagg
gttgagatgggcgaggcggctgccatcttcatgaccgccacgccaccaggaacccgtgacgcatttccggactccaactcaccaattat
ggacaccgaagtggaagtcccagagagagcctggagctcaggcttgattgggtgacggatcattctggaaaaacagtttggttttgttc
caagcgtgaggaacggcaatgagatcgcagcttgtctgacaaaggctggaaaacgggtcatacagctcagcagaaagacttttgagaca
gagttccagaaaacaaaacatcaagagtgggactttgtcgtgacaactgacatttcagagatgggcgccaactttaaagctgaccgtgt
catagattccaggagatgcctaaagccggtcatacttgatggcgagagagtcattctggctggacccatgcctgtcacacatgccagcg
ctgcccagaggagggggcgcataggcaggaatcccaacaaacctggagatgagtatctgtatggaggtgggtgcgcagagactgacgaa
gaccatgcacactggcttgaagcaagaatgctccttgacaatatttacctccaagatggcctcatagcctcgctctatcgacctgaggc
cgacaaagtagcagccattgagggagagttcaagcttaggacggagcaaaggaagacctttgtgaactcatgaaaagaggagatcttc
agtttggctggcctatcaggttgcatctgccggaataacctacacagatagaagatggtgattgatggcacgaccaacaacaccataat
ggaagacagtgtgccggcagaggtgtggaccagacacggagagaaaagagtgctcaaaccgaggtggatggacgccagagtttgttcag
atcatgcgccctgaagtcattcaaggagtttgccgctgggaaaagaggagcggcttttggagtgatggaagccctgggaacactgcca
```

```
ggacacatgacagagagattccaggaagccattgacaacctcgctgtgctcatgcgggcagagactggaagcaggccttacaaagccgc
ggcggcccaattgccggagacActagagacAataatgcttttgggggttgctgggaacagtctcgctgggaatcttcttcgtcttgatga
ggaacaagggcatagggaagatgggattggaatggtgactcttggggccagcgcatggctcatgtggctctcggaaattgagccagcca
gaattgcatgtgtcctcattgttgtgttcctattgctggtggtgctcatacctgagccagaaaagcaaagatctccccaggacaaccaa
atggcaatcatcatcatggtagcagtaggtcttctgggcttgattaccgccaatgaactcggatggttggagagaacaaagagtgacct
aagccatctaatgggaaggagagaggaggggggcaaccataggattctcaatggacattgacctgcggccagcctcagcttgggccatct
atgctgccttgacaactttcattaccccagccgtccaacatgcagtgaccacctcatacaacaactactccttaatggcgatggccacg
caagctggagtgttgtttggcatgggcaaagggatgccattctacgcatgggactttggagtcccgctgctaatgataggttgctactc
acaattaacacccctgaccctaatagtggccatcattttgctcgtggcgcactacatgtacttgatcccagggctgcaggcagcagctg
cgcgtgctgcccagaagagaacggcagctggcatcatgaagaaccctgttgtggatggaatagtggtgactgacattgacacaatgaca
attgaccccaagtggagaaaaagatgggacaggtgctactcatagcagtagccgtctccagcgccatactgtcgcggaccgcctgggg
gtgggggaggctgggctctgatcacagccgcaacttccactttgtgggaaggctctccgaacaagtactggaactcctctacagcca
cttcactgtgtaacatttttaggggaagttacttggctggagcttctctaatctacacagtaacaagaaacgctggcttggtcaagaga
cgtgggggtggaacaggagaAaccctgggagagaaatggaaggcccgcttgaaccagatgtcggccctggagttctactcctacaaaaa
gtcaggcatcaccgaggtgtgcagagaagaggcccgccgcgccctcaaggacggtgtggcaacgggaggccatgctgtgtcccgaggaa
gtgcaaagctgagatggttggtggagcgggatacctgcagccctatggaaaggtcattgatcttggatgtggcagaggggctggagt
tactacgCcgccaccatccgcaaagttcaagaagtgaaaggatacacaaaaggaggccctggtcatgaagaacccgtgttggtgcaaag
ctatgggtggaacatagtccgtcttaagagtggggtggacgtattcatatggcggctgagccgtgtgacacgttgctgtgtgacatagg
tgagtcatcatctagtcctgaagtggaagaagcacggacgctcagagtcctctccatggtgggggattggcttgaaaaaagaccaggag
cctttgtataaaagtgttgtgcccatacaccagcactatgatggaaaccctggagcgactgcagcgtaggtatgggggaggactggtc
agagtgccactctcccgcaactctacacatgagatgtactgggtGtctggagcgaaaagcaacaccataaaagtgtgtccaccacgag
ccagctcctcttgggcgcatggacgggcctaggaggccagtgaaatatgaggaggatgtgaatctcggctctggcacgcgggctgtgg
taagctgcgctgaagctcccaacatgaagatcattggtaaccgcattgaaaggatccgcagtgagcacgcggaaacgtggttctttgac
gagaaccacccatataggacatgggcttaccatggaagctatgaggcccccacacaagggtcagcgtcctctctaataaacgggttgt
caggctcctgtcaaaaccctgggatgtggtgactggagtcacaggaatagccatgaccgacaccacaccgtatggtcagcaaagagttt
tcaaggaaaaagtggacactagggtgccagaccccaagaaggcactcgtcaggttatgagcatggtGtcttcctggttgtggaaagag
ctaggcaaacacaaacggccacgagtctgcaccaaagaagagttcatcaacaaggttcgtagcaatgcagcattaggggcaatatttga
agaggaaaaagagtggaagactgcagtggaagctgtgaacgatccaaggttctgggctctagtggacaaggaaagagagcaccacctga
gaggagagtgccagagctgtgtgtacaacatgatgggaaaaagagaaaagaaacaaggggaatttggaaaggccaagggcagccgcgcc
atctggtatatgtggctaggggctagatttctagagttcgaagcccttggattcttgaacgaggatcactggatggggagagagaactc
aggaggtggtgttgaagggctgggattacaaagactcggatatgtcctagaagagatgagtcgtataccaggaggaaggatgtatgcag
atgacactgctggctgggacacccgcattagcaggtttgatctggagaatgaagctctaatcaccaaccaaatggagaaagggcacagg
gccttggcattggccataatcaagtacacataccaaaacaaagtggtaaaggtccttagaccagctgaaaaagggaaaacagttatgga
cattatttcgagacaagaccaaaggggggagcggacaagttgtcacttacgctcttaacacatttaccaacctagtggtgcaactcattc
ggaatatggaggctgaggaagttctagagatgcaagacttgtggctgctgcggaggtcagagaaagtgaccaactggttgcagagcaac
ggatgggataggctcaaacgaatggcagtcagtggagatgattgcgttgtgaagccaattgatgataggtttgcacatgccctcaggtt
cttgaatgatatgggaaaagttaggaaggacacacaagagtggaaaccctcaactggatgggacaactgggaagaagttccgttttgct
cccaccacttcaacaagctccatctcaaggacggggaggtccattgtggttccctgccgccaccaagatgaactgattggccgggcccgc
gtctctccaggggcgggatggagcatccgggagactgcttgcctagcaaaatcatatgcgcaaatgtggcagctcctttatttccacag
aagggacctccgactgatggccaatgccatttgttcatctgtgccagttgactgggttccaactgggagaactacctggtcaatccatg
gaaagggagaatggatgaccactgaagacatgcttgtggtgtggaacagagtgtggattgaggagaacgaccacatggaagacaagacc
```

-continued ccagttacgaaatggacagacattccctatttgggaaaaagggaagacttgtggtgtggatctctcatagggcacagaccgcgcaccac
ctgggctgagaacattaaaaacacagtcaacatggtgcgcaggatcataggtgatgaagaaaagtacatggactacctatccacccaag
ttcgctacttgggtgaagaagggtctacacctggagtgctgtaagcaccaatcttaatgttgtcaggcctgctagtcagccacagcttg
gggaaagctgtgcagcctgtgaccccccaggagaagctgggaaaccaagcctatagtcaggccgagaacgccatggcacggaagaagc
catgctgcctgtgagcccctcagaggacactgagtcaaaaaaccccacgcgcttggaggcgcaggatgggaaagaaggtggcgacctt
ccccacccttcaatctggggcctgaactggagatcagctgtggatctccagaagagggactagtggttagaggaGACCCCCCGGAAAAC
GCAAAACAGCATATTGACGCTGGGAAAGACCAGAGACTCCATGAGTTTCCaccacgctggccgccaggcacagatcgccgaacagcggc
ggccggtgtggggaaatccatggtttct PR15 E-W/W/Min

SEQ ID NO: 5

Agttgttgatctgtgtgaatcagactgcgacagttcgagtttgaagcgaaagctagcaacagtatcaacaggttttattttggatttgg
aaacgagagtttctggtcatgaaaaacccaaaaaagaaatccggaggattccggattgtcaatatgctaaaacgcggagtagcccgtgt
gagcccctttgggggcttgaagaggctgccagccggacttctgctgggtcatgggcccatcaggatggtcttggcgattctagccttt
tgagattcacggcaatcaagccatcactgggtctcatcaatagatggggttcagtggggaaaaagaggctatggaaaTaataaagaag
ttcaagaaagatctggctgccatgctgagaataatcaatgctaggaaggagaagaagagacgaggcgcagatactagtgtcggaattgt
tggcctcctgctgaccacagctatggcagcggaggtcactagacgtgggagtgcatactatatgtacttggacagaaacgatgctgggg
aggccatatcttttccaaccacattggggatgaataagtgttatatacagatcatggatcttggacacatgtgtgatgccaccatgagc
tatgaatgccctatgctggatgaggggtggaaccagatgacgtcgattgttggtgcaacacgacgtcaacttgggttgtgtacggaac
ctgccatcacaaaaaaggtgaagcacggagatctagaagGgctgtgacgctcccctcccattccaccaggaagctgcaaacgcggtcgc
aaacctggttggaatcaagagaatacacaaagcacttgattagagtcgaaaattggatattcaggaaccctggcttcgcgttagcagca
gctgccatcgcttggcttttgggaagctcaacgagccaaaaagtcatatacttggtcatgatactgctgattgccccggcatacagcat
caggtgcataggagtcagcaatagggactttgtggaaggtatgtcaggtgggacttgggttgatgttgtcttggaacatggaggttgtg
tcaccgtaatggcacaggacaaaccgactgtcgacatagagctggttacaacaacagtcagcaacatggcggaggtaagatcctactgc
tatgaggcatcaatatcagacatggcttctgacagccgctgcccaacacaaggtgaagcctaccttgacaagcaatcagacactcaata
tgtctgcaaaagaacgttagtggacagaggctggggaaatggatgtggactttttggcaagggagcctggtgacatgcgctaagtttg
catgctccaagaaaatgaccggCaagagcatccagccagagaatctggagtaccggataatgctgtcagttcatggctcccagcacagt
gggatgatcgttaatgacacaggacatgaaactgatgagaatagagcgaaagttgagataacgcccaattcaccgagagccgaagccac
cctgggggttttggaagcctaggacttgattgtgaaccgaggacaggccttgacttttcagatttgtattacttgactatgaataaca
agcactggttggttcacaaggagtggttccacgacattccattaccttggcacgctggggcagacaccggaactccacactggaacaac
aaagaagcactggtagagttcaaggacgcacatgccaaaaggcaaactgtcgtggttctagggagtcaagaaggagcagttcacacggc
ccttgctggagctctggaggctgagatggatggtgcaaagggGAGACTGTCTAGCGGACACCTTAAGTGTAGACTGAAAATGGACAAAC
TGAGACTTAAGGGAGTGTCATACTCACTGTGTACTGCCGCATTTACGTTTACGAAGATACCCGCCGAAACATTGCACGGAACCGTTACA
GTCGAAGTGCAATACGCCGGAACCGACGGACCATGTAAGGTGCCAGCGCAAATGGCAGTCGATATGCAAACACTGACACCAGTCGGTAG
ACTGATTACCGCTAACCCAGTGATAACCGAATCCACTGAGAATTCGAAAATGATGCTTGAGCTTGACCCACCATTCGGCGATAGCTATA
TCGTTATCGGAGTCGGCGAAAAAAAGATTACACACCATTGGCATAGATCCGGATCTACAATCGGTAAGGCATTCGAAGCTACCGTTAGG
GGCGCTAAGCGTATGGCCGTATTGGGCGATACCGCTTGGGATTTCGGATCCGTCGGAGGCGCACTGAATTCCCTAGGTAAGGGGATACA
CCAAATATTCGGCGCAGCGTTTAAGTCATTGTTCGGAGGGATGTCATGGTTTAGTCAGATACTGATCGGAACATTGCTTATGTGGTTAG
GGTTGAACACTAAGAACGGATCAATCTCATTGATGTGTCTTGCGTTAGGGGGGGTGTTGATCTTTCTGTCAACCGCCGTTAGCGCAgat
gtggggtgctcggtggacttctcaaagaaggagacgagatgcggtacaggggtgttcgtctataacgacgttgaagcctggagggacag
gtacaagtaccatcctgactcccccgtagattggcagcagcagtcaagcaagcctgggaagatggtatctgcgggatctcctctgttt
caagaatggaaaacatcatgtggagatcagtgagaggggagctcaacgcaatcctggaagagaatggagttcaactgacggtcgttgtg -continued

```
ggatctgtaaaaaacccatgtggagaggtccacagagattgcccgtgcctgtgaacgagctgccccacggctggaaggcttggggaa atcgtatttcgtcagagcagcaaagacaaataacagattgtcgtggatggtgacacactgaaggaatgcccactcaaacatagagcatg gaacagattcttgtggaggatcatgggttcggggtatttcacactagtgtctggctcaaggttagagaagattattcattagagtgtga tccagccgttattggaacagctgttaaggaaaggaggctgtacacagtgatctaggctactggattgagagtgagaagaatgacacat ggaggctgaagagggcccatctgatcgagatgaaaacatgtgaatggccaaagtcccacacattgtggacagatggaatagaagagagt gatctgatcatacccaagtctttagctgggccactcagccatcacaataccagagagggctacaggacccaaatgaaagggccatggca cagtgaagaActtgaaattcggtttgaggaatgcccaggcactaaggtccacgtggaggaaacatgtggaacaagaggaccatctctga gatcaaccactgcaagcggaagggtgatcgaggaatggtgctgcagggagtgcacaatgccccactgtcgttccgggctaaagatggc tgttggtatggaatggagataaggcccaggaaagaaccagaaagcaacttagtaaggtcaatggtgactgcaggatcaactgatcacat ggaccacttctcccttggagtgcttgtgatcctgctcatggtgcaggaagggctgaagaagagaatgaccacaaagatcatcataagca catcaatggcagtgctggtagctatgatcctggaggattttcaatgagtgacctggctaagcttgcaattttgatgggtgccaccttc gcggaaatgaacactggaggagatgtagctcatctggcgctgatagcggcattcaaagtcagaccagcgttgctggtatattcatcttc agagctaattggacaccccgtgaaagcatgctgctggccttggcctcgtgtcttttgcaaactgcgatctccgccttggaaggcgacct gatggttctcatcaatggttttgctttggcctggttggcaatacgagcgatggttgttccacgcactgataacatccttggcaatcc tggctgctctgacaccactggcccggggcacactgcttgtggcgtggagagcaggccttgctacttgcgggggtttatgctcctctct ctgaagggaaaaggcagtgtgaagaagaacttaccatttgtcatggccctgggactaaccgctgtgaggctggtcgacccatcaacgt ggtgggactgctgttgctcacaaggagtgggaagcggagctggcccctagcgaagtactcacagctgttggcctgatatgcgcattgg ctggagggttcgccaaggcagatatagagatggctgggcccatggccgcggtcggtctgctaattgtcagttacgtggtGtcaggaaag agtgtggacatgtacattgaaagagcaggAgacatcacatgggaaaaagatgcggaagtcactggaaacagtccccggctcgatgtggc gctagatgagagtggtgatttctccctggtggaggatgacggtcccccatgagagagatcatactcaaggtggtcctgatgaccatct gtggcatgaacccaatagccataccattgcagctggagcgtggtacgtatacgtgaagactggaaaaaggagtggtgctctatgggatg tgcctgctcccaaggaagtaaaaaaggggggaAccacagatggagtgtacagagtaatgactcgtagactgctaggttcaacacaagtt ggagtgggagttatgcaagaggggtctttcacactatgtggcacgtcacaaaaggatccgcgctgagaagcggtgaagggagacttga tccatactggggagatgtcaagcaggatctggtgtcatactgtggtccatggaagctagatgccgcctgggatgggcacagcgaggtgc agctcttggccgtgcccccggagagagagcgaggaacatccagactctgcccggaatatttaagacaaaggatggggacattggagcg gttgcgctggattacccagcaggaacttcaggatctccaatcctagacaagtgtgggagagtgataggactttatggcaatggggtcgt gatcaaaaacgggagttatgttagtgccatcacccaagggaggagggaggaagagactcctgttgagtgcttcgagccctcgatgctga agaagaagcagctaactgtcttagacttgcatcctggagctgggaaaaccaggagagttcttcctgaaatagtccgtgaagccataaaa acaagactccgtactgtgatcttagctccaaccagggttgtcgctgctgaaatggaggaggcccttagagggcttccagtgcgttatat gacaacagcagtcaatgtcacccactctggaacagaaatcgtcgacttaatgtgccatgccaccttcacttcacgtctactacagccaa tcagagtccccaactataatctgtatattatggatgaggcccacttcacagatccctcaagtatagcagcaagaggatacatttcaaca agggttgagatgggcgaggcggctgccatcttcatgaccgccacgccaccaggaacccgtgacgcatttccggactccaactcaccaat tatggacaccgaagtggaagtcccagagagagcctggagctcaggctttgattgggtgacggatcattctggaaaaacagtttggtttg ttccaagcgtgaggaacggcaatgagatcgcagcttgtctgacaaaggctggaaaacgggtcatacagctcagcagaaagacttttgag acagagttccagaaaacaaaacatcaagagtgggactttgtcgtgacaactgacatttcagagatgggcgccaactttaaagctgaccg tgtcatagattccaggagatgcctaaagccggtcatacttgatggcgagagagtcattctggctggacccatgcctgtcacacatgcca gcgctgcccagaggaggggcgcataggcaggaatcccaacaaacctggagatgagtatctgtatggaggtgggtgcgcagagactgac gaagaccatgcacactggcttgaagcaagaatgctccttgacaatatttacctccaagatggcctcatagcctcgctctatcgacctga ggccgacaaagtagcagccattgagggagagttcaagcttaggacggagcaaaggaagacctttgtggaactcatgaaaagaggagatc ttcagtttggctggcctatcaggttgcatctgccggaataacctacacagatagaagatggtgattgatggcacgaccaacaacaccat aatggaagacagtgtgccggcagaggtgtggaccagacacggagagaaaagagtgctcaaaccgaggtggatggacgccagagtttgtt
```

```
cagatcatgcggccctgaagtcattcaaggagtttgccgctgggaaaagaggagcggcttttggagtgatggaagccctgggaacactg
ccaggacacatgacagagagattccaggaagccattgacaacctcgctgtgctcatgcgggcagagactggaagcaggccttacaaagc
cgcggcggcccaattgccggagacActagagacAataatgcttttggggttgctgggaacagtctcgctgggaatcttcttcgtcttga
tgaggaacaagggcataggaagatgggctttggaatggtgactcttggggccagcgcatggctcatgtggctctcggaaattgagcca
gccagaattgcatgtgtcctcattgttgtgttcctattgctggtggtgctcatacctgagccagaaaagcaaagatctccccaggacaa
ccaaatggcaatcatcatcatggtagcagtaggtcttctgggcttgattaccgccaatgaactcggatggttggagagaacaaagagtg
acctaagccatctaatgggaaggagagaggaggggggcaaccataggattctcaatggacattgacctgcggccagcctcagcttgggcc
atctatgctgccttgacaactttcattaccccagccgtccaacatgcagtgaccacctcatacaacaactactccttaatggcgatggc
cacgcaagctggagtgttgtttggcatgggcaaagggatgccattctacgcatgggactttggagtcccgctgctaatgataggttgct
actcacaattaacacccctgaccctaatagtggccatcattttgctcgtggcgcactacatgtacttgatcccagggctgcaggcagca
gctgcgcgtgctgcccagaagagaacggcagctggcatcatgaagaaccctgttgtggatggaatagtggtgactgacattgacacaat
gacaattgaccccaagtggagaaaaagatgggacaggtgctactcatagcagtagccgtctccagcgccatactgtcgcggaccgcct
gggggtgggggagctggggctctgatcacagccgcaacttccactttgtgggaaggctctccgaacaagtactggaactcctctaca
gccacttcactgtgtaacatttttaggggaagttacttggctggagcttctctaatctacacagtaacaagaaacgctggcttggtcaa
gagacgtggggtggaacaggagaAaccctgggagagaaatggaaggcccgcttgaaccagatgtcggccctggagttctactcctaca
aaagtcaggcatcaccgaggtgtgcagagaagaggcccgccgcgccctcaaggacggtgtggcaacgggaggccatgctgtgtcccga
ggaagtgcaaagctgagatggttggtggagcgggatacctgcagccctatggaaaggtcattgatcttggatgtggcagaggggctg
gagttactacgCcgccaccatccgcaaagttcaagaagtgaaaggatacacaaaaggaggccctggtcatgaagaacccgtgttggtgc
aaagctatgggtggaacatagtccgtcttaagagtggggtggacgtattcatatggcggctgagccgtgtgacacgttgctgtgtgaca
taggtgagtcatcatctagtcctgaagtggaagaagcacggacgctcagagtcctctccatggtgggggattggcttgaaaaaagacca
ggagccttttgtataaaagtgttgtgcccatacaccagcactatgatggaaaccctggagcgactgcagcgtaggtatggggaggact
ggtcagagtgccactctcccgcaactctacacatgagatgtactgggGtctggagcgaaaagcaacaccataaaaagtgtgtccacca
cgagccagctcctcttggggcgcatggacgggcctaggaggccagtgaaatatgaggaggatgtgaatctcggctctggcacgcgggct
gtggtaagctgcgctgaagctcccaacatgaagatcattggtaaccgcattgaaaggatccgcagtgagcacgcggaaacgtggttatt
gacgagaaccacccatataggacatgggcttaccatggaagctatgaggcccccacacaagggtcagcgtcctctctaataaacggggt
tgtcaggctcctgtcaaaaccctgggatgtggtgactggagtcacaggaatagccatgaccgacaccacaccgtatggtcagcaaagag
ttttcaaggaaaaagtggacactagggtgccagaccccccaagaaggcactcgtcaggttatgagcatggtGtcttcctggttgtggaaa
gagctaggcaaacacaaacggccacgagtctgcaccaaagaagagttcatcaacaaggttcgtagcaatgcagcattaggggcaatatt
tgaagaggaaaagagtggaagactgcagtggaagctgtgaacgatccaaggttctgggctctagtggacaaggaaagagagcaccacc
tgagaggagagtgccagagctgtgtgtacaacatgatgggaaaagagaaaagaaacaaggggaatttggaaaggccaagggcagccgc
gccatctggtatatgtggctaggggctagatttctagagttcgaagcccttggattcttgaacgaggatcactggatggggagagagaa
ctcaggaggtggtgttgaagggctgggattacaaagactcggatatgtcctagaagagatgagtcgtataccaggaggaaggatgtatg
cagatgacactgctggctgggacaccgcattagcaggtttgatctggagaatgaagctctaatcaccaaccaaatggagaaagggcac
agggccttggcattggccataatcaagtacacataccaaaacaaagtggtaaaggtccttagaccagctgaaaaagggaaaacagttat
ggacattatttcgagacaagaccaaaggggagcggacaagttgtcacttacgctcttaacacatttaccaacctagtggtgcaactca
ttcggaatatggaggctgaggaagttctagagatgcaagacttgtggctgctgcggaggtcagagaaagtgaccaactggttgcagagc
aacgatgggataggctcaaacgaatggcagtcagtggagatgattgcgttgtgaagccaattgatgataggtttgcacatgccctcag
gttcttgaatgatatgggaaaagttaggaaggacacacaagagtggaaaccctcaactggatgggacaactgggaagaagttccgtttt
gctcccaccacttcaacaagctccatctcaaggacgggaggtccattgtggttccctgccgccaccaagatgaactgattggccgggcc
cgcgtctctccaggggcgggatggagcatccgggagactgcttgcctagcaaaatcatatgcgcaaatgtggcagctcctttatttcca
```

-continued cagaagggacctccgactgatggccaatgccatttgttcatctgtgccagttgactgggttccaactgggagaactacctggtcaatcc atggaaagggagaatggatgaccactgaagacatgcttgtggtgtggaacagagtgtggattgaggagaacgaccacatggaagacaag accccagttacgaaatggacagacattccctatttgggaaaaagggaagacttgtggtgtggatctctcatagggcacagaccgcgcac cacctgggctgagaacattaaaaacacagtcaacatggtgcgcaggatcataggtgatgaagaaaagtacatggactacctatccaccc aagttcgctacttgggtgaagaagggtctacacctggagtgctgtaagcaccaatcttaatgttgtcaggcctgctagtcagccacagc ttggggaaagctgtgcagcctgtgaccccccaggagaagctgggaaaccaagcctatagtcaggccgagaacgccatggcacggaaga agccatgctgcctgtgagcccctcagaggacactgagtcaaaaaaccccacgcgcttggaggcgcaggatgggaaaagaaggtggcgac cttcccaccccttcaatctggggcctgaactggagatcagctgtggatctccagaagagggactagtggttagaggaGACCCCCCGGAA AACGCAAACAGCATATTGACGCTGGGAAAGACCAGAGACTCCATGAGTTTCCaccacgctggccgccaggcacagatcgccgaacagc ggcggccggtgtggggaaatccatggtttct MR766 Syn WT

SEQ ID NO: 6

-continued

```
aagaatggaaaacatcatgtggaaatcagtagaaggggagctcaatgctatcctagaggagaatggagttcaactgacagttgttgtgg
gatctgtaaaaaacccccatgtggagaggtccacaaagattgccagtgcctgtgaatgagctgccccatggctggaaagcctgggggaaa
tcgtattttgttagggcggcaaagaccaacaacagttttgttgtcgacggtgacacactgaaggaatgtccgcttgagcacagagcatg
gaatagttttcttgtggaggatcacgggtttggagtcttccacaccagtgtctggcttaaggtcagagaagattactcattagaatgtg
acccagccgtcataggaacagctgttaagggaagggaggccgcgcacagtgatctgggctattggattgaaagtgaaaagaatgacaca
tggaggctgaagagggcccacctgattgagatgaaaacatgtgaatggccaaagtctcacacattgtggacagatggagtagaagaaag
tgatcttatcatacccaagtctttagctggtccactcagccaccacaacaccagagagggttacagaacccaagtgaaagggccatggc
acagtgaagaActtgaaatccggtttgaggaatgtccaggcaccaaggtttacgtggaggagacatgcggaactagaggaccatctctg
agatcaactactgcaagtggaagggtcattgaggaatggtgctgtagggaatgcacaatgcccccactatcgtttcgagcaaaagacgg
ctgctggtatggaatggagataaggcccaggaaagaaccagagagcaacttagtgaggtcaatggtgacagcggggtcaaccgatcata
tggaccacttctctcttggagtgcttgtgattctactcatggtgcaggaggggttgaagaagagaatgaccacaaagatcatcatgagc
acatcaatggcagtgctggtagtcatgatcttggaggattttcaatgagtgacctggccaagcttgtgatcctgatgggtgctactttt
cgcagaaatgaacactggaggagatgtagctcacttggcattggtagcggcatttaaagtcagaccagccttgctggtGtccttcattt
tcagagccaattggacaccccgtgagagcatgctgctagccctggcttcgtgtcttctgcaaactgcgatctctgctcttgaaggtgac
ttgatggtcctcattaatggatttgattggcctggttggcaattcgagcaatggccgtgccacgcactgacaacatcgctctaccaatc
ttggctgctctaacaccactagctcgaggcacactgctcgtggcatggagagcgggcctggctacttgtggagggatcatgctcctctc
cctgaaagggaaaggtagtgtgaagaagaacctgccatttgtcatggccctgggattgacagctgtgagggtagtagaccctattaatg
tggtaggactactgttactcacaaggagtgggaagcggagctggccccctagtgaagttctcacagccgttggcctgatatgtgcactg
gccggagggtttgccaaggcagacattgagatggctggacccatggctgcagtaggccttgctaattgtcagctatgtggtGtcgggaaa
gagtgtggacatgtacattgaaagagcaggAgacatcacatgggaaaaggacgcggaagtcactggaaacagtcctcggcttgacgtgg
cactggatgagagtggtgatttctccttggtagaggaagatggtccacccatgagagagatcatactcaaggtggtcctgatggccatc
tgtggcatgaacccaatagctatacctttgctgcaggagcgtggtatgtgtatgtgaagactgggaaaaggagtggcgccctctggga
cgtgcctgctcccaaagaagtgaagaaaggagaAaccacagatggagtgtacagagtgatgactcgcagactgctaggttcaacacagg
ttggagtgggagtcatgcaagagggagtcttccacaccatgtggcacgttacaaaaggagccgcactgaggagcggtgagggaagactt
gatccatactgggggatgtcaagcaggacttggtgtcatactgtgggccttggaagttggatgcagcttgggatggactcagcgaggt
acagcttttggccgtacctcccggagagagggccagaaacattcagaccctgcctggaatattcaagacaaaggacggggacatcggag
cagttgctctggactaccctgcagggacctcaggatctccgatcctagacaaatgtggaagagtgataggactctatggcaatgggggtt
gtgatcaagaatggaagctatgttagtgctataacccagggaaagagggaggaggagactccggttgaatgtttcgaaccctcgatgct
gaagaagaagcagctaactgtcttggatctgcatccaggagccgaaaaaccaggagagttcttcctgaaatagtccgtgaagccataa
aaaagagactccggacagtgatcttggcaccaactagggttgtcgctgctgagatggaggaggccttgagaggacttccggtgcgttac
atgacaacagcagtcaacgtcacccattctgggacagaaatcgttgatttgatgtgccatgccacttcacttcacgcttactacaacc
catcagagtccctaattacaatctcAacatcatggatgaagcccacttcacagacccctcaagtatagctgcaagaggatacatatcaa
caagggttgaaatgggcgaggcggctgccatttttatgactgccacaccaccaggaacccgtgatgcgtttcctgactctaactcacca
atcatggacacagaagtggaagtcccagagagagcctggagctcaggctttgattgggtgacagaccattctgggaaaacagtttggtt
cgttccaagcgtgagaaacggaaatgaaatcgcagcctgtctgacaaaggctggaaagcgggtcatacagctcagcaggaagacttttg
agacagaatttcagaaaacaaaaaatcaagagtgggactttgtcataacaactgacatctcagagatgggcgccaacttcaaggctgac
cgggtcatagactctaggagatgcctaaaaccagtcatacttgatggtgagagagtcatcttggctgggcccatgcctgtcacgcatgc
tagtgctgctcagaggagaggacgtataggcaggaaccctaacaaacctggagatgagtacatgtatggaggtgggtgtgcagagactg
atgaaggccatgcacactggcttgaagcaagaatgcttcttgacaacatctacctccaggatggcctcatagcctcgctctatcggcct
gaggccgataaggtagccgccattgagggagagtttaagctgaggacagagcaaaggaagaccttcgtggaactcatgaagagaggGga
```

-continued ccttcccgtctggctagcctatcaggttgcatctgccggaataacttacacagacagaagatggtgattgatggcacaaccaacaac
cataatggaagacagcgtaccagcagaggtgtggacaaagtatggagagaagagagtgctcaaaccgagatggatggatgctagggtct
gttcagaccatgcggccctgaagtcgttcaaagaattcgccgctggaaaaagaggagcggattgggagtaatggaggccctgggaacac
tgccaggacacatgacagagaggtttcaggaagccattgacaacctcgccgtgctcatgcgagcagagactggaagcaggccttataag
gcagcggcagcccaactgccggagacTctagagacAattatgctcttaggtttgctgggaacagtttcactggggatcttcttcgtctt
gatgcggaataagggcatcggggaagatggggattggaatggtaaccccttggggccagtgcatggctcatgtggattcggaaattgaacca
gccagaattgcatgtgtcctcattgttgtgtttttattactggtggtgctcatacccgagccagagaagcaaagatctccccaagataa
ccagatggcaattatcatcatggtggcagtgggccttctaggtttgataactgcaaacgaacttggatggctggaaagaacaaaaaatg
acatagctcatctaatgggaaggagagaagaaggagcaaccatgggattctcaatggacattgatctgcggccagcctccgcctgggct
atctatgccgcattgacaactctcatcacccccagctgtccaacatgcggtaaccacttcatacaacaactactccttaatggcgatggc
cacacaagctggagtgctgtttggcatgggcaaagggatgccattttatgcatgggaccttggagtcccgctgctaatgatgggttgct
attcacaattaacaccccctgactctgatagtagctatcattctgcttgtggcgcactacatgtacttgatcccaggcctacaagcggca
gcagcgcgtgctgcccagaaaaggacagcagctggcatcatgaagaatcccgttgtggatggaatagtggtaactgacattgacacaat
gacaatagaccccaggtggagaagaagatgggacaagtgttactcatagcagtagccatctccagtgctgtgctgctgcggaccgcct
ggggatgggggaggctggagctctgatcacagcagcgacctccaccttgtgggaaggctctccaaacaaatactggaactcctctaca
gccacctcactgtgcaacatcttcagaggaagctatctggcaggagcttcccttatctatacagtgacgagaaacgctggcctggttaa
gagacgtggaggtgggacgggagagactctgggagagaagtggaaagctcgtctgaatcagatgtcggccctggagttctactcttata
aaaagtcaggtatcactgaagtgtgtagagaggaggctcgccgtgccctcaaggatggagtggccacaggaggacatgccgtatcccgg
ggaagtgcaaagctcagatggttggtggagagaggatatctgcagccctatgggaaggttgttgacctcggatgtggcagaggggctg
gagctattatgccgccaccatccgcaaagtgcaggaggtgagaggatacacaaagggaggtcccggtcatgaagaacccatgctggtgc
aaagctatgggtggaacatagttcgtctcaagagtggagtggacgtcttccacatggcggctgagccgtgtgacactctgctgtgtgac
ataggtgagtcatcatctagtcctgaagtggaagagacacgaacactcagagtgctctctatggtgggggactggcttgaaaaaagacc
aggggccttctgtataaaggtgctgtgcccatacaccagcactatgatggaaaccatggagcgactgcaacgtaggcatgggggaggat
tagtcagagtgccattgtctcgcaactccacacatgagatgtactgggtGtctggggcaaagagcaacatcataaaaagtgtgtccacc
acaagtcagctcctcctgggacgcatggatggccccaggaggccagtgaaatatgaggaggatgtgaacctcggctcgggtacacgagc
tgtggcaagctgtgctgaggctcctaacatgaaaatcatcggcaggcgcattgagagaatccgcaatgaacatgcagaaacatggtttc
ttgatgaaaaccacccatacaggacatgggcctaccatgggagctacgaagcccccacgcaaggatcagcgtcttccctcgtgaacggg
gttgttagactcctgtcaaagccttgggacgtggtgactggagttacaggaatagccatgactgacaccacaccatacgccaacaaag
agtcttcaaagaaaaagtggacaccagggtgccagatccccaagaaggcactcgccaggtaatgaacatagtctcttcctggctgtgga
aggagctggggaaacgcaagcggccacgcgtctgcaccaaagaagagtttatcaacaaggtgcgcagcaatgcagcactgggagcaata
tttgaagaggaaaagaatggaagacggctgtggaagctgtgaatgatccaaggttttgggccctagtggatagggagagagaacacca
cctgagaggagagtgtcacagctgtgtgtacaacatgatgggaaaaagagaaaagaagcaaggagagttcgggaaagcaaaaggtagcc
gcgccatctggtacatgtggttgggagccagattcttggagtttgaagcccttggattcttgaacgaggaccattggatgggaagagaa
aactcaggaggtggagtcgaagggttaggattgcaaagacttggatacattctagaagaaatgaatcgggcaccaggaggaaagatgta
cgcagatgacactgctggctgggacacccgcattagtaagtttgatctggagaatgaagctctgattaccaaccaaatggaggaagggc
acagaactctggcgttggccgtgattaaatacacataccaaaacaaagtggtgaaggttctcagaccagctgaaggaggaaaaacagtt
atggacatcatttcaagacaagaccagagaggagtggacaagttgtcacttatgctctcaacacattccaccttggtggtgcagct
tatccggaacatggaagctgaggaagtgttagagatgcaagacttatggttgttgaggaagccagagaaagtgaccagatggttgcaga
gcaatggatgggatagactcaaacgaatggcggtcagtggagatgactgcgttgtgaagccaatcgatgataggtttgcacatgccctc
aggttcttgaatgacatgggaaaagttaggaaagacacacaggagtggaaaccctcgactggatggagcaattgggaagaagtcccgtt
ctgctcccaccacttcaacaagctgtacctcaaggatgggagatccattgtggtcccttgccgccaccaagatgaactgattggccgag -continued ctcgcgtctcaccaggggcaggatggagcatccgggagactgcctgtcttgcaaaatcatatgcgcagatgtggcagctcattatttcc acagaagGgaccttcgactgatggctaatgccatttgctcggctgtgccagttgactgggtTccaactgggagaaccacctggtcaatc catggaaagggagaatggatgaccactgaggacatgctcatggtgtggaatagagtgtggattgaggagaacgaccatatggaggacaa gactcctgtaacaaaatggacagacattccctatctaggaaaaagggaggacttatggtgtggatcccttatagggcacagaccccgca ccacttgggctgaaaacatcaaagacacagtcaacatggtgcgcaggatcataggtgatgaagaaaagtacatggactatctatccacc caagtccgctacttgggtgaggaagggtccacacccggagtgttgtaagcaccaattttagtgttgtcaggcctgctagtcagccacag tttggggaaagctgtgcagcctgtaaccccccaggagaagctgggaaaccaagctcatagtcaggccgagaacgccatggcacggaag aagccatgctgcctgtgagcccctcagaggacactgagtcaaaaaaccccacgcgcttggaagcgcaggatgggaaaagaaggtggcga ccttccccacccttcaatctggggcctgaactggagactagctgtgaatctccagcagagggactagtggttagaggagacccccgga aaacgcacaacagcatattgacgctgggaaagaccagagactccatgagtttccaccacgctggccgccaggcacagatcgccgaacTT

CGGCGGCCGGTGTGGGGAAATCCATGGTTTCT

MR766 E-Min

SEQ ID NO: 7

AGTTGTTGATCTGTGTGAGTCAGACTGCGACAGTTCGAGTCTGAAGCGAGAGCTAACAACAGTATCAACAGGTTTAATTTGGATTTGGA

AACGAGAGTTTCTGGTCATGAAAAACCCAAAGAAGAAATCCGGAGGATTCCGGATTGTCAATATGCTAAAACGCGGAGTAGCCCGTGTA

AACCCCTTGGGAGGTTTGAAGAGGTTGCCAGCCGGACTTCTGCTGGGTCATGGACCCATCAGAATGGTTTTGGCGATACTAGCCTTTTT

GAGATTTACAGCAATCAAGCCATCACTGGGCCTTATCAACAGATGGGGTTCCGTGGGGAAAAAAGAGGCTATGGAAATAATAAAGAAGT

TCAAGAAAGATCTTGCTGCCATGTTGAGAATAATCAATGCTAGGAAAGAGAGGAAGAGACGTGGCGCAGACACCAGCATCGGAATCATT

GGCCTCCTGCTGACTACAGCCATGGCAGCCGAAATTACGAGAAGGGGGTCCGCATACTATATGTATCTGGATAGGTCCGACGCCGGTAA

GGCAATCTCATTCGCAACGACACTCGGAGTGAATAAGTGTCACGTTCAGATTATGGACTTAGGGCATATGTGCGACGCTACTATGTCAT

ACGAATGCCCTATGCTTGACGAAGGCGTTGAGCCAGACGACGTCGACTGTTGGTGCAATACGACTAGCACATGGGTCGTGTACGGTACA

TGCCATCACAAAAAGGGCGAAGCGAGACGGTCTAGAAGGGCCGTTACGTTGCCGTCACACTCTACGAGAAAGTTGCAGACTAGGTCTCA

GACTTGGTTGGAGTCACGCGAATACACTAAGCATCTGATTAAGGTCGAGAATTGGATTTTTAGGAACCCAGGGTTCGCACTAGTCGCCG

TCGCAATCGCTTGGTTGTTGGGGTCTAGTACGAGTCAGAAAGTGATATACTTAGTGATGATACTGTTGATCGCACCCGCATACTCTATT

AGGTGTATCGGAGTGAGTAATCGCGATTTCGTCGAGGGTATGAGCGGAGGGACATGGGTCGACGTTGTGCTTGAGCACGGGGGGTGCGT

TACCGTTATGGCCCAAGACAAACCGACAGTCGATATCGAACTGGTTACGACTACCGTTTCGAACATGGCCGAAGTGAGATCGTATTGTT

ACGAGGCTAGCATAAGCGATATGGCTAGCGATAGTAGGTGCCCAACACAGGGCGAAGCGTATCTCGATAAGCAATCCGATACGCAATAC

GTTTGCAAACGGACATTGGTCGATAGGGGGTGGGGTAACGGATGCGGACTGTTCGGTAAGGGGTCACTAGTGACATGCGCTAAGTTTAC

ATGCTCTAAAAAAATGACCGGTAAGTCAATCCAACCCGAAAACCTTGAGTATAGGATTATGTTGAGCGTACACGGATCGCAACACTCCG

GTATGATCGTTAACGATACCGGATACGAGACTGACGAGAATAGGGCTAAGGTCGAGGTGACACCTAACTCACCTAGAGCCGAAGCGACA

TTGGGGGGGTTCGGATCTCTCGGACTGGATTGCGAACCTAGAACCGGATTGGACTTTAGCGATCTGTACTATCTGACTATGAACAATAA

GCATTGGTTGGTGCATAAGGAGTGGTTTCACGACATACCACTGCCATGGCACGCCGGAGCCGATACCGGTACGCCACATTGGAATAACA

AAGAGGCACTAGTCGAGTTTAAGGACGCTCACGCTAAGAGACAGACCGTAGTCGTGTTGGGGTCACAGGAGGGAGCCGTGCATACCGCA

CTAGCCGGCGCACTCGAGGCCGAAATGGACGGAGCGAAAGGGAGACTGTTTAGCGGACACCTTAAGTGTAGACTGAAAATGGACAAGTT

GCGACTTAAGGGCGTTAGCTATAGCCTATGTACCGCCGCATTTACGTTTACGAAAGTGCCAGCCGAAACGTTGCACGGAACCGTTACCG

TCGAGGTGCAATACGCCGGAACCGACGGACCATGCAAGATACCCGTGCAAATGGCCGTCGATATGCAGACACTGACACCAGTCGGACGG

TTGATTACCGCTAACCCAGTGATAACCGAGTCAACCGAAAACTCTAAGATGATGCTCGAGCTTGACCCACCATTCGGCGACTCATATAT

CGTTATCGGAGTCGGCGACAAAAAGATTACGCATCATTGGCATAGATCCGGATCGACAATCGGTAAGGCATTCGAAGCGACAGTGAGAG

GCGCTAAGCGTATGGCCGTATTGGGCGATACCGCATGGGACTTCGGATCCGTCGGCGGAGTGTTTAACTCACTCGGTAAGGGGATACAC

CAGATATTCGGAGCCGCATTCAAATCGTTGTTCGGCGGAATGTCATGGTTTAGTCAGATACTGATCGGAACACTGCTTGTGTGGTTGGG

GTTGAACACTAAGAACGGATCGATTAGTCTGACATGCTTAGCCTTAGGCGGAGTGATGATTTTTCTGTCAACCGCCGTTAGCGCAGACG

-continued

```
TGGGGTGCTCAGTGGACttctcaaaaaaggaaacgagatgtggcacgggggtattcatctataatgatgttgaagcctggagggaccgg tacaagtaccatcctgactcccccccgcagattggcagcagcagtcaagcaggcctgggaagaggggatctgtgggatctcatccgtttc aagaatggaaaacatcatgtggaaatcagtagaaggggagctcaatgctatcctagaggagaatggagttcaactgacagttgttgtgg gatctgtaaaaaacccatgtggagaggtccacaaagattgccagtgcctgtgaatgagctgccccatggctggaaagcctgggggaaa tcgtattttgttagggcggcaaagaccaacaacagttttgttgtcgacggtgacacactgaaggaatgtccgcttgagcacagagcatg gaatagttttcttgtggaggatcacgggtttggagtcttccacaccagtgtctggcttaaggtcagagaagattactcattagaatgtg acccagccgtcataggaacagctgttaagggaagggaggccgcgcacagtgatctgggctattggattgaaagtgaaaagaatgacaca tggaggctgaagagggcccacctgattgagatgaaaacatgtgaatggccaaagtctcacacattgtggacagatggagtagaagaaag tgatcttatcatacccaagtctttagctggtccactcagccaccacaacaccagagagggttacagaacccaagtgaaagggccatggc acagtgaagaActtgaaatccggtttgaggaatgtccaggcaccaaggtttacgtggaggagacatgcggaactagaggaccatctctg agatcaactactgcaagtggaagggtcattgaggaatggtgctgtagggaatgcacaatgcccccactatcgtttcgagcaaaagacgg ctgctggtatggaatggagataaggcccaggaagaaccagagagcaacttagtgaggtcaatggtgacagcggggtcaaccgatcata tggaccacttctctcttggagtgcttgtgattctactcatggtgcaggaggggttgaagaagagaatgaccacaaagatcatcatgagc acatcaatggcagtgctggtagtcatgatcttggaggattttcaatgagtgacctggccaagcttgtgatcctgatgggtgctacttt cgcagaaatgaacactggaggagatgtagctcacttggcattggtagcggcatttaaagtcagaccagccttgctggtGtccttcattt tcagagccaattggacaccccgtgagagcatgctgctagccctggcttcgtgtcttctgcaaactgcgatctctgctcttgaaggtgac ttgatggtcctcattaatggatttgattggcctggttggcaattcgagcaatggccgtgccacgcactgacaacatcgctctaccaatc ttggctgctctaacaccactagctcgaggcacactgctcgtggcatggagagcgggcctggctacttgtggagggatcatgctcctctc cctgaaagggaaaggtagtgtgaagaagaacctgccatttgtcatggccctgggattgacagctgtgagggtagtagaccctattaatg tggtaggactactgttactcacaaggagtgggaagcggagctggcccccctagtgaagttctcacagccgttggcctgatatgtgcactg gccggagggtttgccaaggcagacattgagatggctggacccatggctgcagtaggcttgctaattgtcagctatgtggtGtcgggaaa gagtgtggacatgtacattgaaagagcaggAgacatcacatgggaaaaggacgcggaagtcactggaaacagtcctcggcttgacgtgg cactggatgagagtggtgatttctccttggtagaggaagatggtccacccatgagagagatcatactcaaggtggtcctgatggccatc tgtggcatgaacccaatagctatacatttgctgcaggagcgtggtatgtgtatgtgaagactgggaaaaggagtggcgccctctgggac gtgcctgctcccaaagaagtgaagaaaggagaAaccacagatggagtgtacagagtgatgactcgcagactgctaggttcaacacaggt tggagtgggagtcatgcaagagggagtcttccacaccatgtggcacgttacaaaaggagccgcactgaggagcggtgagggaagacttg atccatactgggggatgtcaagcaggacttggtgtcatactgtgggccttggaagttggatgcagcttgggatggactcagcgaggta cagcttttggccgtacctcccggagagagggccagaaacattcagaccctgcctggaatattcaagacaaaggacggggacatcggagc agttgctctggactaccctgcaggacctcaggatctccgatcctagacaaatgtggaagagtgataggactctatggcaatggggttg tgatcaagaatggaagctatgttagtgctataacccagggaaagaggggaggaggagactccggttgaatgtttcgaaccctcgatgctg aagaagaagcagctaactgtcttggatctgcatccaggagccggaaaaaccaggagagttcttcctgaaatagtccgtgaagccataaa aaagagactccggacagtgatcttggcaccaactagggttgtcgctgctgagatggaggaggccttgagaggacttccggtgcgttaca tgacaacagcagtcaacgtcacccattctgggacagaaatcgttgatttgatgtgccatgccactttcacttcacgcttactacaaccc atcagagtccctaattacaatctcAacatcatggatgaagcccacttcacagacccctcaagtatagctgcaagaggatacatatcaac aagggttgaaatgggcgaggcggctgccattttttatgactgccacaccaccaggaacccgtgatgcgtttcctgactctaactcaccaa tcatggacacagaagtggaagtcccagagagagcctggagctcaggattgattgggtgacagaccattctgggaaaacagtttggttcg ttccaagcgtgagaaacggaaatgaaatcgcagcctgtctgacaaaggctggaaagcgggtcatacagctcagcaggaagacttttgag acagaatttcagaaaacaaaaaatcaagagtgggactttgtcataacaactgacatctcagagatgggcgccaacttcaaggctgaccg ggtcatagactctaggagatgcctaaaaccagtcatacttgatggtgagagagtcatcttggctgggcccatgcctgtcacgcatgcta gtgctgctcagaggagaggacgtataggcaggaacccctaacaaacctggagatgagtacatgtatggaggtgggtgtgcagagactgat gaaggccatgcacactggcttgaagcaagaatgcttcttgacaacatctacctccaggatggcctcatagcctcgctctatcggcctga
```

-continued

```
ggccgataaggtagccgccattgagggagagtttaagctgaggacagagcaaaggaagaccttcgtggaactcatgaagagaggGgacc
ttcccgtctggctagcctatcaggttgcatctgccggaataacttacacagacagaagatggtgctttgatggcacaaccaacaacacc
ataatggaagacagcgtaccagcagaggtgtggacaaagtatggagagaagagagtgctcaaaccgagatggatggatgctagggtctg
ttcagaccatgcggccctgaagtcgttcaaagaattcgccgctgaaaaagaggagcggattgggagtaatggaggccctgggaacact
gccaggacacatgacagagaggtttcaggaagccattgacaacctcgccgtgctcatgcgagcagagactggaagcaggccttataagg
cagcggcagcccaactgccggagacTctagagacAattatgctcttaggtttgctgggaacagtttcactggggatcttcttcgtcttg
atgcggaataagggcatcgggaagatgggattggaatggtaaccctt ggggccagtgcatggctcatgtggattcggaaattgaaccag
ccagaattgcatgtgtcctcattgttgtgttttattactggtggtgctcatacccgagccagagaagcaaagatctccccaagataac
cagatggcaattatcatcatggtggcagtgggccttctaggtttgataactgcaaacgaacttggatggctggaaagaacaaaaatga
catagctcatctaatgggaaggagagaagaaggagcaaccatgggattctcaatggacattgatctgcggccagcctccgcctgggcta
tctatgccgcattgacaactctcatcaccccagctgtccaacatgcggtaaccacttcatacaacaactactccttaatggcgatggcc
acacaagctggagtgagtttggcatgggcaaagggatgccatttttatgcatgggaccttggagtcccgctgctaatgatgggttgctat
tcacaattaacacccctgactctgatagtagctatcattctgcttgtggcgcactacatgtacttgatcccaggcctacaagcggcagc
agcgcgtgctgcccagaaaaggacagcagctggcatcatgaagaatcccgttgtggatggaatagtggtaactgacattgacacaatga
caatagacccccaggtggagaagaagatgggacaagtgttactcatagcagtagccatctccagtgctgtgctgctgcggaccgcctgg
ggatggggggaggctggagctctgatcacagcagcgacctccaccttgtgggaaggctctccaaacaaatactggaactcctctacagc
cacctcactgtgcaacatcttcagaggaagctatctggcaggagcttcccttatctatacagtgacgagaaacgctggcctggttaaga
gacgtggaggtgggacgggagagactctgggagagaagtggaaagctcgtctgaatcagatgtcggccctggagttctactcttataaa
aagtcaggtatcactgaagtgtgtagagaggaggctcgccgtgccctcaaggatggagtggccacaggaggacatgccgtatcccgggg
aagtgcaaagctcagatggttggtggagagaggatatctgcagccctatgggaaggttgttgacctcggatgtggcagaggggggctgga
gctattatgccgccaccatccgcaaagtgcaggaggtgagaggatacacaaagggaggtcccggtcatgaagaacccatgctggtgcaa
agctatgggtggaacatagttcgtctcaagagtggagtggacgtcttccacatggcggctgagccgtgtgacactctgctgtgtgacat
aggtgagtcatcatctagtcctgaagtggaagagacacgaacactcagagtgctctctatggtggggactggcttgaaaaaagaccag
gggccttctgtataaaggtgctgtgcccatacaccagcactatgatggaaaccatggagcgactgcaacgtaggcatgggggaggatta
gtcagagtgccattgtctcgcaactccacacatgagatgtactgggtGtctggggcaaagagcaacatcataaaagtgtgtccaccac
aagtcagctcctcctgggacgcatggatggccccaggaggccagtgaaatatgaggaggatgtgaacctcggctcgggtacacgagctg
tggcaagctgtgctgaggctcctaacatgaaaatcatcggcaggcgcattgagagaatccgcaatgaacatgcagaaacatggtttctt
gatgaaaaccacccatacaggacatgggcctaccatgggagctacgaagcccccacgcaaggatcagcgtcttccctcgtgaacggggt
tgttagactcctgtcaaagccttgggacgtggtgactggagttacaggaatagccatgactgacaccacaccatacggccaacaaagag
tcttcaaagaaaaagtggacaccagggtgccagatccccaagaaggcactcgccaggtaatgaacatagtctcttcctggctgtggaag
gagctggggaaacgcaagcggccacgcgtctgcaccaaagaagagtttatcaacaaggtgcgcagcaatgcagcactgggagcaatatt
tgaagaggaaaaagaatggaagacggctgtggaagctgtgaatgatccaaggttttgggccctagtggatagggagagagaacaccacc
tgagaggagagtgtcacagctgtgtgtacaacatgatgggaaaaagagaaaagaagcaaggagagttcgggaaagcaaaaggtagccgc
gccatctggtacatgtggttgggagccagattcttggagtttgaagcccttggattcttgaacgaggaccattggatgggaagagaaaa
ctcaggaggtggagtcgaagggttaggattgcaaagacttggatacattctagaagaaatgaatcggcaccaggaggaaagatgtacg
cagatgacactgctggctgggacacccgcattagtaagtttgatctggagaatgaagctctgattaccaaccaaatggaggaagggcac
agaactctggcgttggccgtgattaaatacacataccaaaacaaagtggtgaaggttctcagaccagctgaaggaggaaaaacagttat
ggacatcatttcaagacaagaccagagagggagtggacaagttgtcacttatgctctcaacacattccaccttggtggtgcagctta
tccggaacatggaagctgaggaagtgttagagatgcaagacttatggttgttgaggaagccagagaaagtgaccagatggttgcagagc
aatggatgggatagactcaaacgaatggcggtcagtggagatgactgcgttgtgaagccaatcgatgataggtttgcacatgccctcag
```

-continued gttcttgaatgacatgggaaaagttaggaaagacacacaggagtggaaaccctcgactggatggagcaattgggaagaagtcccgttct gctcccaccacttcaacaagctgtacctcaaggatgggagatccattgtggtcccttgccgccaccaagatgaactgattggccgagct cgcgtctcaccaggggcaggatggagcatccgggagactgcctgtcttgcaaaatcatatgcgcagatgtggcagctcctttatttcca cagaagGgaccttcgactgatggctaatgccatttgctcggctgtgccagttgactgggtTccaactgggagaaccacctggtcaatcc atggaaagggagaatggatgaccactgaggacatgctcatggtgtggaatagagtgtggattgaggagaacgaccatatggaggacaag actcctgtaacaaaatggacagacattccctatctaggaaaaagggaggacttatggtgtggatcccttatagggcacagaccccgcac cacttgggctgaaaacatcaaagacacagtcaacatggtgcgcaggatcataggtgatgaagaaaagtacatggactatctatccaccc aagtccgctacttgggtgaggaagggtccacacccggagtgttgtaagcaccaattttagtgttgtcaggcctgctagtcagccacagt ttggggaaagctgtgcagcctgtaaccccccaggagaagctgggaaaccaagctcatagtcaggccgagaacgccatggcacggaaga agccatgctgcctgtgagcccctcagaggacactgagtcaaaaaacccccacgcgcttggaagcgcaggatgggaaaagaaggtggcgac cttccccacccttcaatctggggcctgaactggagactagctgtgaatctccagcagagggactagtggttagaggagaccccccggaa aacgcacaacagcatattgacgctgggaaagaccagagactccatgagtttccaccacgctggccgccaggcacagatcgccgaacTTC

GGCGGCCGGTGTGGGGAAATCCATGGTTTCT

MR766 E-W/Min

SEQ ID NO: 8
AGTTGTTgatctgtgtgagtcagactgcgacagttcgagtctgaagcgagagctaacaacagtatcaacaggtttaatttggatttgga aacgagagtttctggtcatgaaaaacccaaagaagaaatccggaggattccggattgtcaatatgctaaaacgcggagtagcccgtgta aacccctttggggaggtttgaagaggttgccagccggacttctgctgggtcatggacccatcagaatggttttggcgatactagccttttt gagatttacagcaatcaagccatcactgggccttatcaacagatggggttccgtggggaaaaaagaggctatggaaataataaagaagt tcaagaaagatcttgctgccatgttgagaataatcaatgctaggaaagagaggaagagacgtggcgcagacaccagcatcggaatcatt ggcctcctgctgactacagccatggcagcagagatcactagacgcgggagtgcatactacatgtacttggataggagcgatgccgggaa ggccatttcgtttgctaccacattgggagtgaacaagtgccacgtacagatcatggacctcgggcacatgtgtgacgccaccatgagtt atgagtgccctatgctggatgagggagtggaaccagatgatgtcgattgctggtgcaacacgacatcaacttgggttgtgtacggaacc tgtcatcacaaaaaaggtgaggcacggcgatctagGagagccgtgacgctcccttctcactctacaaggaagttgcaaacgcggtcgca gacctggttagaatcaagagaatacacgaagcacttgatcaaggttgaaaactggatattcaggaaccccgggtttgcgctagtggccg ttgccattgcctggctttttgggaagctcgacgagccaaaaagtcatatacttggtcatgatactgctgattgccccggcatacagtatc aggtgcattggagtcagcaatagagacttcgtggagggcatgtcaggtgggacctgggttgatgttgtcttggaacatggaggctgcgt taccgtgatggcacaggacaagccaacagttgacatagagttggtcacgacgacggttagtaacatggccgaggtaagatcctattgct acgaggcatcgatatcggacatggcttcggacagtcgttgcccaacacaaggtgaagcctaccttgacaagcaatcagacactcaatat gtctgcaaaagaacattagtggacagaggttggggaaacggttgtggactttttggcaaagggagcttggtgacatgtgccaagtttac gtgttctaagaagatgaccggCaagagcattcaaccggaaaatctggagtatcggataatgctatcagtgcatggctcccagcatagcg ggatgattgtcaatgatacaggatatgaaactgacgaaaatagagcgaaagtcgaggttacgCCTAACTCACCTAGAGCCGAAGCGACA TTGGGGGGGTTCGGATCTCTCGGACTGGATTGCGAACCTAGAACCGGATTGGACTTTAGCGATCTGTACTATCTGACTATGAACAATAA GCATTGGTTGGTGCATAAGGAGTGGTTTCACGACATACCACTGCCATGGCACGCCGGAGCCGATACCGGTACGCCACATTGGAATAACA AAGAGGCACTAGTCGAGTTTAAGGACGCTCACGCTAAGAGACAGACCGTAGTCGTGTTGGGGTCACAGGAGGGAGCCGTGCATACCGCA CTAGCCGGCGCACTCGAGGCCGAAATGGACGGAGCGAAAGGGAGACTGTTTAGCGGACACCTTAAGTGTAGACTGAAAATGGACAAGTT GCGACTTAAGGGCGTTAGCTATAGCCTATGTACCGCCGCATTTACGTTTACGAAAGTGCCAGCCGAAACGTTGCACGGAACCGTTACCG TCGAGGTGCAATACGCCGGAACCGACGGACCATGCAAGATACCCGTGCAAATGGCCGTCGATATGCAGACACTGACACCAGTCGGACGG TTGATTACCGCTAACCCAGTGATAACCGAGTCAACCGAAAACTCTAAGATGATGCTCGAGCTTGACCCACCATTCGGCGACTCATATAT CGTTATCGGAGTCGGCGACAAAAAGATTACGCATCATTGGCATAGATCCGGATCGACAATCGGTAAGGCATTCGAAGCGACAGTGAGAG GCGCTAAGCGTATGGCCGTATTGGGCGATACCGCATGGGACTTCGGATCCGTCGGCGGAGTGTTTAACTCACTCGGTAAGGGGATACAC CAGATATTCGGAGCCGCATTCAAATCGTTGTTCGGCGGAATGTCATGGTTTAGTCAGATACTGATCGGAACACTGCTTGTGTGGTTGGG -continued

```
GTTGAACACTAAGAACGGATCGATTAGTCTGACATGCTTAGCCTTAGGCGGAGTGATGATTTTTCTGTCAACCGCCGTTAGCGCAGACG
TGGGGTGCTCAGTGGACTTCTCAAAAAAGGAAACGAGATGTGGCACGGGGGTATTCATCTATAATGATGTTGAAGCCTGGAGGGACCGG
TACAAGTACCATCCTGACTCCCCCCGCAGATTGGCAGCAGCAGTCAAGCAGGCCTGGGAAGAGGGGATCTGTGGGATCTCATCCGTTTC
AAGAATGGAAAACATCATGTGGAAATCAGTAGAAGGGAGCTCAATGCTATCCTAGAGGAGAATGGAGTTCAACTGACAGTTGTTGTGG
GATCTGTAAAAAACCCCATGTGGAGAGGTCCACAAAGATTGCCAGTGCCTGTGAATGAGCTGCCCCATGGCTGGAAAGCCTGGGGGAAA
TCGTATTTTGTTAGGGCGGCAAAGACCAACAACAGTTTTGTTGTCGACGGTGACACACTGAAGGAATGTCCGCTTGAGCACAGAGCATG
GAATAGTTTTCTTGTGGAGGATCACGGGTTTGGAGTCTTCCACACCAGTGTCtggcttaaggtcagagaagattactcattagaatgtg
acccagccgtcataggaacagctgttaagggaagggaggccgcgcacagtgatctgggctattggattgaaagtgaaaagaatgacaca
tggaggctgaagagggcccacctgattgagatgaaaacatgtgaatggccaaagtctcacacattgtggacagatggagtagaagaaag
tgatcttatcatacccaagtctttagctggtccactcagccaccacaacaccagagagggttacagaacccaagtgaaagggccatggc
acagtgaagaActtgaaatccggtttgaggaatgtccaggcaccaaggtttacgtggaggagacatgcggaactagaggaccatctctg
agatcaactactgcaagtggaagggtcattgaggaatggtgctgtagggaatgcacaatgccccactatcgtttcgagcaaaagacgg
ctgctggtatggaatggagataaggcccaggaaagaaccagagagcaacttagtgaggtcaatggtgacagcggggtcaaccgatcata
tggaccacttctctcttggagtgcttgtgattctactcatggtgcaggaggggttgaagaagagaatgaccacaaagatcatcatgagc
acatcaatggcagtgctggtagtcatgatcttggaggattttcaatgagtgacctggccaagcttgtgatcctgatgggtgctacttt
cgcagaaatgaacactggaggagatgtagctcacttggcattggtagcggcatttaaagtcagaccagccttgctggtGtccttcattt
tcagagccaattggacaccccgtgagagcatgctgctagccctggcttcgtgtcttctgcaaactgcgatctctgctcttgaaggtgac
ttgatggtcctcattaatggatttgctttggcctggttggcaattcgagcaatggccgtgccacgcactgacaacatcgctctaccaat
cttggctgctctaacaccactagctcgaggcacactgctcgtggcatggagagcgggcctggctacttgtggagggatcatgctcctct
ccctgaaagggaaaggtagtgtgaagaagaacctgccatttgtcatggccctgggattgacagctgtgagggtagtagaccctattaat
gtggtaggactactgttactcacaaggagtgggaagcggagctggcccctagtgaagttctcacagccgttggcctgatatgtgcact
ggccggagggttgccaaggcagacattgagatggctggacccatggctgcagtaggcttgctaattgtcagctatgtggtGtcgggaa
agagtgtggacatgtacattgaaagagcaggAgacatcacatgggaaaaggacgcggaagtcactggaaacagtcctcggcttgacgtg
gcactggatgagagtggtgatttctccttggtagaggaagatggtccacccatgagagagatcatactcaaggtggtcctgatggccat
ctgtggcatgaacccaatagctataccttttgctgcaggagcgtggtatgtgtatgtgaagactgggaaaaggagtggcgccctctggg
acgtgcctgctcccaaagaagtgaagaaaggagaAaccacagatggagtgtacagagtgatgactcgcagactgctaggttcaacacag
gttggagtgggagtcatgcaagagggagtcttccacaccatgtggcacgttacaaaaggagccgcactgaggagcggtgagggaagact
tgatccatactgggggatgtcaagcaggacttggtgtcatactgtgggccttggaagttggatgcagcttgggatggactcagcgagg
tacagcttttggccgtacctcccggagagagggccagaaacattcagaccctgcctggaatattcaagacaaaggacggggacatcgga
gcagttgctctggactaccctgcagggacctcaggatctccgatcctagacaaatgtggaagagtgataggactctatggcaatgggt
tgtgatcaagaatggaagctatgttagtgctataacccagggaaagagggaggaggagactccggttgaatgtttcgaaccctcgatgc
tgaagaagaagcagctaactgtcttggatctgcatccaggagccggaaaaaccaggagagttcttcctgaaatagtccgtgaagccata
aaaaagagactccggacagtgatcttggcaccaactagggttgtcgctgctgagatggaggaggccttgagaggacttccggtgcgtta
catgacaacagcagtcaacgtcacccattctgggacagaaatcgttgatttgatgtgccatgccactttcacttcacgcttactacaac
ccatcagagtccctaattacaatctcAacatcatggatgaagcccacttcacagacccctcaagtatagctgcaagaggatacatatca
acaagggttgaaatgggcgaggcggctgccatttttatgactgccacaccaccaggaacccgtgatgcgtttcctgactctaactcacc
aatcatggacacagaagtgaagtcccagagagagcctggagctcaggattgattgggtgacagaccattctgggaaaacagtttggtt
cgttccaagcgtgagaaacggaaatgaaatcgcagcctgtctgacaaaggctggaaagcgggtcatacagctcagcaggaagacttttg
agacagaatttcagaaaacaaaaaatcaagagtgggactttgtcataacaactgacatctcagagatgggcgccaacttcaaggctgac
cgggtcatagactctaggagatgcctaaaaccagtcatacttgatggtgagagagtcatcttggctgggcccatgcctgtcacgcatgc
```

-continued

```
tagtgctgctcagaggagaggacgtataggcaggaaccctaacaaacctggagatgagtacatgtatggaggtgggtgtgcagagactg
atgaaggccatgcacactggcttgaagcaagaatgcttcttgacaacatctacctccaggatggcctcatagcctcgctctatcggcct
gaggccgataaggtagccgccattgagggagagtttaagctgaggacagagcaaaggaagaccttcgtggaactcatgaagagaggGga
ccttcccgtctggctagcctatcaggttgcatctgccggaataacttacacagacagaagatggtgattgatggcacaaccaacaacac
cataatggaagacagcgtaccagcagaggtgtggacaaagtatggagagaagagagtgctcaaaccgagatggatggatgctagggtct
gttcagaccatgcggccctgaagtcgttcaaagaattcgccgctggaaaaagaggagcggctttgggagtaatggaggccctgggaaca
ctgccaggacacatgacagagaggtttcaggaagccattgacaacctcgccgtgctcatgcgagcagagactggaagcaggccttataa
ggcagcggcagcccaactgccggagacTctagagacAattatgctcttaggtttgctgggaacagtttcactggggatcttcttcgtct
tgatgcggaataagggcatcggaagatgggattggaatggtaacccttggggccagtgcatggctcatgtggctttcggaaattgaac
cagccagaattgcatgtgtcctcattgttgtgttttattactggtggtgctcataccgagccagagaagcaaagatctccccaagat
aaccagatggcaattatcatcatggtggcagtgggccttctaggtttgataactgcaaacgaacttggatggctggaaagaacaaaaaa
tgacatagctcatctaatgggaaggagagaagaaggagcaaccatgggattctcaatggacattgatctgcggccagcctccgcctggg
ctatctatgccgcattgacaactctcatcaccccagctgtccaacatgcggtaaccacttcatacaacaactactccttaatggcgatg
gccacacaagctggagtgctgtttggcatgggcaaagggatgccatttatgcatgggaccttggagtcccgctgctaatgatgggttg
ctattcacaattaacaccccctgactctgatagtagctatcattctgcttgtggcgcactacatgtacttgatcccaggcctacaagcgg
cagcagcgcgtgctgcccagaaaaggacagcagctggcatcatgaagaatcccgttgtggatggaatagtggtaactgacattgacaca
atgacaatagaccccccaggtggagaagaagatgggacaagtgttactcatagcagtagccatctccagtgctgtgctgctgcggaccgc
ctggggatggggggaggctggagctctgatcacagcagcgacctccaccttgtgggaaggctctccaaacaaatactggaactcctcta
cagccacctcactgtgcaacatcttcagaggaagctatctggcaggagcttcccttatctatacagtgacgagaaacgctggcctggtt
aagagacgtggaggtgggacgggagagactctgggagagaagtggaaagctcgtctgaatcagatgtcggccctggagttctactctta
taaaaagtcaggtatcactgaagtgtgtagagaggaggctcgccgtgccctcaaggatggagtggccacaggaggacatgccgtatccc
ggggaagtgcaaagctcagatggttggtggagagaggatatctgcagcccatgggaaggttgttgacctcggatgtggcagaggggc
tggagctattatgccgccaccatccgcaaagtgcaggaggtgagaggatacacaaagggaggtcccggtcatgaagaacccatgctggt
gcaaagctatgggtggaacatagttcgtctcaagagtggagtggacgtcttccacatggcggctgagccgtgtgacactctgctgtgtg
acataggtgagtcatcatctagtcctgaagtggaagagacacgaacactcagagtgctctctatggtgggggactggcttgaaaaaaga
ccaggggccttctgtataaaggtgctgtgcccatacaccagcactatgatggaaaccatggagcgactgcaacgtaggcatgggggagg
attagtcagagtgccattgtctcgcaactccacacatgagatgtactgggtGtctggggcaaagagcaacatcataaaaagtgtgtcca
ccacaagtcagctcctcctgggacgcatggatggccccaggaggccagtgaaatatgaggaggatgtgaacctcggctcgggtacacga
gctgtggcaagctgtgctgaggctcctaacatgaaaatcatcggcaggcgcattgagagaatccgcaatgaacatgcagaaacatggtt
tcttgatgaaaaccacccatacaggacatgggcctaccatgggagctacgaagcccccacgcaaggatcagcgtcttccctcgtgaacg
gggttgttagactcctgtcaaagccttgggacgtggtgactggagttacaggaatagccatgactgacaccacaccatacgccaacaa
agagtcttcaaagaaaaagtggacaccagggtgccagatccccaagaaggcactcgccaggtaatgaacatagtctcttcctggctgtg
gaaggagctggggaaacgcaagcggccacgcgtctgcaccaaagaagagtttatcaacaaggtgcgcagcaatgcagcactgggagcaa
tatttgaagaggaaaaagaatggaagacggctgtggaagctgtgaatgatccaaggttttgggccctagtggatagggagagagaacac
cacctgagaggagagtgtcacagctgtgtgtacaacatgatgggaaaaagagaaaagaagcaaggagagttcgggaaagcaaaaggtag
ccgcgccatctggtacatgtggttgggagccagattcttggagtttgaagcccttggattcttgaacgaggaccattggatgggaagag
aaaactcaggaggtggagtcgaagggttaggattgcaaagacttggatacattctagaagaaatgaatcgggcaccaggaggaaagatg
tacgcagatgacactgctggctgggacacccgcattagtaagtttgatctggagaatgaagctctgattaccaaccaaatggaggaagg
gcacagaactctggcgttggccgtgattaaatacacataccaaaacaaagtggtgaaggttctcagaccagctgaaggaggaaaaacag
ttatggacatcatttcaagacaagaccagagagggagtggacaagttgtcacttatgctctcaacacattcaccaacttggtggtgcag
cttatccggaacatggaagctgaggaagtgttagagatgcaagacttatggttgttgaggaagccagagaaagtgaccagatggttgca
``` gagcaatggatgggatagactcaaacgaatggcggtcagtggagatgactgcgttgtgaagccaatcgatgataggtttgcacatgccc tcaggttcttgaatgacatgggaaaagttaggaaagacacacaggagtggaaaccctcgactggatggagcaattgggaagaagtcccg ttctgctcccaccacttcaacaagctgtacctcaaggatgggagatccattgtggtcccttgccgccaccaagatgaactgattggccg agctcgcgtctcaccagggcaggatggagcatccgggagactgcctgtcttgcaaaatcatatgcgcagatgtggcagctcctttatt tccacagaagGgaccttcgactgatggctaatgccatttgctcggctgtgccagttgactgggTccaactgggagaaccacctggtca atccatggaaagggagaatggatgaccactgaggacatgctcatggtgtggaatagagtgtggattgaggagaacgaccatatggagga caagactcctgtaacaaatggacagacattccctatctaggaaaaagggaggacttatggtgtggatcccttatagggcacagacccc gcaccacttgggctgaaaacatcaaagacacagtcaacatggtgcgcaggatcataggtgatgaagaaaagtacatggactatctatcc acccaagtccgctacttgggtgaggaagggtccacacccggagtgttgtaagcaccaattttagtgttgtcaggcctgctagtcagcca cagtttggggaaagctgtgcagcctgtaaccccccaggagaagctggggaaccaagctcatagtcaggccgagaacgccatggcacgg aagaagccatgctgctgtgagcccctcaggagacactgagtcaaaaaaccccacgcgcttggaagcgcaggatgggaaaagaaggtgg cgaccttccccaccccttcaatctggggcctgaactggagactagctgtgaatctccagcagagggactagtggttagaggagacccccc ggaaaacgcacaacagcatattgacgctgggaagaccagagactccatgagtttccaccacgctggccgccaggcacagatcgccgaa cTTCGGCGGCCGGTGTGGGGAAATCCATGGTTTCT

MR766 E-W/

```
GCGCTAAGCGTATGGCCGTATTGGGCGATACCGCATGGGACTTCGGATCCGTCGGCGGAGTGTTTAACTCACTCGGTAAGGGGATACAC
CAGATATTCGGAGCCGCATTCAAATCGTTGTTCGGCGGAATGTCATGGTTTAGTCAGATACTGATCGGAACACTGCTTGTGTGGTTGGG
GTTGAACACTAAGAACGGATCGATTAGTCTGACATGCTTAGCCTTAGGCGGAGTGATGATTTTTCTGTCAACCGCCGTTAGCGCAGACG
TGGGGTGCTCAGTGGACTTCTCAAAAAAGGAAACGAGATGTGGCACGGGGGTATTCATCTATAATGATGTTGAAGCCTGGAGGGACCGG
TACAAGTACCATCCTGACTCCCCCCGCAGATTGGCAGCAGCAGTCAAGCAGGCCTGGGAAGAGGGGATCTGTGGGATCTCATCCGTTTC
AAGAATGGAAAACATCATGTGGAAATCAGTAGAAGGGAGCTCAATGCTATCCTAGAGGAGAATGGAGTTCAACTGACAGTTGTTGTGG
GATCTGTAAAAAACCCCATGTGGAGAGGTCCACAAAGATTGCCAGTGCCTGTGAATGAGCTGCCCCATGGCTGGAAAGCCTGGGGGAAA
TCGTATTTTGTTAGGGCGGCAAAGACCAACAACAGTTTTGTTGTCGACGGTGACACACTGAAGGAATGTCCGCTTGAGCACAGAGCATG
GAATAGTTTTCTTGTGGAGGATCACGGGTTTGGAGTCTTCCACACCAGTGTCtggcttaaggtcagagaagattactcattagaatgtg
acccagccgtcataggaacagctgttaagggaagggaggccgcgcacagtgatctgggctattggattgaaagtgaaaagaatgacaca
tggaggctgaagagggcccacctgattgagatgaaaacatgtgaatggccaaagtctcacacattgtggacagatggagtagaagaaag
tgatcttatcatacccaagtctttagctggtccactcagccaccacaacaccagagagggttacagaacccaagtgaaagggccatggc
acagtgaagaActtgaaatccggtttgaggaatgtccaggcaccaaggtttacgtggaggagacatgcggaactagaggaccatctctg
agatcaactactgcaagtggaagggtcattgaggaatggtgctgtagggaatgcacaatgcccccactatcgtttcgagcaaaagacgg
ctgctggtatggaatggagataaggcccaggaaagaaccagagagcaacttagtgaggtcaatggtgacagcggggtcaaccgatcata
tggaccacttctctcttggagtgcttgtgattctactcatggtgcaggaggggttgaagaagagaatgaccacaaagatcatcatgagc
acatcaatggcagtgctggtagtcatgatcttggaggattttcaatgagtgacctggccaagcttgtgatcctgatgggtgctactttt
cgcagaaatgaacactggaggagatgtagctcacttggcattggtagcggcatttaaagtcagaccagccttgctggtGtccttcatttt
tcagagccaattggacacccgtgagagcatgctgctagccctggcttcgtgtcttctgcaaactgcgatctctgctcttgaaggtgac
ttgatggtcctcattaatggatttgctttggcctggttggcaattcgagcaatggccgtgccacgcactgacaacatcgctctaccaat
cttggctgctctaacaccactagctcgaggcacactgctcgtggcatggagagcgggcctggctacttgtggagggatcatgctcctct
ccctgaaagggaaaggtagtgtgaagaagaacctgccatttgtcatggccctgggattgacagctgtgagggtagtagaccctattaat
gtggtaggactactgttactcacaaggagtgggaagcggagctggcccctagtgaagttctcacagccgttggcctgatatgtgcact
ggccggagggtttgccaaggcagacattgagatggctggacccatggctgcagtaggcttgctaattgtcagctatgtggtGtcgggaa
agagtgtggacatgtacattgaaagagcaggAgacatcacatgggaaaaggacgcggaagtcactggaaacagtcctcggccttgacgtg
gcactggatgagagtggtgatttctccttggtagaggaagatggtccacccatgagagagatcatactcaaggtggtcctgatggccat
ctgtggcatgaacccaatagctataccttttgctgcaggagcgtggtatgtgtatgtgaagactgggaaaaggagtggcgccctctggg
acgtgcctgctcccaaagaagtgaagaaaggagaAaccacagatggagtgtacagagtgatgactcgcagactgctaggttcaacacag
gttggagtgggagtcatgcaagagggagtcttccacaccatgtggcacgttacaaaaggagccgcactgaggagcggtgagggaagact
tgatccatactgggggatgtcaagcaggacttggtgtcatactgtgggccttggaagttggatgcagcttgggatggactcagcgagg
tacagcttttggccgtacctcccggagagagggccagaaacattcagaccctgcctggaatattcaagacaaaggacggggacatcgga
gcagttgctctggactaccctgcagggacctcaggatctccgatcctagacaaatgtggaagagtgataggactctatggcaatgggt
tgtgatcaagaatggaagctatgttagtgctataacccagggaaagaggaggaggagactccggttgaatgtttcgaaccctcgatgc
tgaagaagaagcagctaactgtcttggatctgcatccaggagccggaaaaaccaggagagttcttcctgaaatagtccgtgaagccata
aaaaagagactccggacagtgatcttggcaccaactagggttgtcgctgctgagatggaggaggccttgagaggacttccggtgcgtta
catgacaacagcagtcaacgtcacccattctgggacagaaatcgttgatttgatgtgccatgccactttcacttcacgcttactacaac
ccatcagagtccctaattacaatctcAacatcatggatgaagcccacttcacagacccctcaagtatagctgcaagaggatacatatca
acaagggttgaaatgggcgaggcggctgccattttatgactgccacaccaccaggaacccgtgatgcgtttcctgactctaactcacc
aatcatggacacagaagtggaagtcccagagagagcctggagctcaggattgattgggtgacagaccattctgggaaaacagtttggtt
cgttccaagcgtgagaaacggaaatgaaatcgcagcctgtctgacaaaggctggaaagcgggtcatacagctcagcaggaagacttttg
agacagaatttcagaaaacaaaaaatcaagagtgggactttgtcataacaactgacatctcagagatgggcgccaacttcaaggctgac
```

-continued

```
cgggtcatagactctaggagatgcctaaaaccagtcatacttgatggtgagagagtcatcttggctgggcccatgcctgtcacgcatgc
tagtgctgctcagaggagaggacgtataggcaggaaccctaacaaacctggagatgagtacatgtatggaggtgggtgtgcagagactg
atgaaggccatgcacactggcttgaagcaagaatgcttcttgacaacatctacctccaggatggcctcatagcctcgctctatcggcct
gaggccgataaggtagccgccattgagggagagtttaagctgaggacagagcaaaggaagaccttcgtggaactcatgaagagaggGga
ccttcccgtctggctagcctatcaggttgcatctgccggaataacttacacagacagaagatggtgctttgatggcacaaccaacaaca
ccataatggaagacagcgtaccagcagaggtgtggacaaagtatggagagaagagagtgctcaaaccgagatggatggatgctagggtc
tgttcagaccatgcggccctgaagtcgttcaaagaattcgccgctggaaaaagaggagcggattgggagtaatggaggccctgggaaca
ctgccaggacacatgacagagaggtttcaggaagccattgacaacctcgccgtgctcatgcgagcagagactggaagcaggccttataa
ggcagcggcagcccaactgccggagacTctagagacAattatgctcttaggtttgctgggaacagtttcactggggatcttcttcgtct
tgatgcgaataagggcatcggaagatgggattggaatggtaaccttggggccagtgcatggctcatgtggattcggaaattgaacc
agccagaattgcatgtgtcctcattgttgtgttttattactggtggtgctcatacccgagccagagaagcaaagatctccccaagata
accagatggcaattatcatcatggtggcagtgggccttctaggtttgataactgcaaacgaacttggatggctgaaagaacaaaaaat
gacatagctcatctaatgggaaggagagaagaaggagcaaccatgggattctcaatggacattgatctgcggccagcctccgcctgggc
tatctatgccgcattgacaactctcatcaccccagctgtccaacatgcggtaaccacttcataacaactactccttaatggcgatgg
ccacacaagctggagtgctgtttggcatgggcaaagggatgccatttatgcatgggaccttggagtcccgctgctaatgatgggttgc
tattcacaattaacaccctgactctgatagtagctatcattctgcttgtggcgcactacatgtacttgatcccaggcctacaagcggc
agcagcgcgtgctgcccagaaaaggacagcagctggcatcatgaagaatcccgttgtggatggaatagtggtaactgacattgacacaa
tgacaatagaccccaggtggagaagaagatgggacaagtgttactcatagcagtagccatctccagtgctgtgctgctgcggaccgcc
tggggatgggggaggctggagctctgatcacagcagcgacctccaccttgtgggaaggctctccaaacaaatactggaactcctctac
agccacctcactgtgcaacatcttcagaggaagctatctggcaggagcttcccttatctatacagtgacgagaaacgctggcctggtta
agagacgtggaggtgggacgggagagactctgggagagaagtggaaagctcgtctgaatcagatgtcggccctggagttctactcttat
aaaaagtcaggtatcactgaagtgtgtagagaggaggctcgccgtgccctcaaggatggagtggccacaggaggacatgccgtatcccg
gggaagtgcaaagctcagatggttggtggagagaggatatctgcagcccatgggaaggttgttgacctcggatgtggcagagggggct
ggagctattatgccgccaccatccgcaaagtgcaggaggtgagaggatacacaaagggaggtcccggtcatgaagaacccatgctggtg
caaagctatgggtggaacatagttcgtctcaagagtggagtggacgtcttccacatggcggctgagccgtgtgacactctgctgtgtga
cataggtgagtcatcatctagtcctgaagtggaagagacacgaacactcagagtgctctctatggtgggggactggcttgaaaaaagac
caggggccttctgtataaaggtgctgtgcccatacaccagcactatgatggaaaccatggagcgactgcaacgtaggcatggggagga
ttagtcagagtgccattgtctcgcaactccacacatgagatgtactgggtGtctggggcaaagagcaacatcataaaaagtgtgtccac
cacaagtcagctcctcctgggacgcatggatggcccaggaggccagtgaaatatgaggaggatgtgaacctcggctcgggtacacgag
ctgtggcaagctgtgctgaggctcctaacatgaaaatcatcggcaggcgcattgagagaatccgcaatgaacatgcagaaacatggttt
cttgatgaaaaccacccatacaggacatgggcctaccatgggagctacgaagcccccacgcaaggatcagcgtcttccctcgtgaacgg
ggttgttagactcctgtcaaagccttgggacgtggtgactggagttacaggaatagccatgactgacaccacaccatacggccaacaaa
gagtcttcaaagaaaaagtggacaccagggtgccagatccccaagaaggcactcgccaggtaatgaacatagtctcttcctggctgtgg
aaggagctggggaaacgcaagcggccacgcgtctgcaccaaagaagagtttatcaacaaggtgcgcagcaatgcagcactgggagcaat
atttgaagaggaaaaagaatggaagacggctgtggaagctgtgaatgatccaaggttttgggccctagtggataggagagagaacacc
acctgagaggagagtgtcacagctgtgtgtacaacatgatgggaaaaagagaaaagaagcaaggagagttcgggaaagcaaaaggtagc
cgcgccatctggtacatgtggttgggagccagattcttggagtttgaagcccttggattcttgaacgaggaccattggatgggaagaga
aaactcaggaggtggagtcgaagggttaggattgcaaagacttggatacattctagaagaaatgaatcgggcaccaggaggaaagatgt
acgcagatgacactgctggctgggacacccgcattagtaagtttgatctggagaatgaagctctgattaccaaccaaatggaggaaggg
cacagaactctggcgttggccgtgattaaatacacataccaaaacaaagtggtgaaggttctcagaccagctgaaggaggaaaaacagt
```

-continued tatggacatcatttcaagacaagaccagagagggagtggacaagttgtcacttatgctctcaacacattcaccaacttggtggtgcagc ttatccggaacatggaagctgaggaagtgttagagatgcaagacttatggttgttgaggaagccagagaaagtgaccagatggttgcag agcaatggatgggatagactcaaacgaatggcggtcagtggagatgactgcgttgtgaagccaatcgatgataggtttgcacatgccct caggttcttgaatgacatgggaaaagttaggaaagacacacaggagtggaaaccctcgactggatggagcaatgggaagaagtcccgt tctgctcccaccacttcaacaagctgtacctcaaggatgggagatccattgtggtccccttgccgccaccaagatgaactgattggccga gctcgcgtctcaccaggggcaggatggagcatccgggagactgcctgtcttgcaaaatcatatgcgcagatgtggcagctcctttattt ccacagaagGgaccttcgactgatggctaatgccatttgctcggctgtgccagttgactgggtTccaactgggagaaccacctggtcaa tccatggaaagggagaatggatgaccactgaggacatgctcatggtgtggaatagagtgtggattgaggagaacgaccatatggaggac aagactcctgtaacaaaatggacagacattccctatctaggaaaaagggaggacttatggtgtggatcccttatagggcacagacccccg caccacttgggctgaaaacatcaaagacacagtcaacatggtgcgcaggatcataggtgatgaagaaaagtacatggactatctatcca cccaagtccgctacttgggtgaggaagggtccacacccgagtgttgtaagcaccaattttagtgttgtcaggcctgctagtcagccac agtttggggaaagctgtgcagcctgtaaccccccaggagaagctgggaaaccaagctcatagtcaggccgagaacgccatggcacgga agaagccatgctgcctgtgagcccctcagaggacactgagtcaaaaaaccccacgcgcttggaagcgcaggatgggaaaagaaggtggc gaccttccccaccccttcaatctggggcctgaactggagactagctgtgaatctccagcagagggactagtggttagaggagaccccccg gaaaacgcacaacagcatattgacgctgggaaagaccagagactccatgagtttccaccacgctggccgccaggcacagatcgccgaac

TTCGGCGGCCGGTGTGGGGAAATCCATGGTTTCT

MR766 NS3-Min

SEQ ID NO: 10

AGTTGTTgatctgtgtgagtcagactgcgacagttcgagtctgaagcgagagctaacaacagtatcaacaggtttaatttggatttgga aacgagagtttctggtcatgaaaaacccaaagaagaaatccggaggattccggattgtcaatatgctaaaacgcggagtagcccgtgta aacccctttgggaggtttgaagaggttgccagccggacttctgctgggtcatggacccatcagaatggttttggcgatactagccttttt gagatttacagcaatcaagccatcactgggccttatcaacagatggggttccgtggggaaaaaagaggctatggaaataataaagaagt tcaagaaagatcttgctgccatgttgagaataatcaatgctaggaaagagaggaagagacgtggcgcagacaccagcatcggaatcatt ggcctcctgctgactacagccatggcagcagagatcactagacgcggagtgcatactacatgtacttggataggagcgatgccgggaa ggccatttcgtttgctaccacattgggagtgaacaagtgccacgtacagatcatggacctcgggcacatgtgtgacgccaccatgagtt atgagtgccctatgctggatgagggagtggaaccagatgatgtcgattgctggtgcaacacgacatcaacttgggttgtgtacggaacc tgtcatcacaaaaaggtgaggcacggcgatctagagagccgtgacgctccccttctcactctacaaggaagttgcaaacgcggtcgca gacctggttagaatcaagagaatacacgaagcacttgatcaaggttgaaaactggatattcaggaaccccgggttttgcgctagtggccg ttgccattgcctggcttttgggaagctcgacgagccaaaaagtcatatacttggtcatgatactgctgattgccccggcatacagtatc aggtgcattggagtcagcaatagagacttcgtggagggcatgtcaggtgggacctgggttgatgttgtcttggaacatggaggctgcgt taccgtgatggcacaggacaagccaacagttgacatagagttggtcacgacgacggttagtaacatggccgaggtaagatcctattgct acgaggcatcgatatcggacatggcttcggacagtcgttgcccaacacaaggtgaagcctaccttgacaagcaatcagacactcaatat gtctgcaaaagaacattagtggacagaggttggggaaacggttgtggacttttggcaaagggagcttggtgacatgtgccaagtttac gtgttctaagaagatgaccggCaagagcattcaaccggaaaatctggagtatcggataatgctatcagtgcatggctcccagcatagcg ggatgattgtcaatgatacaggatatgaaactgacgaaaatagagcgaaagtcgaggttacgcctaattcaccaagagcggaagcaacc ttgggaggctttggaagcttaggacttgactgtgaaccaaggacaggccttgacttttcagatctgtattacctgaccatgaacaataa gcattggttggtgcacaaagagtggtttcatgacatcccattgccttggcatgctggggcagacaccggaactccacactggaacaaca aagaggcattggtagaattcaaggatgccacgccaagaggcaaaccgtcgtcgttctggggagccaggaaggagccgttcacacggct ctcgctggagctctagaggctgagatggatggtgcaaaggggaGgctgttctctggcctttgaaatgccgcctaaaaatggacaagct tagattgaagggcgtgtcatattccttgtgcactgcggcattcacattcaccaaggtcccagctgaaacactgcatggaacagtcacag tggaaggtgcagtatgcagggacagatggacctgcaagatcccagtccagatggcggtggacatgcagaccctgaccccagttggaagg ctgataaccgccaacccgtgattactgaaagcactgagaactcaaagatgatgttggagcttgacccaccatttgggattcttacat -continued tgtcataggagttggggacaagaaaatcacccaccactggcataggagtggtagcaccatcggaaaggcatttgaggccactgtgagag gcgccaagagaatggcagtcctggggggatacagcctgggacttcggatcagtcggggtgtgttcaactcactgggtaagggcattcac cagattttggagcagccttcaaatcactgtttggaggaatgtcctggttctcacagatcctcataggcacgctgctagtgtggttagg tttgaacacaaagaatggatctatctccctcacatgcttggccctggggggagtgatgatcttcctctccacggctgtttctgctgacg tggggtgctcagtggacttctcaaaaaaggaaacgagatgtggcacgggggtattcatctataatgatgttgaagcctggagggaccgg tacaagtaccatcctgactccccccgcagattggcagcagcagtcaagcaggcctgggaagaggggatctgtgggatctcatccgtttc aagaatggaaaacatcatgtggaaatcagtagaaggggagctcaatgctatcctagaggagaatggagttcaactgacagttgttgtgg gatctgtaaaaaacccatgtggagaggtccacaaagattgccagtgcctgtgaatgagctgccccatggctggaaagcctgggggaaa tcgtattttgttagggcggcaaagaccaacaacagttttgttgtcgacggtgacacactgaaggaatgtccgcttgagcacagagcatg gaatagttttcttgtggaggatcacgggtttggagtcttccacaccagtgtctggcttaaggtcagagaagattactcattagaatgtg accCAGCCGTCATAGGAACAGCTGTTAAGGGAAGGGAGGCCGCGCACAGTGATCTGGGCTATTGGATTGAAAGTGAAAAGAATGACACA TGGAGGCTGAAGAGGGCCCACCTGATTGAGATGAAAACATGTGAATGGCCAAAGTCTCACACATTGTGGACAGATGGAGTAGAAGAAAG TGATCTTATCATACCCAAGTCTTTAGCTGGTCCACTCAGCCACCACAACACCAGAGAGGGTTACAGAACCCAAGTGAAAGGGCCATGGC ACAGTGAAGAACTTGAAATCCGGTTTGAGGAATGTCCAGGCACCAAGGTTTACGTGGAGGAGACATGCGGAACTAGAGGACCATCTCTG AGATCAACTACTGCAAGTGGAAGGGTCATTGAGGAATGGTGCTGTAGGGAATGCACAATGCCCCCACTATCGTTTCGAGCAAAAGACGG CTGCTGGTATGGAATGGAGATAAGGCCCAGGAAAGAACCAGAGAGCAACTTAGTGAGGTCAATGGTGACAGCGGGGTCAACCGATCATA TGGACCACTTCTCTCTTGGAGTGCTTGTGATTCTACTCATGGTGCAGGAGGGGTTGAAGAAGAGAATGACCACAAAGATCATCATGAGC ACATCAATGGCAGTGCTGGTAGTCATGATCTTGGGAGGATTTTCAATGAGTGACCTGGCCAAGCTTGTGATCCTGATGGGTGCTACTTT CGCAGAAATGAACACTGGAGGAGATGTAGCTCACTTGGCATTGGTAGCGGCATTTAAAGTCAGACCAGCCTTGCTGGTGTCCTTCATTT TCAGAGCCAATTGGACACCCCGTGAGAGCATGCTGCTAGCCCTGGCTTCGTGTCTTCTGCAAACTGCGATCTCTGCTCTTGAAGGTGAC TTGATGGTCCTCATTAATGGATTTGCTTTGGCCTGGTTGGCAATTCGAGCAATGGCCGTGCCACGCACTGACAACATCGCTCTACCAAT CTTGGCTGCTCTAACACCACTAGCTCGAGGCACACTGCTCGTGGCATGGAGAGCGGGCCTGGCTACTTGTGGAGGGATCATGCTCCTCT CCCTGAAAGGGAAAGGTAGTGTGAAGAAGAACCTGCCATTTGTCATGGCCCTGGGATTGACAGCTGTGAGGGTAGTAGACCCTATTAAT GTGGTAGGACTACTGTTACTCACAAGGAGTGGGAAGCGGAGCTGGCCCCCTAGTGAAGTTCTCACAGCCGTTGGCCTGATATGTGCACT GGCCGGAGGGTTTGCCAAGGCAGACATTGAGATGGCTGGACCCATGGCTGCAGTAGGCCTTGCTAATTGTCAGCTATGTGGTGTCGGGAA AGAGTGTGGACATGTACATTGAAAGAGCAGGAGACATCACATGGGAAAAGGACGCGGAAGTCACTGGAAACAGTCCTCGGCTTGACGTG GCACTGGATGAGAGTGGTGATTTCTCCTTGGTAGAGGAAGATGGTCCACCCATGAGAGAGATCATACTCAAGGTGGTCCTGATGGCCAT CTGTGGCATGAACCCAATAGCTATACCTTTTGCTGCAGGAGCGTGGTATGTGTATGTGAAGACTGGGAAAAGGTCTGGCGCACTATGGG ACGTACCCGCTCCTAAAGAGGTCAAAAAAGGCGAAACAACCGACGGAGTGTATAGGGTTATGACTAGACGGTTGCTCGGATCGACACAG GTCGGAGTCGGAGTGATGCAAGAGGGAGTGTTTCATACAATGTGGCATGTGACTAAGGGAGCCGCACTTAGATCAGGCGAAGGGAGACT CGATCCATACTGGGGGGACGTTAAGCAGGACCTAGTCTCATATTGCGGACCTTGGAAACTCGACGCCGCATGGGACGGACTGTCAGAGG TCCAACTGTTAGCCGTACCACCAGGCGAAAGAGCGAGAAACATACAGACATTGCCCGGAATCTTTAAGACTAAGGACGGAGACATAGGC GCAGTCGCACTCGATTACCCTGCCGGAACTAGCGGATCACCGATACTCGATAAGTGCGGAAGGGTTATCGGATTGTACGAAACGGAGT CGTTATCAAAAACGGATCATACGTTAGCGCTATAACACAGGGGAAACGCGAAGAGGAGACACCAGTCGAGTGTTTCGAACCTAGTATGC TTAAAAAAAACAGCTAACCGTACTCGATCTGCATCCCGGAGCCGGTAAGACACGTAGAGTGTTGCCCGAAATCGTTAGGGAGGCTATC AAAAAACGGTTGCGTACAGTGATACTCGCACCTACTAGGGTCGTCGCCGCCGAAATGGAGGAAGCGCTTAGGGGGTTGCCCGTTAGGTA TATGACAACCGCCGTTAACGTTACGCATAGCGGAACAGAGATAGTCGATCTGATGTGTCACGCTACATTTACATCTAGACTGTTGCAGC CAATTAGGGTGCCTAATTACAATCTGAATATAATGGACGAAGCGCATTTTACCGATCCGTCATCAATCGCCGCTAGGGGGTACATATCG ACTAGAGTCGAGATGGGCGAAGCCGCCGCAATCTTTATGACCGCTACACCTCCCGGAACTAGGGACGCATTCCCAGACTCTAACTCACC TATTATGGATACCGAAGTCGAGGTCCCCGAACGCGCTTGGTCTAGCGGATTCGATTGGGTTACCGATCATAGCGGTAAGACCGTTTGGT -continued

```
TCGTACCTAGCGTTAGAAACGGAAACGAGATAGCCGCATGTCTGACTAAGGCCGGTAAGAGAGTGATACAGCTATCTAGAAAGACATTC
GAAACAGAGTTTCAGAAGACTAAGAATCAGGAGTGGGACTTCGTTATAACAACCGATATCTCTGAGATGGGCGCTAACTTTAAGGCCGA
TAGGGTGATCGATAGTAGACGGTGTCTTAAGCCAGTGATACTCGACGGAGAGAGAGTGATACTCGCCGGACCTATGCCAGTGACACACG
CTAGCGCCGCACAACGTAGGGGGAGAATCGGACGGAATCCTAACAAACCGGGAGACGAATATATGTACGGGGGGGGTGCGCTGAGACA
GACGAAGGGCACGCTCATTGGCTTGAGGCTAGAATGCTACTCGATAACATATACTTGCAGGACGGACTAATCGCTAGTCTGTATAGACC
GGAAGCCGATAAGGTCGCCGCTATCGAGGGAGAGTTTAAGCTTAGAACCGAGCAACGTAAGACATTCGTCGAGCTTATGAAAAGAGGCG
ATCTGCCAGTGTGGCTCGCATACCAGGTCGCTAGTGCCGGAATAACATATACCGATAGGAGATGGTGTTTCGACGGAACAACTAACAAT
ACAATTATGGAGGACTCAGTCCCAGCCGAAGTGTGGACTAAGTACGGCGAAAAGAGAGTGCTTAAGCCTAGATGGATGGACGCTAGGGT
GTGTTCGGATCACGCCGCACTTAAGTCATTCAAAGAGTTCGCAGCCGGTAAGAGAGGAGCGGCTTTGGGAGTAATGGAGGCCCTGGGAA
CACTGCCAGGACACATGACAGAGAGGTTTCAGGAAGCCATTGACAACCTCGCCGTGCTCATGCGAGCAGAGACTGGAAGCAGGCCTTAT
AAGGCAGCGGCAGCCCAACTGCCGGAGACTCTAGAGACAATTATGCTCTTAGGTTTGCTGGGAACAGTTTCACTGGGGATCTTCTTCGT
CTTGATGCGGAATAAGGGCATCGGGAAGATGGGCTTTGGAATGGTAACCCTTGGGGCCAGTGCATGGCTCATGTGGCTTTCGGAAATTG
AACCAGCCAGAATTGCATGTGTCCTCATTGTTGTGTTTTATTACTGGTGGTGCTCATACCCGAGCCAGAGAAGCAAAGATCTCCCCAA
GATAACCAGATGGCAATTATCATCATGGTGGCAGTGGGCCTTCTAGGTTTGATAACTGCAAACGAACTTGGATGGCTGGAAAGAACAAA
AAATGACATAGCTCATCtaatgggaaggagagaagaaggagcaaccatgggattctcaatggacattgatctgcggccagcctccgcct
gggctatctatgccgcattgacaactctcatcaccccagctgtccaacatgcggtaaccacttcatacaacaactactccttaatggcg
atggccacacaagctggagtgctgtttggcatgggcaaagggatgccattttatgcatgggaccttggagtcccgctgctaatgatggg
ttgctattcacaattaacacccctgactctgatagtagctatcattctgcttgtggcgcactacatgtacttgatcccaggcctacaag
cggcagcagcgcgtgctgcccagaaaaggacagcagctggcatcatgaagaatcccgttgtggatgaatagtggtaactgacattgac
acaatgacaatagaccccccaggtggagaagaagatgggacaagtgttactcatagcagtagccatctccagtgctgtgctgctgcggac
cgcctggggatgggggaggctggagctctgatcacagcagcgacctccaccttgtgggaaggctctccaaacaaatactggaactcct
ctacagccacctcactgtgcaacatcttcagaggaagctatctggcaggagcttcccttatctatacagtgacgagaaacgctggcctg
gttaagagacgtggaggtgggacgggagagactctgggagagaagtggaaagctcgtctgaatcagatgtcggccctggagttctactc
ttataaaagtcaggtatcactgaagtgtgtagagaggaggctcgccgtgccctcaaggatggagtggccacaggaggacatgccgtat
cccgggaagtgcaaagctcagatggttggtggagagaggatatctgcagccctatgggaaggttgttgacctcggatgtggcagaggg
ggctggagctattatgccgccaccatccgcaaagtgcaggaggtgagaggatacacaaagggaggtcccggtcatgaagaacccatgct
ggtgcaaagctatgggtggaacatagttcgtctcaagagtggagtggacgtcttccacatggcggctgagccgtgtgacactctgctgt
gtgacataggtgagtcatcatctagtcctgaagtggaagagacacgaacactcagagtgctctctatggtgggggactggcttgaaaaa
agaccaggggccttctgtataaaggtgctgtgcccatacaccagcactatgatggaaaccatggagcgactgcaacgtaggcatgggggg
aggattagtcagagtgccattgtctcgcaactccacacatgagatgtactgggtGtctggggcaaagagcaacatcataaaaagtgtgt
ccaccacaagtcagctcctcctgggacgcatggatgccccaggaggccagtgaaatatgaggaggatgtgaacctcggctcgggtaca
cgagctgtggcaagctgtgctgaggctcctaacatgaaaatcatcggcaggcgcattgagagaatccgcaatgaacatgcagaaacatg
gtttcttgatgaaaaccacccatacaggacatgggcctaccatgggagctacgaagcccccacgcaaggatcagcgtcttccctcgtga
acggggttgttagactcctgtcaaagccttgggacgtggtgactggagttacaggaatagccatgactgacaccacaccatacgccaa
caaagagtcttcaaagaaaaagtggacaccagggtgccagatccccaagaaggcactcgccaggtaatgaacatagtctcttcctggct
gtggaaggagctgggaaacgcaagcggccacgcgtctgcaccaaagaagagtttatcaacaaggtgcgcagcaatgcagcactgggag
caatatttgaagaggaaaaagaatggaagacggctgtggaagctgtgaatgatccaaggttttgggccctagtggatagggagagagaa
caccacctgagaggagagtgtcacagctgtgtgtacaacatgatgggaaaaagagaaaagaagcaaggagagttcgggaaagcaaaagg
tagccgcgccatctggtacatgtggttgggagccagattcttggagtttgaagcccttggattcttgaacgaggaccattggatgggaa
gagaaaactcaggaggtggagtcgaagggttaggattgcaaagacttggatacattctagaagaaatgaatcgggcaccaggaggaaag
atgtacgcagatgacactgctggctgggacacccgcattagtaagtttgatctggagaatgaagctctgattaccaaccaaatggagga
```

-continued agggcacagaactctggcgttggccgtgattaaatacacataccaaaacaaagtggtgaaggttctcagaccagctgaaggaggaaaaa
cagttatggacatcatttcaagacaagaccagagagggagtggacaagttgtcacttatgctctcaacacattcaccaacttggtggtg
cagcttatccggaacatggaagctgaggaagtgttagagatgcaagacttatggttgttgaggaagccagagaaagtgaccagatggtt
gcagagcaatggatgggatagactcaaacgaatggccggtcagtggagatgactgcgttgtgaagccaatcgatgataggtttgcacatg
ccctcaggttcttgaatgacatgggaaaagttaggaaagacacacaggagtggaaaccctcgactggatggagcaattgggaagaagtc
ccgttctgctcccaccacttcaacaagctgtacctcaaggatggggagatccattgtggtcccttgccgccaccaagatgaactgattgg
ccgagctcgcgtctcaccaggggcaggatggagcatccgggagactgcctgtcttgcaaaatcatatgcgcagatgtggcagctcctttt
atttccacagaagGgaccttcgactgatggctaatgccatttgctcggctgtgccagttgactgggTccaactgggagaaccacctgg
tcaatccatggaaagggagaatggatgaccactgaggacatgctcatggtgtggaatagagtgtggattgaggagaacgaccatatgga
ggacaagactcctgtaacaaaatggacagacattccctatctaggaaaaagggaggacttatggtgtggatcccttatagggcacagac
cccgcaccacttgggctgaaaacatcaaagacacagtcaacatggtgcgcaggatcataggtgatgaagaaaagtacatggactatcta
tccacccaagtccgctacttgggtgaggaagggtccacacccggagtgttgtaagcaccaatttagtgttgtcaggcctgctagtcag
ccacagtttggggaaagctgtgcagcctgtaacccccccaggagaagctgggaaaccaagctcatagtcaggccgagaacgccatggca
cggaagaagccatgctgcctgtgagccctcagaggacactgagtcaaaaaaccccacgcgcttggaagcgcaggatgggaaaagaagg
tggcgaccttccccacccttcaatctggggcctgaactggagactagctgtgaatctccagcagagggactagtggttagaggagaccc
cccggaaaacgcacaacagcatattgacgctgggaaagaccagagactccatgagtttccaccacgctggccgccaggcacagatcgcc
gaacTTCGGCGGCCGGTGTGGGGAAATCCATGGTTTCT MR766 NS3-W/Min

SEQ ID N

-continued

```
TCGAGGTGCAATACGCCGGAACCGACGGACCATGCAAGATACCCGTGCAAATGGCCGTCGATATGCAGACACTGACACCAGTCGGACGG
TTGATTACCGCTAACCCAGTGATAACCGAGTCAACCGAAAACTCTAAGATGATGCTCGAGCTTGACCCACCATTCGGCGACTCATATAT
CGTTATCGGAGTCGGCGACAAAAAGATTACGCATCATTGGCATAGATCCGGATCGACAATCGGTAAGGCATTCGAAGCGACAGTGAGAG
GCGCTAAGCGTATGGCCGTATTGGGCGATACCGCATGGGACTTCGGATCCGTCGGCGGAGTGTTTAACTCACTCGGTAAGGGGATACAC
CAGATATTCGGAGCCGCATTCAAATCGTTGTTCGGCGGAATGTCATGGTTTAGTCAGATACTGATCGGAACACTGCTTGTGTGGTTGGG
GTTGAACACTAAGAACGGATCGATTAGTCTGACATGCTTAGCCTTAGGCGGAGTGATGATTTTTCTGTCAACCGCCGTTAGCGCAGACG
TGGGGTGCTCAGTGGACTTCTCAAAAAAGGAAACGAGATGTGGCACGGGGGTATTCATCTATAATGATGTTGAAGCCTGGAGGGACCGG
TACAAGTACCATCCTGACTCCCCCCGCAGATTGGCAGCAGCAGTCAAGCAGGCCTGGGAAGAGGGGATCTGTGGGATCTCATCCGTTTC
AAGAATGGAAAACATCATGTGGAAATCAGTAGAAGGGGAGCTCAATGCTATCCTAGAGGAGAATGGAGTTCAACTGACAGTTGTTGTGG
GATCTGTAAAAAACCCCATGTGGAGAGGTCCACAAAGATTGCCAGTGCCTGTGAATGAGCTGCCCCATGGCTGGAAAGCCTGGGGGAAA
TCGTATTTTGTTAGGGCGGCAAAGACCAACAACAGTTTTGTTGTCGACGGTGACACACTGAAGGAATGTCCGCTTGAGCACAGAGCATG
GAATAGTTTTCTTGTGGAGGATCACGGGTTTGGAGTCTTCCACACCAGTGTCtggcttaaggtcagagaagattactcattagaatgtg
acccagccgtcataggaacagctgttaagggaagggaggccgcgcacagtgatctgggctattggattgaaagtgaaaagaatgacaca
tggaggctgaagagggcccacctgattgagatgaaaacatgtgaatggccaaagtctcacacattgtggacagatggagtagaagaaag
tgatcttatcatacccaagtctttagctggtccactcagccaccacaacaccagagagggttacagaacccaagtgaaagggccatggc
acagtgaagaActtgaaatccggtttgaggaatgtccaggcaccaaggtttacgtggaggagacatgcggaactagaggaccatctctg
agatcaactactgcaagtggaaggtgtcattgaggaatggtgctgtagggaatgcacaatgcccccactatcgtttcgagcaaaagacgg
ctgctggtatggaatggagataaggcccaggaaagaaccagagagcaacttagtgaggtcaatggtgacagcggggtcaaccgatcata
tggaccacttctctcttggagtgcttgtgattctactcatggtgcaggaggggttgaagaagagaatgaccacaaagatcatcatgagc
acatcaatggcagtgctggtagtcatgatcttggaggattttcaatgagtgacctggccaagcttgtgatcctgatgggtgctactttt
cgcagaaatgaacactggaggagatgtagctcacttggcattggtagcggcatttaaagtcagaccagccttgctggtGtccttcattt
tcagagccaattggacaccccgtgagagcatgctgctagccctggcttcgtgtcttctgcaaactgcgatctctgctcttgaaggtgac
ttgatggtcctcattaatggatttgctttggcctggttggcaattcgagcaatggccgtgccacgcactgacaacatcgctctaccaat
cttggctgctctaacaccactagctcgaggcacactgctcgtggcatggagagcgggcctggctacttgtggagggatcatgctcctct
ccctgaaagggaaaggtagtgtgaagaagaacctgccatttgtcatggccctgggattgacagctgtgagggtagtagaccctattaat
gtggtaggactactgttactcacaaggagtgggaagcggagctggcccctagtgaagttctcacagccgttggcctgatatgtgcact
ggccggagggtttgccaaggcagacattgagatggctggacccatggctgcagtaggcttgctaattgtcagctatgtggtGtcgggaa
agagtgtggacatgtacattgaaagagcaggAgacatcacatgggaaaaggacgcggaagtcactggaaacagtcctcggcttgacgtg
gcactggatgagagtggtgatttctccttggtagaggaagatggtccacccatgagagagatcatactcaaggtggtcctgatggccat
ctgtggcatgaacccaatagctataccttttgctgcaggagcgtggtatgtgtatgtgaagactgggaaaaggagtggcgccctctggg
acgtgcctgctcccaaagaagtgaagaaaggagaAaccacagatggagtgtacagagtgatgactcgcagactgctaggttcaacacag
gttggagtgggagtcatgcaagagggagtcttccacaccatgtggcacgttacaaaaggagccgcactgaggagcggtgagggaagact
tgatccatactgggggatgtcaagcaggacttggtgtcatactgtgggccttggaagttggatgcagcttgggatggactcagcgagg
tacagcttttggccgtacctcccggagagagggccagaaacattcagaccctgcctggaatattcaagacaaaggacggggacatcgga
gcagttgctctggactaccctgcagggacctcaggatctccgatcctagacaaatgtggaagagtgataggactctatggcaatggggt
tgtgatcaagaatggaagctatgttagtgctataacccagggaaagagggaggaggagactccggttgaatgtttcgaaccctcgatgc
tgaagaagaagcagctaactgtcttggatctgcatccaggagccggaaaaaccaggagagttcttcctgaaatagtccgtgaagccata
aaaaagagactccggacagtgatcttggcaccaactagggttgtcgctgctgagatggaggaggccttgagaggacttccggtgcgtta
catgacaacagcagtcaacgtcacccattctgggacagaaatcgttgatttgatgtgccatgccactttcacttcacgcttactacaac
ccatcagagtccctaattacaatctcAacatcatggatgaagcccacttcacagaccccctcaagtatagctgcaagaggatacatatca
acaagggttgaaatgggcgaggcggctgccattttttatgactgccacaccaccaggaacccgtgatgcgtttcctgactctaactcacc
```

-continued

```
aatcatggacacagaagtggaagtcccagagagagcctggagctcaggattgattgggtgacagaccattctgggaaaacagtttggtt cgttccaagcgtgagaaacggaaatgaaatcgcagcctgtctgacaaaggctggaaagcgggtcatacagctcagcaggaagacttttg agacagaatttcagaaaacaaaaaatcaagagtgggactttgtcataacaactgacatctcagagatgggcgccaacttcaaggctgac cgggtcatagactctaggagatgcctaaaaccagtcatacttgatggtgagagagtcatcttggctgggccatgcctgtcacgcatgc tagtgctgctcagaggagaggacgtataggcaggaaccctaacaaacctggagatgagtacatgtatggaggtgggtgtgcagagactg atgaaggccatgcacactggcttgaagcaagaatgcttcttgacaacatctacctccaggatggcctcatagcctcgctctatcggcct gaggccgataaggtagccgccattgagggagagtttaagctgaggacagagcaaaggaagaccttcgtggaactcatgaagagaggGga ccttcccgtctggctagcctatcaggttgcatctgccggaataacttacacagacagaagatggtgattgatggcacaaccaacaacac cataatggaagacagcgtaccagcagaggtgtggacaaagtatggagagaagagagtgctcaaaccgagatggatggatgctagggtct gttcagaccatgcgccctgaagtcgttcaaagaattcgccgctggaaaaagaggagcggctttgggagtaatggaggccctgggaaca ctgccaggacacatgacagagaggtttcaggaagccattgacaacctcgccgtgctcatgcgagcagagactggaagcaggccttataa ggcagcggcagcccaactgccggagacTctagagacAattatgctcttaggtttgctgggaacagtttcactggggatcttcttcgtct tgatgcggaataagggcatcggaagatgggattggaatggtaaccctggggccagtgcatggctcatgtggctttcggaaattgaac cagccagaattgcatgtgtcctcattgttgtgttttattactggtggtgctcatacccgagccagagaagcaaagatctccccaagat aaccagatggcaattatcatcatggtggcagtgggccttctaggtttgataactgcaaacgaacttggatggctggaaagaacaaaaaa tgacatagctcatctaatgggaaggagagaagaaggagcaaccatgggattctcaatggacattgatctgcggccagcctccgcctggg ctatctatgccgcattgacaactctcatcaccccagctgtccaacatgcggtaaccacttcatacaacaactactccttaatggcgatg gccacacaagctggagtgctgtttggcatgggcaaagggatgccattttatgcatgggaccttggagtcccgctgctaatgatggttg ctattcacaattaacacccctgactctgatagtagctatcattctgcttgtggcgcactacatgtacttgatcccaggcctacaagcgg cagcagcgcgtgctgcccagaaaaggacagcagctggcatcatgaagaatcccgttgtggatggaatagtggtaactgacattgacaca atgacaatagacccccaggtggagaagaagatgggacaagtgttactcatagcagtagccatctccagtgctgtgctgctgcggaccgc ctggggatggggggaggctggagctctgatcacagcagcgacctccaccttgtgggaaggctctccaaacaaatactggaactcctcta cagccacctcactgtgcaacatcttcagaggaagctatctggcaggagcttcccttatctatacagtgacgagaaacgctggcctggtt aagagacgtggaggtgggacgggagagactctgggagagaagtggaaagctcgtctgaatcagatgtcggccctggagttctactctta taaaaagtcaggtatcactgaagtgtgtagagaggaggctcgccgtgccctcaaggatggagtggccacaggaggacatgccgtatccc ggggaagtgcaaagctcagatggttggtggagagaggatatctgcagccctatggaaggttgttgacctcggatgtggcagaggggc tggagctattatgccgccaccatccgcaaagtgcaggaggtgagaggatacacaaagggaggtcccggtcatgaagaacccatgctggt gcaaagctatgggtggaacatagttcgtctcaagagtggagtggacgtcttccacatggcggctgagccgtgtgacactctgctgtgtg acataggtgagtcatcatctagtcctgaagtggaagagacacgaacactcagagtgctctctatggtggggactggcttgaaaaaaga ccaggggccttctgtataaaggtgctgtgcccatacaccagcactatgatggaaaccatggagcgactgcaacgtaggcatgggggagg attagtcagagtgccattgtctcgcaactccacacatgatgatgtactgggGtctggggcaaagagcaacatcataaaaagtgtgtcca ccacaagtcagctcctcctgggacgcatggatggccccaggaggccagtgaaatatgaggaggatgtgaacctcggctcgggtacacga gctgtggcaagctgtgctgaggctcctaacatgaaaatcatcggcaggcgcattgagagaatccgcaatgaacatgcagaaacatggtt tcttgatgaaaaccacccatacaggacatgggcctaccatgggagctacgaagcccccacgcaaggatcagcgtcttccctcgtgaacg gggttgttagactcctgtcaaagccttgggacgtggtgactggagttacaggaatagccatgactgacaccacaccatacgccaacaa agagtcttcaaagaaaaagtggacaccagggtgccagatccccaagaaggcactcgccaggtaatgaacatagtctcttcctggctgtg gaaggagctggggaaacgcaagcggccacgcgtctgcaccaaagaagagtttatcaacaaggtgcgcagcaatgcagcactgggagcaa tatttgaagaggaaaaagaatggaagacggctgtggaagctgtgaatgatccaaggttttgggccctagtggatagggagagagaacac cacctgagaggagagtgtcacagctgtgtgtacaacatgatgggaaaaagagaaaagaagcaaggagagttcggaaagcaaaaggtag ccgcgccatctggtacatgtggtttgggagccagattcttggagtttgaagcccttggattcttgaacgaggaccattggatgggaagag
```

-continued aaaactcaggaggtggagtcgaagggttaggattgcaaagacttggatacattctagaagaaatgaatcgggcaccaggaggaaagatg
tacgcagatgacactgctggctgggacacccgcattagtaagtttgatctggagaatgaagctctgattaccaaccaaatggaggaagg
gcacagaactctggcgttggccgtgattaaatacacataccaaaacaaagtggtgaaggttctcagaccagctgaaggaggaaaaacag
ttatggacatcatttcaagacaagaccagagagggagtggacaagttgtcacttatgctctcaacacattccaccttggtggtgcag
cttatccggaacatggaagctgaggaagtgttagagatgcaagacttatggttgttgaggaagccagagaaagtgaccagatggttgca
gagcaatggatgggatagactcaaacgaatggcggtcagtggagatgactgcgttgtgaagccaatcgatgataggtttgcacatgccc
tcaggttcttgaatgacatgggaaaagttaggaaagacacacaggagtggaaaccctcgactggatggagcaattgggaagaagtcccg
ttctgctcccaccacttcaacaagctgtacctcaaggatgggagatccattgtggtcccttgccgccaccaagatgaactgattggccg
agctcgcgtctcaccaggggcaggatggagcatccgggagactgcctgtcttgcaaaatcatatgcgcagatgtggcagctcctttatt
tccacagaagGgaccttcgactgatggctaatgccatttgctcggctgtgccagttgactgggtTccaactgggagaaccacctggtca
atccatggaaagggagaatggatgaccactgaggacatgctcatggtgtggaatagagtgtggattgaggagaacgaccatatggagga
caagactcctgtaacaaaatggacagacattccctatctaggaaaaagggaggacttatggtgtggatcccttatagggcacagacccc
gcaccacttgggctgaaaacatcaaagacacagtcaacatggtgcgcaggatcataggtgatgaagaaagtacatggactatctatcc
acccaagtccgctactggggtgaggaagggtccacacccggagtgttgtaagcaccaattttagtgttgtcaggcctgctagtcagcca
cagtttggggaaagctgtgcagcctgtaaccccccaggagaagctgggaaaccaagctcatagtcaggccgagaacgccatggcacgg
aagaagccatgctgcctgtgagcccctcaggacactgagtcaaaaaccccacgcgcttggaagcgcaggatgggaaagaaggtgg
cgaccttccccacccttcaatctgggcctgaactggagactagctgtgaatctccagcagagggactagtggttagaggagacccccc
ggaaaacgcacaacagcatattgacgctgggaaagaccagagactccatgagtttccaccacgctggccgccaggcacagatcgccgaa
cTTCGGCGGCCGGTGTGGGGAAATCCATGGTTTCT

MR766 NS3-W

-continued

```
tagattgaagggcgtgtcatattccttgtgcactgcggcattcacattcaccaaggtcccagctgaaacactgcatggaacagtcacag
tggaggtgcagtatgcagggacagatggaccctgcaagatcccagtccagatggcggtggacatgcagaccctgaccccagttggaagg
ctgataaccgccaaccccgtgattactgaaagcactgagaactcaaagatgatgttggagcttgacccaccatttggggattcttacat
tgtcataggagttggggacaagaaaatcacccaccactggcataggagtggtagcaccatcggaaaggcatttgaggccactgtgagag
gcgccaagagaatggcagtcctgggggatacagcctgggacttcggatcagtcggggtgtgttcaactcactgggtaagggcattcac
cagattttggagcagccttcaaatcactgtttggaggaatgtcctggttctcacagatcctcataggcacgctgctagtgtggttagg
tttgaacacaaagaatggatctatctccctcacatgcttggccctgggggagtgatgatcttcctctccacggctgtttctgctgacg
tggggtgctcagtggacttctcaaaaaaggaaacgagatgtggcacgggggtattcatctataatgatgttgaagcctggagggaccgg
tacaagtaccatcctgactcccccgcagattggcagcagcagtcaagcaggcctgggaagaggggatctgtgggatctcatccgtttc
aagaatggaaaacatcatgtggaaatcagtagaagggagctcaatgctatcctagaggagaatggagttcaactgacagttgttgtgg
gatctgtaaaaaaccccatgtggagaggtccacaaagattgccagtgcctgtgaatgagctgccccatggctggaaagcctgggggaaa
tcgtattttgttagggcggcaaagaccaacaacagttttgttgtcgacggtgacacactgaaggaatgtccgcttgagcacagagcatg
gaatagttttcttgtggaggatcacgggtttggagtcttccacaccagtgtctggcttaaggtcagagaagattactcattagaatgtg
acccagccgtcataggaacagctgttaagggaagggaggccgcgcacagtgatctgggctattggattgaaagtgaaaagaatgacaca
tggaggctgaagagggcccacctgattgagatgaaaacatgtgaatggccaaagtctcacacattgtggacagatggagtagaagaaag
tgatcttatcatacccaagtctttagctggtccactcagccaccacaacaccagagagggttacagaacccaagtgaaagggccatggc
acagtgaagaActtgaaatccggtttgaggaatgtccaggcaccaaggtttacgtggaggagacatgcggaactagaggaccatctctg
agatcaactactgcaagtggaaggtcattgaggaatggtgctagggaatgcacaatgccccactatcgtttcgagcaaaagacgg
ctgctggtatggaatggagataaggcccaggaaagaaccagagagcaacttagtgaggtcaatggtgacagcggggtcaaccgatcata
tggaccacttctctcttggagtgcttgtgattctactcatggtgcaggaggggttgaagaagagaatgaccacaaagatcatcatgagc
acatcaatggcagtgctggtagtcatgatcttggaggattttcaatgagtgacctggccaagcttgtgatcctgatgggtgctacttt
cgcagaaatgaacactggaggagatgtagctcacttggcattggtagcggcatttaaagtcagaccagccttgctggtGtccttcattt
tcagagccaattggacaccccgtgagagcatgctgctagccctggcttcgtgtcttctgcaaactgcgatctctgctcttgaaggtgac
ttgatggtcctcattaatggatttgattggcctggttggcaattcgagcaatggccgtgccacgcactgacaacatcgctctaccaatc
ttggctgctctaacaccactagctcgaggcacactgctcgtggcatggagagcgggcctggctacttgtggagggatcatgctcctctc
cctgaaagggaaaggtagtgtgaagaagaacctgccatttgtcatggccctgggattgacagctgtgagggtagtagaccctattaatg
tggtaggactactgttactcacaaggagtgggaagcggagctggccccctagtgaagttctcacagccgttggcctgatatgtgcactg
gccggagggtttgccaaggcagacattgagatggctggacccatggctgcagtaggcttgctaattgtcagctatgtggtGtcgggaaa
gagtgtggacatgtacattgaaagagcaggAgacatcacatgggaaaaggacgcggaagtcactggaaacagtcctcggcttgacgtgg
cactggatgagagtggtgatttctccttggtagaggaagatggtccacccatgagagagatcatactcaaggtggtcctgatggccatc
tgtggcatgaacccaatagctatacctttgctgcaggacgtggtatgtgtatgtgaagactgggaaaaggagtggcgccctctggga
cgtgcctgctcccaaagaagtgaagaaaggagaAaccacagatggagtgtacagagtgatgactcgcagactgctaggttcaacacagg
ttggagtgggagtcatgcaagagggagtcttccacaccatgtggcacgttacaaaaggagccgcactgaggagcggtgagggaagactt
gatccatactgggggatgtcaagcaggacttggtgtcatactgtgggccttggaagttggatgcagcttgggatggactcagcgaggt
acagcttttggccgtacctcccggagagagggccagaaacattcagaccctgcctggaatattcaagacaaaggacgggacatcggag
cagttgctctggactaccctgcagggacctcaggatctccgatcctagacaaatgtggaagagtgataggactctatggcaatgggtt
gtgatcaagaatggaagctatgttagtgctataacccagggaaagagggaggaggagactccggttgaatgtttcgaaccctcgatgct
gaagaagaagcagctaactgtcttggatctgcatccaggagccggaaaaaccaggagagttcttcctgaaatagtccgtgaagccataa
aaagagactccggacagtgatcttggcaccaactagggttgtcgctgctgagatggaggaggccttgagaggacttccggtgcgttac
atgacaacagcagtcaacgtcacccattctgggacagaaatcgttgatttgatgtgccatgccactttcacttcacgcttactacaacc
```

-continued catcagagtccctaattacaatctcAacatcatgatgaagcccacttcacagaccctcaagtatagctgcaagaggatacatatcaa caagggttgaaatgggcgaggcggctgccatttttatgactgccacaccaccaggaacccgtgatgcgtttcctgactctaactcacca atcatggacacagaagtggaagtcccagagagagcctggagctcaggctttgattgggtgacagaccattctgggaaaacagtttggtt cgttccaagcgtgagaaacggaaatgaaatcgcagcctgtctgacaaaggctggaaagcgggtcatacagctcagcaggaagacttttg agacagaatttcagaaaacaaaaaatcaagagtgggactttgtcataacaactgacatctcTGAGATGGGCGCTAACTTTAAGGCCGAT AGGGTGATCGATAGTAGACGGTGTCTTAAGCCAGTGATACTCGACGGAGAGAGAGTGATACTCGCCGGACCTATGCCAGTGACACACGC TAGCGCCGCACAACGTAGGGGGAGAATCGGACGGAATCCTAACAAACCGGGAGACGAATATATGTACGGGGGGGGTGCGCTGAGACAG ACGAAGGGCACGCTCATTGGCTTGAGGCTAGAATGCTACTCGATAACATATACTTGCAGGACGGACTAATCGCTAGTCTGTATAGACCG GAAGCCGATAAGGTCGCCGCTATCGAGGGAGAGTTTAAGCTTAGAACCGAGCAACGTAAGACATTCGTCGAGCTTATGAAAAGAGGCGA TCTGCCAGTGTGGCTCGCATACCAGGTCGCTAGTGCCGGAATAACATATACCGATAGGAGATGGTGTTTCGACGGAACAACTAACAATA CAATTATGGAGGACTCAGTCCCAGCCGAAGTGTGGACTAAGTACGGCGAAAAGAGAGTGCTTAAGCCTAGATGGATGGACGCTAGGGTG TGTTCGGATCACGCCGCACTTAAGTCATTCAAAGAGTTCGCAGCCGGTAAGAGAGGAGCGGCTTTGGGAGTAATGGAGGCCCTGGGAAC ACTGCCAGGACACATGACAGAGAGGTTTCAGGAAGCCATTGACAACCTCGCCGTGCTCATGCGAGCAGAGACTGGAAGCAGGCCTTATA AGGCAGCGGCAGCCCAACTGCCGGAGACTCTAGAGACAATTATGCTCTTAGGTTTGCTGGGAACAGTTTCACTGGGGATCTTCTTCGTC TTGATGCGGAATAAGGGCATCGGGAAGATGGGCTTTGGAATGGTAACCCTTGGGGCCAGTGCATGGCTCATGTGGCTTTCGGAAATTGA ACCAGCCAGAATTGCATGTGTCCTCATTGTTGTGTTTTTATTACTGGTGGTGCTCATACCCGAGCCAGAGAAGCAAAGATCTCCCCAAG ATAACCAGATGGCAATTATCATCATGGTGGCAGTGGGCCTTCTAGGTTTGATAACTGCAAACGAACTTGGATGGCTGGAAAGAACAAAA AATGACATAGCTCATCtaatgggaaggagagaagaaggagcaaccatgggattctcaatggacattgatctgcggccagcctccgcctg ggctatctatgccgcattgacaactctcatcaccccagctgtccaacatgcggtaaccacttcatacaacaactactccttaatggcga tggccacacaagctggagtgctgtttggcatgggcaaagggatgccatttatgcatgggaccttggagtcccgctgctaatgatgggt tgctattcacaattaacacccctgactctgatagtagctatcattctgcttgtggcgcactacatgtacttgatcccaggcctacaagc ggcagcagcgcgtgctgcccagaaaaggacagcagctggcatcatgaagaatcccgttgtggatggaatagtggtaactgacattgaca caatgacaatagaccccaggtggagaagaagatgggacaagtgttactcatagcagtagccatctccagtgctgtgctgctgcggacc gcctggggatgggggaggctggagctctgatcacagcagcgacctccaccttgtgggaaggctctccaaacaaatactggaactcctc tacagccacctcactgtgcaacatcttcagaggaagctatctggcaggagcttcccttatctatacagtgacgagaaacgctggcctgg ttaagagacgtggaggtgggacgggagagactctgggagagaagtggaaagctcgtctgaatcagatgtcggccctggagttctactct tataaaaagtcaggtatcactgaagtgtgtagagaggaggctcgccgtgccctcaaggatggagtggccacaggaggacatgccgtatc ccgggggaagtgcaaagctcagatggttggtggagagaggatatctgcagccctatgggaaggttgttgacctcggatgtggcagagggg gctggagctattatgccgccaccatccgcaaagtgcaggaggtgagaggatacacaaagggaggtcccggtcatgaagaacccatgctg gtgcaaagctatgggtggaacatagttcgtctcaagagtggagtggacgtcttccacatggcggctgagccgtgtgacactctgctgtg tgacataggtgagtcatcatctagtcctgaagtggaagagacacgaacactcagagtgctctctatggtgggggactggcttgaaaaaa gaccaggggccttctgtataaaggtgctgtgcccatacaccagcactatgatggaaaccatggagcgactgcaacgtaggcatggggga ggattagtcagagtgccattgtctcgcaactccacacatgagatgtactgggGtctggggcaaagagcaacatcataaaaagtgtgtc caccacaagtcagctcctcctgggacgcatggatggccccaggaggccagtgaaatatgaggaggatgtgaacctcggctcgggtacac gagctgtggcaagctgtgctgaggctcctaacatgaaaatcatcggcaggcgcattgagagaatccgcaatgaacatgcagaaacatgg tttcttgatgaaaaccacccatacaggacatgggcctaccatgggagctacgaagcccccacgcaaggatcagcgtcttccctcgtgaa cggggttgttagactcctgtcaaagccttgggacgtggtgactggagttacaggaatagccatgactgacaccacaccatacggccaac aaagagtcttcaaagaaaaagtggacaccagggtgccagatccccaagaaggcactcgccaggtaatgaacatagtctcttcctggctg tggaaggagctggggaaacgcaagcggccacgcgtctgcaccaaagaagagtttatcaacaaggtgcgcagcaatgcagcactgggagc aatatttgaagaggaaaagaatggaagacggctgtggaagctgtgaatgatccaaggttttgggccctagtggataggagagagaac accacctgagaggagagtgtcacagctgtgtgtacaacatgatgggaaaaagagaaaagaagcaaggagagttcgggaaagcaaaaggt -continued

```
agccgcgccatctggtacatgtggtgggagccagattcttggagtttgaagcccttggattcttgaacgaggaccattggatgggaag agaaaactcaggaggtggagtcgaagggttaggattgcaaagacttggatacattctagaagaaatgaatcgggcaccaggaggaaaga tgtacgcagatgacactgctggctgggacacccgcattagtaagtttgatctggagaatgaagctctgattaccaaccaaatggaggaa gggcacagaactctggcgttggccgtgattaaatacacataccaaaacaaagtggtgaaggttctcagaccagctgaaggaggaaaaac agttatggacatcatttcaagacaagaccagagagggagtggacaagttgtcacttatgctctcaacacattcaccaacttggtggtgc agcttatccggaacatggaagctgaggaagtgttagagatgcaagacttatggttgttgaggaagccagagaaagtgaccagatggttg cagagcaatggatgggatagactcaaacgaatggcggtcagtggagatgactgcgttgtgaagccaatcgatgataggtttgcacatgc cctcaggttcttgaatgacatgggaaaagttaggaaagacacacaggagtggaaaccctcgactggatggagcaattgggaagaagtcc cgttctgctcccaccacttcaacaagctgtacctcaaggatgggagatccattgtggtcccttgccgccaccaagatgaactgattggc cgagctcgcgtctcaccaggggcaggatggagcatccggagactgcctgtcttgcaaaatcatatgcgcagatgtggcagctccttta tttccacagaagGgaccttcgactgatggctaatgccatttgctcggctgtgccagttgactgggtTccaactgggagaaccacctggt caatccatggaaagggagaatggatgaccactgaggacatgctcatggtgtggaatagagtgtggattgaggagaacgaccatatggag gacaagactcctgtaacaaaatggacagacattccctatctaggaaaaagggaggacttatggtgtggatcccttatagggcacagacc ccgcaccacttgggctgaaaacatcaaagacacagtcaacatggtgcgcaggatcataggtgatgaagaaagtacatggactatctat ccacccaagtccgctacttgggtgaggaagggtccacacccggagtgttgtaagcaccaattttagtgttgtcaggcctgctagtcagc cacagtttggggaaagctgtgcagcctgtaaccccccaggagaagctgggaaaccaagctcatagtcaggccgagaacgccatggcac ggaagaagccatgctgcctgtgagccctcagaggacactgagtcaaaaaacccacgcgcttggaagcgcaggatgggaaaagaaggt ggcgaccttccccacccttcaatctggggcctgaactggagactagctgtgaatctccagcagagggactagtggttagaggagacccc ccggaaaacgcacaacagcatattgacgctgggaaagaccagagactccatgagtttccaccacgctggccgccaggcacagatcgccg aacTTCGGCGGCCGGTGTGGGGAAATCCATGGTTTCT
```

The present invention provides a vaccine composition for inducing an immune response in a subject comprising any of the attenuated viruses described herein and a pharmaceutically acceptable car Methods of Eliciting an Immune Response Various embodiments provide for a method of eliciting an immune response in a subject comprising administering to the subject a prophylactically or therapeutically effective dose of a vaccine composition comprising a modified Flavivirus of the present invention. Particular embodiments provide for a method of eliciting a protective immune response in a subject comprising administering to the subject a prophylactically or therapeutically effective dose of a vaccine composition comprising a modified Flavivirus of the present invention. In various embodiments, the immune response is cross-protective against a heterologous Flavivirus virus.

In various embodiments, the method further comprises administering to the subject at least one adjuvant. Non-limiting examples of adjuvants are discussed herein. Particular embodiments provide for a method of eliciting an immune response in a subject, comprising: administering to the subject a prophylactically or therapeutically effective dose of a vaccine composition comprising a modified Zika virus the present invention.

Various embodiments provide for a method of eliciting a protective immune response in a subject, comprising: administering to the subject a prophylactically or therapeutically effective dose of a vaccine composition comprising a modified Zika virus the present invention.

In various embodiments, the method further comprises administering to the subject at least one adjuvant. Non-limiting examples of adjuvants are described herein.

In various embodiments, the immune response is cross-protective against a heterologous Zika virus.

Various embodiments of the present invention provide for a method of eliciting an immune response in a subject in need thereof, comprising: administering a prime dose of an attenuated Flavivirus produced by a method other than codon-pair deoptimization or a modified Flavivirus in which expression of viral proteins is reduced compared to a parent virus, wherein the reduction in expression is the result of recoding the prM, or envelope (E) region, or the nonstructural protein 3 (NS3) region or both the E and NS3 regions; and administering one or more boost dose of the attenuated Flavivirus by methods other than codon-pair deoptimization or the modified Flavivirus to the subject in need thereof, wherein at least the prime dose or the one or more boost dose is the modified virus. In various embodiments, a first of the one or more boost dose is administered about 2 weeks after the prime dose.

In various embodiments, the Flavivirus is a Zika virus. In other embodiments, the Flavivirus is selected from the group consisting of dengue fever virus, West Nile virus, yellow fever virus, Japanese encephalitis virus, Spondweni virus, Saint Louis encephalitis virus, and Powassan virus.

In various embodiments, one or both of the E protein-encoding sequence and the NS3 protein-encoding sequence are recoded by reducing the codon pair bias or codon usage bias of the protein-encoding sequence. In various embodiments, reducing the codon-pair bias comprises identifying a codon pair in the parent protein-encoding sequence having a codon-pair score that can be reduced, and reducing the codon-pair bias by substituting the codon pair with a codon pair that has a lower codon-pair score.

In various embodiments, reducing the codon-pair bias comprises rearranging the codons of a parent protein-encoding sequence. In various embodiments, one or both of the E protein-encoding sequence and the NS3 protein-encoding sequence are recoded by increasing the number of CpG or UpA di nucleotides compared to a parent virus. In various embodiments, each of the recoded prM/E protein-encoding sequence and the recoded NS3 protein-encoding sequence have a codon pair bias less than, −0.05, −0.1, or less than −0.2, or less than −0.3, or less than −0.4. In various embodiments, one or both of the E protein-encoding sequence and the NS3 protein-encoding sequence are recoded by replacing one or more codons with synonymous codons that are less frequent in the viral host.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. "Exposed" to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, "administering" means delivering using any of the various methods and delivery systems known to those skilled in the art. Administering can be performed, for example, intranasally, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

In various embodiments, the present invention provides for a method of eliciting an immune response in a subject in need thereof, comprising: administering a prime dose of an attenuated Flavivirus produced by a method other than codon-pair deoptimization or a modified Flavivirus in which expression of viral proteins is reduced compared to a parent virus, wherein the reduction in expression is the result of recoding the prM, or envelope (E) region, or the nonstructural protein 3 (NS3) region or both the E and NS3 regions; and administering one or more boost dose of the attenuated Flavivirus by methods other than codon-pair deoptimization or the modified Flavivirus to the subject in need thereof, wherein at least the prime dose or the one or more boost dose is the modified virus.

In various embodiments, the one or more boost dose is administered about 2 weeks after a prime dose. In various embodiments, 2, 3, 4, or 5 boost doses are administered. In various embodiments, the intervals between the boost doses can be 1, 2, 3, 4, 5, 6, 7, 8, 9, or 10 weeks. In additional embodiments, the intervals between the boost doses can be 1, 2, 3, 4, 5, 6, 7, 8, 9, 10, 11 or 12 months. As a non-limiting example, the prime dose can be administered, about two weeks thereafter a first boost dose can be administered, about one month after the first boost dose, a second boost dose can be administered, about 6 months after the second boost dose, a third boost dose can be administered. As another non-limiting example, the prime dose can be administered, about two weeks thereafter a first boost dose can be administered, about six months after the first boost dose, a second boost dose can be administered, about 12 months after the second boost dose, a third boost dose can be administered. In further embodiments, additional boost dosages can be periodically administered; for example, every 5 years, every 10 years, etc.

In various embodiments, the Flavivirus is a Zika virus. In various embodiments, the Flavivirus is selected from the group consisting of dengue fever virus, West Nile virus, yellow fever virus, Japanese encephalitis virus, Spondweni virus, Saint Louis encephalitis virus, and Powassan virus.

In various embodiments, one or both of the E protein-encoding sequence and the NS3 protein-encoding sequence are recoded by lowering the codon pair bias or codon usage bias of the protein-encoding sequence. In various embodiments, one or both of the E protein-encoding sequence and the NS3 protein-encoding sequence are recoded by increasing the number of CpG or UpA di nucleotides compared to a parent virus.

In various embodiments, reducing the codon-pair bias comprises identifying a codon pair in the parent protein-encoding sequence having a codon-pair score that can be reduced, and reducing the codon-pair bias by substituting the codon pair with a codon pair that has a lower codon-pair score.

In various embodiments, reducing the codon-pair bias comprises rearranging the codons of a parent protein-encoding sequence. In various embodiments it includes the increase of the CpG dinucleotide in the modified virus. In various embodiments it includes the increase of the UpA dinucleotide in the modified virus.

In various embodiments, each of the recoded prM/E protein-encoding sequence and the recoded NS3 protein-encoding sequence have a codon pair bias less than, −0.05, −0.1, or less than −0.2, or less than −0.3, or less than −0.4.

In various embodiments, one or both of the E protein-encoding sequence and the NS3 protein-encoding sequence are recoded by replacing one or more codons with synonymous codons that are less frequent in the viral host.

In various embodiments, the prime dose is administered subcutaneously, intramuscularly, intradermally, or intranasally. In various embodiments, the one or more boost dose is administered intratumorally, intravenously, or intrathecally.

The timing between the prime and boost dosages can vary, for example, depending on the stage of infection or disease (e.g., non-infected, infected, number of days post infection), and the patient's health. In various embodiments, the one or more boost dose is administered about 2 weeks after the prime dose. That is, the prime dose is administered and about two weeks thereafter, a boost dose is administered.

In various embodiments, the dosage amount can vary between the prime and boost dosages. As a non-limiting example, the prime dose can contain fewer copies of the virus compared to the boost dose.

In other embodiments, the type of attenuated virus produced by a method other than codon-pair deoptimization or modified virus of the present invention can vary between the prime and boost dosages. In one non-limiting example, a modified virus of the present invention can be used in the prime dose and an attenuated virus (produced by a method other than codon-pair deoptimization) of the same or different family, genus, species, group or order can be used in the boost dose.

In other embodiments, the route of administration can vary between the prime and the boost dose. In a non-limiting example, the prime dose can be administered subcutaneously, and the boost dose can be administered via injection into the tumor; for tumors that are in accessible, or are difficult to access, the boost dose can be administered intravenously.

A "subject" means any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human poliovirus receptor CD155. In a preferred embodiment, the subject is a human. Preferred embodiments of birds are domesticated poultry species, including, but not limited to, chickens, turkeys, ducks, and geese.

A "prophylactically effective dose" is any amount of a vaccine that, when administered to a subject prone to viral infection or prone to affliction with a virus-associated disorder, induces in the subject an immune response that protects the subject from becoming infected by the virus or afflicted with the disorder. "Protecting" the subject means either reducing the likelihood of the subject's becoming infected with the virus, or lessening the likelihood of the disorder's onset in the subject, by at least two-fold, preferably at least ten-fold. For example, if a subject has a 1% chance of becoming infected with a virus, a two-fold reduction in the likelihood of the subject becoming infected with the virus would result in the subject having a 0.5% chance of becoming infected with the virus. Most preferably, a "prophylactically effective dose" induces in the subject an immune response that completely prevents the subject from becoming infected by the virus or prevents the onset of the disorder in the subject entirely.

As used herein, a "therapeutically effective dose" is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An "adjuvant" shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more dengue virus, one or more Japanese encephalitis virus, one or more West Nile virus, one or more yellow fever virus, one or more Zika virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains. However, the citation of a reference herein should not be construed as an acknowledgement that such reference is prior art to the present invention.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994). All references mentioned herein are incorporated in their entirety by reference into this application. The contents of WO 2008/121992 and WO 2011/044561 are incorporated by reference.

EXAMPLES

Example 1

Construction and Characterization of E, NS3 and E-NS3 Codon Pair-Bias Reduced Zika Virus in Tissue Culture To achieve attenuation of Zika virus strains PRVABC59 and MR766, codon pair bias of the prM/E and NS3 genes was reduced (introducing underrepresented codon pairs) in viral genes according to computer algorithms and chemical synthesis in order to reduce the expression level of the viral genes (FIG. 1).

TABLE 6

| CpG and UpA increase | | |
|---|---|---|
| Virus | CpG (%) | UpA (%) |
| PR15 SYN WT | 24 (2.39%) | 26 (2.59%) |
| PR15 E-W/W/Min | 59 (5.88%) | 52 (5.18%) |

Example 2

Leveraging SAVE Platform Flexibility to Create Second-Generation Zika Virus Vaccine Candidates To fine-tune attenuation and immunogenicity, a second generation of Zika virus vaccine candidates were constructed using the SAVE platform (FIG. 2). Based on the E-Min design (FIG. 1), the new vaccine candidates contained a smaller proportion of deoptimized sequence lowered from 2014 base-pairs (E-Min) to either 997 base-pairs (E-W/Min) or 664 base-pairs (E-W/W/Min) with the remainder restored to wild-type sequence.

The sequences of the three candidates MR766 E-Min (SEQ ID NO: 7), W-E-Min (SEQ ID NO: 8), and E-W/W/Min (SEQ ID NO: 9) are provided herein as examples.

Example 3

Characterization of Reduced Codon-Pair Bias Variants' Attenuation in Vero Cells

Figure 3:
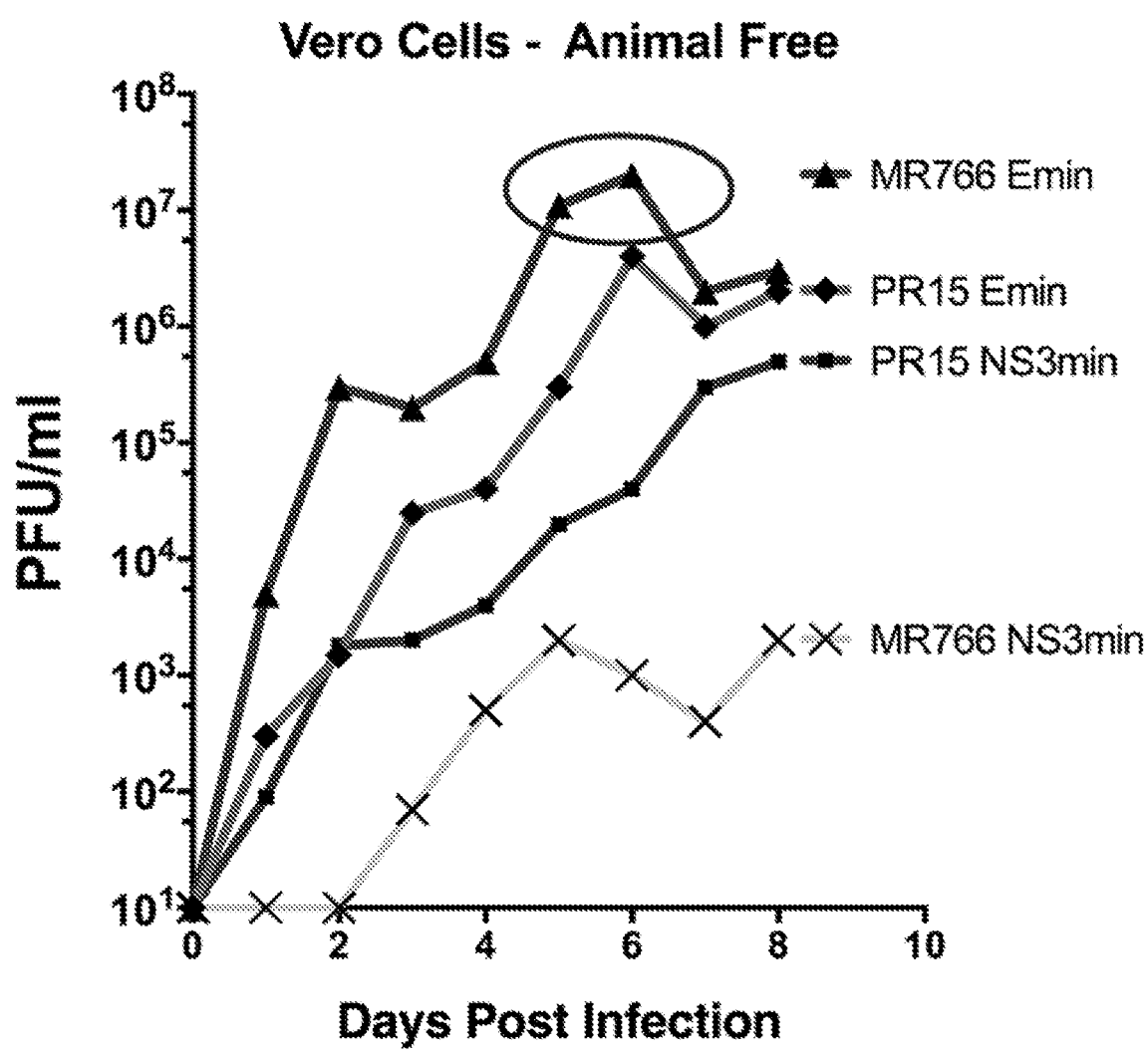
FIG. 3 depicts growth of Zika vaccine candidates in Vero cells under animal component-free conditions. The 6 chimera Zika vaccine strains were used to infect Vero cells under animal-component free conditions at a MOI of 0.1. Of the six strains, four grew to detectable titers in Vero cells under these conditions. MR766-Emin grew to a peak titer of $5 \times 10^7$ PFU/ml after five days and PR15-EhMin to a peak titer of $5 \times 10^6$ PFU/ml after 5 days in Vero cells grown in animal-free conditions.

MR766-EMin replicated with similar kinetics compared to wildtype MR766 in Vero cells, reaching a titer of $\geq 2 \times 10^7$ PFU/mL. PR15 E-Min was more attenuated, reaching a titer of $\sim 2 \times 10^6$ PFU/mL in Vero cells. The N53-Min variants were more highly attenuated; with maximum titers of $1 \times 10^3$ PFU/mL and $5 \times 10^5$ PFU/mL for MR766 N53-Min and PR15 N53-Min respectively (FIG. 3).

Example 4

Figure 4:
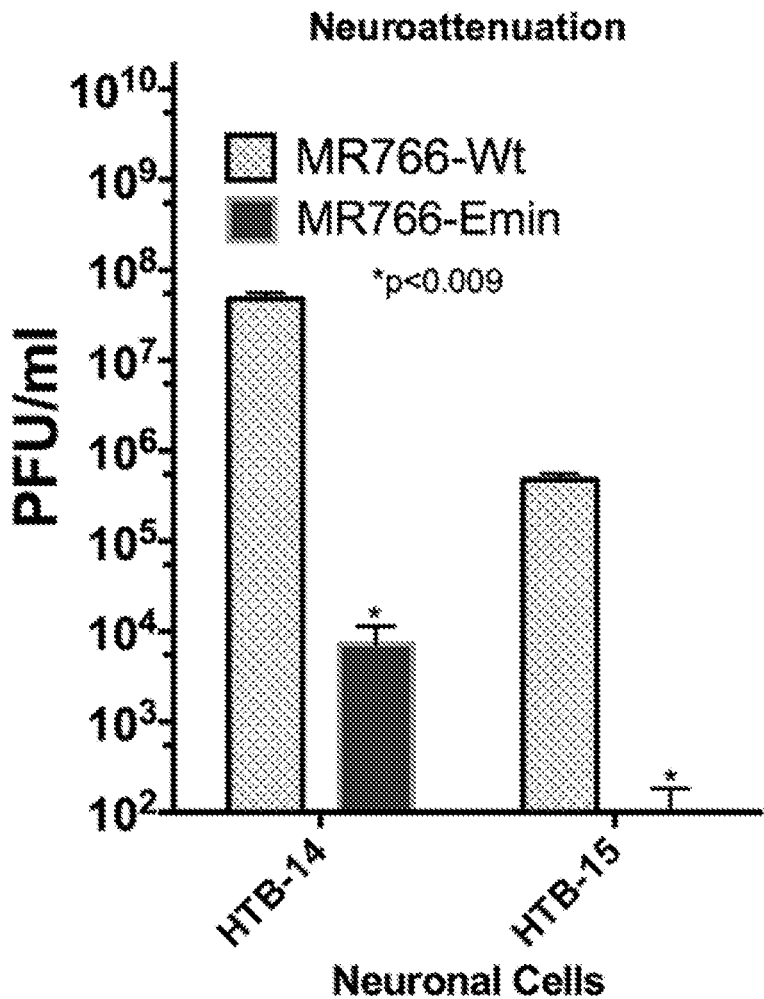
FIG. 4 depicts neuro-attenuation of MR766-EMin in human neuronal cells. The human neuronal cell lines HTB-14 and HTB-15 which have been used previously to characterize wt Zika virus cell tropism in the developing human brain were infected at a MOI of 0.1 and 4 days post infection, replicating virus was titrated on BHK cells, with wt MR766 growing to high titers ($5 \times 10^7$ PFU/mL for HTB-14 and $8 \times 10^5$ PFU/mL for HTB-15. The lead candidate, MR766 E-Min, was approximately 10,000-fold attenuated in both of these cell lines, indicating a high level of neuro-attenuation in human cells.

Neuroattenuation of Reduced Codon-Pair Bias Variants' in Human Neuronal Cell Lines Unlike the older ZIKV strains such as MR766, the current strains of ZIKV cause neurological disease such as microcephaly and Guillain-Barre syndrome. Thus, based on our pre, pre-IND meeting with the FDA, any live-attenuated Zika vaccine would need to demonstrate neuro-attenuation in human neuronal cells in vitro and neuro-attenuation in nonhuman primates in vivo (proposed Phase II work). To begin the pre-clinical development of our lead candidate, we infected two well-characterized human neuronal cell lines HTB-14 (also known as U-87) and HTB-15 (also known as U-118), which have been used previously to characterize Zika virus cell tropism in the developing human brain and to test potential anti-Zika inhibitors. We infected human neuronal cell lines HTB-14 and HTB-15 and quantified peak titers after 4 days. We observed that in human HTB-14 cells, MR766 E-Min was nearly 4 $Log_{10}$s attenuated and in human HTB-15 cells, growth was either undetectable in two independent experiments or at the limit of detection in one experiment (100 PFU/ml) also representing a nearly 4 $Log_{10}$ level of neuro attenuation in vitro (FIG. 4)

Example 5

Levels of Protein are Reduced in PRVABC59 or MR766 Derived E-Min Infected Cells

Western Blot of whole cell lysates taken from ZIKV infected cells were used to compare levels of protein expression between different PRVABC59 and MR766 variants. For virus infection, Vero cells were grown in the OptiPRO medium at 37° C. till 90% confluent. Zika viruses, including synthetic wildtype and de-optimized (E-Min) MR766 and PRVABC59, were diluted to an MOI of 0.5 and were added to the cells. The cells were rocked for 15 min at R.T., then incubated at 33° C. for 2 hrs. Next, the inocula were removed, and the infected cells were continued to culture in OptiPRO medium at 33 C for 24 hrs.

For whole cell lysate preparation after 24 hr incubation, cells were briefly rinsed with cold PBS, then lysed on ice with RIPA buffer (150 mM NaCl, 5 mM b-mercaptoethanol, 1% NP-40, 0.1% sodium dodecyl sulfate, 50 mM Tris-HCl, pH8.0). Whole cell lysates were collected, directly mixed with 6× Laemmli buffer with b-mercaptoethanol, boiled and aliquoted for storage.

For Western blot, an equal volume of WCL from each sample was fractionated by SDS-PAGE and transferred to a nitrocellulose membrane. The membrane was blocked with 5% bovine calf serum (BCS) in PBS for 1 hr at R.T., then incubated with a mouse monoclonal antibody against dengue type-2 envelope(E) protein 4G2 overnight at 4 C, washed three times with PBS-Tween, subsequently incubated with HRP conjugated anti-mouse secondary antibody in 5% BCS for 1 hr at R.T. The membrane was washed three times, and proteins were visualized using Pierce 1-Step Ultra TMB Blotting solution.

Figure 5:
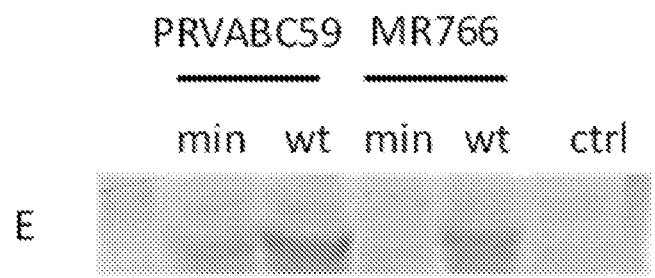
FIG. 5 depicts reduction of protein and RNA expression in ZIKV infected cells. Western blot was used to measure envelope glycoprotein expression in Vero cells infected by E-Min (min) and wildtype (WT) variants of ZIKV strains PRVABC59 and MR766 after being incubated for 24 hours at 33° C. In both strains of ZIKV, envelope glycoprotein expression was greatly reduced for the E-Min variants.

Levels of the envelope glycoprotein were found to be reduced in E-Min variants of PRVABC59 and MR766 strains of ZIKV compared to wildtype (FIG. 5).

Example 6

Attenuation in AG129 Mice

Figure 6:
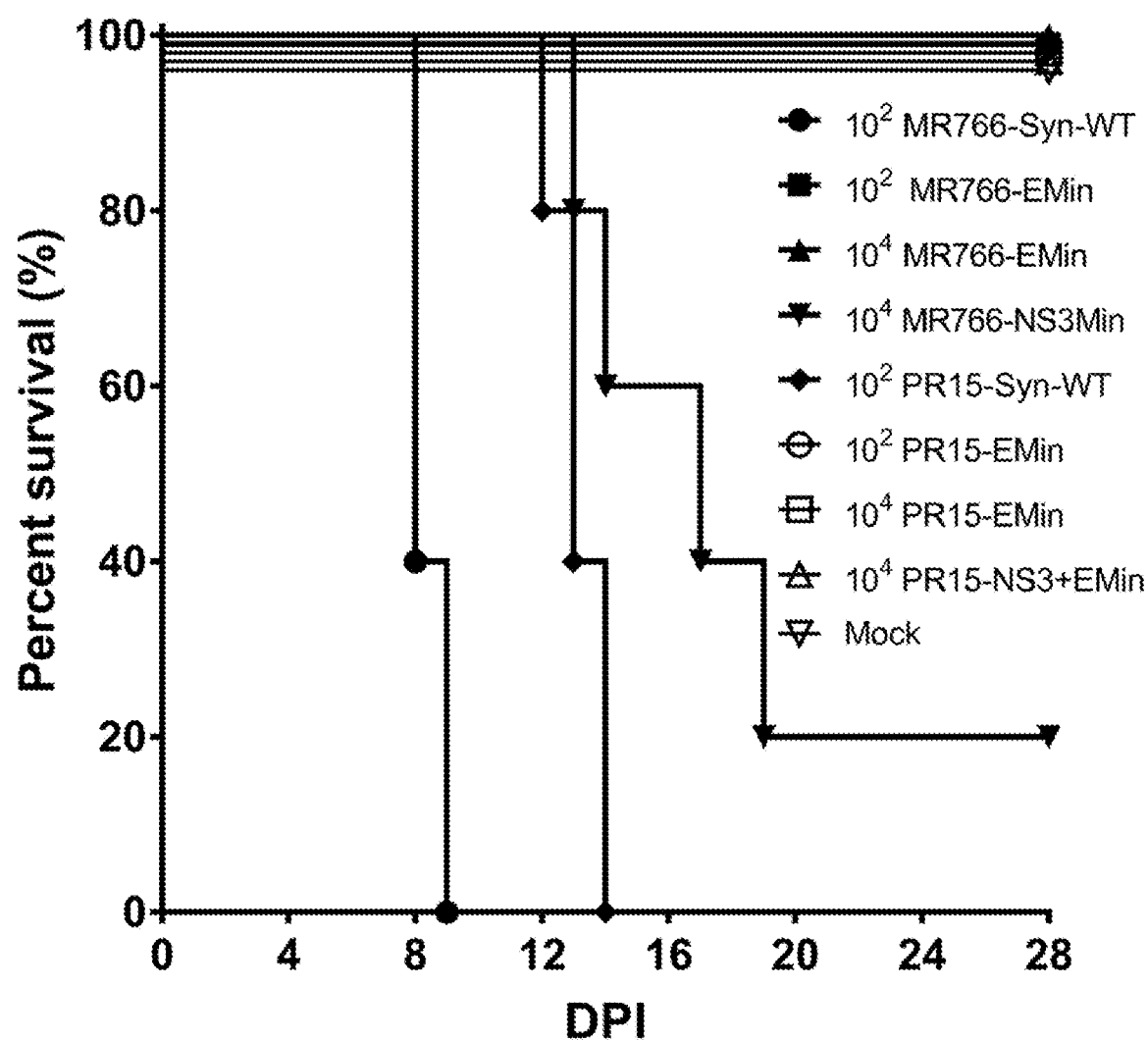
FIG. 6 depicts virus phenotypes in infected mice. Attenuation of SAVE ZIKV vaccine candidates in AG129 mice. AG129 mice were injected with either: i) synthetically derived wild-type virus MR766 and PR15 virus at a dose of $10^2$ (positive control); ii) either a dose of $10^4$ or $10^2$ PFU of the vaccine candidates PR15 E-Min or MR766 E-Min and NS3-Min; iii) a single dose of $10^4$ of the vaccine candidate PR15 NS3+E-Min; all delivered in 100 µl subcutaneously. Injected mice were examined for mortality and morbidity (weight loss). All mice inoculated with $10^2$ wt virus and 80% of mice inoculated with $10^4$ MR766-NS3-Min succumbed to infection. All other mice survived including all mice vaccinated with $10^4$ PFU of the lead candidate MR 766 E-Min and none exhibited any weight loss.

As described above, the AG129 adult mouse model is gaining acceptance for studies of flavivirus vaccines and therapeutics. We used AG129 mice to test: 1) each synthetically derived wild-type virus MR766 and PR15 virus at a dose of $10^2$ (positive control); 2) two doses ($10^4$ and $10^2$ PFU) of the vaccine candidates PR15 E-Min or MR766 E-Min and NS3-Min; and 3) a single dose of $10^4$ of the vaccine candidates PR15 NS3/E-Min. In this study we examined attenuation, efficacy, and immunogenicity. Animals were randomly assigned to groups of 5 animals. Groups were infected with various attenuated and synthetic wild-type viruses. Two rounds of vaccination were performed on Day 0 and Day 28 to vaccinate mice. To measure attenuation, survival and weight was measured post-vaccination (FIG. 6).

Survival, weight, and clinical sign data were collected daily throughout the course of the experiment. SAVE deoptimized PRVABC59 and MR766 strains were highly attenuated compared to synthetic wild-type viruses, with only the MR766 NS3-Min at a dose of $10^4$ inducing death in 40% of mice. Thus, all other strains are at least 500-fold attenuated. Mice infected with $10^2$ PFU of synthetic wild-type PR15 or MR766 ZIKV experienced a dramatic weight loss just prior to death, similar to the pattern observed with "natural" wild-type ZIKV. Mice infected with $10^4$ PFU of the candidate MR766 E-Min did not experience significant weight loss or mortality (FIG. 6).

The growth phenotype and pathogenesis of the PRVABC59 E-Min and E+NS3-Min variant as well as the MR766 E-Min and NS3-Min was examined in an animal model. Groups of five AG129 mice received each virus at doses of $10^2$ or $10^4$ PFU subcutaneously, and body weight and survival of the animals was monitored continuously for 28 days p.i. Morbidity and mortality (weight loss, reduced activity, death) was monitored. The Lethal Dose 50 ($LD_{50}$) of the wildtype virus and the vaccine candidates was calculated by the method of Reed and Muench (Reed, L. J.; Muench, H., 1938, The American Journal of Hygiene 27: 493-497). Remarkably, the E-Min variants for PRVABC59 and MR766 and the PRVABC59 E+NS3-Min virus did not induce apparent disease after a dose up to $10^4$ PFU with no mortality and minimal weight loss. Therefore, the theoretical LD50 of the E-Min variants was calculated to be equal or greater than $3.16 \times 10^4$ PFU, which exceeds that of wt PRVABC59 or MR766 by a factor of at least 1,000 (Table 5). The LD50 of the MR766 NS3-Min virus was calculated to be ≤42.

TABLE 5

$LD_{50}$ and $PD_{50}$ of Attenuated Virus

| Virus | LD50 | PD50 |
|---|---|---|
| WT MR766 | $<3.16 \times 10^1$ | NA |
| MR766 E-Min | $>3.16 \times 10^4$ | $6.81 \times 10^1$ |
| MR766 NS3-Min | $<4.20 \times 10^1$ | $<6.81 \times 10^3$ |
| WT PRVABC59 | $<3.16 \times 10^1$ | NA |
| PRVABC59 E-Min | $3.16 \times 10^4$ | $1.47 \times 10^2$ |
| PRVABC59 E+NS3-Min | $3.16 \times 10^4$ | $<6.81 \times 10^3$ |

Example 7

Immunogenicity in AG129 Mice

Figure 7:
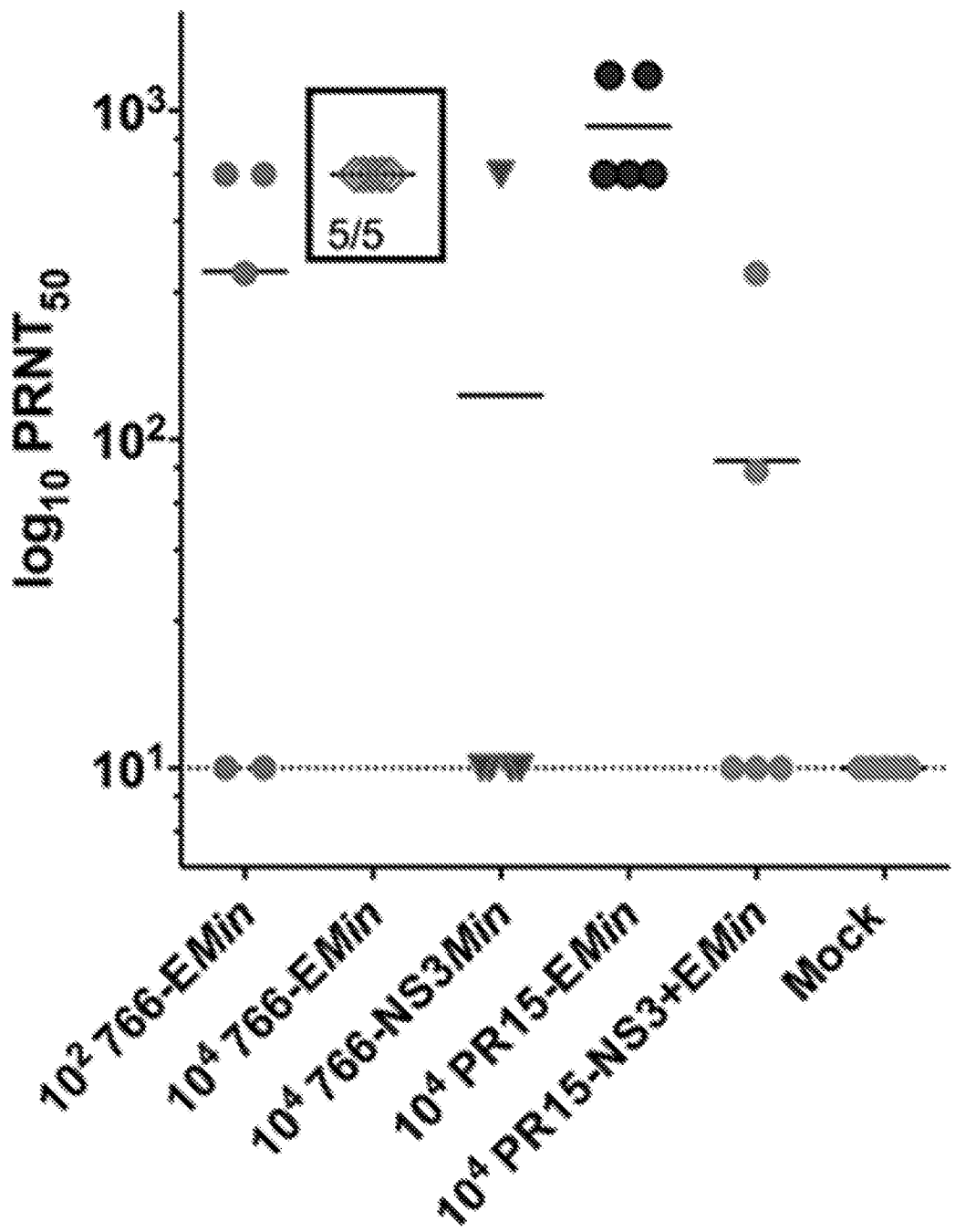
FIG. 7 depicts SAVE-attenuated ZIKV vaccine candidates induce high levels of neutralizing antibodies and protect from lethal challenge in AG129 mice. A) Anti-PR15 Zika antibodies after a single dose. Serum from vaccinated animals was harvested on Day 28 and antibodies were quantified against ZIKV strain Puerto Rico 2015 PRVABC-59 via $PRNT_{50}$ assay on Vero cells. Mice vaccinated with both PR15 E-Min and MR766 E-Min at the $10^4$ dose developed high levels of neutralizing antibodies (2.8 $\log_{10}$ PRNT50).

Vaccine candidates should be capable of providing, at low dose, long-term protection from challenge with a lethal dose of wt virus equal to $10^{2.3}$ cell-culture infectious dose ($CCID_{50}$) per animal. Although the E-Min variants were highly attenuated in cell culture and in AG129 mice, they were successful in preventing mortality in AG129 mice after challenge with as little as 68 PFU (MR766 E-Min) or 147 PFU (PRVABC59 E-Min). We tested vaccine efficacy in the survivors of each mouse from the attenuation study. First, serum was harvested from survivors via superficial temporal vein on Day 28 and animals were boosted with the same vaccine dose a second time on Day 28. Serum was also collected on day 49 (21 days post-boost). Neutralizing antibodies from these animals were quantified using a 50% plaque reduction neutralization titer ($PRNT_{50}$) assay of serum harvested at 14, 28, and 49 days post vaccination. One half serial dilutions, starting at a 1/10 dilution, of test sera were made. Dilutions were then mixed 1:1 with $10^{2.4}$ PFU of ZIKV strain PRVABC59 (PR15). The virus-serum mixture was then added to individual wells of a 12-well tissue culture plate with Vero 76 cells. The reciprocal of the dilution of test serum that resulted in ≥50% reduction in average plaques from virus control was recorded as the $PRNT_{50}$ value. On day 28 and after only a single vaccination, MR766 E-Min was able to generate a robust antibody response to the current PR15 strain in all animals (FIG. 7). Similarly, PR15 E-Min also provided a robust antibody response after only a single vaccination.

Example 8

Protective Efficacy in AG129 Mice

On Day 49 after initial vaccination, each group was challenged with a lethal dose ($10^{2.3}$ $CCID_{50}$/animal) of PR15 WT virus in 0.1 mL delivered s.c. Challenge virus was provided to Utah State via BEI Resources (Manassas, Va.). Mice were observed at least twice daily for mortality, and weights were taken every other day from 7-21 days post challenge to track weight change. Codagenix's SAVE vaccine candidates were successful in preventing or reducing mortality and morbidity (weight loss, not shown) in challenged AG129 mice. MR766 E-Min and PR15 E-Min at a dose of $10^4$ could both protect all mice and induce a robust antibody response, whereas other vaccine variants (e.g. PR15 E+NS3-Min) could only provide partial protection (FIG. 8). The protective-dose 50% (PD$_{50}$) for MR766 E-Min was <10$^2$ PFU, at least 1000-fold less than MR766 E-Min's LD$_{50}$, indicating at least a 3-orders of magnitude safety margin.

Example 9

Efficacy in Non-Human Primates

Figure 9:
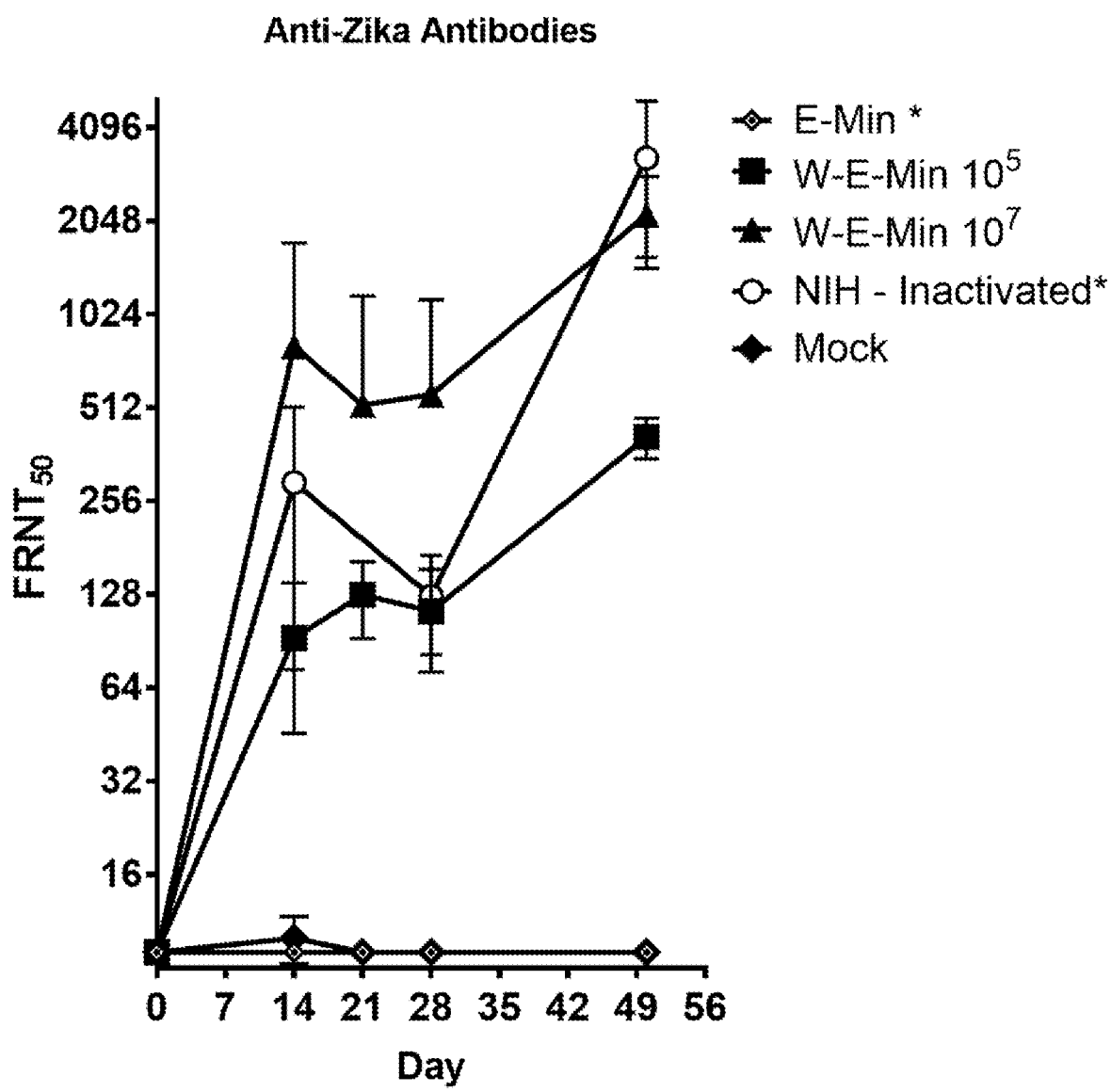
FIG. 9 depicts immunogenicity of E-W/Min vaccination in Cynomolgus macaques. Zika virus seronegative macaques were vaccinated with either $10^5$ or $10^7$ plaque-forming units (PFU) or E-W/Min delivered subcutaneously in a volume of 0.5 ml. Mock vaccinated animals were injected with 0.5 mL of vaccine diluent. Macaques were initially vaccinated on day 0, and then boosted on day 28. Serum samples were collected on days 0, 14, 21, 28, and 50 and tested for neutralizing activity against wildtype ZIKV strain MR766 using a focus-reduction neutralization 50% ($FRNT_{50}$) assay in Vero cells. Vaccination with $10^7$ PFU E-W/Min was found to be superior to the NIH inactivated ZIKV vaccine candidate after the first vaccination and comparable post-boost. The lower $10^5$ PFU dose was also effective in triggering neutralizing antibodies. All animals vaccinated with E-W/Min seroconverted by day 14 post-vaccination.
Figure 10:
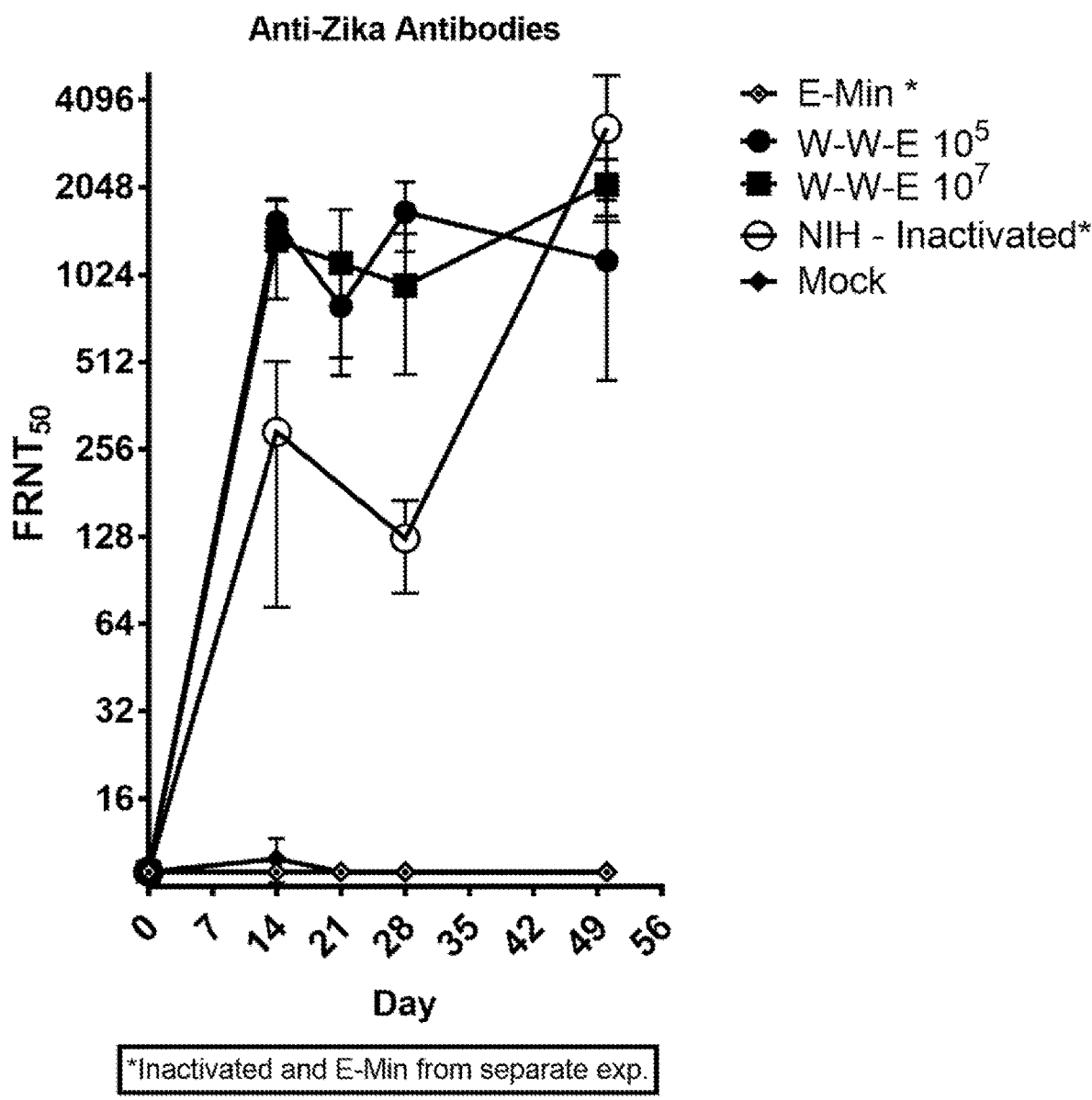
FIG. 10 depicts immunogenicity of E-W/W/Min vaccination in Cynomolgus macaques. Zika virus seronegative macaques were vaccinated with either $10^5$ or $10^7$ plaque-forming units (PFU) or E-W/W/Min delivered subcutaneously in a volume of 0.5 mL. Mock vaccinated animals were injected with 0.5 mL of vaccine diluent. Macaques were initially vaccinated on day 0, and then boosted on day 28. Serum samples were collected on days 0, 14, 21, 28, and 50 and tested for neutralizing activity against wildtype ZIKV strain MR766 using a focus-reduction neutralization 50% ($FRNT_{50}$) assay in Vero cells. Vaccination with $10^7$ or $10^5$ PFU E-W/W/Min was found to be superior to the NIH inactivated ZIKV vaccine candidate after the first vaccination and the two doses triggered comparable levels of neutralizing antibodies. All animals vaccinated with E-W/Min seroconverted by day 14 post-vaccination. No increase in $FRNT_{50}$ titer was observed post-boost on day 28, indicating sterilizing immunity that prevented secondary infection from triggering an anamnestic response. This further indicates that a single, relatively low dose, of W-W-E-Min may be sufficient for triggering high levels (≥1,028 $FRNT_{50}$).

Cynomolgus macaques (CM) are commonly used as a model for evaluating flavivirus infection including Yellow Fever, Dengue, West Nile and ZIKV. ZIKV isolates have also been recovered from naturally infected Cynomolgus macaques. Previous work suggests that while experimental ZIKV infection of CM is not likely to produce clinical disease, ZIKV can replicate and be found in blood, urine and other tissues. In a non-GLP study conducted by Southern Research, we evaluated the efficacy of live attenuated Zika virus (ZIKV) vaccine candidates in naïve CM. A total of fifteen (15) (10 male and 5 female) ZIKV seronegative CMs were randomized into five (5) treatment groups. CMs in Groups 1-4 were vaccinated using a prime-boost regimen (Days 0 and 28) by subcutaneous (SC) injection with attenuated viruses (MR776 E-W/Min or MR776 E-W/W/Min) at doses of 10$^7$ or 10$^5$ PFU in a volume of 500 µL. CMs assigned to the mock control group (Group 5) received PBS via SC injection. The presence of vaccine induced anti-ZIKV neutralizing antibody (Nab) was assessed on Day 14, 21, 28, 50 and 61 by focus reduction neutralization test (FRNT). FRNT values were 2-4 times higher for both MR766 E-W/Min (FIG. 9) and MR766 E-W/W/Min (FIG. 10) vaccinated macaques compared to the NIH Inactivated vaccine after a single dose. FRNT values in E-W/W/Min vaccinated macaques did not increase after the boost on day 28, indicating that the vaccines induced sterilizing immunity that prevented further infection by the boosting virus. All animals vaccinated with E-W/Min or E-W/W/Min seroconverted by day 14 post-vaccination. This data indicates that a single, relatively low dose, of E-W/W/Min may be sufficient for triggering high levels (≥1,028 FRNT$_{50}$).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A modified Zika virus in which expression of viral proteins is reduced compared to a parent virus, wherein the reduction in expression is the result of recoding at least the envelope (E) region,
   wherein recoding at least the envelope (E) region comprises reducing the codon pair bias;
   wherein less than the entire of the E region is deoptimized,
   wherein the modified virus has a safety factor of at least $10^2$, wherein the safety factor is defined by the ratio of $LD_{50}/PD_{50}$, wherein the envelope (E) region is encoded by a nucleic acid having SEQ ID NO:8 or SEQ ID NO:9.

2. A method of eliciting an immune response in a subject, comprising prophylactically administering to the an effective dose of an immunogenic composition comprising a modified virus of claim 1.

3. The method of claim 2, further comprising administering to the subject at least one adjuvant.

4. The method of claim 2, wherein the immune response is cross-reactive with a heterologous Zika virus.

5. The modified Zika virus of claim 1, wherein the envelope (E) region is encoded by a nucleic acid having SEQ ID NO:8.

6. A method of eliciting an immune response in a subject, comprising prophylactically administering to the subject an effective dose of an immunogenic composition comprising a modified virus of claim 5.

7. The method of claim 6, further comprising administering to the subject at least one adjuvant.

8. The method of claim 6, wherein the immune response is cross-reactive with a heterologous Zika virus.

9. The modified Zika virus of claim 1, wherein the envelope (E) region is encoded by a nucleic acid having SEQ ID NO:9.

10. A method of eliciting an immune response in a subject, comprising prophylactically administering to the subject an effective dose of an immunogenic composition comprising a modified virus of claim 9.

11. The method of claim 10, further comprising administering to the subject at least one adjuvant.

12. The method of claim 10, wherein the immune response is cross-reactive with a heterologous Zika virus.

* * * * *